US006534546B1

(12) United States Patent
Honda et al.

(10) Patent No.: US 6,534,546 B1
(45) Date of Patent: Mar. 18, 2003

(54) ANILINE DERIVATIVES POSSESSING AN INHIBITORY EFFECT OF NITRIC OXIDE SYNTHASE

(75) Inventors: Toshio Honda, Tokyo (JP); Toshihiko Makino, Shizuoka-ken (JP); Toshiaki Nagafuji, Shizuoka-ken (JP); Yasushi Kitoh, Shizuoka-ken (JP); Nobuaki Kimura, Shizuoka-ken (JP)

(73) Assignee: Chugai Seiyaku Kabushiki Kaisha (JP)

( * ) Notice: Subject to any disclaimer, the term of this patent is extended or adjusted under 35 U.S.C. 154(b) by 0 days.

(21) Appl. No.: 08/849,400

(22) PCT Filed: Dec. 12, 1995

(86) PCT No.: PCT/JP95/02540

§ 371 (c)(1), (2), (4) Date: Jun. 6, 1997

(87) PCT Pub. No.: WO96/18608

PCT Pub. Date: Jun. 20, 1996

Related U.S. Application Data

(63) Continuation of application No. PCT/JP95/01135, filed on Jun. 7, 1995.

(30) Foreign Application Priority Data

Dec. 12, 1994 (JP) ........................................... 6-336795

(51) Int. Cl.[7] ....................... A61K 31/17; A61K 31/44; A61K 31/40; A61K 31/27

(52) U.S. Cl. ....................... 514/586; 514/357; 514/428; 514/429; 514/479; 514/485; 514/509; 514/530; 514/531; 514/543; 514/544; 514/587; 514/637; 514/641; 560/16; 560/24; 560/25; 560/34; 560/35; 564/27; 564/244; 564/245; 564/246

(58) Field of Search .......................... 564/27, 245, 537, 564/539, 244, 246, 247; 560/16, 24, 25, 34, 35; 514/485, 586, 587, 637, 357, 428, 429, 478, 509, 530, 531, 543, 544, 641; 546/331, 332; 548/566, 577

(56) References Cited

U.S. PATENT DOCUMENTS

| | | | | |
|---|---|---|---|---|
| 4,156,734 A | | 5/1979 | Stone | 424/273 R |
| 4,537,896 A | * | 8/1985 | Claeson et al. | 514/330 |
| 5,656,660 A | * | 8/1997 | Lum et al. | 514/467 |

FOREIGN PATENT DOCUMENTS

| | | |
|---|---|---|
| JP | 52-99227 | 8/1977 |
| JP | 59-31757 | 2/1984 |
| WO | WO 94/21621 | 9/1994 |
| WO | 9500505 | 1/1995 |
| WO | 9509619 | 4/1995 |
| WO | 9609286 | 3/1996 |

OTHER PUBLICATIONS

Toshiaki Nagafuji et al., "Blockade of Nitric Oxide Formation by $N^{w}$–nitro–L–arginine Mitigates Ischemic Brain Edema and Subsequent Cerebral Infarction in Rats", Neuroscience Letters, vol. 147, p. 159–162, 1992.

Toshiaki Nagafuji et al., "A Narrow therapeutical Window of a Nitric Oxide Synthase Inhibitor Against Transient Ischemic Brain Injury", European Journal of Pharmacology, Environmental Toxicology and Pharmacology Section, vol. 248, p. 325–328, 1993.

T. Nagafuji et al., "Temporal Profiles of $Ca^{2+}$/Calmodulin–Dependent and –Independent Nitric Oxide Synthase Activity in the Rat Brain Microvessels Following Cerebral Ishcemia", Acta Neurochir, Suppl. 60, p. 285–288, 1994.

Toshiaki Nagafuji et al., "Nitric Oxide Synthase in Cerebral Ischemia", Molecular and Chemical Neuropathology, vol. 26, pp. 107–157, 1995.

Atwell et al, "Relationships between structure and kinetics of cyclization of 2–aminoaryl amides: potential prodrugs of cyclization–activated aromatic mustards"; *Chemical Abstracts* 120(17) Abst. No. 216381 (*J. Med. Chem.* 37(3):371–380 (1994).

(List continued on next page.)

*Primary Examiner*—Peter O'Sullivan
(74) *Attorney, Agent, or Firm*—Browdy and Neimark, P.L.L.C.

(57) ABSTRACT

Compounds represented by the general formula (1):

(1)

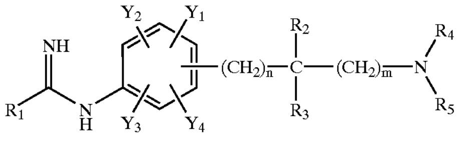

(where $R_1$ is $SR_6$ or $NR_7R_8$, where $R_6$ is typically an alkyl group having 1–6 carbon atoms, $R_7$ is a hydrogen atom, an alkyl group having 1–6 carbon atoms or a nitro group, and $R_8$ is a hydrogen atom or an alkyl group having 1–6 carbon atoms; $R_2$ and $R_3$ are each typically a hydrogen atom or an alkyl group having 1–6 carbon atoms; $R_4$ is a hydrogen atom, an alkyl group having 1–6 carbon atoms or an amidino group of which the amine portion may be substituted by an alkyl or nitro group; $R_5$ is a hydrogen atom or an alkyl group having 1–6 carbon atoms; $Y_1$, $Y_2$, $Y_3$ and $Y_4$ which may be the same or different are each typically a hydrogen atom, a halogen atom or an alkoxy group having 1–6 carbon atoms; n and m are each an integer of 0 or 1), or possible stereoisomers or optically active forms of the compounds or pharmaceutically acceptable salts thereof. The compounds possess a potent nitric oxide synthase inhibiting activity and are useful as therapeutics of cerebrovascular diseases.

45 Claims, 2 Drawing Sheets

OTHER PUBLICATIONS

Sastry et al, "Synthesis of 6-(1,4,5, 6-tetrahydro-6-oxo-3-pyridazinyl)-2H-1, 4-benzoxazin-3(4H)-ones as possible cardiotonic agents"; *Chemical Abstracts* 112(21) Abst. No. 198278 (*Indian J. Chem. Sect. B.* 28B(10):882-884 (1989).

Simon et al, "New reaction of thionyl chloride with a carboxylic acid in the presence of a tertiary amine. X-ray crystallographic proof of structure o.alpha.-chloro-.alpha.-chlrosulfenyl-4-nitro-2, 5-dimethoxyphenylacetyl chloride"; *Chemical Abstracts* (68(2) Abst. No. 7264 (*J. Amer. Chem. Soc.* 89(23):5838-44 (1987).

Sindelar et al, "(2-Arylthio-4-fluorophenyl) acetic acids", *Chemical Abstracts* 97(11) Abst. No. 91952 (*CS* 191 794 B(Czech) Jul. 31, 1979.

Moore et al, "Synthesis of Analogues of Bradykinin with Replacement of the Arginine Residues by 4-Guanidinophenyl-L-alanine", *J. Chem. Soc. Perkins Transactions I* pp. 2025-2030 (1977).

Weinstock et al, "Synthesis and Evaluation of Non-Catechol D-1 and D-2 Dopamine Receptor Agonists: Benzimidazol-2-one, Benzoxazol-2-one, and the Highly Potent Benzothiazol-2-one 7-Ethylamines", *J. Med. Chem.* 30:1166-1176 (1987).

* cited by examiner

ANILINE DERIVATIVES POSSESSING AN INHIBITORY EFFECT OF NITRIC OXIDE SYNTHASE

This application is a 371 of PCT/JP95/02540 filed Dec. 12, 1995 which is a continuation of PCT/JP95/01135 filed Jun. 7, 1995.

TECHNICAL FIELD

This invention relates to N-substituted aniline derivatives, more specifically to the compounds represented by the general formula (1) which have an inhibitory effect on nitric oxide synthase (NOS) to suppress the production of nitric oxide (NO) and thereby prove effective against the pathology in cerebrovascular diseases, in particular, occlusive cerebrovascular diseases in which excessive NO or NO metabolites would be involved, as well as traumatic brain injuries, seizure, headache and other pains, morphine tolerance and dependence, Alzheimer's disease, Parkinson's disease, septic shocks, chronic rheumatoid arthritis, osteoarthritis, viral or nonviral infections and diabetes; the invention also relates to possible stereoisomers and optically active forms of the compounds, pharmaceutically acceptable salts thereof, as well as to preventives and therapeutics containing them as an effective ingredient.

BACKGROUND ART

Occlusion or lower perfusion pressure in a cerebral artery or carotid artery by a certain mechanism cause ischemic necrosis in the brain tissue and this state is called "cerebral infarction". Cerebral infarction is roughly classified to cerebral embolism and cerebral thrombosis depending upon the mechanism involved.

Cerebral embolism is characterized by the formation of thrombi in a cerebral artery due to detachment of intracardiac blood clots or rarely blood clots on arterial walls, and cerebral thrombosis is primarily based on sclerotic lesions of cerebral arteries, which are complicated by an increased blood viscosity or a reduced perfusion pressure to result in an occlusion of the artery, which may progress to ischemic necrosis of the brain tissue ("NOKEKKAN SHOGAI", compiled under the supervision of Hisao MANABE and Teruo OMAE, published by Life Science, pp. 54–55, 1992).

Irrespective of whether the cause is cerebral embolism or thrombosis, the formation of edema is observed in the ischemic brain tissue either concurrently with or prior to the development of the infarction. Vasogenic brain edema is manifested several hours after the onset of cerebral ischemia and continues for about one week from the onset. Thereafter, the brain edema decreases gradually and, depending on the area of the infarction, the edema persists as an infarct area in one to three months. Since the brain is covered with the rigid skull, brain edema causes an increase in the brain volume. If the brain edema exceeds a certain limit, there occurs an abrupt increase in the tissue pressure and the intracranial pressure, often inducing fatal hernia and eventually aggravating the brain damage to determine the scope of the subsequent infarct volume ("CT, MRI JIDAI NO NOSOTCHUGAKU, PART I in Two Volumes", Kenji INAMURA and Akio TERASHI, published by Nihon Rinshosha, pp.,231–239, 1993). In addition, if a region of the brain becomes infarcted, the functions that have been fulfilled by the affected area, for example, perception, sensation and memory will be lost.

Thus, the treatment of brain edema and infarction which are critical to the quality of patient's life and the prognosis of his disease is clinically a very important objective. As for brain edema, the currently used methods of treatment rely upon hyperpnea, the drainage of cerebrospinal fluid and the use of hypertonic solutions, steroids and others; however, in almost all the effects of cases, these methods are only transient and there is not much promise for the therapeutic efficacy to be finally achieved ("NOSOTCHU CHIRYO MANUAL", ed. by Masakuni KAMEYAMA, published by Igaku Shoin, pp. 34–36, 1991). Therefore, it has been desirable to develop drugs that are operated by an entirely different mechanism than the conventional etiological observation and which will prove effective in the treatment of ischemic cerebrovascular diseases.

A presently dominant theory based on genetic DNA analyses holds that NOS exists in at least three isoforms, namely, calcium-dependent N-cNOS (type 1) which is present constitutively in neurons, calcium-dependent E-cNOS (type 3) which is present constitutively in vascular endothelial cells and apparently calcium-independent iNOS (type 2) which is induced and synthesized by stimulation with cytokines and/or lipopolysaccharides (LPS) in macrophages and many other cells (Nathan et al., FASEB J. 16, 3051–3064, 1992; Nagafuji et al., Mol. Chem. Neuropathol. 26, 107–157, 1995).

A mechanism that has been proposed as being most probable for explaining the brain tissue damage which accompany cerebral ischemia is a pathway comprising the sequence of elevation in the extracellular glutamic acid level, hyperactivation of glutamic acid receptors on the post-synapses, elevation in the intracellular calcium level and activation of calcium-dependent enzymes (Siesjö, J. Cereb. Blood Flow Metab. 1, 155–185, 1981; Siesjö, J. Neurosurg. 60, 883–908, 1984; Choi, Trends Neurosci. 11, 465–469, 1988; Siejö and Bengstsson, J. Cereb. Blood Flow Metab. 9, 127–140, 1989). As already mentioned, N-cNOS is calcium-dependent, so the inhibition of abnormal activation of this type of NOS isoform would contribute to the neuroprotective effects of NOS inhibitors (Dawson et al., Annals Neurol. 32, 297–311, 1992).

As a matter of fact, the mRNA level of N-cNOS and the number of N-cNOS containing neurons start to increase early after cerebral ischemia and their temporal alterations coincide with the development of infarction in rats (Zhang et al., Brain Res. 654, 85–95, 1994). In addition, in a mouse model of focal cerebral ischemia, the percent inhibition of N-cNOS activity and the percent reduction of infarct volume correlate to each other at least in a dose range of L-NNA that reduces infarct volume (Carreau et al., Eur. J. Pharmacol. 256, 241–249, 1994). Further in addition, it has been reported that in N-cNOS knockout mice, the infarct volume observed after focal cerebral ischemia is significantly smaller than that in the control (Huang et al., Science 265, 1883–1885, 1994).

A report has also been made that suggests the involvement of iNOS in the mechanism for the occurrence and development of ischemic brain damage. Briefly, after 12 hours of focal cerebral ischemia in rats, the mRNA of iNOS started to increase in the cerebral cortex of the affected hemisphere and, after 2 days, it reached a maximum concomitantly with iNOS activity, probably originating from polynuclear leukocytes (Iadecola et al., J. Cereb. Blood Flow Metab. 15, 52–59, 1995; Iadecola et al., J. Cereb. Blood Flow Metab. 15, 378–384, 1995). It has been reported that when $N^{G}$-nitro-L-arginine methyl ester (L-NAME) which is one of the NOS inhibitors was administered after 3 hours of ischemia in consideration of the above-described temporal changes, the infarct volume decreased significantly (Zhang et al., J. Cereb. Blood Flow Metab. 15, 595–601, 1995).

Further in addition, it has been reported that the amount of occurrence of iNOS or its enzymatic activity increased in astrocytes or brain microvessels after cerebral ischemia in rats (Endoh et al., Neurosci. Lett. 154, 125–128, 1993; Endoh et al., Brain Res. 651, 92–100, 1994; Nagafuji et al., in Brain Edema IX (Ito et al, eds.), 60, pp285–288, 1994, Springer-Verlag; Toshiaki NAGAFUJI and Toru MATSUI, Jikken Igaku, 13, 127–135, 1995; Nagafuji et al., Mol. Chem. Neuropathol. 26, 107–157, 1995).

These reports suggest that N-CNOS or iNOS may be closely involved in the mechanism for the occurrence and the development of the tissue damage following cerebral ischemia.

Referring now to NO, it is at least one of the essences of endothelium-derived relaxing factor (EDRF) and, hence, is believed to take part in the adjustment of the tension of blood vessels and the blood flow (Moncada et al., Pharmacol. Rev. 43, 109–142, 1991). As a matter of fact, it was reported that when rats were administered high doses of L-NNA, the cerebral blood flow was found to decrease in a dose-dependent manner as the blood pressure increased (Toru MATSUI et al., Jikken Igaku, 11, 55–60, 1993). The brain has a mechanism by which the cerebral blood flow is maintained at a constant level notwithstanding the variations of blood pressure over a specified range (which is commonly referred to as "autoregulation mechanism") ("NOSOTCHU JIKKEN HANDBOOK", compiled by Keiji SANO, published by IPC, 247–249, 1990). The report of Matsui et al. suggests the failure of this "autoregulation mechanism" to operate. Therefore, if E-cNOS is particularly inhibited beyond a certain limit in an episode of brain ischemia, the cerebral blood flow will decrease and the blood pressure will increase, thereby aggravating the dynamics of microcirculation, possibly leading to an expansion of the ischemic lesion.

The present inventors previously found that $N^G$-nitro-L-arginine (L-NNA), known to be a NOS inhibitor, possessd ameliorative effects against brain edema and infarction in a rat model of focal cerebral ischemia (Nagafuji et al., Neurosci. Lett. 147, 159–162, 1992; Japanese Patent Public Disclosure No. 192080/1994), as well as the neuronal cell death in a gerbil model of forebrain ischemia (Nagafuji et al., Eur. J. Pharmacol. Env. Tox. 248, 325–328, 1993). On the other hand, relatively high doses of NOS inhibitors have been reported to be entirely ineffective against ischemic brain damage or sometimes aggravating it (Iadecola et al., J. Cereb. Blood Flow Metab. 14, 175–192, 1994; Toshiaki NAGAFUJI and Toru MATSUI, Jikken Igaku, 13, 127–135, 1995; Nagafuji et al., Mol. Chem. Neuropathol. 26, 107–157, 1995). It should be noted that as a matter of fact, all papers that reported the changes of NO or its metabolites in the brain after permanent or temporary cerebral ischemia agreed in their results to show the increase in the levels of those substances (Toshiaki NAGAFUJI and Toru MATSUI, Jikken Igaku, 13, 127–135, 1995; Nagafuji et al., Mol. Chem. Neuropathol. 26, 107–157, 1995).

One of the reasons for explaining the fact that conflicting reports have been made about the effectiveness of NOS inhibitors in cerebral ischemic models would be the low selectivity of the employed NOS inhibitors for N-cNOS or iNOS. As a matter of fact, no existing NOS inhibitors including L-NNA and L-NAME have a highly selective inhibitory effect on a specific NOS isoform (Nagafuji et al., Neuroreport 6, 1541–1545, 1995; Nagafuji et al., Mol. Chem. Neuropathol. 26, 107–157, 1995). Therefore, it may well be concluded that desirable therapeutics of ischemic cerebrovascular diseases should have a selective inhibitory effect on N-cNOS or iNOS (Nowicki et al., Eur. J. Pharmacol. 204, 339–340, 1991; Dawson et al., Proc. Natl. Acad. Sci. USA 88, 6368–6371, 1991; Iadecola et al., J. Cereb. Blood Flow Metab. 15, 52–59, 1995; Iadecola et al., J. Cereb. Blood Flow Metab. 15, 378–384, 1995; Toshiaki NAGAFUJI and Toru MATSUI, Jikken Igaku 13, 127–135, 1995; Nagafuji et al., Mol. Chem. Neuropathol. 26, 107–157, 1995).

It has also been suggested that N-cNOS inhibitors have the potential for use as therapeutics of traumatic brain injuries (Oury et al., J. Biol. Chem. 268, 15394–15398, 1993; MacKenzie et al., Neuroreport 6, 1789–1794, 1995), seizure (Rigaud-Monnet et al., J. Cereb. Blood Flow Metab. 14, 581–590; 1994), headache and other pains (Moore et al., Br. J. Pharmacol. 102, 198–202, 1991; Olesen., Trends Pharmacol. 15, 149–153, 1994), morphine tolerance and dependence (Kolesnikov et al., Eur. J. Pharmacol. 221, 399–400, 1992; Cappendijk et al., Neurosci. Lett. 162, 97–100, 1993), Alzheimer's disease (Hu and EI-FaKahany, Neuroreport 4, 760–762, 1993; Meda et al., Nature 374, 647–650, 1995) and Parkinson's disease (Youdim et al., Advances Neurol. 60, 259–266, 1993; Schulz et al., J. Neurochem. 64, 936–939, 1995).

Upon stimulation by certain kinds of cytokines and/or LPS, iNOS is induced in immunocytes such as macrophages and glial cells and other cells, and the resulting large amount of NO will dilate blood vessels to cause a fatal drop in blood pressure. Therefore, it is speculated that an iNOS inhibitor may be effective against septic shocks (Kilbourn and Griffith, J. Natl. Cncer Inst. 84, 827–831, 1992; Cobb et al., Crit. Care Med. 21, 1261–1263, 1993; Lorente et al., Crit. Care Med. 21, 1287–1295, 1993).

Further, it has been suggested that iNOS inhibitors are useful as therapeutics of chronic rheumatoid arthritis and osteoarthritis (Farrell et al., Ann, Rheum. Dis. 51, 1219–1222, 1992; Hauselmann et al., FEBS Lett. 352, 361–364, 1994; Islante et al., Br. J. Pharmacol. 110, 701–706, 1993), viral or nonviral infections (Zembvitz and Vane, Proc. Natl. Acad. Sci. USA 89, 2051–2055, 1992; Koprowski et al., Proc. Natl. Acad. Sci. USA 90, 3024–3027, 1993) and diabetes (Kolb et al., Life Sci. PL213–PL217, 1991).

The NOS inhibitors so far reported to have selectivity for N-cNOS are $N^G$-cyclpropyl-L-arginine (L-CPA) (Lamberte et al., Eur. J. Pharmacol. 216, 131–134, 1992), L-NNA (Furfine et al., Biochem. 32, 8512–8517, 1993), S-methyl-L-thiocitrulline (L-MIN) (Narayanan and Griffith, J. Med. Chem. 37, 885–887, 1994; Furfine et al., J. Biol. Chem. 37, 885–887, 1994; Furfine et al., J. Biol. Chem. 269, 26677–26683, 1994; W095/09619; Narayanan et al., J. Biol. Chem. 270, 11103–11110, 1995; Nagafuji et al., Neuroreport 6, 1541–1545, 1995) and S-ethyl-L-thiocitrulline (L-EIN) (Furfine et al., J. Biol. Chem. 269, 26677–26683, 1994; W095/09619; Narayanan et al., J. Biol. Chem. 270, 11103–11110, 1995).

In addition, the inhibitors that have been reported to have selectivity for iNOS are $N_G$-iminoethyl-L-ornithine (L-NIO) (McCall et al., Br. J. Pharmacol. 102, 234–238, 1991) and aminoguanidine (AG) (Griffith et al., Br. J. Pharmacol. 110, 963–968, 1993; Hasan et al. Eur. J. Pharmacol. 249, 101–106, 1993)

DISCLOSURE OF INVENTION

An object of the present invention is to provide novel compounds that have a selective inhibitory effect on calcium-dependent NOS which is present constitutively in the brain, particularly in neurons (N-cNOS), or an apparently calcium-independent and inducible NOS (iNOS) and which are useful as therapeutics of cerebrovascular diseases, Alzheimer's disease, analgesics, morphine tolerance or dependence, sepsis, chronic rheumatoid arthritis, osteoarthritis, viral or nonviral infections, diabetes and Parkinson's disease.

As a result of the intensive studies made in order to attain the stated object, the present inventors found that N-substituted aniline derivatives represented by the general formula (1), or possible stereoisomers or optically active forms of the compounds, as well as pharmaceutically acceptable salts thereof have an inhibitory effect against or selectivity for N-cNOS or iNOS that are superior to the existing NOS inhibitors, thereby exhibiting marked effectiveness as therapeutics of cerebrovascular diseases (especially as therapeutics of occlusive cerebrovascular diseases):

(1)

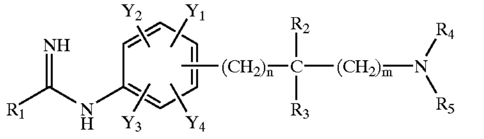

(where $R_1$ is $SR_6$ or $NR_7R_8$;

where $R_6$ is an optionally substituted straight-chained or branched alkyl group having 1–6 carbon atoms or a straight-chained or branched alkenyl group having 2–6 carbon atoms;

$R_7$ is a hydrogen atom, a straight-chained or branched alkyl group having 1–6 carbon atoms, a cyclic alkyl group having 3–8 carbon atoms, a straight-chained or branched alkenyl group having 2–6 carbon atoms, a straight-chained or branched alkynyl group having 3–6 carbon atoms, a straight-chained or branched alkoxy group having 1–6 carbon atoms, a straight-chained or branched alkyl group having 1–6 carbon atoms, or a nitro group;

$R_8$ is a hydrogen atom or a straight-chained or branched alkyl group having 1–6 carbon atoms;

$R_2$ is a hydrogen atom, a straight-chained or branched alkyl group having 1–6 carbon atoms, an alkoxycarbonyl group of which the alkyl portion is a straight-chained or branched alkyl group having 1–6 carbon atoms or a carboxyl group, or may combine with $R_3$ to form a 3- to 8-membered ring;

$R_3$ is a hydrogen atom or a straight-chained or branched alkyl group having 1–6 carbon atoms, or may combine with $R_2$ to form a 3- to 8-membered ring;

$R_4$ is a hydrogen atom, a straight-chained or branched alkyl group having 1–6 carbon atoms, an alkoxycarbonyl group of which the alkyl portion is a straight-chained or branched alkyl group having 1–6 carbon atoms, an optionally substituted acyl group having 1–8 carbon atoms, an amidino group that may be substituted on the nitrogen atom with a straight-chained or branched alkyl group having 1–6 carbon atoms or a cyclic alkyl group having 3–8 carbon atoms or a nitro group, or may combine with $R_5$ to form a 3- to 8-membered ring;

$R_5$ is a hydrogen atom, a straight-chained or branched alkyl group having 1–6 carbon atoms, an alkoxycarbonyl group of which the alkyl portion is a straight-chained or branched alkyl group having 1–6 carbon atoms, an alkoxycabonylamino group of which the alkyl portion is a straight-chained or branched alkyl group having 1–6 carbon atoms or an amino group, or may combine with $R_4$ to form a 3- to 8-membered ring;

$Y_1$, $Y_2$, $Y_3$ and $Y_4$ which may be the same or different are each a hydrogen atom, a halogen atom, a nitro group, a cyano group, a hydroxyl group, a straight-chained or branched alkyl group having 1–6 carbon atoms that may be substituted by 1–3 halogen atoms, a cyclic alkyl group having 3–6 carbon atoms that may be substituted by 1–3 halogen atoms, a straight-chained or branched alkenyl group having 2–6 carbon atoms, a straight-chained or branched alkynyl group having 2–6 carbon atoms, an optionally substituted straight-chained or branched alkoxy group having 1–6 carbon atoms, a straight-chained or branched alkylthio group having 1–6 carbon atoms, $NY_5Y_6$, or $COY_7$;

where $Y_5$ and $Y_6$ which may be the same or different are each a hydrogen atom, an optionally substituted straight-chained or branched alkyl group having 1–6 carbon atoms, or an optionally substituted cyclic alkyl group having 3–6 carbon atoms, an acyl group having 1–8 carbon atoms, an alkoxycarbonyl group of which the alkyl portion is a straight-chained or branched alkyl group having 1–6 carbon atoms, or $Y_5$ and $Y_6$ may combine together to form a 3- to 8-membered ring;

$Y_7$ is a hydrogen atom, a hydroxyl group, a straight-chained or branched alkyl group having 1–6 carbon atoms or a cyclic alkyl group having 3–6 carbon atoms, an alkoxy group of which the alkyl portion is a straight-chained or branched alkyl group having 1–6 carbon atoms or $NY_5Y_6$;

where $Y_5$ and $Y_6$ which may be the same or different are each a hydrogen atom, a straight-chained or branched alkyl group having 1–6 carbon atoms or a cyclic alkyl group having 3–6 carbon atoms; and n and m are each an integer of 0 or 1).

The present invention has been accomplished on the basis of this finding.

The present inventors also found that compounds represented by the general formula (21) are intermediates useful in the synthesis of the compounds represented by the general formula (1):

(21)

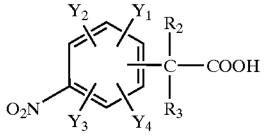

(where $R_2$ is a hydrogen atom, a straight-chained or branched alkyl group having 1–6 carbon atoms or may combine with $R_3$ to form a 3- to 8-membered ring;

$R_3$ is a straight-chained or branched alkyl group having 1–6 carbon atoms or may combine with $R_2$ to form a 3- to 8-membered ring;

$Y_1$, $Y_2$, $Y_3$ and $Y_4$ which may be the same or different are each a hydrogen atom, a halogen atom, a straight-chained or branched alkyl group having 1–6 carbon atoms that may be substituted by 1–3 halogen atoms, a cyclic alkyl group having 3–6 carbon atoms that may be substituted by 1–3 halogen atoms, a straight-chained or branched alkoxy groups having 1–6 carbon atoms of which the alkyl portion may optionally have a substituent, a straight-chained or branched alkylthio group having 1–6 carbon atoms, $NY_5Y_6$ or $COY_7$;

where $Y_5$ and $Y_6$ which may be the same or different are each a hydrogen atom, an optionally substituted straight-chained or branched alkyl group having 1–6 carbon atoms, an acyl group having 1–8 carbon atoms or an alkoxycarbonyl group of which the alkyl portion is a straight-chained or branched alkyl group having 1–6 carbon atoms or, alternatively, $Y_5$ and $Y_6$ may combine together to form a 3- to 8-membered ring;

$Y_7$ is a hydrogen atom, a straight-chained or branched alkyl group having 1–6 carbon atoms, a cyclic alkyl group having 3–6 carbon atoms, a straight-chained or branched alkoxy group having 1–6 carbon atoms, or $NY_5Y_6$;

where $Y_5$ and $Y_6$ which may be the same or different are each a hydrogen atom, a straight-chained or branched alkyl group having 1–6 carbon atoms, or a cyclic alkyl group having 3–6 carbon atoms).

Japanese Patent Public Disclosure No. 13391/1975 ; Clin. Sci. Mol. Med. 53, 355–364, 1977; J. Chem. Eng. Data, 22, 3, 224–245, 1977; Clin. Sci. Mol. Med. 54, 673–677, 1978; J. Biochem. 94, 123–128, 1983 and International Publication WO94/21621 teach compounds that are related to the compounds of the invention which are represented by the general formula (1).

In addition, part of the compounds of the invention which are represented by the general formula (1) are described by generic concept in Japanese Patent Public Disclosure Nos. 97933/1977, 99227/1977 and 158249/1987. However, these patents make no reference whatsoever to the NOS inhibiting action of the compounds corresponding to those of the invention or other aspects thereof such as their use as therapeutics of cerebro-vascular diseases, traumatic brain injuries, seizure, Alzheimer's disease, Parkinson's disease, headache and other pains, morphine tolerance or dependence, septic shocks, chronic rheumatoid arthritis, osteoarthritis, viral or antiviral infections and diabetes.

It should also be noted that International Publication WO95/00505 which was not published before the priority date of the subject application (Dec. 12, 1994) but which was later published, and J. Chem. Soc. Perkin Trans. 1, 2025–2030, 1977 describe part of the compounds of the invention which are represented by the general formula (1), and said International Publication also shows part of the compounds of the invention by generic concept.

Further in addition, International Publication WO95/09619 which was not published before the priority date of the subject application (Dec. 12, 1994) but which was later published shows part of the compounds of the invention of the general formula (1) by generic concept.

As it will be demonstrated by the tests hereinafter, the compounds described in the Examples of the invention have by far superior NOS inhibiting action, as well as extremely high selectivity for both N-cNOS and iNOS compared to the compounds described in International Publication WO95/00505 and WO95/09619.

BEST MODE FOR CARRYING OUT THE INVENTION

Figure 1:
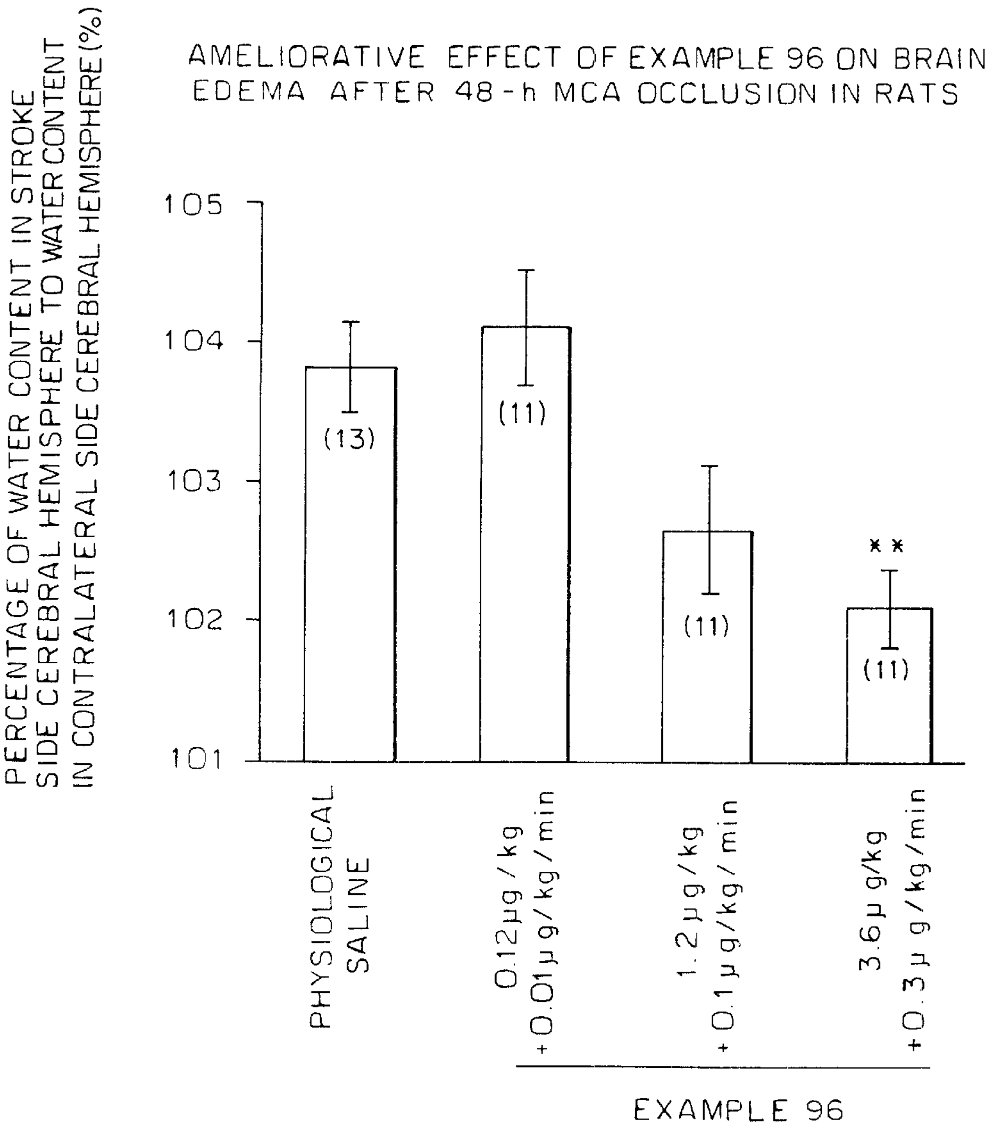
FIG. 1 is a graph showing the efficacy of the compound of Example 96 in ameliorating the brain edema formed after 48-h occlusion of the left middle cerebral artery in rats.

In the present invention, the straight-chained or branched alkyl group having 1–6 carbon atoms may be exemplified by a methyl, ethyl, n-propyl, i-propyl, n-butyl, s-butyl, t-butyl, pentyl or hexyl group or the like;

the straight-chained or branched alkenyl group having 2–6 carbon atoms may be exemplified by a vinyl, allyl, butenyl or pentenyl group or the like;

the cyclic alkyl group having 3–8 carbon atoms may be exemplified by a cyclopropyl, cyclobutyl, cyclopentyl or cyclohexyl group or the like;

the straight-chained or branched alkynyl group having 3–6 carbon atoms may be exemplified by a propynyl, butynyl or pentynyl group or the like;

the straight-chained or branched alkoxy group having 1–6 carbon atoms may be exemplified by a methoxy, ethoxy, i-propoxy or n-propoxy group or the like;

the alkoxycarbonyl group of which the alkyl portion is a straight-chained or branched alkyl group having 1–6 carbon atoms may be exemplified by a methoxycarbonyl, ethoxycarbonyl, n-propoxycarbonyl, i-propoxycarbonyl, n-butoxycarbonyl or t-butoxycarbonyl group or the like;

the acyl group having 1–8 carbon atoms may be exemplified by an acetyl, propionyl, butyryl, isobutyryl or benzoyl group or the like;

the straight-chained or branched alkylthio group having 1–6 carbon atoms may be exemplified by a methylthio, ethylthio or propylthio group or the like;

the substituent in the optionally substituted straight-chained or branched alkyl group having 1–6 carbon atoms, or in the optionally substituted acyl group having 1–8 carbon atoms or in the optionally substituted straight-chained or branched alkoxy group having 1–6 carbon atoms may be exemplified by a halogen atom, a hydrocarbyl group such as a phenyl group or the like;

the optionally substituted straight-chained or branched alkyl group having 1–6 carbon atoms may be exemplified by a methyl, ethyl, 2-fluoroethyl or n-propyl group or the like;

the optionally substituted straight-chained or branched alkoxy group having 1–6 carbon atoms may be exemplified by a methoxy, ethoxy, trifluoromethoxy, propoxy or benzyloxy group or the like;

the optionally substituted acyl group having 1–8 carbon atoms may be exemplified by an acetyl or benzoyl group or the like;

$NY_5Y_6$ may be exemplified by an amino, methylamino, ethylamino, dimethylamino, ethylmethylamino, piperidino, acetamido, N-methylacetamido, t-butoxycarbonylamino or N-methyl-t-butoxycarbonylamino group or the like;

$COY_7$ may be exemplified by a formyl, carboxyl, acetyl, propionyl, cyclobutyryl, methoxycarbonyl, ethoxycarbonyl, t-butoxycarbonyl, aminocarbonyl, methylaminocarbonyl, ethylaminocarbonyl, dimethylaminocarbonyl or ethylmethylaminocarbonyl group or the like;

$R_1$ is preferably a mercapto group substituted by a straight-chained or branched alkyl group having 1–6 carbon atoms or an amino group substituted by a straight-chained or branched alkyl group having 1–6 carbon atoms or a nitroamino group, with a methylthio, ethylthio, ethylamino or nitroamino group being particularly preferred;

$R_2$ is preferably a hydrogen atom or a straight-chained or branched alkyl group having 1–6 carbon atoms, with a hydrogen atom, a methyl group or an ethyl group being particularly preferred;

$R_3$ is preferably a hydrogen atom or a straight-chained or branched alkyl group having 1–6 carbon atoms, with a hydrogen atom or a methyl group being particularly preferred;

the substituent in the case where $R_2$ and $R_3$ combine together to form a 3- to 8-membered ring may be exemplified by a cyclopropyl, cyclobutyl, cyclopentyl or cyclohexyl group;

$R_4$ is preferably a hydrogen atom;

$R_5$ is preferably a hydrogen atom;

m and n are preferably both 0 if the substituents other than $Y_1$, $Y_2$, $Y_3$ and $Y_4$ in the general formula (1) are m-substituted on the benzene nucleus and if the substituents other than $Y_1$, $Y_2$, $Y_3$ and $Y_4$ in the general formula (1) are p-substituted on the benzene nucleus, it is preferred that m is 1 and n is 0 or that m is 0 and n is 1;

$Y_1$, $Y_2$, $Y_3$ and $Y_4$ which may be the same or different are each preferably a hydrogen atom, a halogen atom, a cyano group, a hydroxyl group, a straight-chained or branched alkyl group having 1–6 carbon atoms which may optionally be substituted by 1–3 halogen atoms, a cyclic alkyl group having 3–6 carbon atoms which may optionally be substituted by 1–3 halogen atom, a straight-chained or branched alkenyl group having 2–6 carbon atoms, an optionally substituted straight-chained or branched alkoxy group having 1–6 carbon atoms, a straight-chained or branched alkylthio group having 1–6 carbon atoms, a methylamino group, an ethylamino group, a dimethylamino group or an ethylmethylamino group, and more preferred are a hydrogen atom, a halogen atom, a straight-chained or branched alkyl group having 1–6 carbon atoms that may optionally be substituted by 1–3 halogen atoms, a cyclic alkyl group having 3–6 carbon atoms that may optionally be substituted by 1–3 halogen atoms, a straight-chained or branched alkenyl group having 2–6 carbon atoms, an optionally substituted straight-chained or branched alkoxy group having 1–6 carbon atoms, a straight-chained or branched alkylthio group having 1–6 carbon atoms, a methylamino group, an ethylamino group, a dimethylamino group and an ethylmethylamino group.

The compounds of the invention which are represented by the general formula (1) may typically be synthesized by the following schemes:

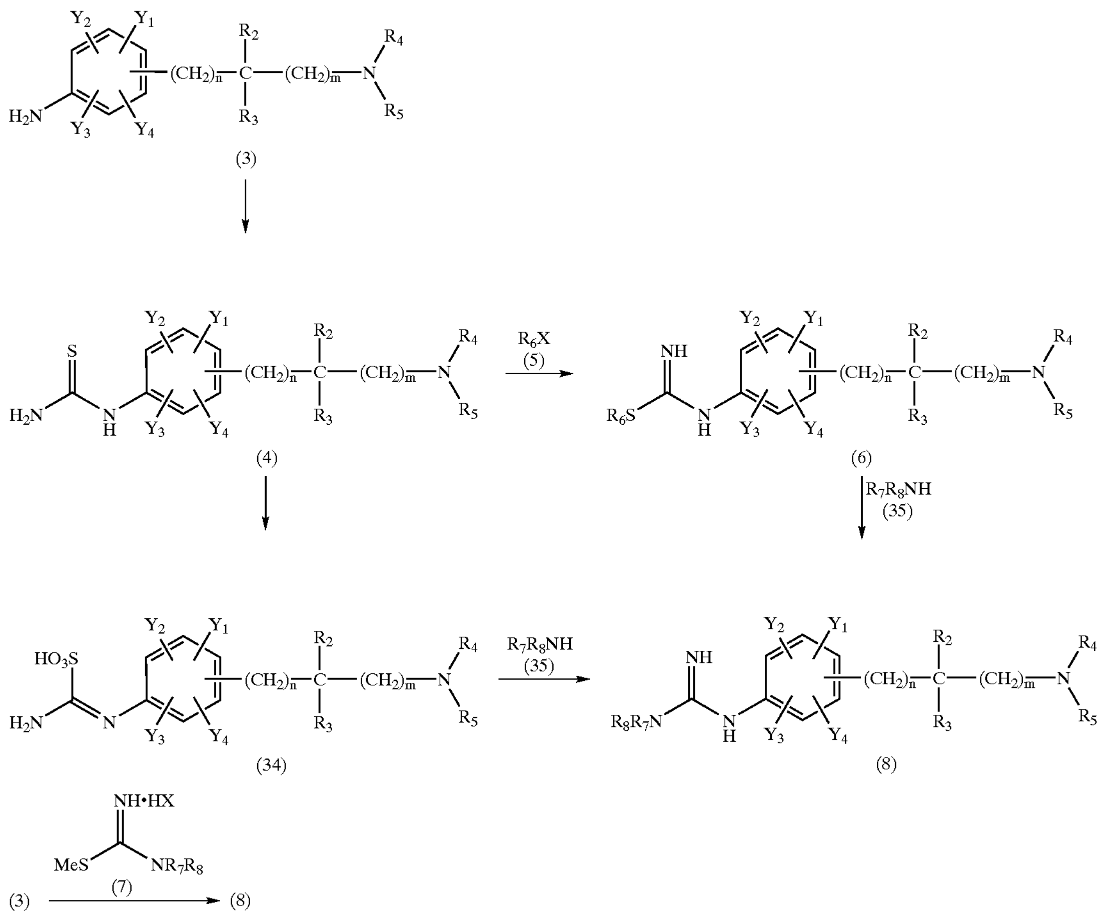

(3) (4) (6) (34) (8)

-continued

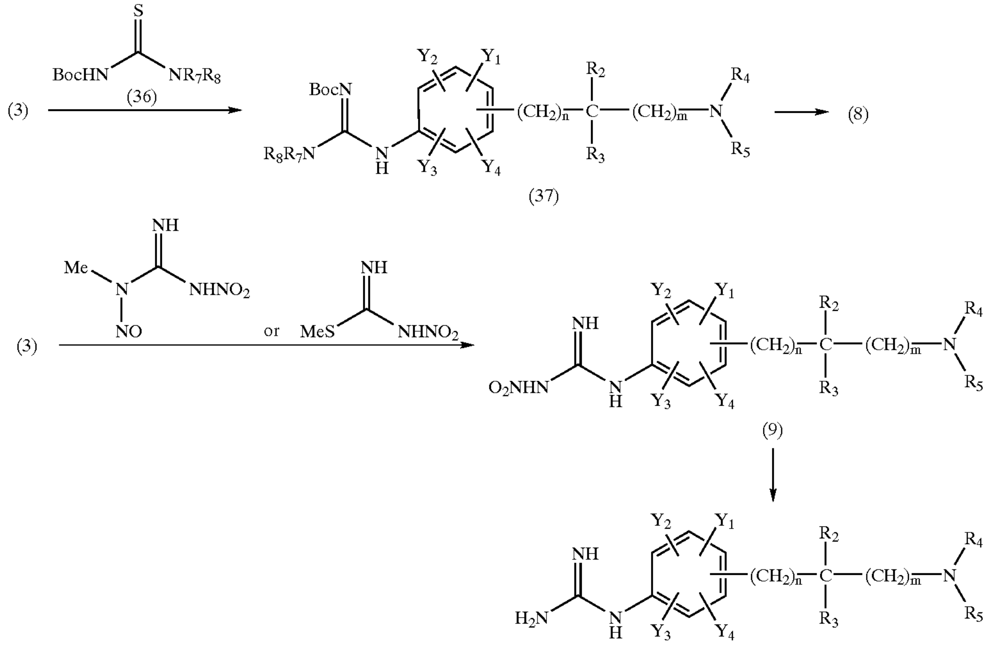

(3) (36) (37) (8)

(3) or (9) (10)

Among the compounds of the formula (1), one which is represented by the formula (6) with $R_1$ being $SR_6$ can be synthesized from a compound of the formula (3) via a compound of the formula (4).

The compound of the formula (6) (where $R_2$ is a hydrogen atom, a straight-chained or branched alkyl group having 1–6 carbon atoms, or an alkoxycarbonyl group of which the alkyl portion is a straight-chained or branched alkyl group having 1–6 carbon atoms or may combine with $R_3$ to form a 3- to 8-membered ring;

$R_3$ is a hydrogen atom or a straight-chained or branched alkyl group having 1–6 carbon atoms or may combine with $R_2$ to form a 3- to 8-membered ring;

$R_4$ is an alkoxycarbonyl group of which the alkyl portion is straight-chained or branched with 1–6 carbon atoms or an optionally substituted acyl group having 1–8 carbon atoms;

$R_5$ is a hydrogen atom, a straight-chained or branched alkyl group having 1–6 carbon atoms, an alkoxycarbonyl group of which the alkyl portion is a straight-chained or branched alkyl group having 1–6 carbon atoms or an alkoxycarbonylamino group of which the alkyl portion is a straight-chained or branched alkyl group having 1–6 carbon atoms;

$R_6$ is an optionally substituted straight-chained or branched alkyl group having 1–6 carbon atoms or a straight-chained or branched alkenyl group having 2–6 carbon atoms;

$Y_1$, $Y_2$, $Y_3$ and $Y_4$ which may be the same or different are each a hydrogen atom, a halogen atom, a straight-chained or branched alkyl group having 1–6 carbon atoms which may be substituted by 1–3 halogen atoms, a cyclic alkyl group having 3–6 carbon atoms which may optionally be substituted by 1–3 halogen atoms, a straight-chained or branched alkoxy group having 1–6 carbon atoms which may have a substituent in the alkyl portion, a straight-chained or branched alkylthio group having 1–6 carbon atoms, $NY_5Y_6$ or $COY_7$;

where $Y_5$ and $Y_6$ which may be the same or different are each a hydrogen atom, an optionally substituted straight-chained or branched alkyl group having 1–6 carbon atoms, an acyl group having 1–8 carbon atoms or an alkoxycarbonyl group of which the alkyl portion is a straight-chained or branched alkyl group having 1–6 carbon atoms or, alternatively, $Y_5$ and $Y_6$ may combine together to form a 3- to 8-membered ring;

$Y_7$ is an optionally substituted straight-chained or branched alkyl group having 1–6 carbon atoms, a cyclic alkyl group having 3–6 carbon atoms, a straight-chained or branched alkoxy group having 1–6 carbon atoms or $NY_5Y_6$;

where $Y_5$ and $Y_6$ which may be the same or different are each a hydrogen atom, a straight-chained or branched alkyl group having 1–6 carbon atoms or a cyclic alkyl group having 3–6 carbon atoms;

m is an integer of 0 or 1; and n is an integer of 0 or 1) may be synthesized in the following manner, provided that $R_2$, $R_3$, $R_4$, $R_5$, $R_6$, $Y_1$, $Y_2$, $Y_3$, $Y_4$, m and n in the following formulae (3), (4), (5) and (6) are each the same as defined above and X is a bromine or iodine atom.

The compound represented by the formula (3) is reacted with thiophosgene in the presence of either an inorganic base such as calcium carbonate or potassium carbonate or an organic base such as triehtylamine or N,N-dimethylaminopyridine, preferably in the presence of calcium carbonate or N,N-dimethylaminopyridine, in a solvent inert to the reaction such as chloroform, methylene chloride, water or dimethylformamide, preferably in methylene chloride or a mixture of methylene chloride and water, at a temperature between 0° C. and the boiling point of the reaction mixture, preferably at room temperature, and the reaction product is thereafter treated with concentrated ammonia solution to yield the compound represented by the formula (4).

Then, the compound of the formula (4) is reacted with a compound of the formula (5) in a solvent inert to the reaction such as acetonitrile, acetone, 1,4-dioxane, methanol or ethanol at a temperature between room temperature and the boiling point of the reaction mixture, preferably in acetonitrile with the reaction mixture being heated under reflux, to thereby yield a compound of the formula (6).

Alternatively, the compound of the formula (6) (where $R_2$ is a hydrogen atom, a straight-chained or branched alkyl group having 1–6 carbon atoms or may combine with $R_3$ to form a 3- to 8-membered ring;

$R_4$ and $R_5$ which may be the same or different are each a straight-chained or branched alkyl group having 1–6 carbon atoms or $R_4$ and $R_5$ may combine together to form a 3- to 8-membered ring;

$R_3$, $Y_1$, $Y_2$, $Y_3$, $Y_4$, X, m and n are each the same as defined above) may be synthesized in the following manner, provided that $R_2$, $R_3$, $R_4$, $R_5$, $R_6$, $Y_1$, $Y_2$, $Y_3$, $Y_4$, X, m and n in the following formulae (3), (4), (5) and (6) are each the same as defined above.

A compound represented by the formula (3) is reacted with benzoyl chloride and ammonium thiocyanate in a solvent inert to the reaction such as acetone at a temperature between room temperature and the boiling point of the reaction mixture, preferably at room temperature and, thereafter, the reaction mixture is heated under reflux together with an aqueous 10% sodium hydroxide solution to thereby yield a compound of the formula (4).

Subsequently, the compound of the formula (4) is reacted with an inorganic acid such as hydrochloric acid, sulfuric acid or nitric acid to form a quaternary ammonium salt, which in turn is reacted with a compound of the formula (5) in a solvent inert to the reaction such as acetonitrile, acetone, 1,4-dioxane, methanol or ethanol, at a temperature between room temperature and the boiling point of the reaction mixture, preferably in acetonitrile with the reaction mixture being heated under reflux to yield the compound of the formula (6).

Among the compounds of the formula (1), one which is represented by the formula (8) with $R_1$ being $NR_7R_8$, (where $R_2$ is a hydrogen atom, a straight-chained or branched alkyl group having 1–6 carbon atoms, an alkoxycarbonyl group of which the alkyl portion is straight-chained or branched with 1–6 carbon atoms or may combine with $R_3$ to form a 3- to 8-membered ring;

$R_4$ is a straight-chained or branched alkyl group having 1–6 carbon atoms, a straight-chained or branched alkoxycarbonyl group having 1–6 carbon atoms, an optionally substituted acyl group having 1–8 carbon atoms or may combine with $R_5$ to form a 3- to 8-membered ring, provided that when $R_5$ is a hydrogen atom, $R_4$ is not an alkyl group;

$R_5$ is a hydrogen atom, a straight-chained or branched alkyl group having 1–6 carbon atoms, an alkoxycarbonyl group of which the alkyl portion is straight-chained or branched with 1–6 carbon atoms or an alkoxycarbonylamino group of which the alkyl portion is straight-chained or branched with 1–6 carbon atoms or may combine with $R_4$ to form a 3- to 8-membered ring;

$R_7$ is a straight-chained, branched or cyclic alkyl group having 1–6 carbon atoms, a straight-chained or branched alkenyl group having 2–6 carbon atoms or a straight-chained or branched alkynyl group having 3–8 carbon atoms;

$R_8$ is a hydrogen atom or a straight-chained or branched alkyl group having 1–6 carbon atoms; and $R_3$, $Y_1$, $Y_2$, $Y_3$, $Y_4$, m and n are each the same as defined above) may be synthesized with compounds of the formulae (6), (4) and (3) being used as starting materials, provided that $R_2$, $R_3$, $R_4$, $R_5$, $R_7$, $R_8$, $Y_1$, $Y_2$, $Y_3$, $Y_4$, X, m and n in the following formulae (3), (4), (5), (6), (7), (34), (35), (36) and (37) are each the same as defined above, with $R_6$ being an optionally substituted straight-chained or branched alkyl group having 1–6 carbon atoms.

The compound of the formula (8) may be obtained by reacting a compound of the formula (6) with an amine of the formula (35) in a solvent inert to the reaction under heating, preferably in dimethylformamide at 80° C.

Alternatively, the compound of the formula (8) may be obtained by converting a compound of the formula (4) to a compound of the formula (34) in accordance with the method of C. A. Maryanoff et al. (J. Org. Chem. 51, 1882–1884, 1986) and thereafter reacting the compound (34) with the amine of the formula (35).

Further in addition, the compound of the formula (8) can be obtained by heating a compound of the formula (3) under reflux together with a compound of the formula (7) in a solvent such as pyridine.

Alternatively, the compound of the formula (8) may be obtained by reacting the compound of the formula (3) with a compound of the formula (36) in accordance with the method of M. A. Poss et al. (Tetrahedron Lett. 33, 5933–5936, 1992) so as to yield a compound of the formula (37) and by then removing the t-butoxycarbonyl protecting group under the conditions to be set forth below.

Among the compounds of the formula (1), one which is represented by the formula (9) with $R_1$ being $NHNO_2$ and one which is represented by the formula (10) with $R_1$ being $NH_2$ can be synthesized with the compound of the formula (3) being used as a starting material, provided that $R_2$, $R_3$, $R_4$, $R_5$, $Y_1$, $Y_2$, $Y_3$, $Y_4$, m and n in the following formulae (3), (9) and (10) are each the same as defined above.

The compound of the formula (9) may be obtained by reacting the compound of the formula (3) with N-methyl-N'-nitro-N-nitrosoguanidine or N-nitro-S-methylisothiourea in a solvent inert to the reaction such as acetonitrile, ethanol, methanol or water, preferably in acetonitrile, at a temperature between room temperature and the boiling point of the reaction mixture, preferably at room temperature, optionally in the presence of triethylamine or acetic acid.

The compound of the formula (10) may be obtained by a reduction of the compound represented by the formula (9). The reduction may be performed in a solvent inert to the reaction such as methanol in the presence of formic acid and palladium-black at room temperature.

Among the compounds of the formula (1), one in which $R_4$ is a hydrogen atom may be synthesized in the following manner.

Among the compounds represented by the formulae (6), (8), (9) or (10), those in which $R_4$ is an alkoxycarbonyl protective group of which the alkyl portion is straight-chained or branched with 1–6 carbon atoms are deprotected by treatment with a deprotecting agent to yield compounds in which $R_4$ is a hydrogen atom. The deprotection may be carried out under those conditions which are customarily used in accordance with the specific type of the protective group to be removed. For instance, if $R_4$ is a t-butoxycarbonyl group, the deprotection is preferably carried out in a solvent inert to the reaction such as methylene chloride, ethyl acetate, methanol, ethanol, 1,4-dioxane or water or in the absence of any solvents at a temperature between 0° C. and room temperature in the presence of a deprotecting agent such as trifluoroacetic acid, hydrochloric acid, sulfuric acid or methanesulfonic acid and it is particularly preferred to use trifluoroacetic acid at room temperature under anhydrous conditions. It should however be noted that those compounds in which $R_2$, $Y_1$, $Y_2$, $Y_3$ and $Y_4$ are each a t-butoxycarbonyl group are converted to such compounds that each of the substituents mentioned above is a carboxyl group whereas those compounds in which $R_5$ is a t-butoxycarbonylamino group are converted by the deprotection to such compounds that $R_5$ is an amino group.

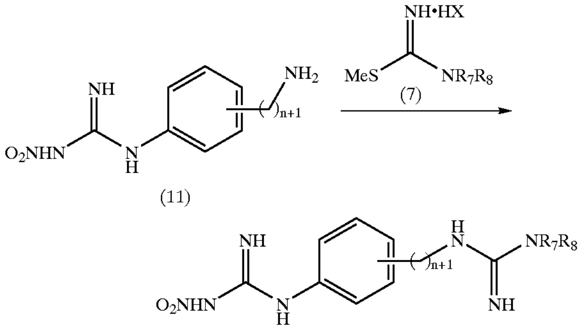

(11)

(12)

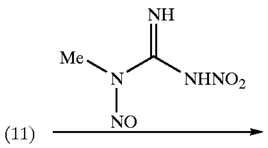

-continued

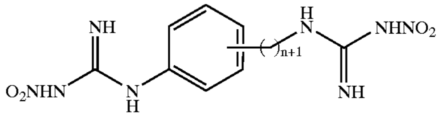

(13)

Among the compounds of the formula (1), those which are represented by the formulae (12) and (13) can be synthesized with a compound of the formula (11) used as a starting material, provided that $R_7$, $R_8$, X and n in the following formulae (7), (12) and (13) are each the same as defined above.

The compound represented by the formula (12) can be obtained by heating the compound of the formula (11) which is a compound of the formula (9) in which $R_2$, $R_3$, $R_4$, $R_5$, $Y_1$, $Y_2$, $Y_3$ and $Y_4$ are each a hydrogen atom and m is 0 under reflux together with a compound of the formula (7) in a solvent such as pyridine.

In addition, the compound represented by the formula (13) can be obtained by reacting the compound of the formula (11) with N-methyl-N'-nitro-N-nitrosoguanidine in a solvent such as pyridine at a temperature between room temperature and the boiling point of the reaction mixture, preferably at room temperature.

The compound of the formula (3) from which the compounds of the formula (1) are to be produced may typically be prepared by the following schemes:

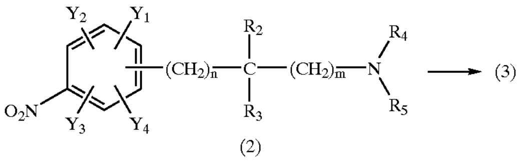

(2)

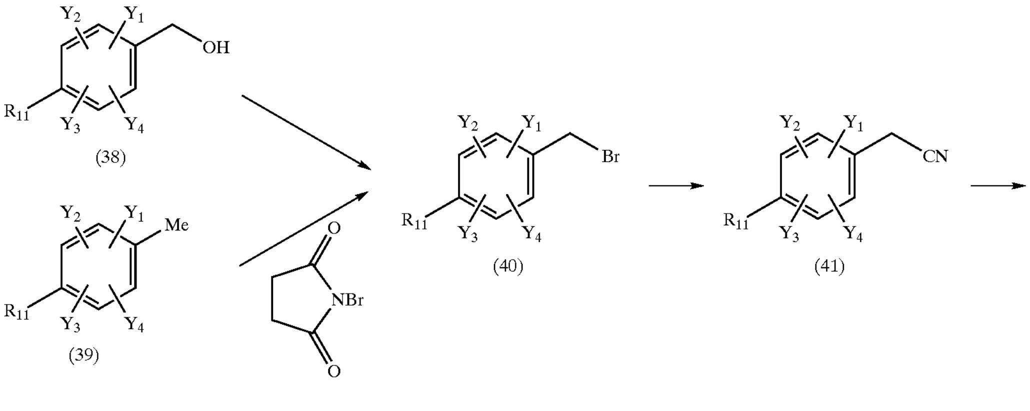

(38)

(39)

(40)

(41)

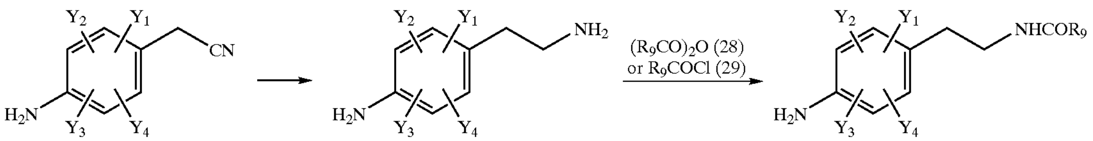

(42)

(43)

(44)

The compound of the formula (3) (where $R_2$ is a hydrogen atom, a straight-chained or branched alkyl group having 1–6 carbon atoms or an alkoxycarbonyl group of which the alkyl portion is a straight-chained or branched alkyl group having 1–6 carbon atoms or it may combine with $R_3$ to form a 3- to 8-membered ring;

$R_3$ is a hydrogen atom or a straight-chained or branched alkyl group having 1–6 carbon atoms or it may combine with $R_2$ to form a 3- to 8-membered ring;

$R_4$ is a straight-chained or branched alkyl group having 1–6 carbon atoms, an alkoxycarbonyl group of which the alkyl portion is a straight-chained or branched alkyl group having 1–6 carbon atoms or an optionally substituted acyl group having 1–8 carbon atoms or it may combine with $R_5$ to form a 3- to 8-membered ring;

$R_5$ is a hydrogen atom, a straight-chained or branched alkyl group having 1–6 carbon atoms, an alkoxycarbonyl group of which the alkyl portion is a straight-chained or branched alkyl group having 1–6 carbon atoms, or an alkoxycarbonylamino group of which the alkyl portion is a straight-chained or branched alkyl group having 1–6 carbon atoms or it may combine with $R_4$ to form a 3- to 8-membered ring;

$Y_1$, $Y_2$, $Y_3$ and $Y_4$ which may be the same or different are each a hydrogen atom, a halogen atom, a straight-chained or branched alkyl group having 1–6 carbon atoms which may optionally be substituted by 1–3 halogen atoms, a cyclic alkyl group having 3–6 carbon atoms which may optionally be substituted by 1–3 halogen atoms, a straight-chained or branched alkoxy group of which the alkyl portion may optionally have a substituent, a straight-chained or branched alkylthio group having 1–6 carbon atoms, $NY_5Y_6$ or $COY_7$;

where $Y_5$ and $Y_6$ which may be the same or different are each a hydrogen atom, an optionally substituted straight-chained or branched alkyl group having 1–6 carbon atoms, an acyl group having 1–8 carbon atoms or an alkoxycarbonyl group of which the alkyl portion is straight-chained or branched with 1–6 carbon atoms, or, alternatively, $Y_5$ and $Y_6$ may combine together to form a 3- to 8-membered ring;

$Y_7$ is a straight-chained or branched alkoxy group having 1–6 carbon atoms or $NY_5Y_6$;

where $Y_5$ and $Y_6$ which may be the same or different are each a hydrogen atom, a straight-chained or branched alkyl group having 1–6 carbon atoms or a cyclic alkyl group having 3–6 carbon atoms;

m is an integer of 0 or 1; and n is an integer of 0 or 1) can be synthesized with a compound of the formula (2) used as a starting material, provided that $R_2$, $R_3$, $R_4$, $R_5$, $Y_1$, $Y_2$, $Y_3$, $Y_4$, m and n in the following formulae (2) and (3) are each the same as defined above.

The compound of the formula (2) is subjected to a catalytic reduction in a solvent inert to the reaction such as ethanol, methanol, ethyl acetate, acetic acid or 1,4-dioxane, preferably in ethanol or methanol, in a hydrogen atmosphere at a temperature between room temperature and the boiling point of the reaction mixture, preferably at room temperature, with palladium-carbon, Raney nickel or platinum oxide being used as a catalyst; alternatively, the compound of the formula (2) is subjected to a reduction with nickel (II) chloride and sodium borohydride, etc.; in either way, the nitro group in the compound of the formula (2) is reduced to yield the compound of the formula (3).

Those compounds of the formula (3) in which $R_4$ is an alkoxycarbonyl group of which the alkyl portion is straight-chained or branched with 1–6 carbon atoms may also be obtained by converting the amino group represented by $NHR_5$ in those compounds of the formula (3) where $R_4$ denotes a hydrogen atom into carbamate. If $R_4$ is a methoxycarbonyl group, above reaction to form carbamate which has an alkoxycarbonyl group of which the alkyl portion is straight-chained or branched with 1–6 carbon atoms can be performed with methyl chloro-carbonate in a solvent inert to the reaction such as methylene chloride, in the presence of an organic base such as triethylamine or N,N-dimethylaminopyridine at a temperature between 0° C. and room temperature. If $R_4$ is a t-butoxycarbonyl group, the reaction can be performed with di-t-butyl dicarbonate in a solvent inert to the reaction such as methylene chloride, dimethylformamide or a mixture of 1,4-dioxane and water in the presence of an organic base such as triethylamine or N,N-dimethylaminopyridine or an inorganic base such as sodium hydroxide or sodium bicarbonate at a temperature between 0° C. and room temperature.

Among the compounds of the formula (3), one which is represented by the formula (44) (where $R_9$ is a straight-chained or branched alkyl group having 1–6 carbon atoms or a straight-chained or branched alkoxy group having 1–6 carbon atoms;

$Y_1$, $Y_2$, $Y_3$ and $Y_4$ which may be the same or different are each a hydrogen atom, a halogen atom, a straight-chained or branched alkyl group having 1–6 carbon atoms that may optionally be substituted by 1–3 halogen atoms, a cyclic alkyl group having 3–6 carbon atoms which may optionally be substituted by 1–3 halogen atoms, a straight-chained or branched alkoxy group having 1–6 carbon atoms which may have a substituent in the alkyl portion, a straight-chained or branched alkylthio group having 1–6 carbon atoms or $NY_5Y_6$;

where $Y_5$ and $Y_6$ which may be the same or different are each an optionally substituted straight-chained or branched alkyl group having 1–6 carbon atoms or, alternatively, $Y_5$ and $Y_6$ may combine together to form a 3- to 8-membered ring) can be synthesized with compounds of the formulae (38) and (39) used as starting materials, provided that $R_9$ in the following formulae (38), (39), (40), (41), (42), (43) and (44) is the same as defined above and $R_{11}$ is an amino group protected with a t-butoxycarbonyl group, a phthaloyl group, a trifluoroacetyl group or the like and further that $Y_1$, $Y_2$, $Y_3$ and $Y_4$ in the following formulae (38), (41), (42), (43) and (44) are each the same as defined above.

By replacing the primary hydroxyl group in the compound of the formula (38) with a bromine atom, one can obtain a compound of the formula (40) (where $Y_1$, $Y_2$, $Y_3$ and $Y_4$ are each the same as defined above). The bromination can be performed in a solvent inert to the reaction such as methylene chloride in the presence of carbon tetrabromide and triphenylphosphine at a temperature between 0° C. and room temperature.

In addition, the compound of the formula (40) (where $Y_1$, $Y_2$, $Y_3$ and $Y_4$ which may be the same or different are each a hydrogen atom, a halogen atom, a straight-chained or branched alkoxy group having 1–6 carbon atoms which may optionally have a substituent in the alkyl portion, a straight-chained or branched alkylthio group having 1–6 carbon atoms or $NY_5Y_6$;

where $Y_5$ and $Y_6$ which may be the same or different are each a hydrogen atom or an optionally substituted straight-chained or branched alkyl group having 1–6 carbon atoms or, alternatively, $Y_5$ and $Y_6$ may combine together to form a 3- to 8-membered ring) can also be obtained by reacting a compound of the formula (39) (where $Y_1$, $Y_2$, $Y_3$ and $Y_4$ are each the same as defined above) with N-bromosuccinimide in a solvent inert to the reaction such as carbon tetrachloride or benzene in the presence of α,α'-azobis(isobutyronitrile) under reflux with heating.

Then, the compound of the formula (40) (where $Y_1$, $Y_2$, $Y_3$ and $Y_4$ which may be the same or different are each a hydrogen atom, a halogen atom, a straight-chained or branched alkyl group having 1–6 carbon atoms which may optionally be substituted by 1–3 halogen atoms, a cyclic alkyl group having 3–6 carbon atoms which may optionally be substituted by 1–3 halogen atoms, a straight-chained or branched alkoxy group having 1–6 carbon atoms which may optionally have a substituent in the alkyl portion, a straight-chained or branched alkylthio group having 1–6 carbon atoms or $NY_5Y_6$;

where $Y_5$ and $Y_6$ which may be the same or different are each an optionally substituted straight-chained or branched alkyl group having 1–6 carbon atoms or, alternatively, $Y_5$ and $Y_6$ may combine together to form a 3- to 8-membered ring) is reacted with sodium cyanide or potassium cyanide to yield a compound of the formula (41). The amino protecting group in the resulting compound of the formula (41) is deprotected to yield a compound of the formula (42), which is then reacted with a hydrogenating reducing agent, preferably lithium aluminum hydride, in the presence of sulfuric acid in a solvent inert to the reaction such as ether or tetrahydrofuran, preferably in ether at a temperature between room temperature and the boiling point of the reaction mixture, preferably under reflux with heat, whereby the cyano group is reduced to yield a compound of the formula (43). The aliphatic amino group in the compound of the formula (43) in turn is acylated or converted to a carbamate with a compound of the formula (28) or (29) to yield a compound of the formula (44). If $R_9$ is a methyl group, the acylation of the amino group can be performed by reacting the compound of the formula (43) with an acetylation agent such as acetyl chloride or acetic anhydride in a solvent inert to the reaction such as methylene chloride in the presence of an organic base such as triethylamine or N,N-dimethylaminopyridine at a temperature between 0° C. and room temperature.

The compounds of the formula (2) from which the compounds of the formula (3) are to be produced can typically be prepared by the following schemes.

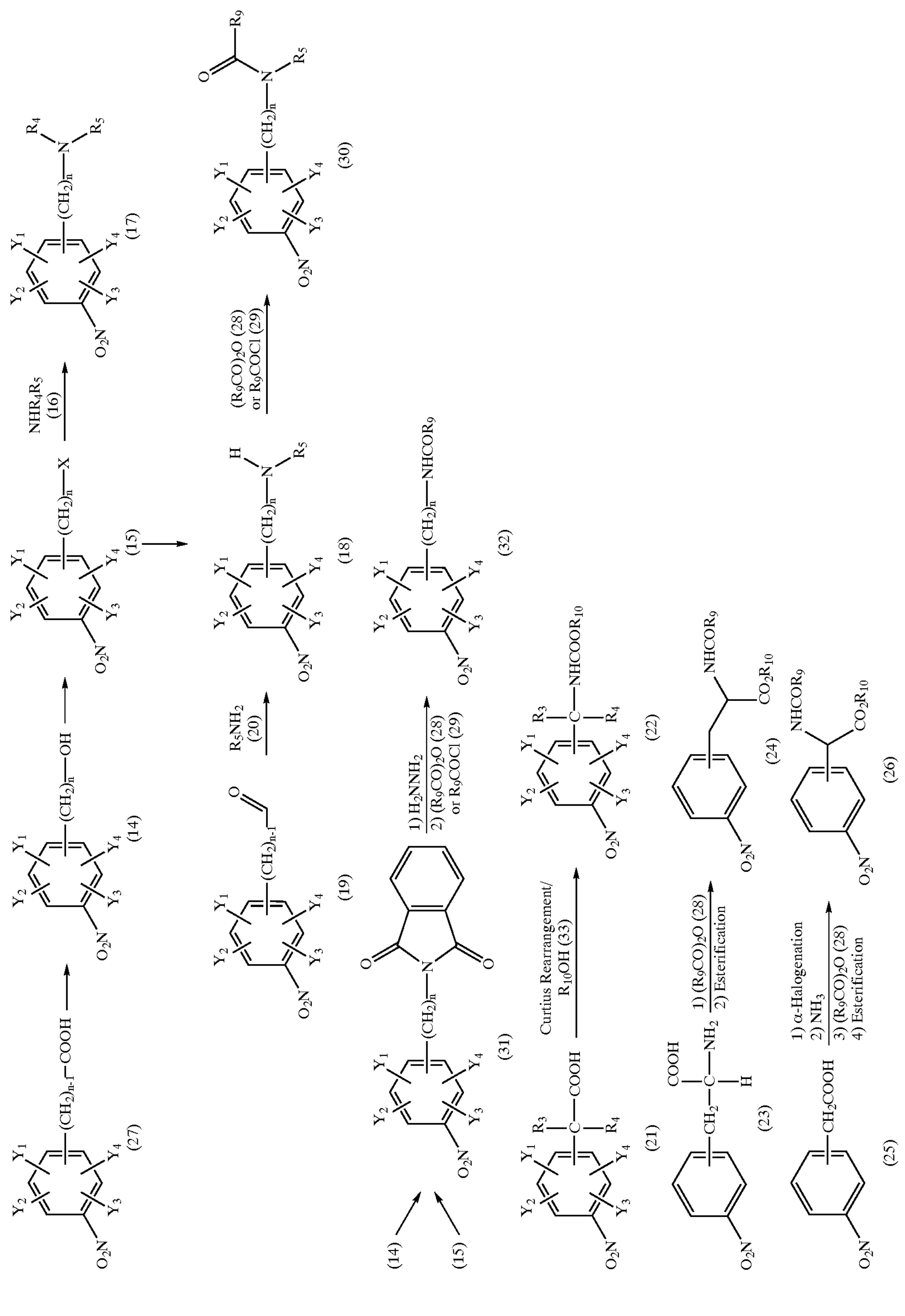
(27)
(14)
(15)
NHR$_4$R$_5$ (16)
(17)
(19)
R$_5$NH$_2$ (20)
(18)
(R$_9$CO)$_2$O (28) or R$_9$COCl (29)
(30)
(14)
(15)
(31)
1) H$_2$NNH$_2$
2) (R$_9$CO)$_2$O (28) or R$_9$COCl (29)
(32)
(21)
Curtius Rearrangement/ R$_{10}$OH (33)
(22)
(23)
1) (R$_9$CO)$_2$O (28)
2) Esterification
(24)
(25)
1) α-Halogenation
2) NH$_3$
3) (R$_9$CO)$_2$O (28)
4) Esterification
(26)

Among the compounds of the formula (2), one which is represented by the formula (17) (where $R_4$ and $R_5$ which may be the same or different are each a straight-chained or branched alkyl group having 1–6 carbon atoms or, alternatively, $R_4$ and $R_5$ may combine together to form a 3- to 8-membered ring;

n is an integer of 1 or 2;

$Y_1$, $Y_2$, $Y_3$ and $Y_4$ are each the same as defined above) can be synthesized from a compound of the formula (27) via compounds of the formulae (14) and (15), provided that $R_4$, $R_5$, $Y_1$, $Y_2$, $Y_3$, $Y_4$ and n in the following formulae (27), (14), (15), (16) and (17) are each the same as defined above and X is a chlorine atom or a bromine atom.

The carboxyl group in the compound of the formula (27) is reduced with a reducing hydrogenating agent, preferably diborane, by heating under reflux in a solvent inert to the reaction, such as tetrahydrofuran, so as to yield the compound of the formula (14).

Then, the primary hydroxyl group in the compound of the formula (14) is replaced by a halogen atom under ordinary reaction conditions to yield the compound of the formula (15). If X is a chlorine atom, the halogenation reaction may be performed with thionyl chloride in a solvent inert to the reaction such as benzene in the presence of a suitable base such as pyridine at a temperature between 0° C. and room temperature.

The resulting compound of the formula (15) in turn is reacted with an amine of the formula (16) in a solvent inert to the reaction such as dimethylformamide in the presence of an organic base such as triethylamine or N,N-dimethylaminopyridine or an inorganic base such as sodium bicarbonate or potassium carbonate at a temperature between 0° C. and room temperature to yield the compound of the formula (17).

Among the compounds of the formula (2), one which is represented by the formula (17) (where $R_4$ and $R_5$ are both an alkoxycarbonyl group of which the alkyl portion is straight-chained or branched with 1–6 carbon atoms;

n is 1; and $Y_1$, $Y_2$, $Y_3$ and $Y_4$ are each the same as defined above) can be synthesized in the following manner, provided that $R_4$, $R_5$, X, $Y_1$, $Y_2$, $Y_3$, $Y_4$ and n in the following formulae (15), (16) and (17) are each the same as defined above.

The compound of the formula (15) is reacted with a compound of the formula (16) in a solvent inert to the reaction such as dimethylformamide in the presence of sodium hydride at a temperature between 0° C. and room temperature to yield the compound of the formula (17).

Among the compounds of the formula (2), one which is represented by the formula (30) (where $R_5$ is a hydrogen atom or a straight-chained or branched alkyl group having 1–6 carbon atoms;

$Y_1$, $Y_2$, $Y_3$ and $Y_4$ which may be the same or different are each a hydrogen atom, a halogen atom, a straight-chained or branched alkyl group having 1–6 carbon atoms which may be substituted by 1–3 halogen atoms, a cyclic alkyl group having 3–6 carbon atoms which may be substituted by 1–3 halogen atoms, a straight-chained or branched alkoxy group which may have a substituent in the alkyl portion, a straight-chained or branched alkylthio group having 1–6 carbon atoms, $NY_5Y_6$ or $COY_7$;

where $Y_5$ and $Y_6$ which may be the same or different are each a hydrogen atom, an optionally substituted straight-chained or branched alkyl group having 1–6 carbon atoms, an acyl group having 1–8 carbon atoms or an alkoxycarbonyl group of which the alkyl portion is a straight-chained or branched alkyl group having 1–6 carbon atoms; or, alternatively, $Y_5$ and $Y_6$ may combine together to form a 3- to 8-membered ring;

$Y_7$ is a straight-chained or branched alkoxy group having 1–6 carbon atoms or $NY_5Y_6$;

where $Y_5$ and $Y_6$ which may be the same or different are each a hydrogen atom, a straight-chained or branched alkyl group having 1–6 carbon atoms or a cyclic alkyl group having 3–6 carbon atoms;

$R_9$ and n are each the same as defined above) can be synthesized from compounds of the formulae (15) and (19) via a compound of the formula (18), provided that X, $Y_1$, $Y_2$, $Y_3$, $Y_4$ and n in the following formulae (15), (18), (19), (20), (28), (29) and (30) are each the same as defined above.

By reacting the compound of the formula (15) with ammonia in a solvent inert to the reaction such as hydrous dimethyl sulfoxide at a temperature between 0° C. and room temperature, one can obtain the compound of the formula (18) (where $R_5$ is a hydrogen atom).

In addition, by subjecting the compound of the formula (19) to a reductive amination with an amine of the formula (20) (where $R_5$ is a straight-chained or branched alkyl group having 1–6 carbon atoms), one can obtain the compound of the formula (18) (where $R_5$ is the same as defined above). The reductive amination can be performed with a suitable reducing agent such as sodium cyanoborohydride in a solvent inert to the reaction such as ethanol or methanol at a temperature between 0° C. and room temperature.

Then, the amino group in the compound of the formula (18) (where $R_5$ is a hydrogen atom or a straight-chained or branched alkyl group having 1–6 carbon atoms) is acylated or converted to a carbamate in the same manner as described above to yield a compound of the formula (30) (where $R_5$ is a hydrogen atom or a straight-chained or branched alkyl group having 1–6 carbon atoms).

Among the compounds of the formula (2), one which is represented by the formula (32) (where $Y_1$, $Y_2$, $Y_3$ and $Y_4$ which may be the same or different are each a hydrogen atom, a straight-chained or branched alkyl group having 1–6 carbon atoms which may be substituted by 1–3 halogen atoms, a cyclic alkyl group having 3–6 carbon atoms which may be substituted by 1–3 halogen atoms, a straight-chained or branched alkoxy group having 1–6 carbon atoms which may have a substituent in the alkyl portion, a straight-chained or branched alkylthio group having 1–6 carbon atoms, $NY_5Y_6$ or $COY_7$;

where $Y_5$ and $Y_6$ which may be the same or different are each a hydrogen atom, an optionally substituted straight-chained or branched alkyl group having 1–6 carbon atoms, an acyl group having 1–8 carbon atoms, or an alkoxycarbonyl group of which the alkyl portion is a straight-chained or branched alkyl group having 1–6 carbon atoms or, alternatively, $Y_5$ and $Y_6$ may combine together to form a 3- to 8-membered ring:

$Y_7$ is a straight-chained or branched alkyl group having 1–6 carbon atoms, a cyclic alkyl group having 3–6 carbon atoms, a straight-chained or branched alkoxy group having 1–6 carbon atoms or $NY_5Y_6$;

where $Y_5$ and $Y_6$ which may be the same or different are each a hydrogen atom, a straight-chained or branched alkyl group having 1–6 carbon atoms or a cyclic alkyl group having 3–6 carbon atoms;

$R_9$ and n are each the same as defined above) can be synthesized from the compounds of the formulae (14) and (15) via a compound of the formula (31), provided that $R_9$, X, $Y_1$, $Y_2$, $Y_3$, $Y_4$ and n in the following formulae (14), (15), (28), (29), (31) and (32) are each the same as defined above.

The compound of the formula (31) can be obtained either by subjecting the compound of the formula (14) and phthalimide to Mitsunobu reaction or by reacting the compound of the formula (15) with potassium phthalimide in a solvent inert to the reaction such as dimethylformamide at room temperature.

Then, the phthalimide protecting group in the compound of the formula (31) is deprotected in the presence of hydrazine and, thereafter, conversion to a carbamate or acylation is performed in the same manner as described above to thereby yield the compound of the formula (32).

Among the compounds of the formula (2), one which is represented by the formula (22) (where $R_2$ and $R_3$ which may be the same or different are each a hydrogen atom or a straight-chained or branched alkyl group having 1–6 carbon atoms or, alternatively, $R_2$ and $R_3$ may combine together to form a 3- to 8-membered ring;

$R_{10}$ is a straight-chained or branched alkyl group having 1–6 carbon atoms;

$Y_1$, $Y_2$, $Y_3$ and $Y_4$ which may be the same or different are each a hydrogen atom, a halogen atom, a straight-chained or branched alkyl group having 1–6 carbon atoms which may be substituted by 1–3 halogen atoms, a cyclic alkyl group having 3–6 carbon atoms which may be substituted by 1–3 halogen atoms, a straight-chained or branched alkoxy group having 1–6 carbon atoms which may have a substituent in the alkyl portion, a straight-chained or branched alkylthio group having 1–6 carbon atoms, $NY_5Y_6$ or $COY_7$;

where $Y_5$ and $Y_6$ which may be the same or different are each a hydrogen atom, an optionally substituted straight-chained or branched alkyl group having 1–6 carbon atoms, an acyl group having 1–8 carbon atoms or an alkoxycarbonyl group of which the alkyl portion is a straight-chained or branched alkyl group having 1–6 carbon atoms, or, alternatively, $Y_5$ and $Y_6$ may combine together to form a 3- to 8-membered ring;

$Y_7$ is a hydrogen atom, a straight-chained or branched alkyl group having 1–6 carbon atoms, a cyclic alkyl group having 3–6 carbon atoms, a straight-chained or branched alkoxy group having 1–6 carbon atoms or $NY_5Y_6$;

where $Y_5$ and $Y_6$ which may be the same or different are each a hydrogen atom, a straight-chained or branched alkyl group having 1–6 carbon atoms or a cyclic alkyl group having 3–6 carbon atoms) can be obtained by subjecting a compound of the formula (21) (where $R_2$, $R_3$, $Y_1$, $Y_2$, $Y_3$ and $Y_4$ are each the same as defined above) to a Curtius rearrangement reaction and to the addition reaction of various alcohols of the formula (33) (where $R_{10}$ is the same as defined above). The Curtius rearrangement reaction and the addition reaction of various alcohols can be performed by reacting the compound of the formula (21) (where $R_2$, $R_3$, $Y_1$, $Y_2$, $Y_3$ and $Y_4$ are each the same as defined above) with a reagent such as diphenylphosphorylazide at room temperature for producing an acid azide from a carboxylic acid and by then reacting the acid azide with an alcohol such as methanol, ethanol or t-butanol under reflux with heat. Alternatively, the reactions may be performed by reacting the compound of the formula (21) with a reagent such as diphenylphosphorylazide under reflux with heat for producing an acid azide from a carboxylic acid in an alcohol such as methanol, ethanol or t-butanol in the presence of an organic base such as triethylamine or N,N-dimethylaminopyridine.

Among the compounds of the formula (2), one which is represented by the formula (24) (where $R_9$ is a straight-chained or branched alkoxy group having 1–6 carbon atoms; and $R_{10}$ is the same as defined above) can be obtained by converting the amino group in a compound of the formula (23) to carbamate in the same manner as described above and thereafter performing an esterification in the usual manner. The esterification can typically be performed using a suitable condensing agent and various alcohols in a solvent inert to the reaction in the presence of an organic base at 0° C.–50° C. In the case of producing a t-butyl ester, the reaction may be performed with 1-ethyl-3-(3-dimethylaminopropyl)carbodiimide hydrochloride and t-butanol in methylene chloride in the presence of an organic base such as triethylamine or N,N-dimethylaminopyridine at 0° C.–50° C., preferably at room temperature. Alternatively, in the case of producing a methyl ester, the reaction may be performed with trimethylsilyldiazomethane in a solvent inert to the reaction such as methanol or ether which are used either individually or in admixture at temperature between 0° C. and room temperature.

Among the compounds of the formula (2), one which is represented by the formula (26) (where $R_9$ and $R_{10}$ are each the same as defined above) can be obtained from a compound of the formula (25) by first converting it to 3- or 4-nitro-DL-phenylglycine in accordance with the method of H. Tsunematsu et al. (Journal of biochemistry 88, 1773–1783, 1980) and thereafter converting the amino group to a carbamate in the same manner as described above and then performing an esterification.

If the compounds of the invention which are represented by the general formula (1) have asymmetric carbons in their structure the pure forms of their stereoisomers and optically active forms thereof can be obtained by known techniques in the art, such as chromatography on optical isomer separating columns and fractional crystallization.

The compounds of the invention which are represented by the general formula (1) may be converted to any pharmaceutically acceptable salts which include, for example, salts with inorganic acids such as hydrochloric acid, sulfuric acid, nitric acid, hydrobromic acid and hydroiodic acid, salts with organic acids such as formic acid, acetic acid, oxalic acid and tartaric acid, salts with alkali metals such as sodium and potassium, and salts with alkaline earth metals such as calcium and magnesium.

The compounds of the invention or salts thereof may be formulated with suitable excipients, adjuvants, lubricants, antiseptics, disintegrators, buffering agents, binders, stabilizers, wetting agents, emulsifiers, coloring agents, flavoring agents, fragrances, etc. to form tablets, granules, subtilized granules, powders, capsules, syrups, elixirs, suspensions, emulsions, injections, etc. for oral or parenteral administration. When the cerebrovascular diseases to be treated are in a hyperacute phase (immediately after the stroke), an acute phase (from the stroke to 2 or 3 days later) or in a subacute phase (2 or 3 days up to 2 weeks after the stroke), the administration is anticipated to be primarily by intramuscular or intravenous injection. In addition, oral administration may be performed in a chronic phase (the third week after stroke and onward) if the patient admits ingestion.

The compounds of the invention or salts thereof may be administered in doses that vary with the physical constitution of the patient, his or her age, physical condition, the severity of the disease, the time of lapse after the onset of the disease and other factors; typical daily doses are anticipated to range from 0.1 to 100 mg/body. It should generally be noted that even if the same dose is administered, the plasma concentration may sometimes vary considerably between patients; hence, an optimal dose of the drug should ideally be determined for each patient on the basis of a monitored plasma concentration of the drug.

If the compounds of the invention or salts thereof are to be formulated as preparations for internal application, lactose, sucrose, sorbitol, mannitol, starches such as potato starch or corn starch, starch derivatives and common additives such as cellulose derivatives or gelatin are suitably used as vehicles, with lubricants such as magnesium stearate, carbowaxes and polyethylene glycol being optionally added concurrently; the resulting mixtures may be formulated in the usual manner into granules, tablets, capsules or other forms suitable for internal application.

If the compounds of the invention or salts thereof are to be formulated as aqueous preparations, effective amounts of the principal ingredients may be dissolved in distilled water for injection, with antioxidants, stabilizers, dissolution aids, buffering agents, preservatives, etc. added as required and, after complete solutions are formed, they are filtered, filled into ampules, sealed and sterilized by a suitable medium such as high-pressure vapor or dry heat so as to prepare injections.

If the compounds of the invention or salts thereof are to be formulated as lyophilized preparations, aqueous solutions having the principal ingredients dissolved in distilled water for injection may be freeze-dried in the usual manner, optionally after the addition of excipients that provide for easy lyophilization, such as sugars (e.g. lactose, maltose and sucrose), sugar alcohols (e.g. mannitol and inositol), glycine and the like.

The production of the compounds of the invention will now be described in greater detail with reference to the following examples but it should be understood that the invention is by no means limited to those examples.

In addition, in order to demonstrate the utility of the invention, the selective inhibitory effect of compounds of the general formula (1) on three NOS isoforms and their ameliorative effect against an occlusive cerebrovascular disease in a rat model of stroke were examined and the results are shown below under the Tests.

EXAMPLES

Tables 1–26 show the formulae for the chemical structures of the compounds prepared in the respective Examples.

TABLE 1

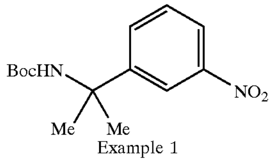

Example 1

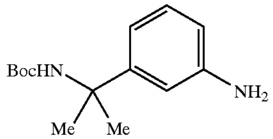

Example 2

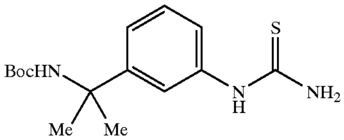

Example 3

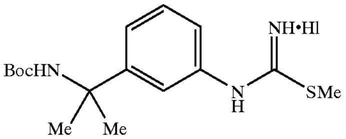

Example 4

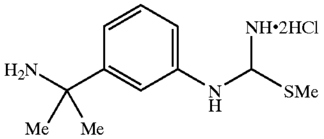

Example 5

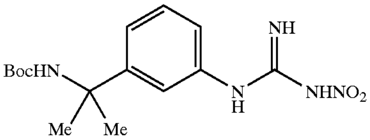

Example 6

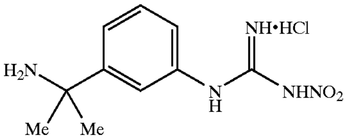

Example 7

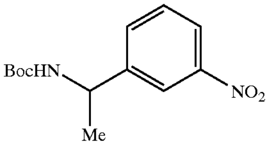

Example 8

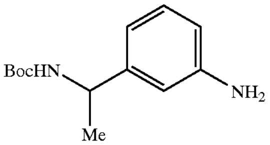

Example 9

TABLE 1-continued
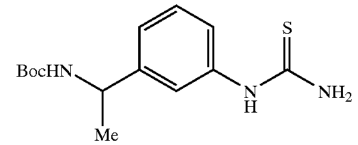
Example 10
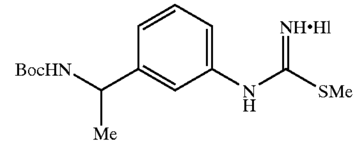
Example 11
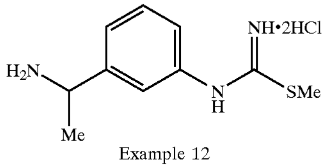
Example 12
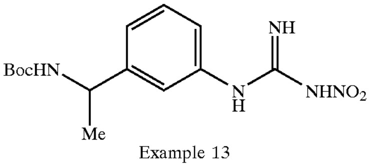
Example 13
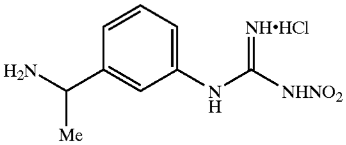
Example 14
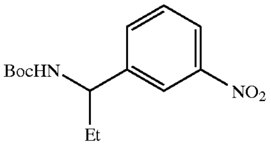
Example 15
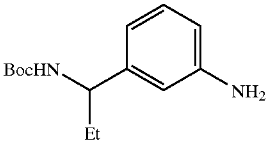
Example 16
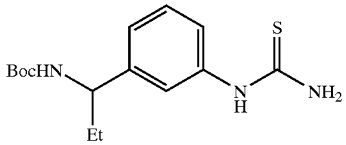
Example 17
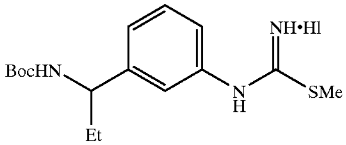
Example 18
TABLE 1-continued
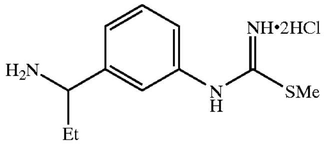
Example 19
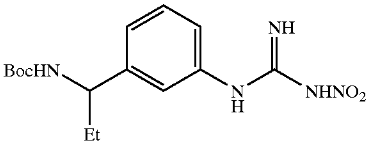
Example 20
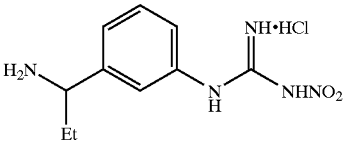
Example 21
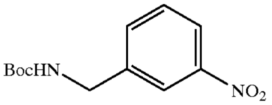
Example 22
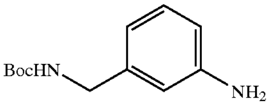
Example 23
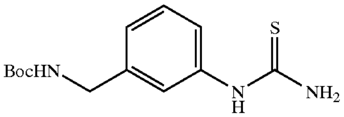
Example 24
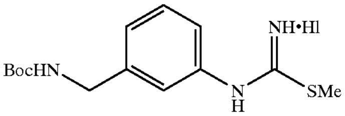
Example 25
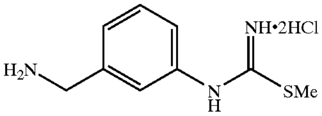
Example 26
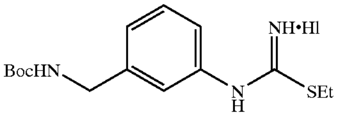
Example 27

TABLE 2
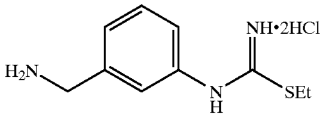
Example 28
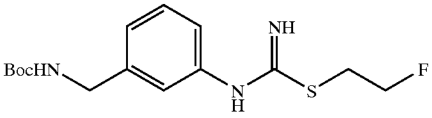
Example 29
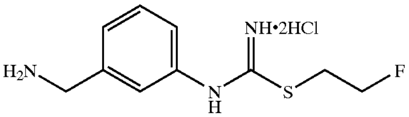
Example 30
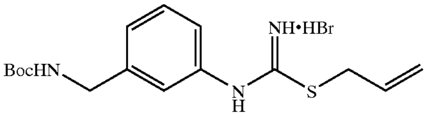
Example 31
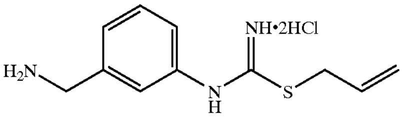
Example 32
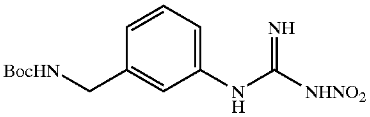
Example 33
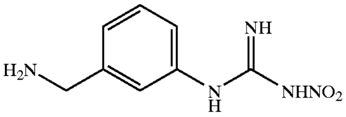
Example 34
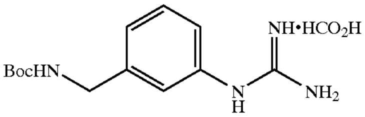
Example 35
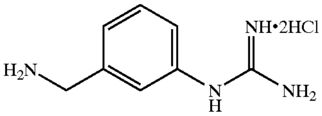
Example 36
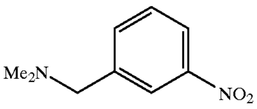
Example 37
TABLE 2-continued
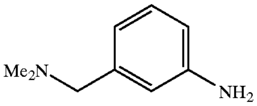
Example 38
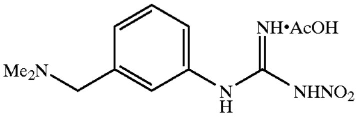
Example 39
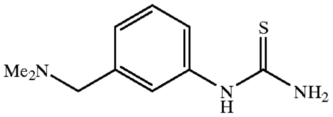
Example 40
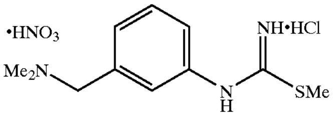
Example 41
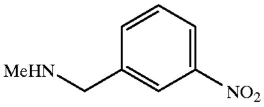
Example 42
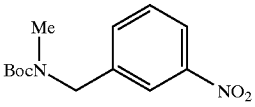
Example 43
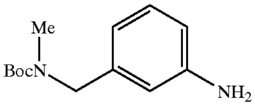
Example 44
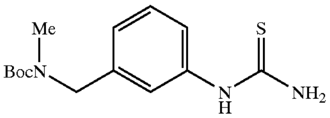
Example 45
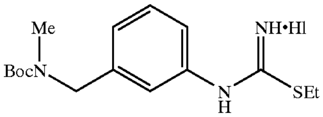
Example 46
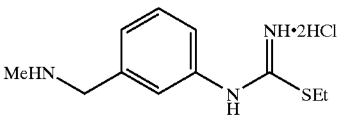
Example 47

TABLE 2-continued
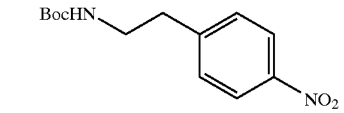
Example 48
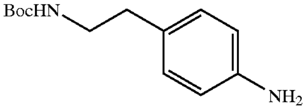
Example 49
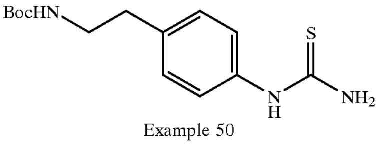
Example 50
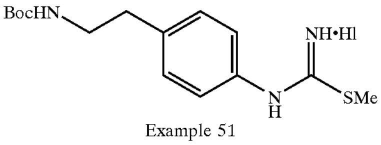
Example 51
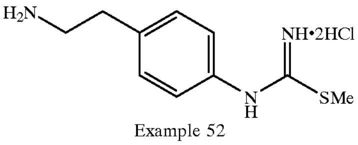
Example 52
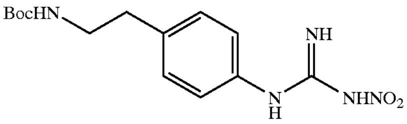
Example 53
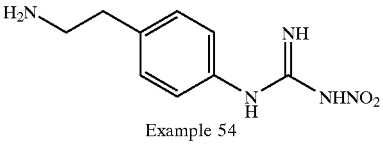
Example 54
TABLE 3
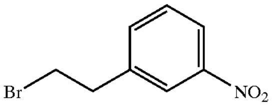
Example 55
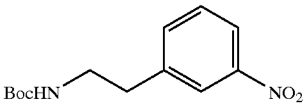
Example 56
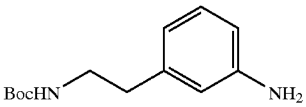
Example 57
TABLE 3-continued
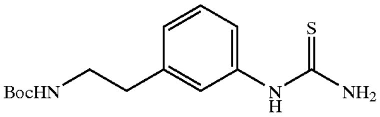
Example 58
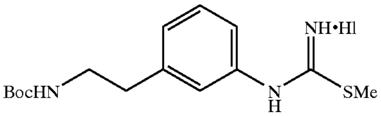
Example 59
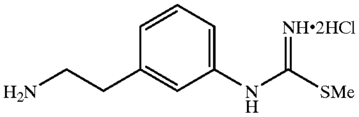
Example 60
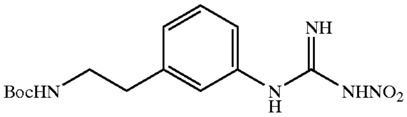
Example 61
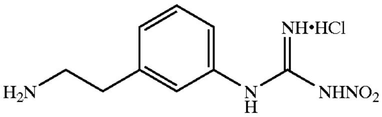
Example 62
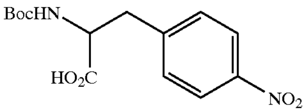
Example 63
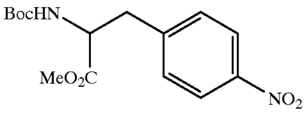
Example 64
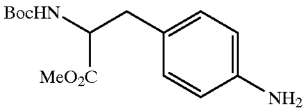
Example 65
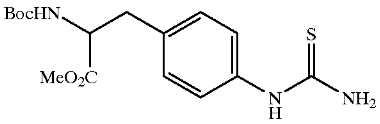
Example 66
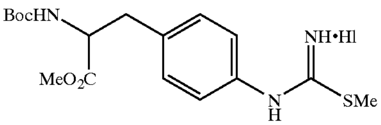
Example 67

TABLE 3-continued
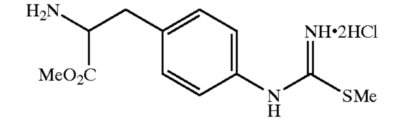
Example 68
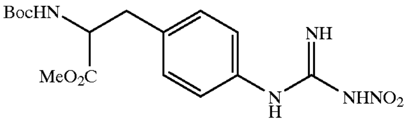
Example 69
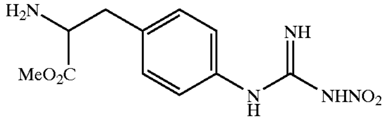
Example 70
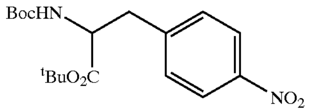
Example 71
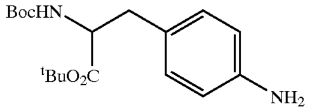
Example 72
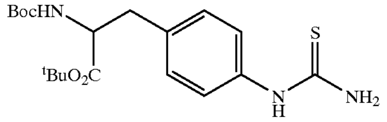
Example 73
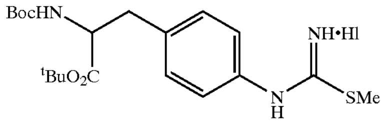
Example 74
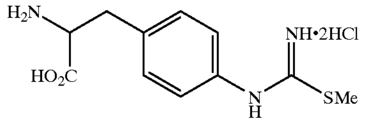
Example 75
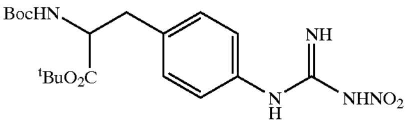
Example 76
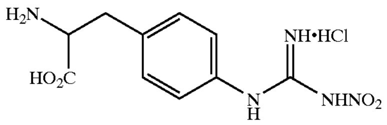
Example 77
TABLE 3-continued
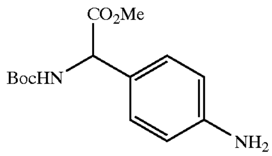
Example 78
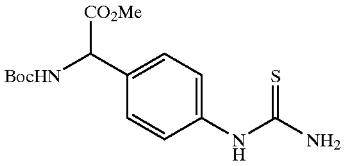
Example 79
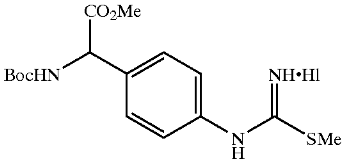
Example 80
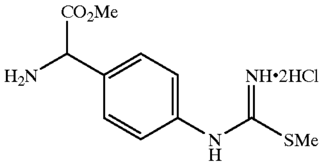
Example 81
TABLE 4
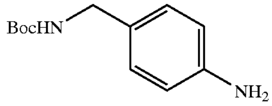
Example 82
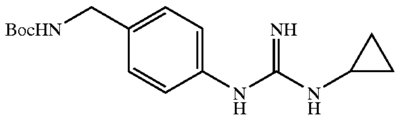
Example 83
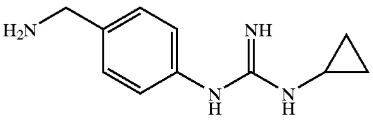
Example 84
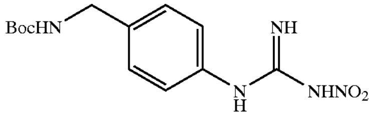
Example 85

TABLE 4-continued
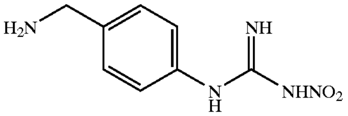
Example 86
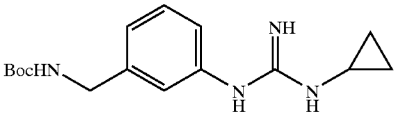
Example 87
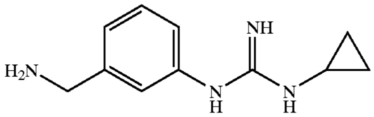
Example 88
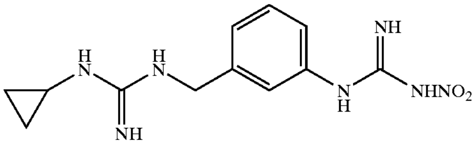
Example 89
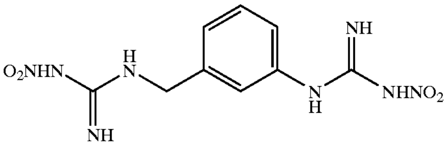
Example 90
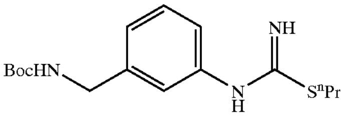
Example 91
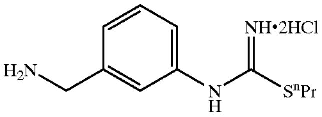
Example 92
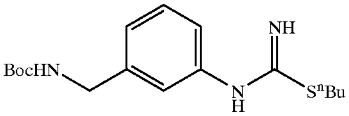
Example 93
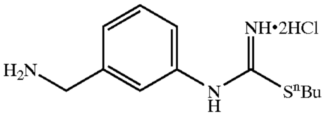
Example 94
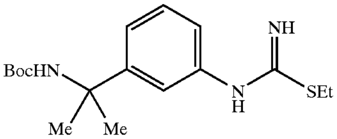
Example 95
TABLE 4-continued
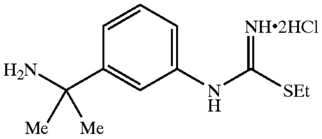
Example 96
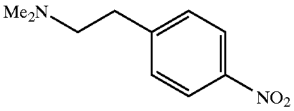
Example 97
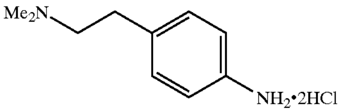
Example 98
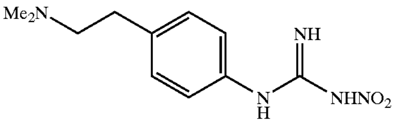
Example 99
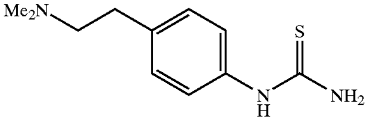
Example 100
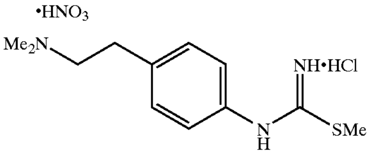
Example 101
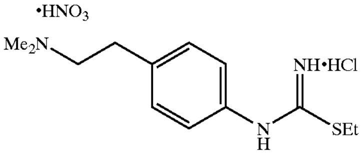
Example 102
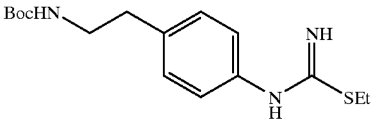
Example 103
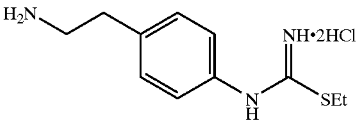
Example 104

TABLE 5
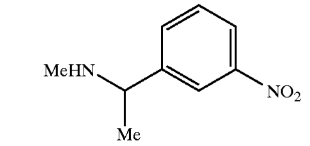
Example 105
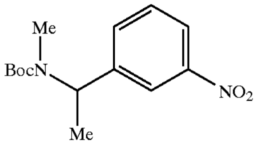
Example 106
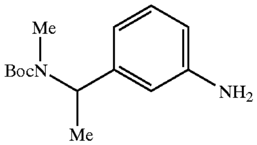
Example 107
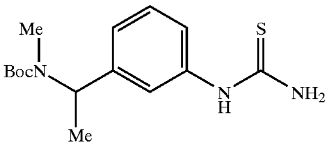
Example 108
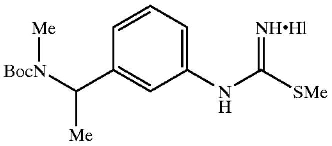
Example 109
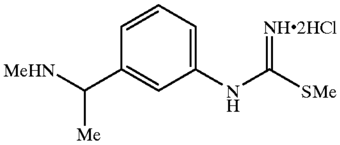
Example 110
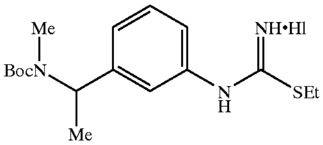
Example 111
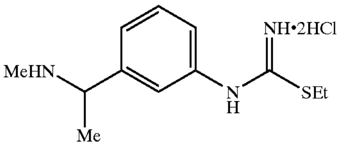
Example 112
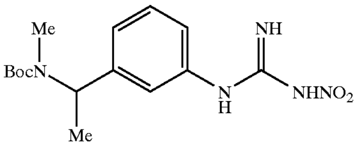
Example 113
TABLE 5-continued
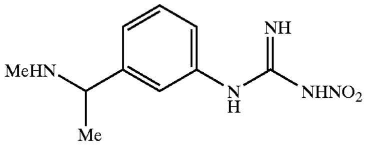
Example 114
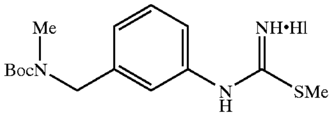
Example 115
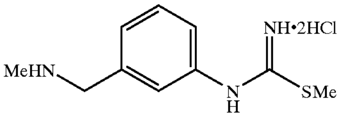
Example 116
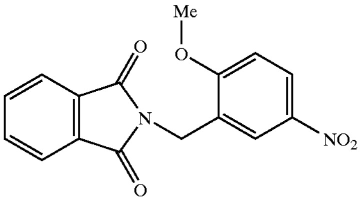
Example 117
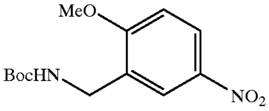
Example 118
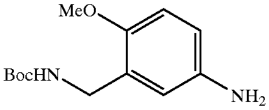
Example 119
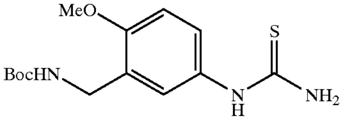
Example 120
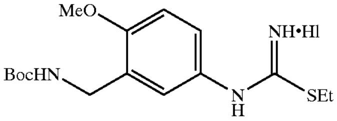
Example 121
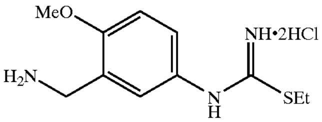
Example 122

TABLE 5-continued
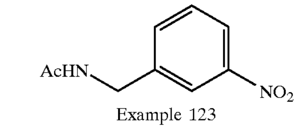
Example 123
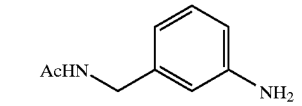
Example 124
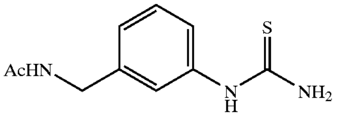
Example 125
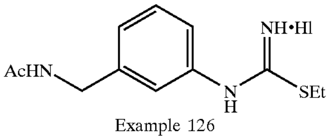
Example 126
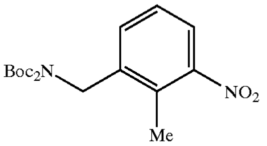
Example 127
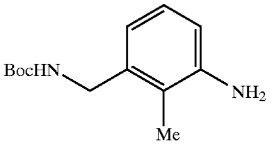
Example 128
TABLE 6
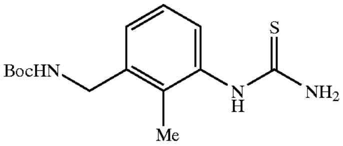
Example 129
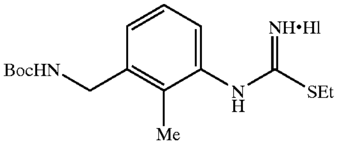
Example 130
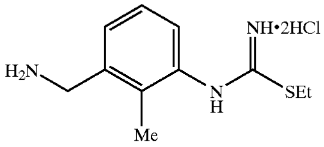
Example 131
TABLE 6-continued
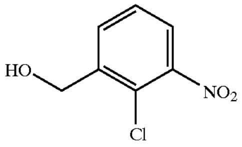
Example 132
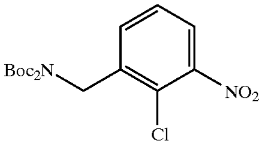
Example 133
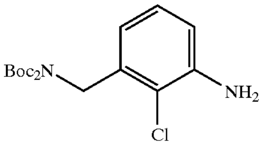
Example 134
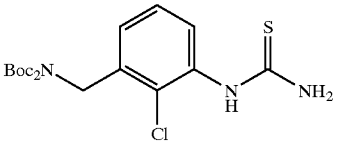
Example 135
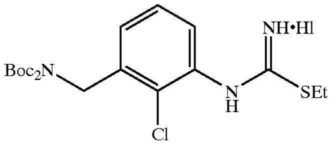
Example 136
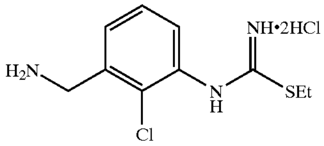
Example 137
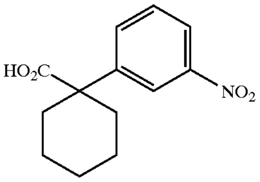
Example 138a
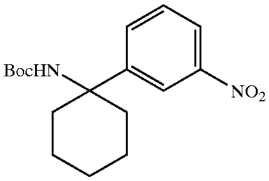
Example 138b TABLE 6-continued
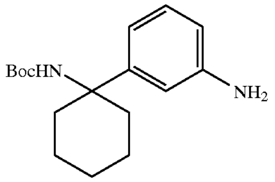
Example 139
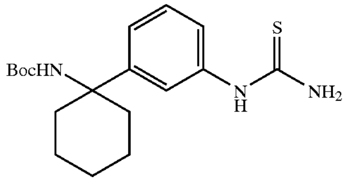
Example 140
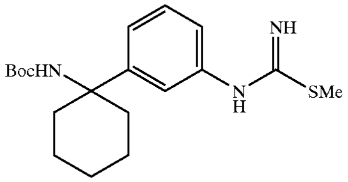
Example 141
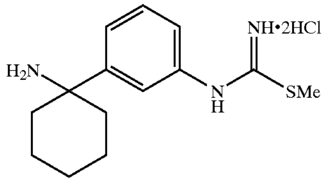
Example 142
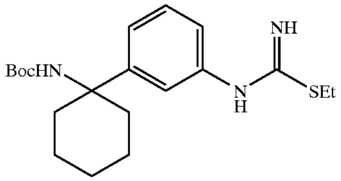
Example 143
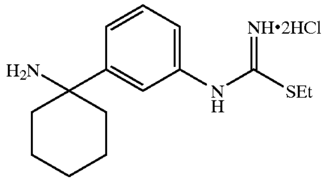
Example 144
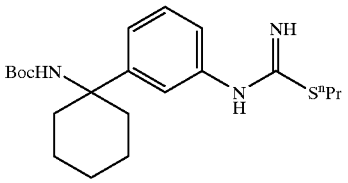
Example 145
TABLE 6-continued
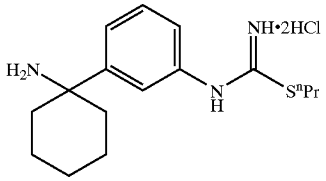
Example 146
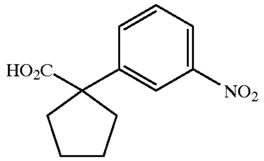
Example 147a
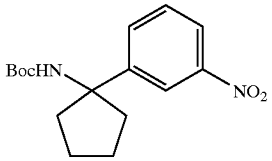
Example 147b
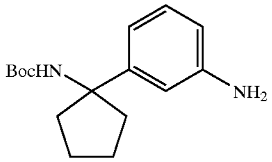
Example 148
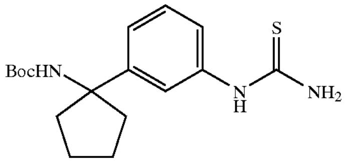
Example 149
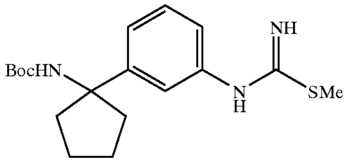
Example 150
TABLE 7
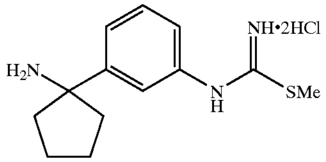
Example 151

TABLE 7-continued
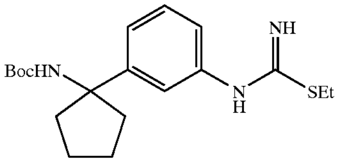
Example 152
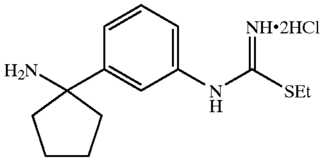
Example 153
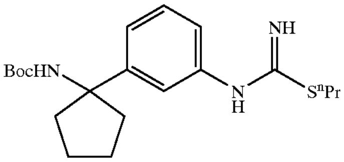
Example 154
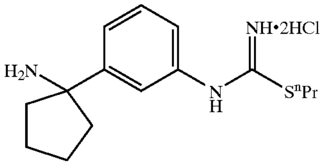
Example 155
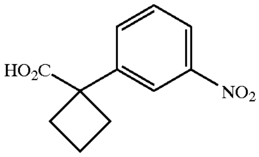
Example 156a
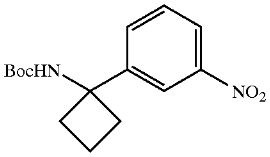
Example 156b
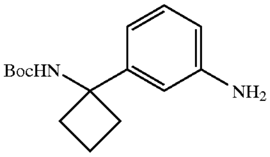
Example 157
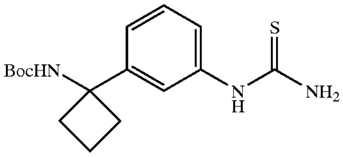
Example 158
TABLE 7-continued
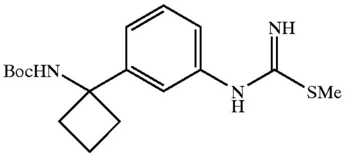
Example 159
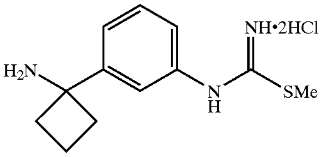
Example 160
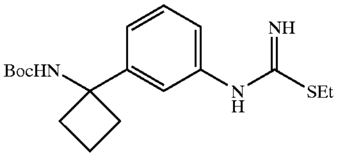
Example 161
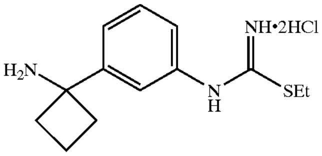
Example 162
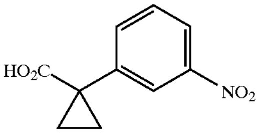
Example 163a
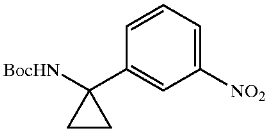
Example 163b
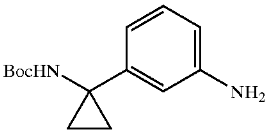
Example 164
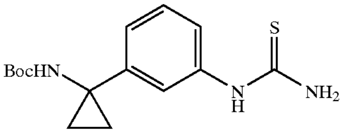
Example 165
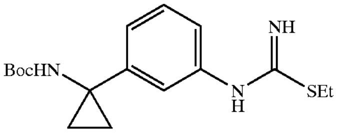
Example 166

TABLE 7-continued
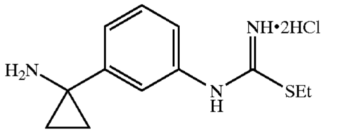
Example 167
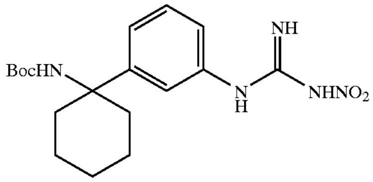
Example 168
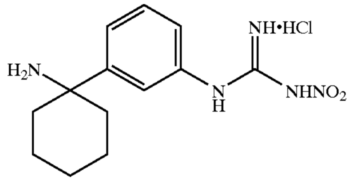
Example 169
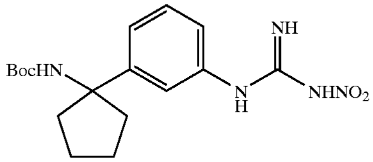
Example 170
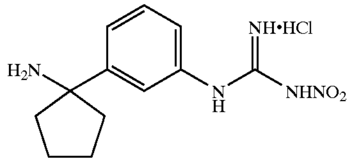
Example 171
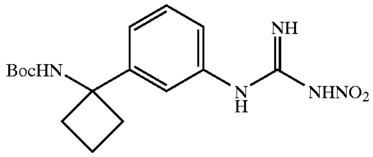
Example 172
TABLE 8
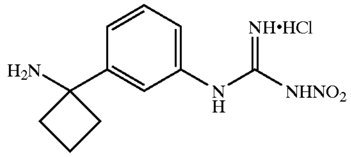
Example 173
TABLE 8-continued
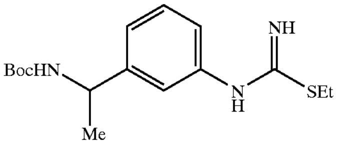
Example 174
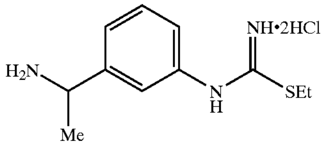
Example 175
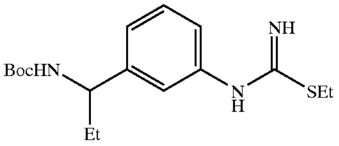
Example 176
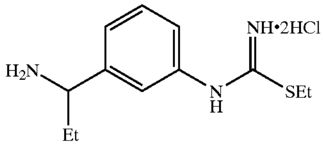
Example 177
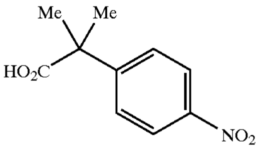
Example 178a
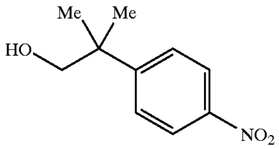
Example 178b
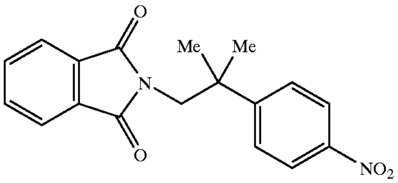
Example 179
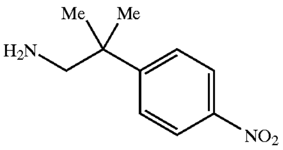
Example 180

TABLE 8-continued
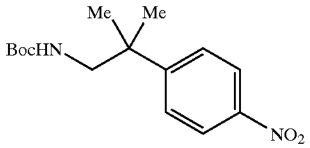
Example 181
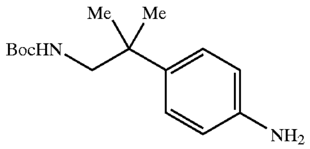
Example 182
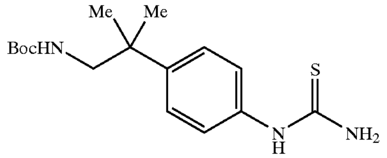
Example 183
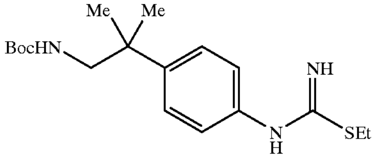
Example 184
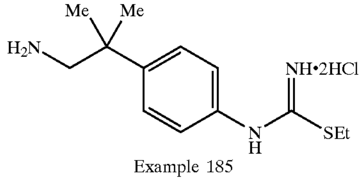
Example 185
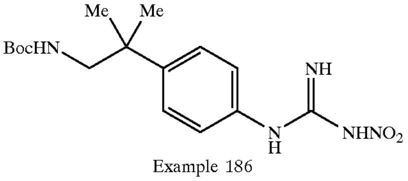
Example 186
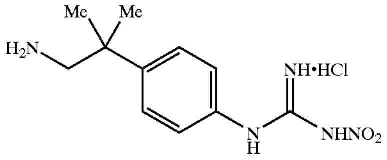
Example 187
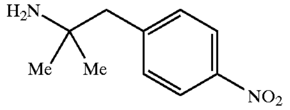
Example 188
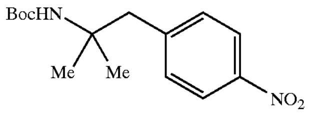
Example 189
TABLE 8-continued
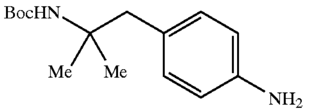
Example 190
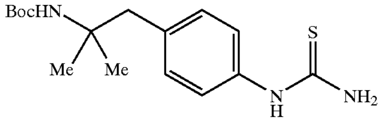
Example 191
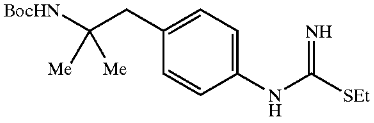
Example 192
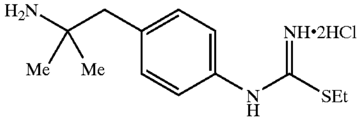
Example 193
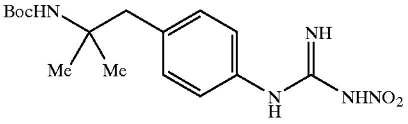
Example 194
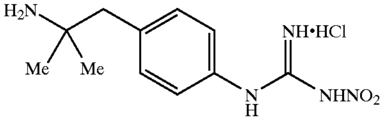
Example 195
TABLE 9
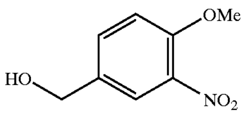
Example 196
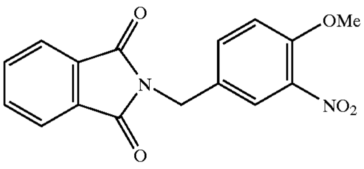
Example 197
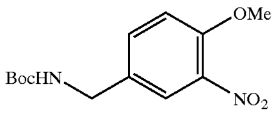
Example 198

TABLE 9-continued
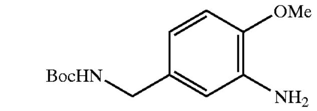
Example 199
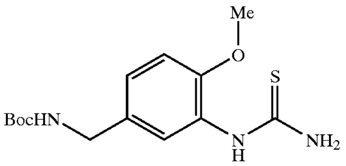
Example 200
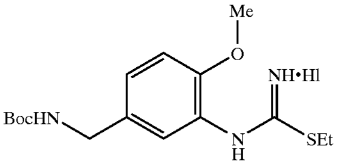
Example 201
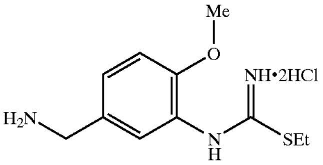
Example 202
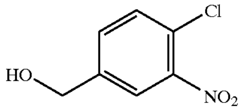
Example 203
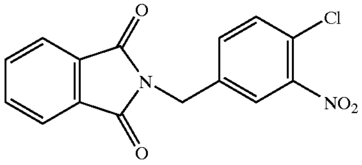
Example 204
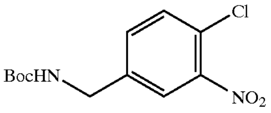
Example 205
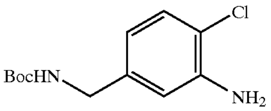
Example 206
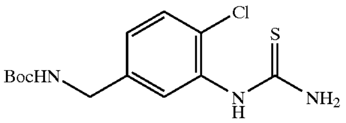
Example 207
TABLE 9-continued
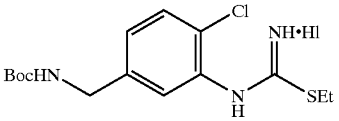
Example 208
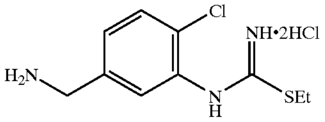
Example 209
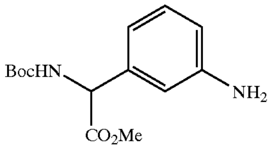
Example 210
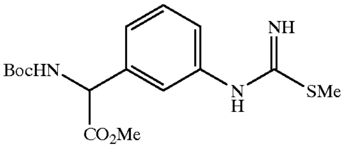
Example 211
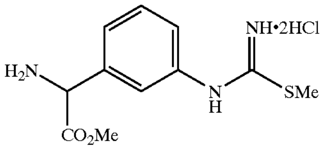
Example 212
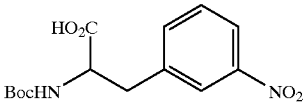
Example 213
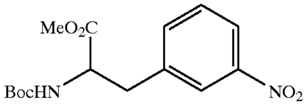
Example 214
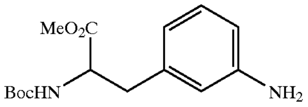
Example 215
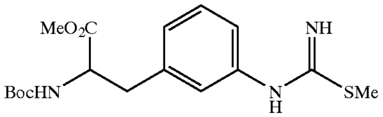
Example 216
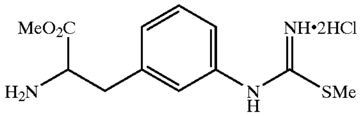
Example 217

TABLE 9-continued
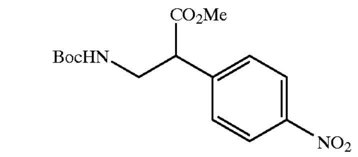
Example 218
TABLE 10
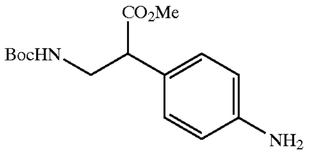
Example 219
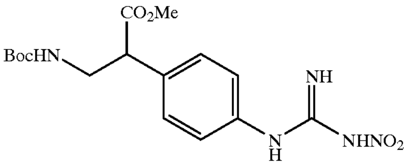
Example 220
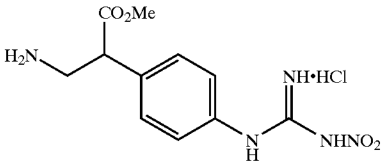
Example 221
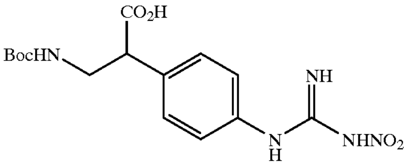
Example 222
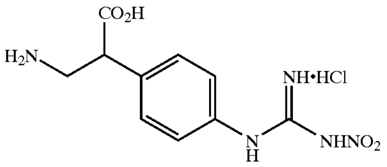
Example 223
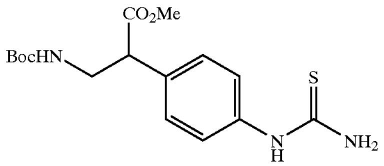
Example 224
TABLE 10-continued
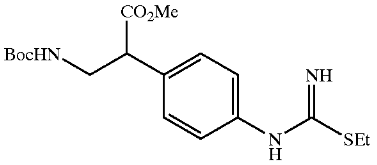
Example 225
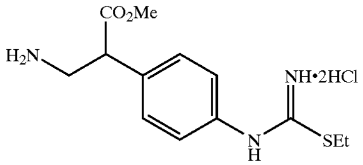
Example 226
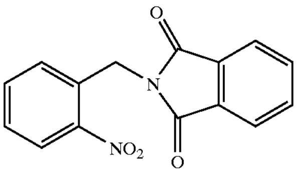
Example 227
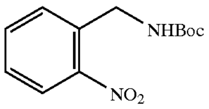
Example 228
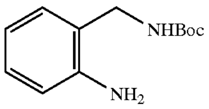
Example 229
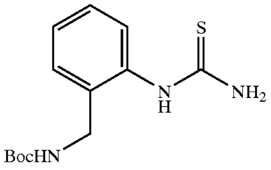
Example 230
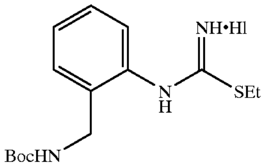
Example 231
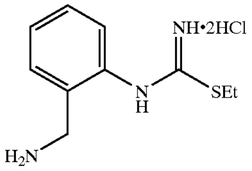
Example 232

TABLE 10-continued
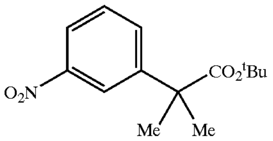
Example 1a
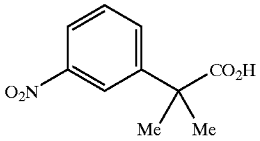
Example 1b
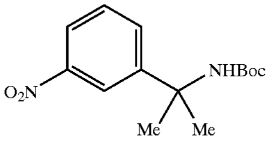
Example 1c
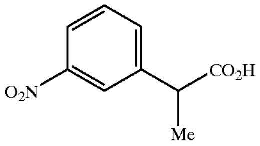
Example 8a
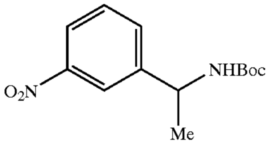
Example 8b
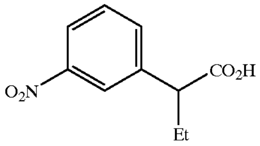
Example 15a
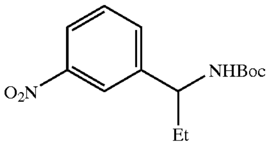
Example 15b
TABLE 11
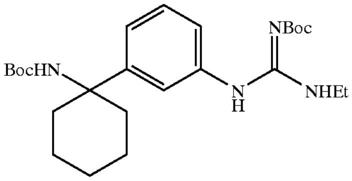
Example 233
TABLE 11-continued
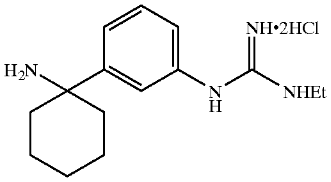
Example 234
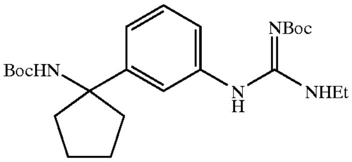
Example 235
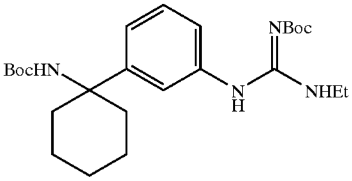
Example 236
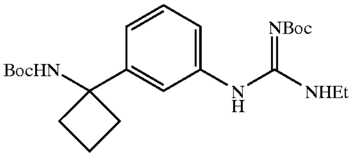
Example 237
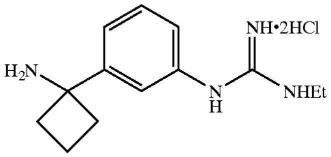
Example 238
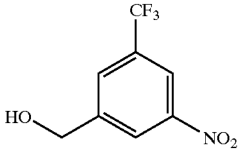
Example 239
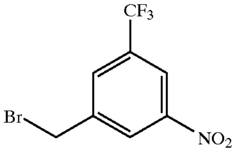
Example 240
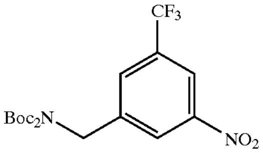
Example 241

TABLE 11-continued
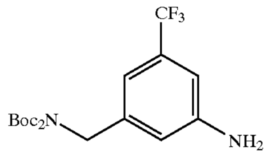
Example 242
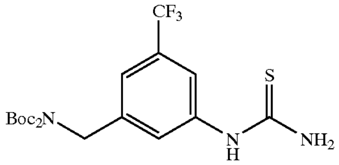
Example 243
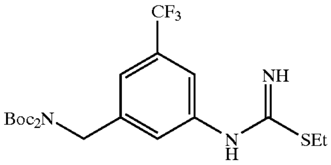
Example 244
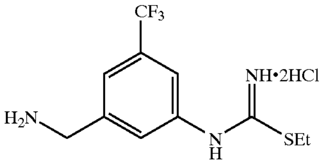
Example 245
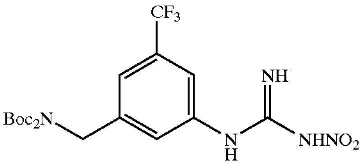
Example 246
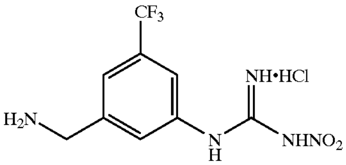
Example 247
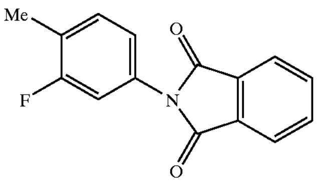
Example 248
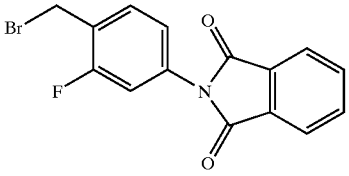
Example 249
TABLE 11-continued
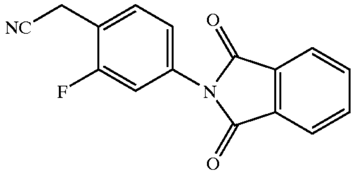
Example 250
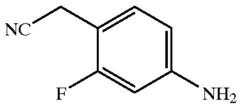
Example 251
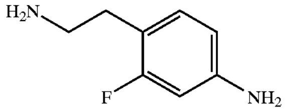
Example 252
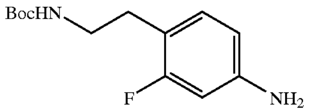
Example 253
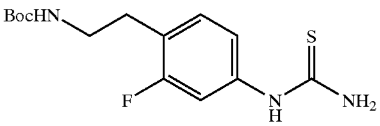
Example 254
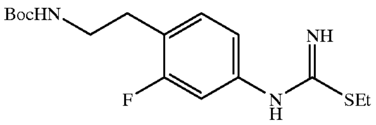
Example 255
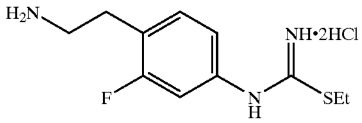
Example 256
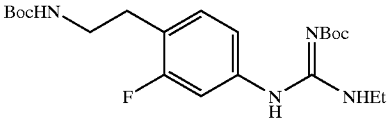
Example 257
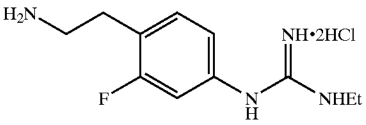
Example 258
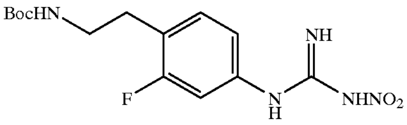
Example 259

TABLE 12
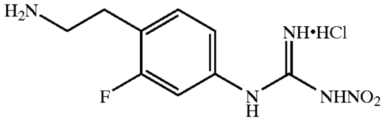
Example 260
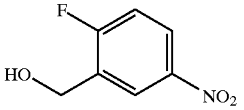
Example 262
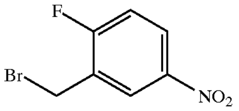
Example 262
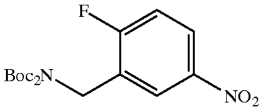
Example 263
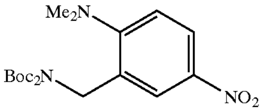
Example 264
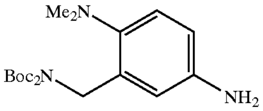
Example 265
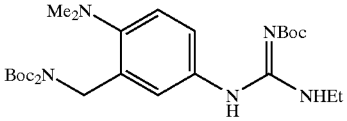
Example 266
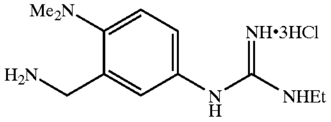
Example 267
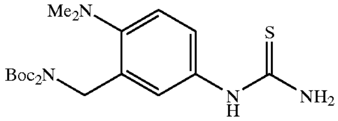
Example 268
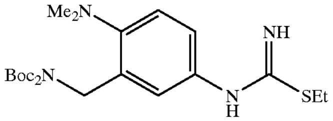
Example 269
TABLE 12-continued
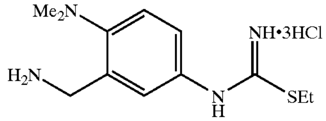
Example 270
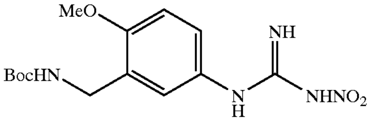
Example 271
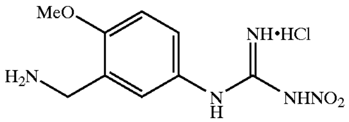
Example 272
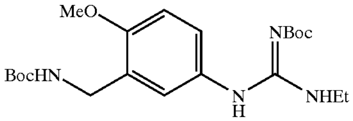
Example 273
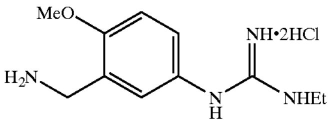
Example 274
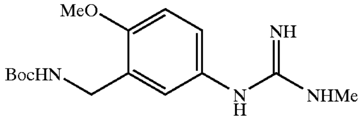
Example 275
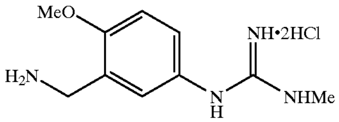
Example 276
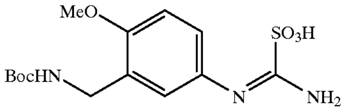
Example 277
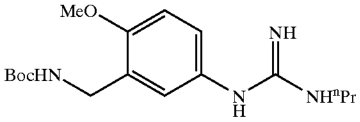
Example 278
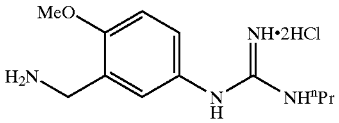
Example 279

TABLE 12-continued
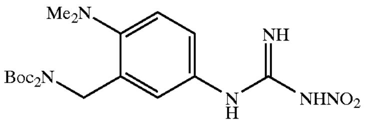
Example 280
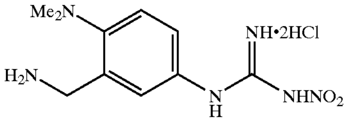
Example 281
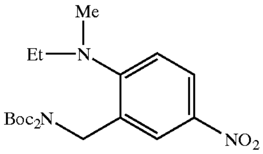
Example 282
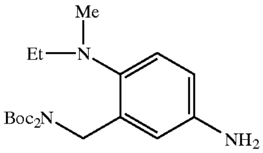
Example 283
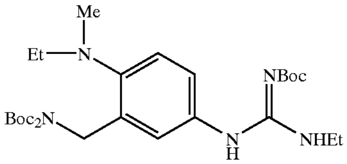
Example 284
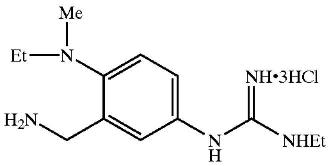
Example 285
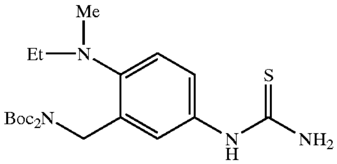
Example 286
TABLE 13
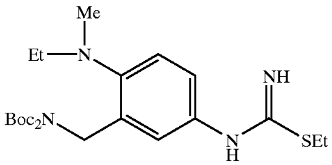
Example 287
TABLE 13-continued
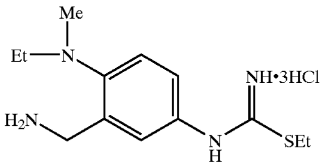
Example 288
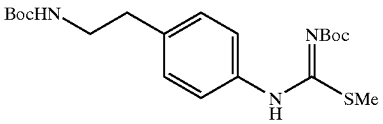
Example 289
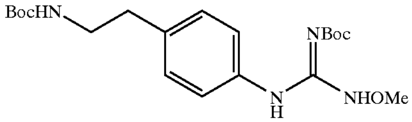
Example 290
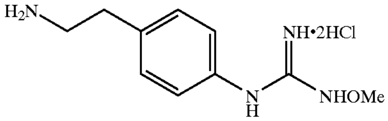
Example 291
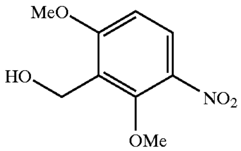
Example 292
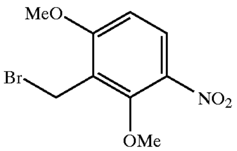
Example 293
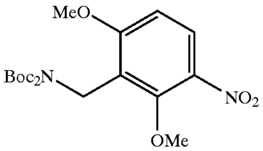
Example 294
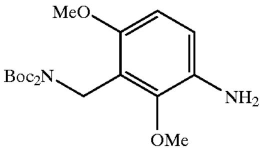
Example 295
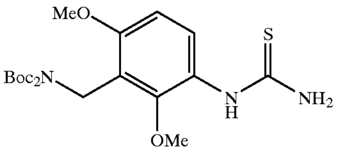
Example 296

TABLE 13-continued
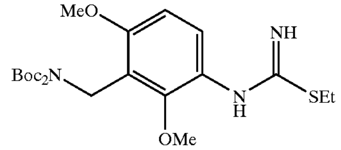
Example 297
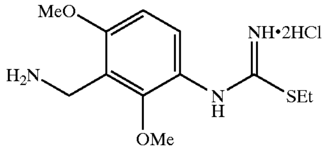
Example 298
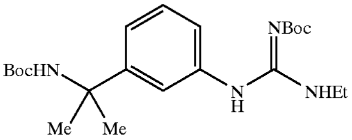
Example 299
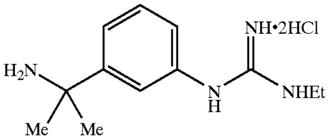
Example 300
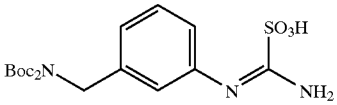
Example 301
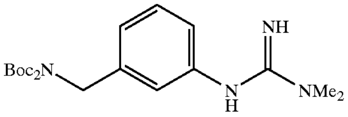
Example 302
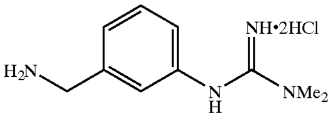
Example 303
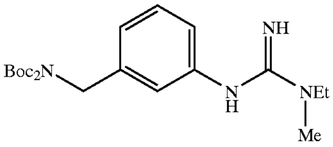
Example 304
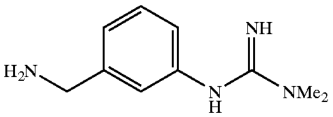
Example 305
TABLE 13-continued
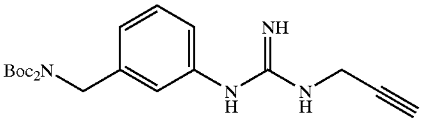
Example 306
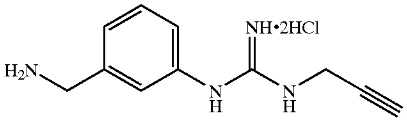
Example 307
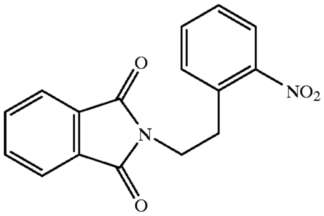
Example 308
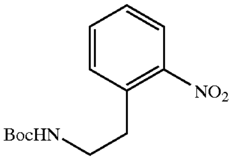
Example 309
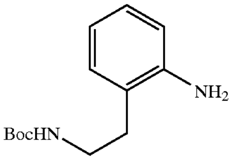
Example 310
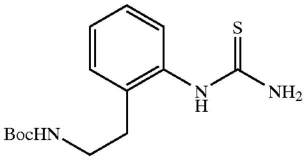
Example 311
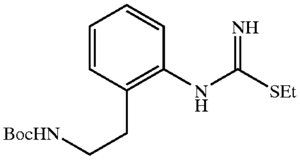
Example 312
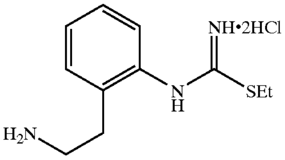
Example 313

TABLE 14
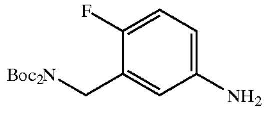
Example 314
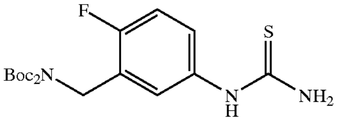
Example 315
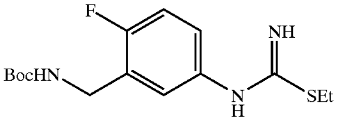
Example 316
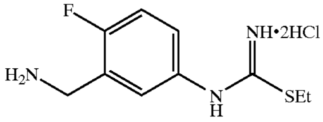
Example 317
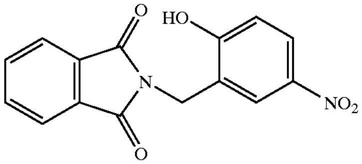
Example 318
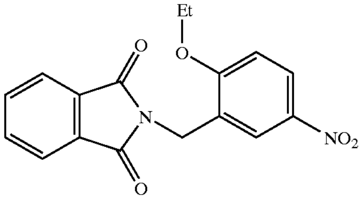
Example 319
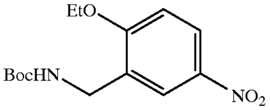
Example 320
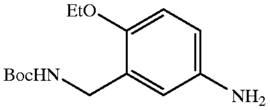
Example 321
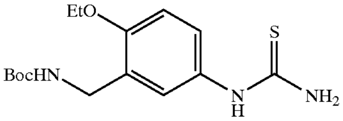
Example 322
TABLE 14-continued
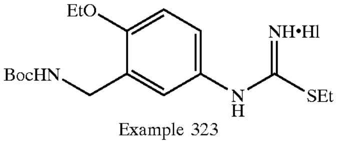
Example 323
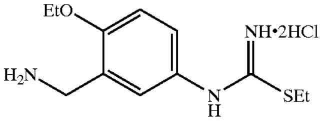
Example 324
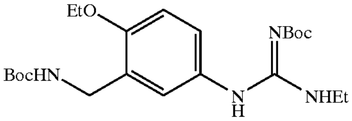
Example 325
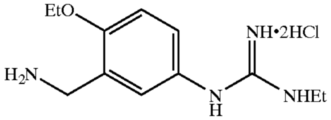
Example 326
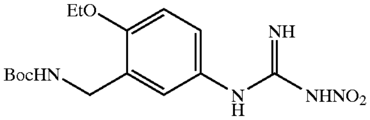
Example 327
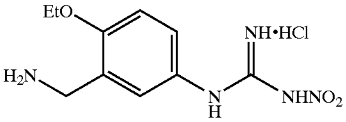
Example 328
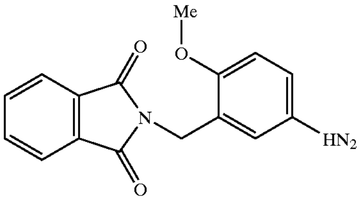
Example 329
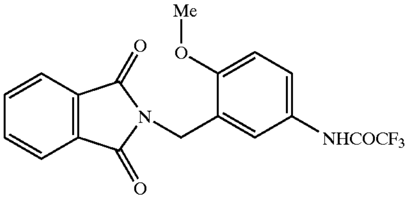
Example 330
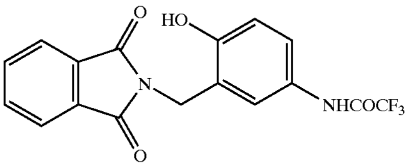
Example 331

TABLE 14-continued
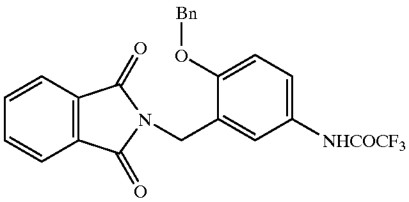
Example 332
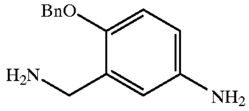
Example 333
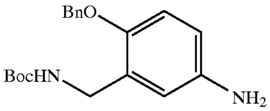
Example 334
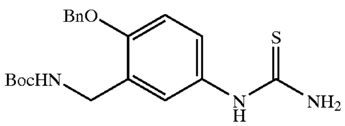
Example 335
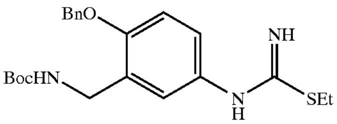
Example 336
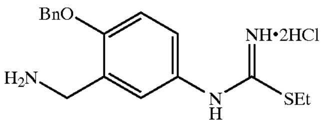
Example 337
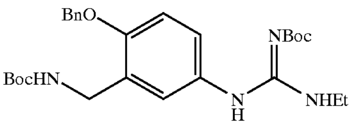
Example 338
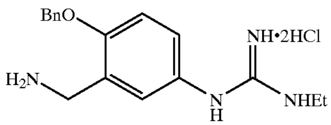
Example 339
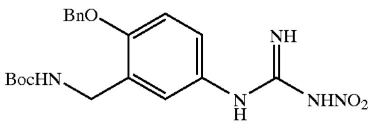
Example 340
TABLE 15
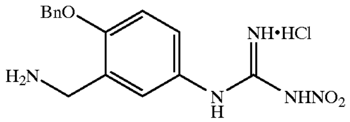
Example 341
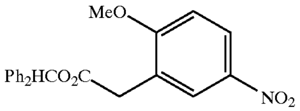
Example 342
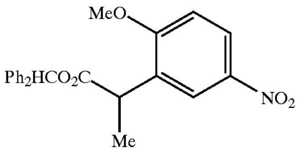
Example 343
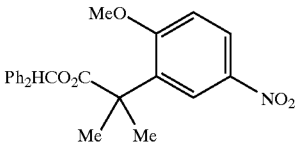
Example 344
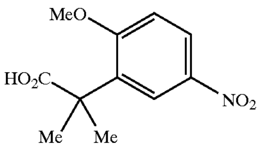
Example 345
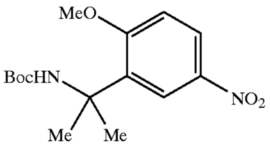
Example 346
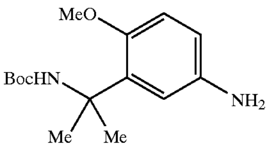
Example 347
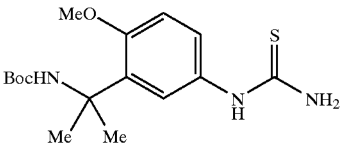
Example 348
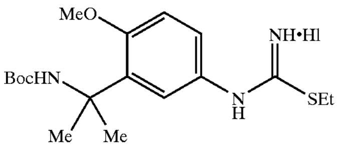
Example 349

TABLE 15-continued
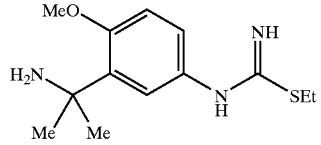
Example 350
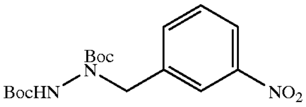
Example 351
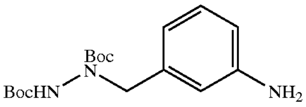
Example 352
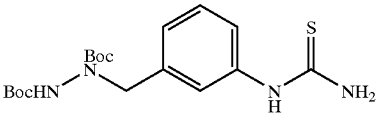
Example 353
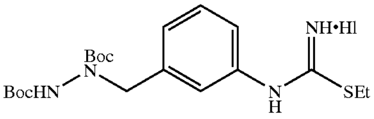
Example 354
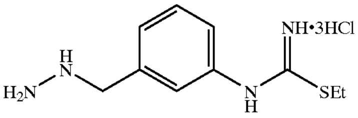
Example 355
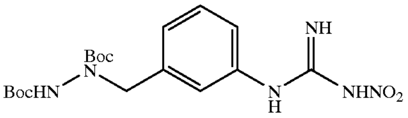
Example 356
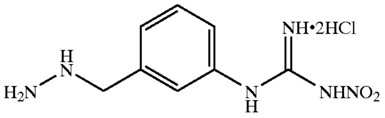
Example 357
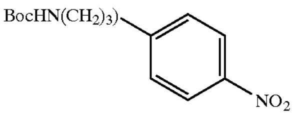
Example 358
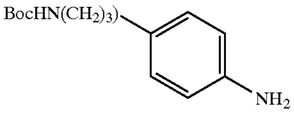
Example 359
TABLE 15-continued
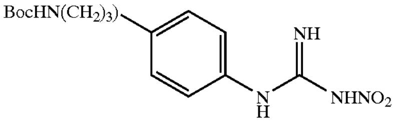
Example 360
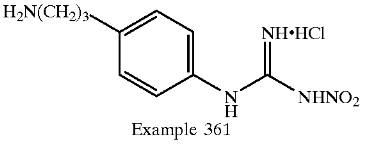
Example 361
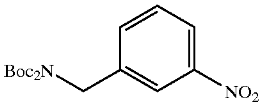
Example 362
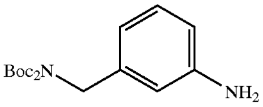
Example 363
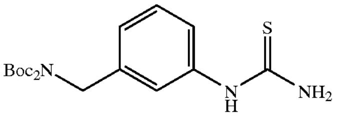
Example 364
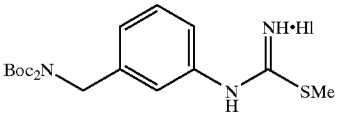
Example 365
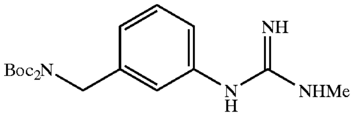
Example 366
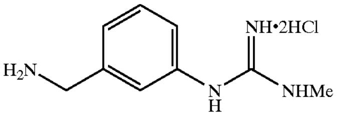
Example 367
TABLE 16
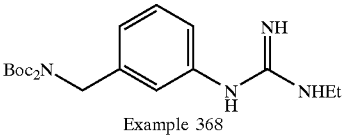
Example 368
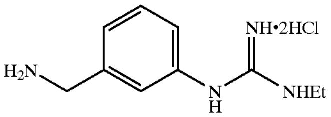
Example 369

TABLE 16-continued
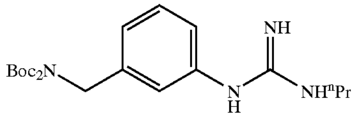
Example 370
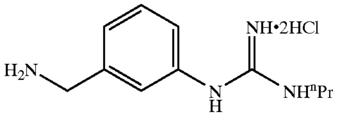
Example 371
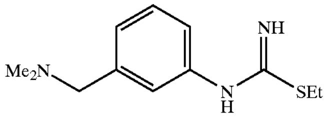
Example 372
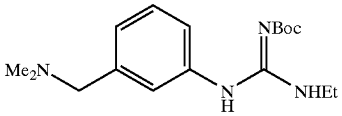
Example 373
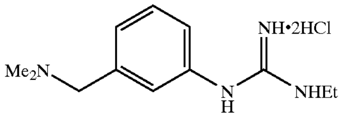
Example 374
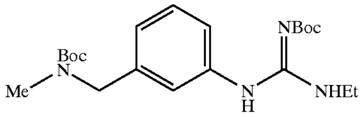
Example 375
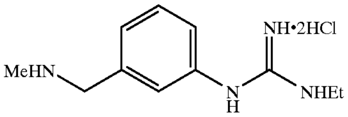
Example 376
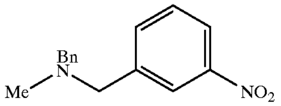
Example 377
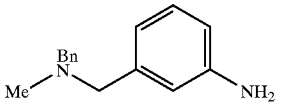
Example 378
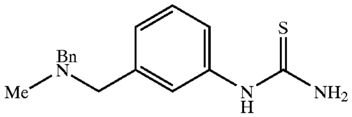
Example 379
TABLE 16-continued
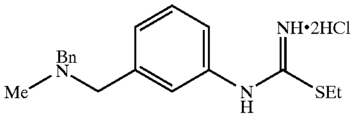
Example 380
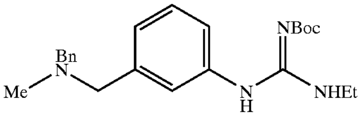
Example 381
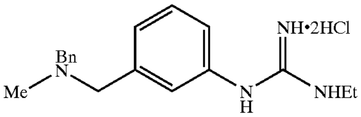
Example 382
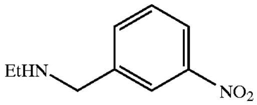
Example 383
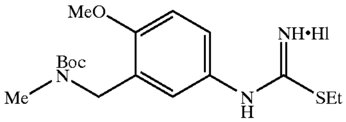
Example 384
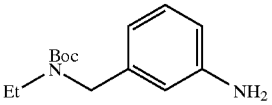
Example 385
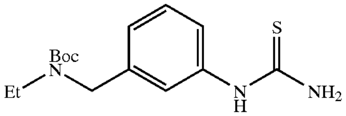
Example 386
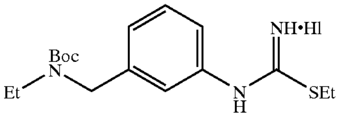
Example 387
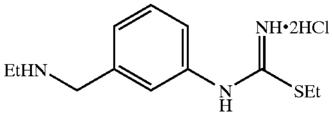
Example 388
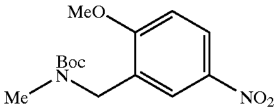
Example 389

TABLE 16-continued
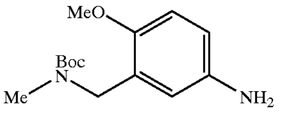
Example 390
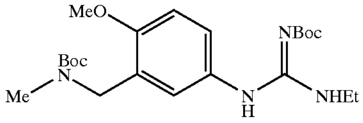
Example 391
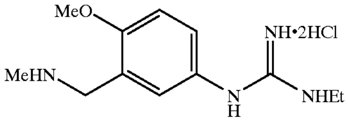
Example 392
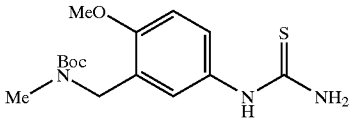
Example 393
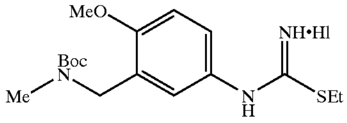
Example 394
TABLE 17
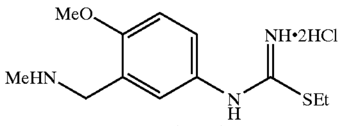
Example 395
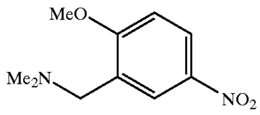
Example 396
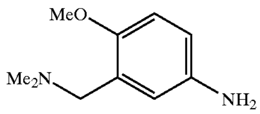
Example 397
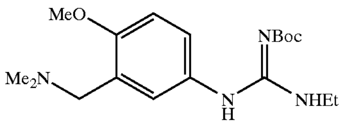
Example 398
TABLE 17-continued
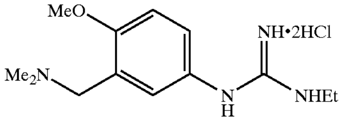
Example 399
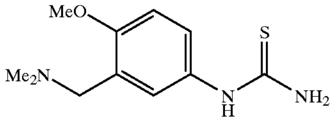
Example 400
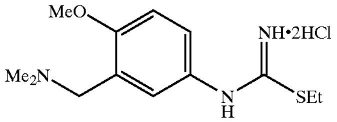
Example 401
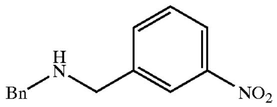
Example 402
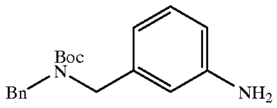
Example 403
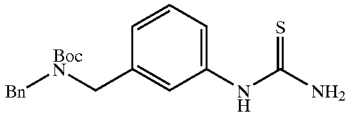
Example 404
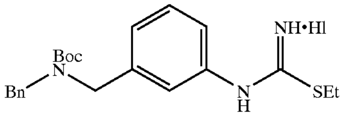
Example 405
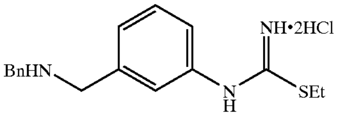
Example 406
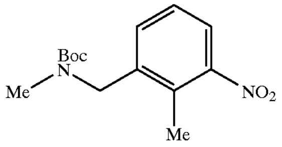
Example 407
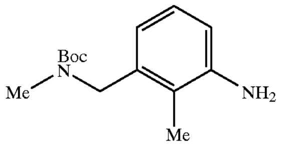
Example 408

TABLE 17-continued
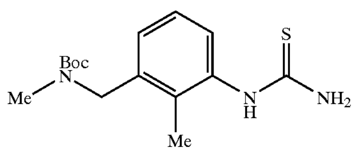
Example 409
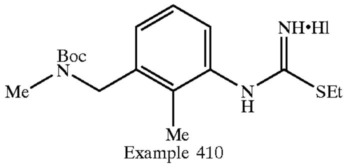
Example 410
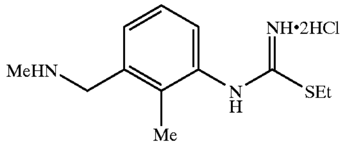
Example 411
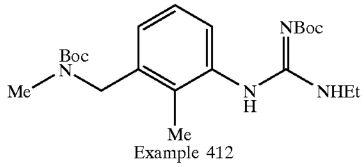
Example 412
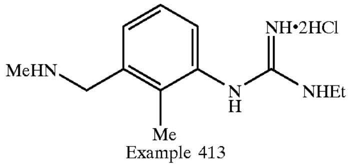
Example 413
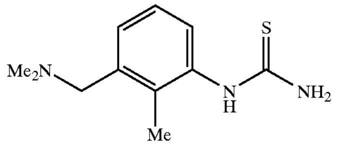
Example 414
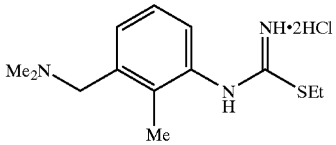
Example 415
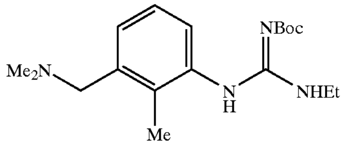
Example 416
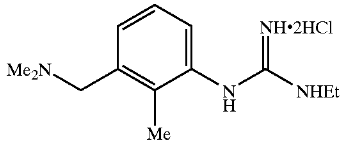
Example 417
TABLE 17-continued
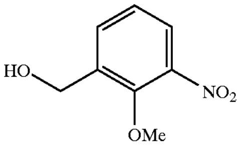
Example 418
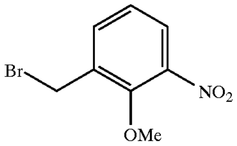
Example 419
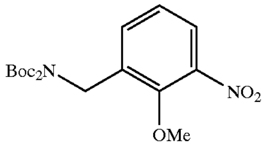
Example 420
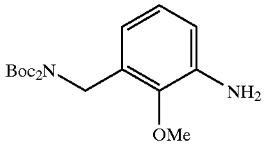
Example 421
TABLE 18
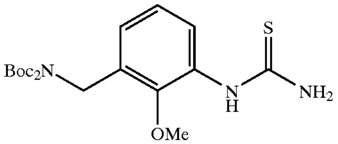
Example 422
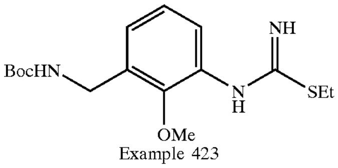
Example 423
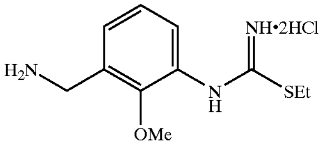
Example 424
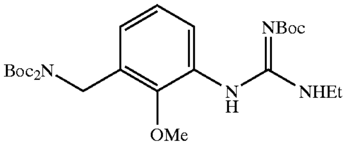
Example 425

TABLE 18-continued
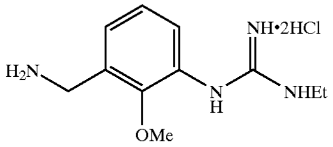
Example 426
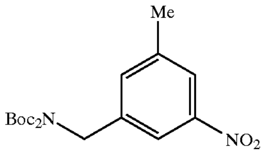
Example 427
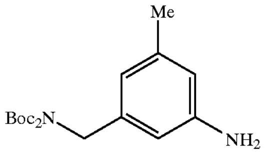
Example 428
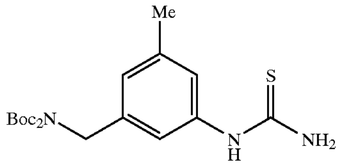
Example 429
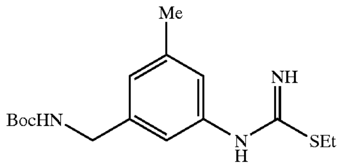
Example 430
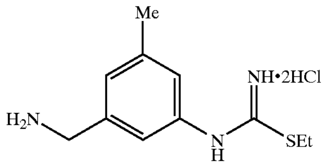
Example 431
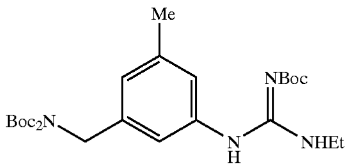
Example 432
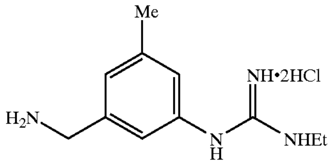
Example 433
TABLE 18-continued
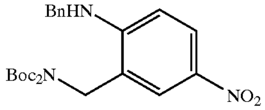
Example 434
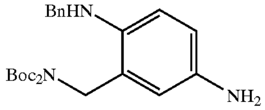
Example 435
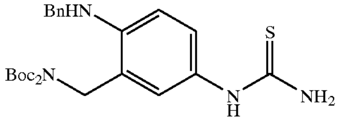
Example 436
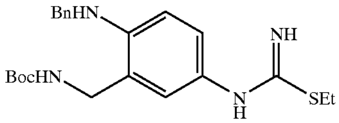
Example 437
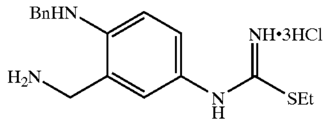
Example 438
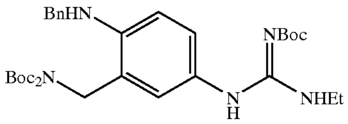
Example 439
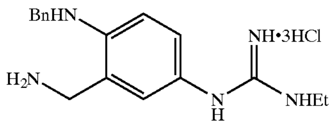
Example 440
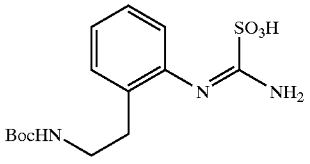
Example 441
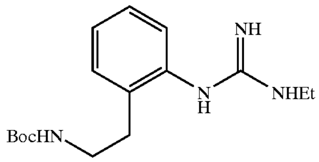
Example 442

TABLE 18-continued
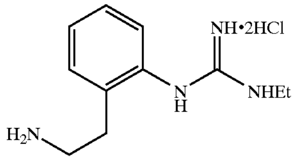
Example 443
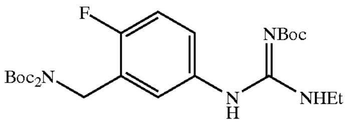
Example 444
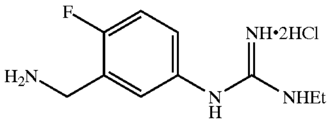
Example 445
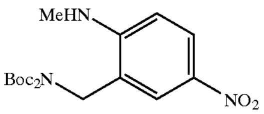
Example 446
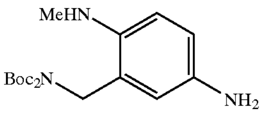
Example 447
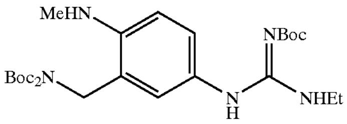
Example 448
TABLE 19
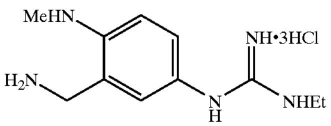
Example 449
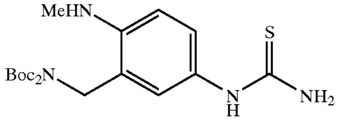
Example 450
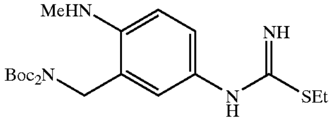
Example 451
TABLE 19-continued
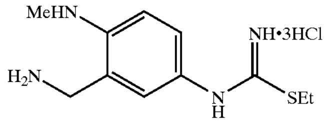
Example 452
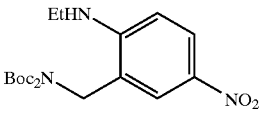
Example 453
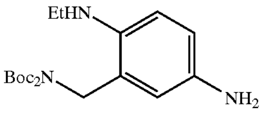
Example 454
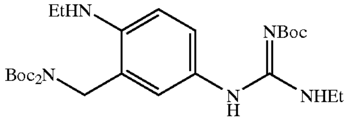
Example 455
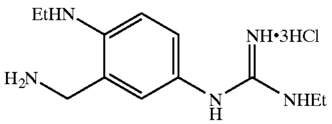
Example 456
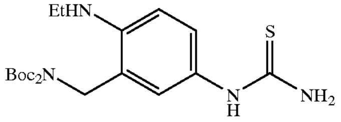
Example 457
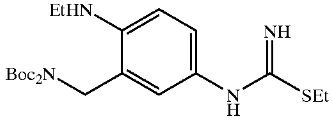
Example 458
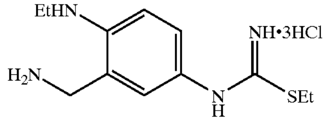
Example 459
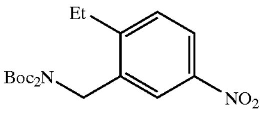
Example 460
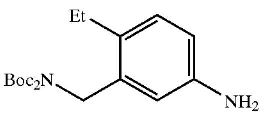
Example 461

TABLE 19-continued
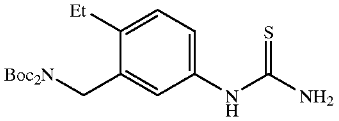
Example 462
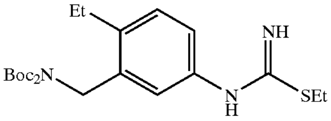
Example 463
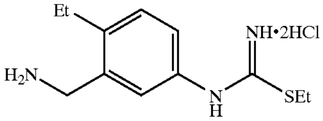
Example 464
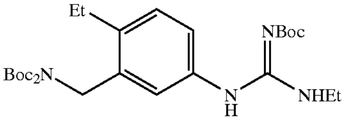
Example 465
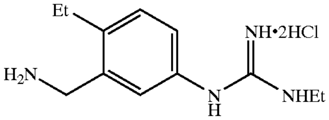
Example 466
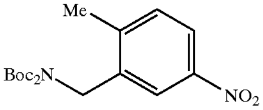
Example 467
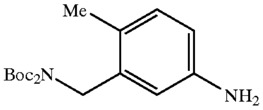
Example 468
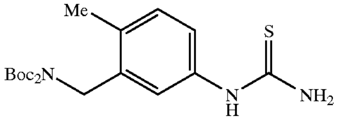
Example 469
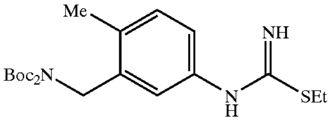
Example 470
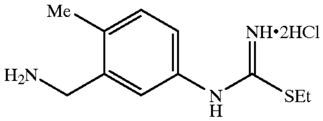
Example 471
TABLE 19-continued
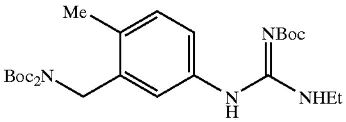
Example 472
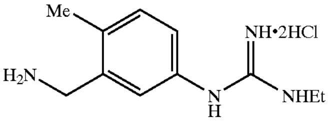
Example 473
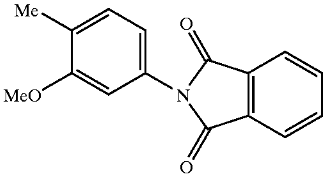
Example 474
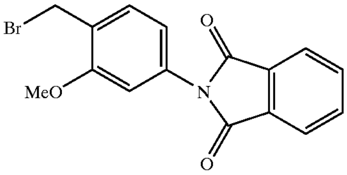
Example 475
TABLE 20
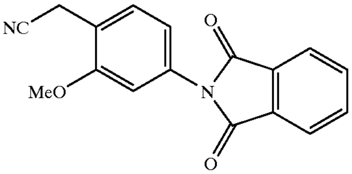
Example 476
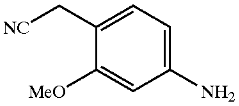
Example 477
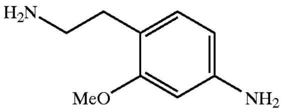
Example 478
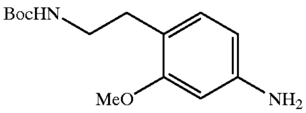
Example 479

TABLE 20-continued
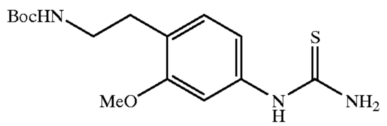
Example 480
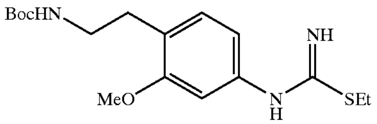
Example 481
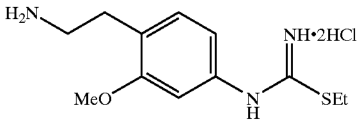
Example 482
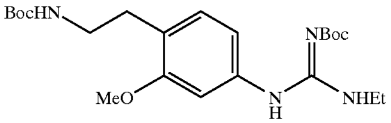
Example 483
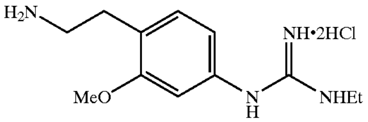
Example 484
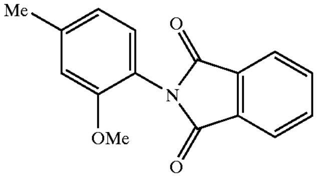
Example 485
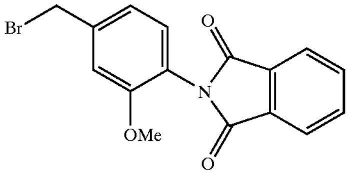
Example 486
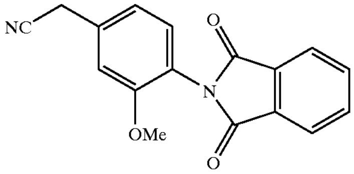
Example 487
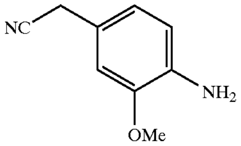
Example 488
TABLE 20-continued
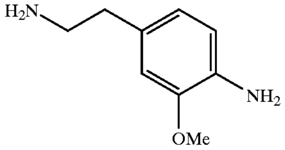
Example 489
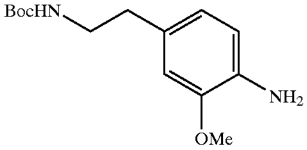
Example 490
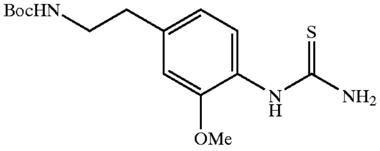
Example 491
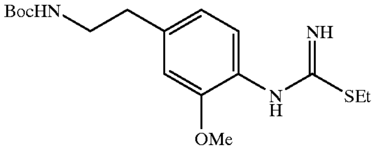
Example 492
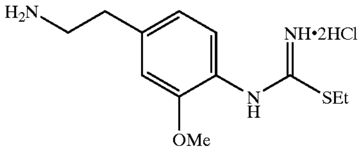
Example 493
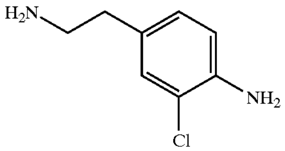
Example 494
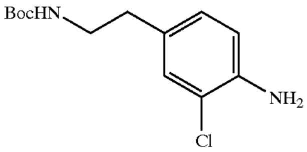
Example 495
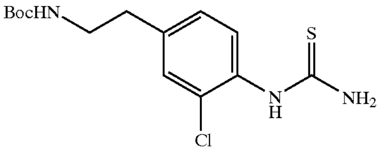
Example 496

TABLE 20-continued
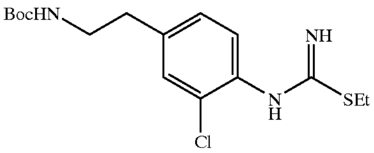
Example 497
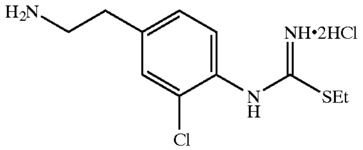
Example 498
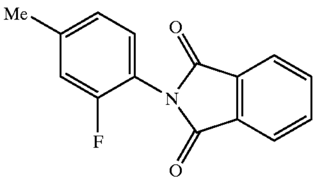
Example 499
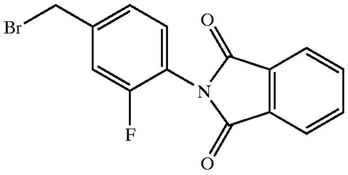
Example 500
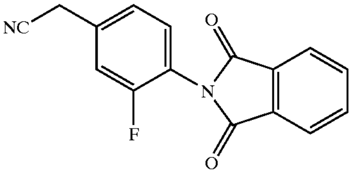
Example 501
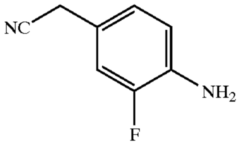
Example 502
TABLE 21
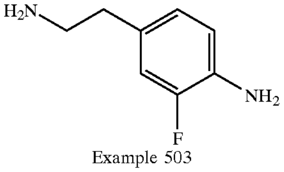
Example 503
TABLE 21-continued
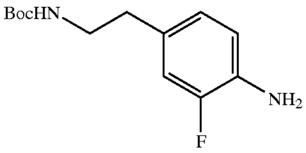
Example 504
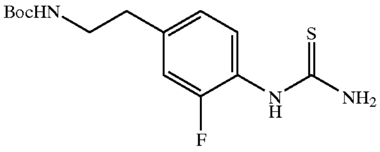
Example 505
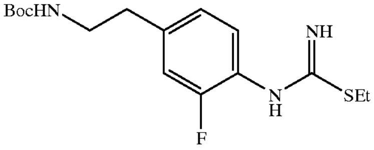
Example 506
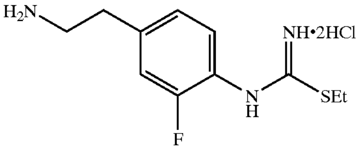
Example 507
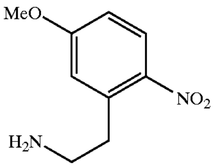
Example 508
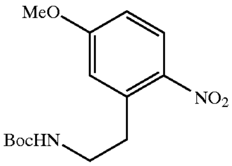
Example 509
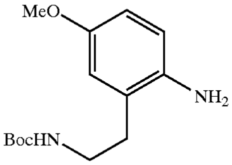
Example 510
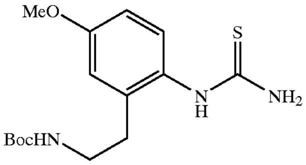
Example 511

TABLE 21-continued
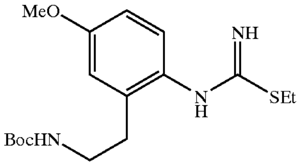
Example 512
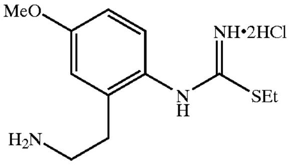
Example 513
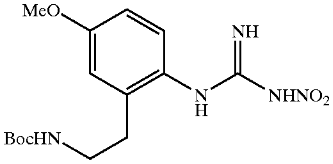
Example 514
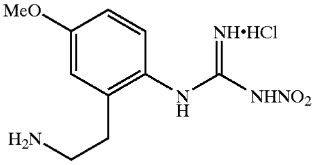
Example 515
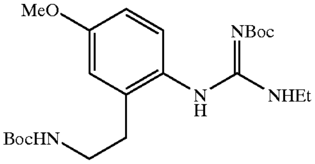
Example 516
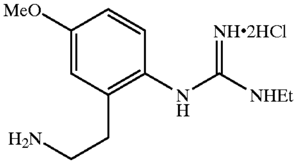
Example 517
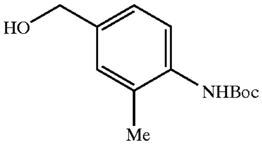
Example 518
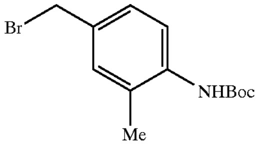
Example 519
TABLE 21-continued
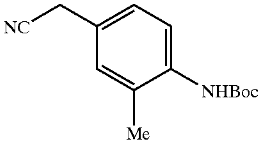
Example 520
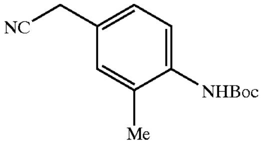
Example 521
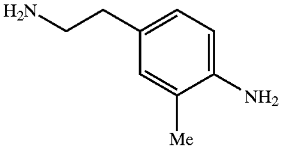
Example 522
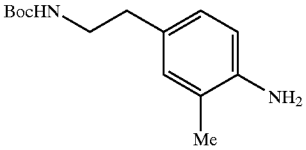
Example 523
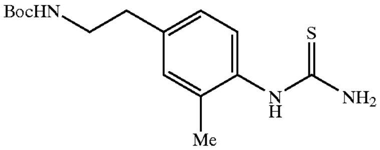
Example 524
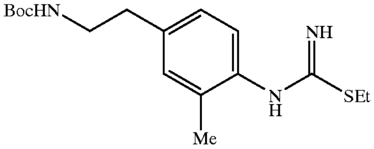
Example 525
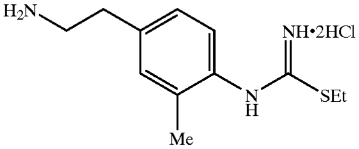
Example 526
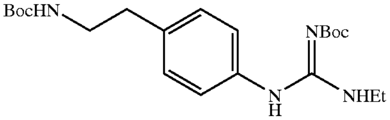
Example 527
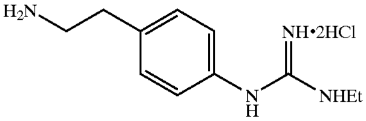
Example 528

TABLE 21-continued
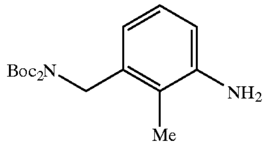
Example 529
TABLE 22
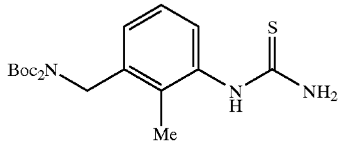
Example 530
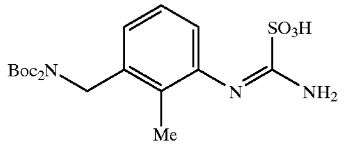
Example 531
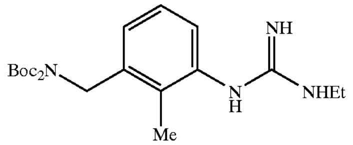
Example 532
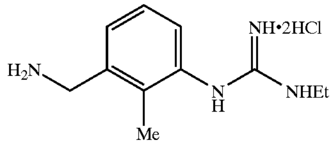
Example 533
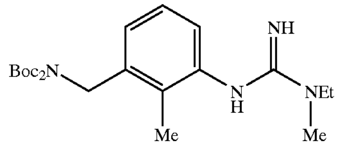
Example 534
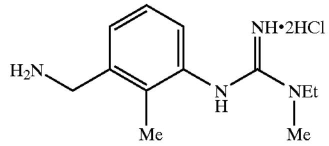
Example 535
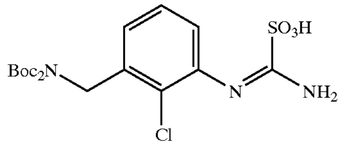
Example 536
TABLE 22-continued
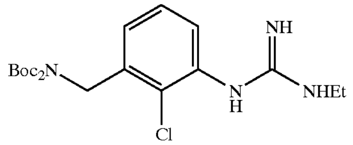
Example 537
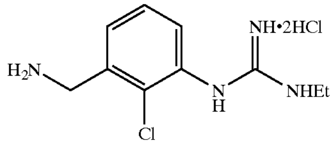
Example 538
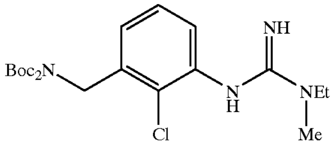
Example 539
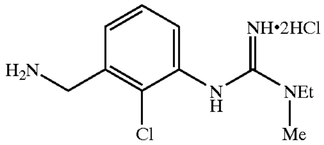
Example 540
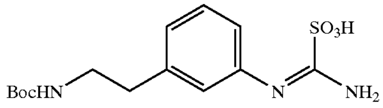
Example 541
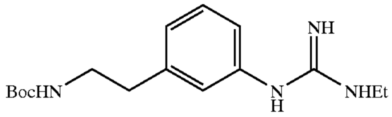
Example 542
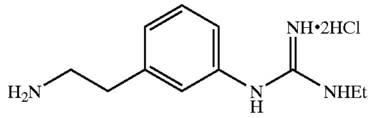
Example 543
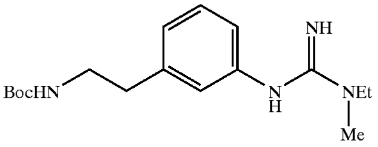
Example 544
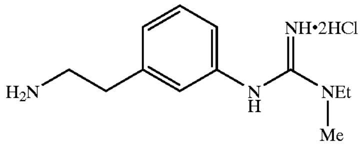
Example 545

TABLE 22-continued
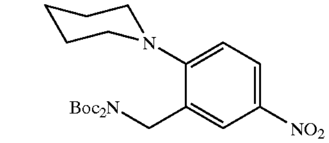
Example 546
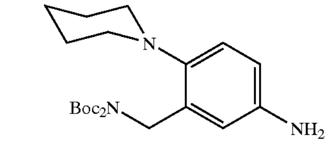
Example 547
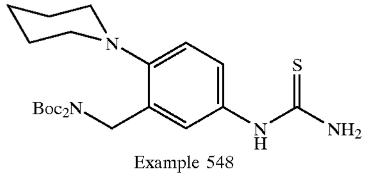
Example 548
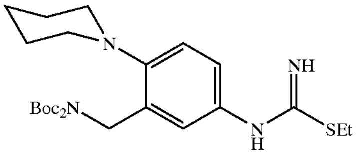
Example 549
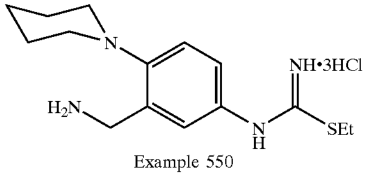
Example 550
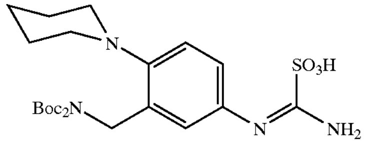
Example 551
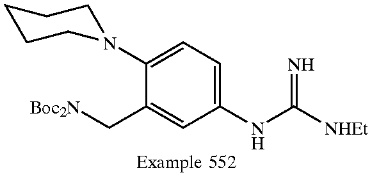
Example 552
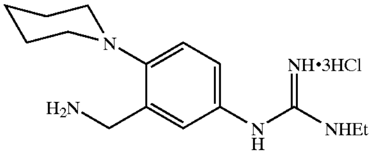
Example 553
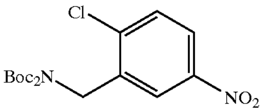
Example 554
TABLE 22-continued
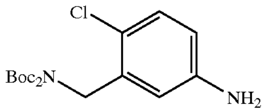
Example 555
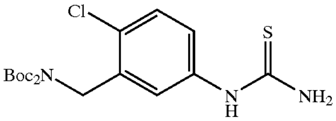
Example 556
TABLE 23
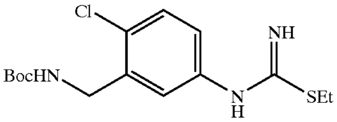
Example 557
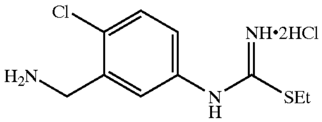
Example 558
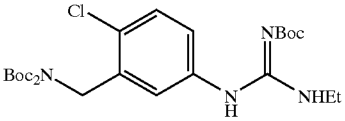
Example 559
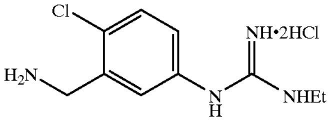
Example 560
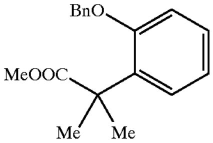
Example 561
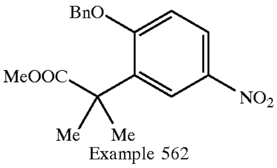
Example 562
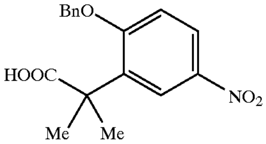
Example 563

TABLE 23-continued
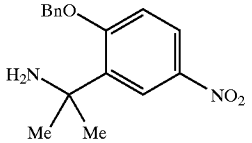
Example 564
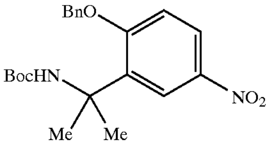
Example 565
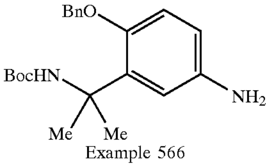
Example 566
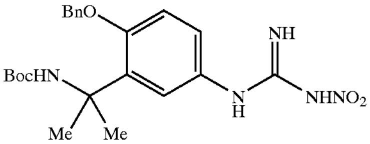
Example 567
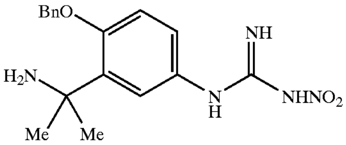
Example 568
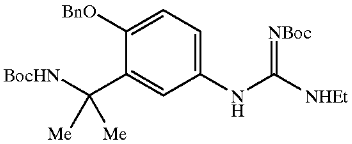
Example 569
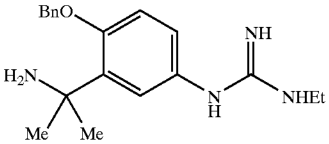
Example 570
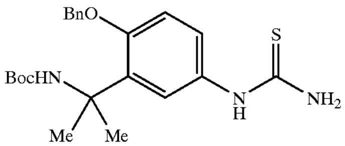
Example 571
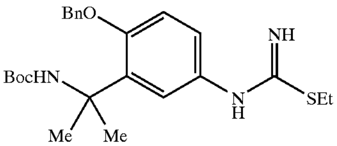
Example 572
TABLE 23-continued
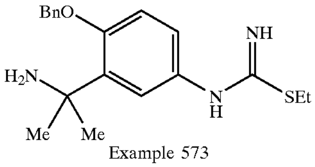
Example 573
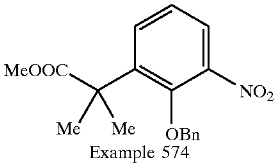
Example 574
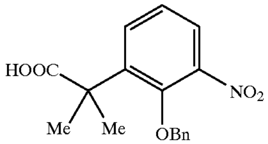
Example 575
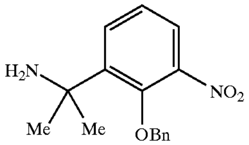
Example 576
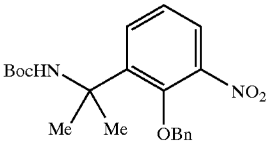
Example 577
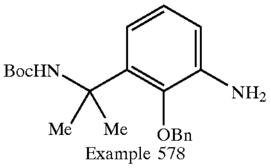
Example 578
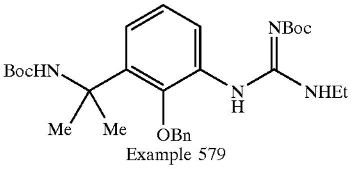
Example 579
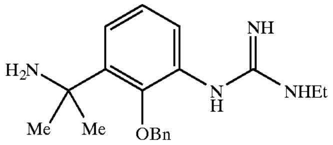
Example 580
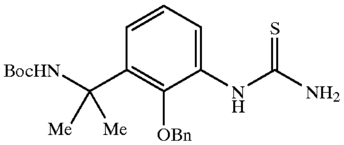
Example 581

TABLE 23-continued
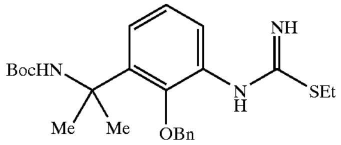
Example 582
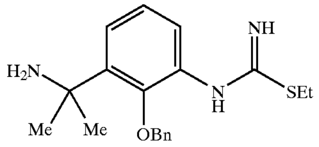
Example 583
TABLE 24
Example 584
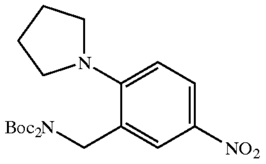
Example 585
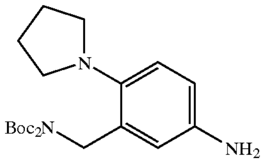
Example 586
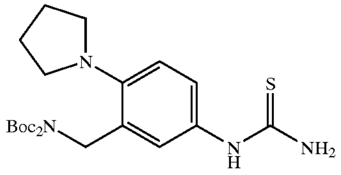
Example 587
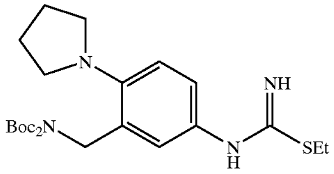
Example 588
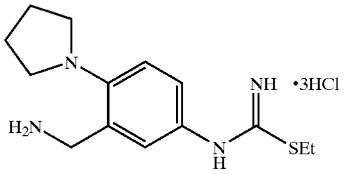
TABLE 24-continued
Example 589
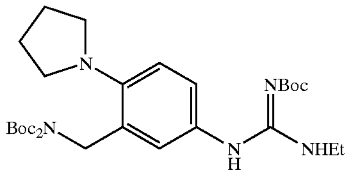
Example 590
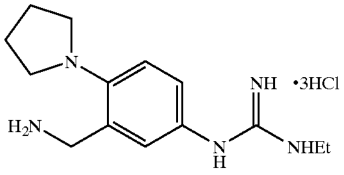
Example 591
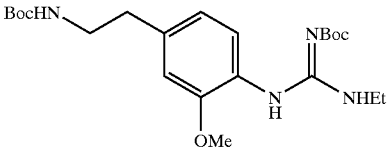
Example 592
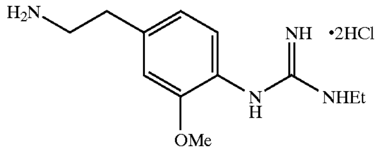
Example 593
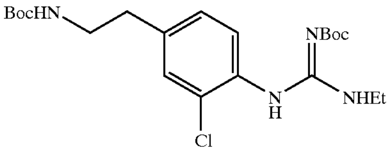
Example 594
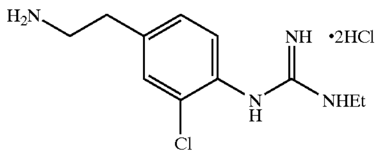
Example 595
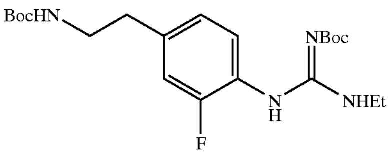

TABLE 24-continued
Example 596
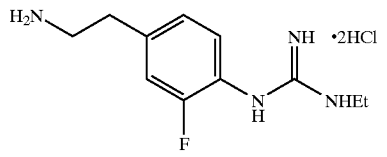
Example 597
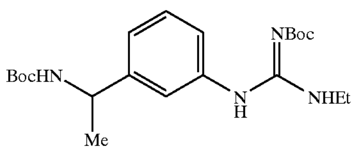
Example 598
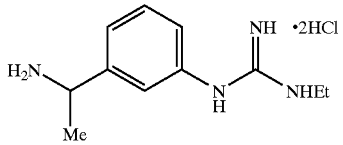
Example 599
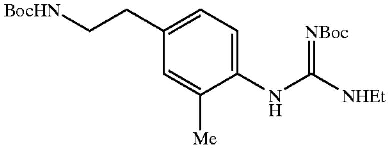
Example 600
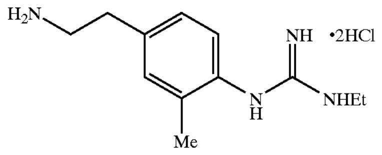
Example 601
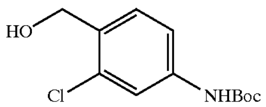
Example 602
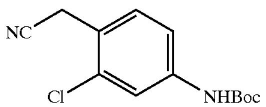
Example 603
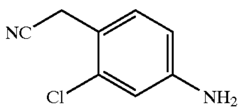
TABLE 24-continued
Example 604
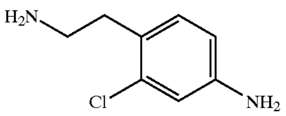
Example 605
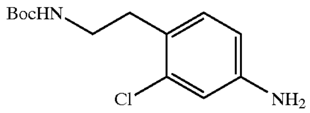
Example 606
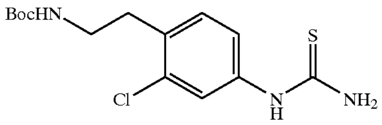
Example 607
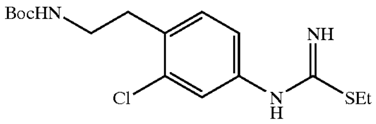
Example 608
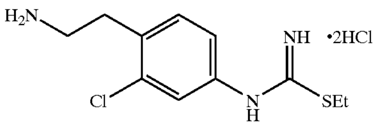
Example 609
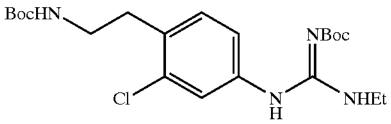
Example 610
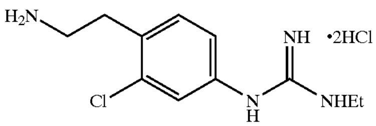
TABLE 25
Example 611
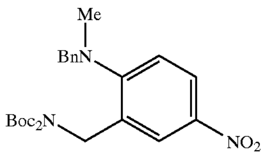

TABLE 25-continued
Example 612
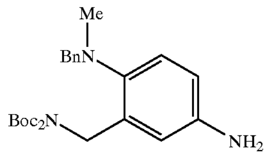
Example 613
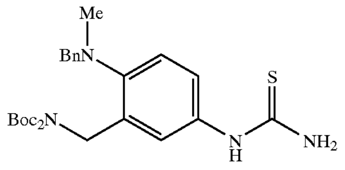
Example 614
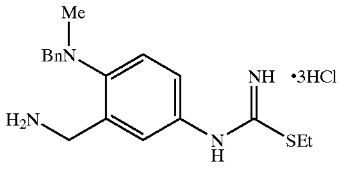
Example 615
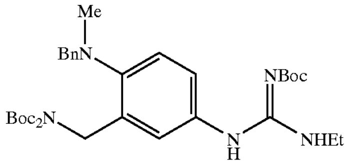
Example 616
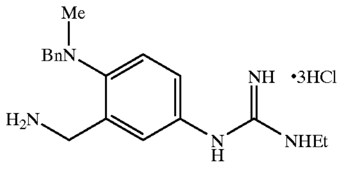
Example 617
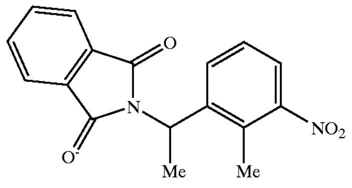
Example 618
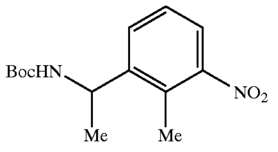
TABLE 25-continued
Example 619
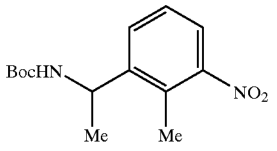
Example 620
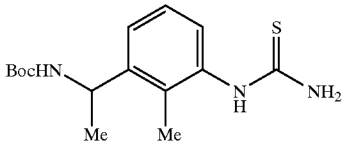
Example 621
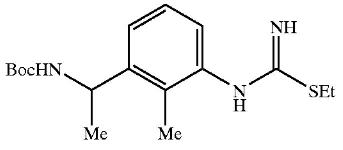
Example 622
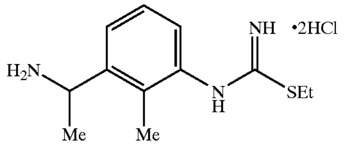
Example 623
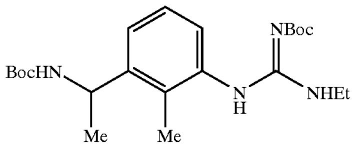
Example 624
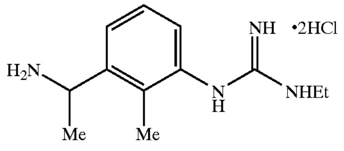
Example 625
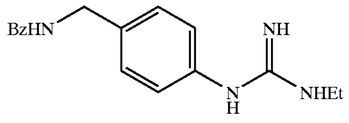
Example 626
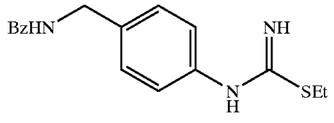

TABLE 25-continued
Example 627
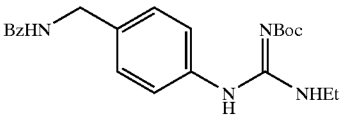
Example 628
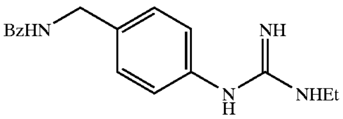
Example 629
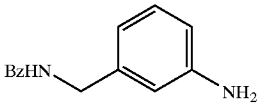
Example 630
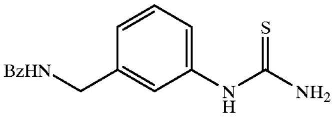
Example 631
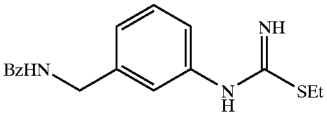
Example 632
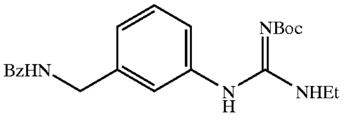
Example 633
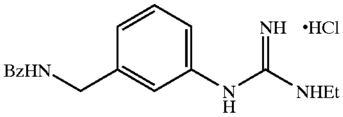
Example 634
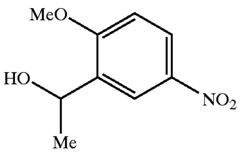
TABLE 25-continued
Example 635
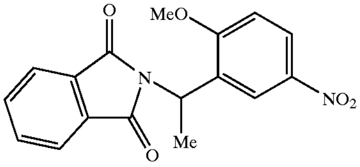
Example 636
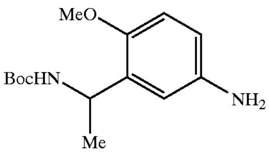
Example 637
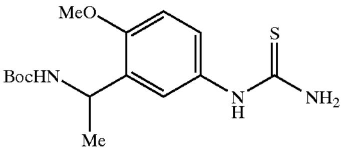
TABLE 26
Example 638
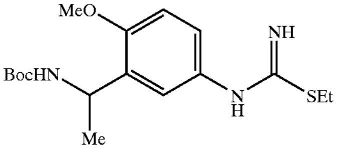
Example 639
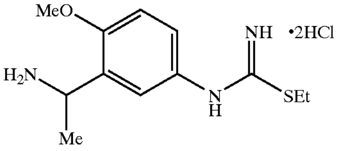
Example 640
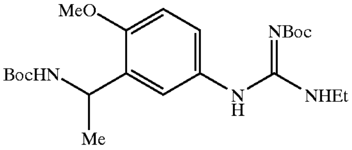
Example 641
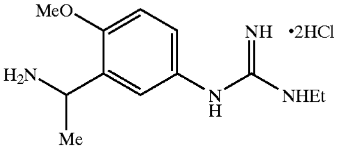

TABLE 26-continued
Example 642
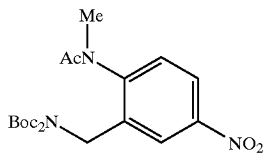
Example 643
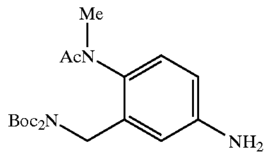
Example 644
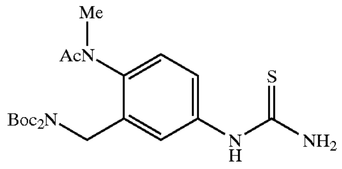
Example 645
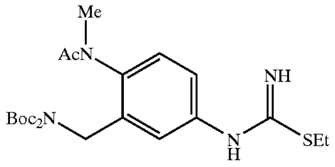
Example 646
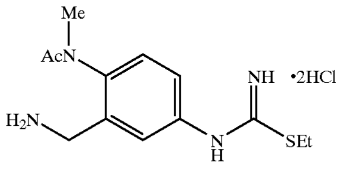
Example 647
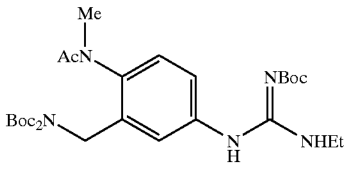
Example 648
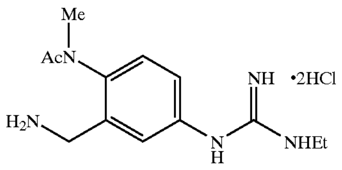
TABLE 26-continued
Example 649
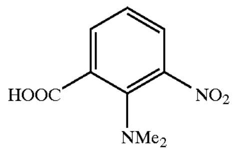
Example 650
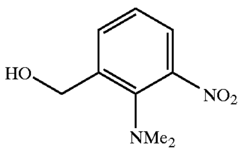
Example 651
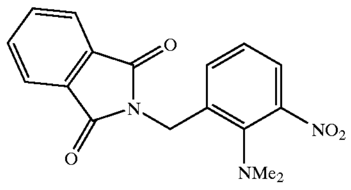
Example 652
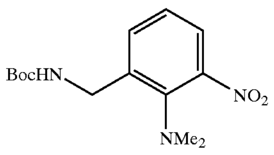
Example 653
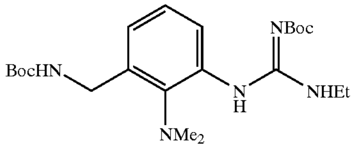
Example 654
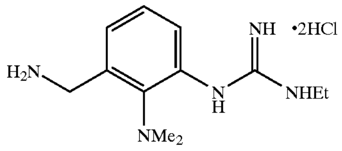
Example 655
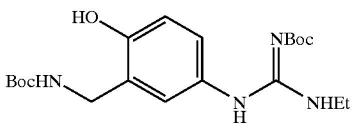

TABLE 26-continued

Example 656

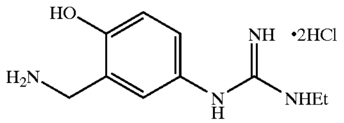

Example 657

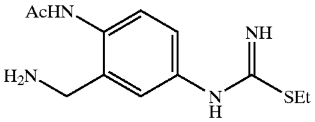

Example 658

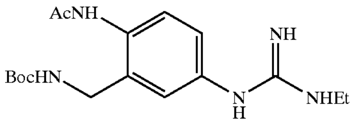

Example 659

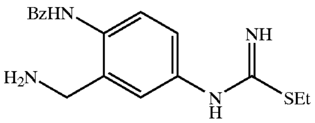

Example 660

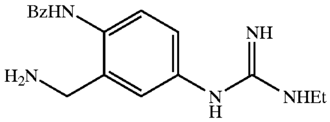

Example 661

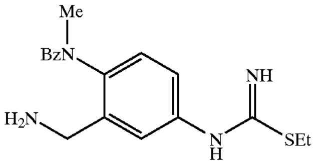

Example 662

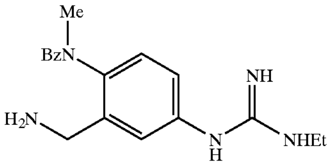

Example 663

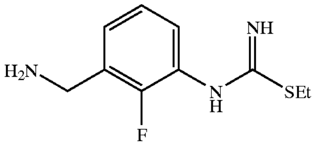

Example 664

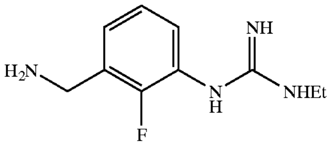

Among the compounds synthesized in the Examples, those which are represented by the general formula (1) are listed below in Tables 27–48.

TABLE 27

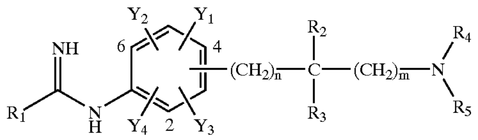

acid

| Example No. | $R_1$ | $Y_1$* | $Y_2$* | $Y_3$* | $Y_4$* | Z★ position | n | $R_2$ | $R_3$ | m | $R_4$ | $R_5$ | Acid |
|---|---|---|---|---|---|---|---|---|---|---|---|---|---|
| 4 | SMe | 2-H | 4-H | 5-H | 6-H | 3 | 0 | Me | Me | 0 | $^t$BuOCO | H | HI |
| 5 | SMe | 2-H | 4-H | 5-H | 6-H | 3 | 0 | Me | Me | 0 | H | H | HCl |
| 6 | $NHNO_2$ | 2-H | 4-H | 5-H | 6-H | 3 | 0 | Me | Me | 0 | $^t$BuOCO | H | — |
| 7 | $NHNO_2$ | 2-H | 4-H | 5-H | 6-H | 3 | 0 | Me | Me | 0 | H | H | HCl |
| 11 | SMe | 2-H | 4-H | 5-H | 6-H | 3 | 0 | Me | H | 0 | $^t$BuOCO | H | HI |
| 12 | SMe | 2-H | 4-H | 5-H | 6-H | 3 | 0 | Me | H | 0 | H | H | HCl |
| 13 | $NHNO_2$ | 2-H | 4-H | 5-H | 6-H | 3 | 0 | Me | H | 0 | $^t$BuOCO | H | — |
| 14 | $NHNO_2$ | 2-H | 4-H | 5-H | 6-H | 3 | 0 | Me | H | 0 | H | H | HCl |
| 18 | SMe | 2-H | 4-H | 5-H | 6-H | 3 | 0 | Et | H | 0 | $^t$BuOCO | H | HI |
| 19 | SMe | 2-H | 4-H | 5-H | 6-H | 3 | 0 | Et | H | 0 | H | H | HCl |
| 20 | $NHNO_2$ | 2-H | 4-H | 5-H | 6-H | 3 | 0 | Et | H | 0 | $^t$BuOCO | H | — |
| 21 | $NHNO_2$ | 2-H | 4-H | 5-H | 6-H | 3 | 0 | Et | H | 0 | H | H | HCl |
| 25 | SMe | 2-H | 4-H | 5-H | 6-H | 3 | 0 | H | H | 0 | $^t$BuOCO | H | HI |

TABLE 27-continued

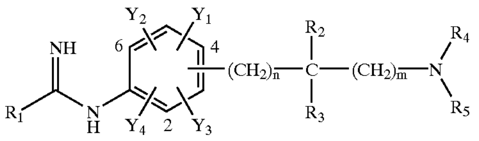

acid

| Example No. | $R_1$ | $Y_1$* | $Y_2$* | $Y_3$* | $Y_4$* | Z★ position | n | $R_2$ | $R_3$ | m | $R_4$ | $R_5$ | Acid |
|---|---|---|---|---|---|---|---|---|---|---|---|---|---|
| 26 | SMe | 2-H | 4-H | 5-H | 6-H | 3 | 0 | H | H | 0 | H | H | HCl |
| 27 | SEt | 2-H | 4-H | 5-H | 6-H | 3 | 0 | H | H | 0 | $^t$BuOCO | H | HI |

*Numeral represents the position of substitution on the benzene ring.

★

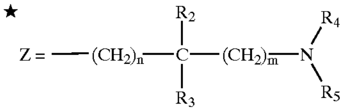

TABLE 28

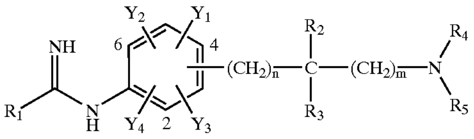

acid

| Example No. | $R_1$ | $Y_1$* | $Y_2$* | $Y_3$* | $Y_4$* | Z★ position | n | $R_2$ | $R_3$ | m | $R_4$ | $R_5$ | Acid |
|---|---|---|---|---|---|---|---|---|---|---|---|---|---|
| 28 | SEt | 2-H | 4-H | 5-H | 6-H | 3 | 0 | H | H | 0 | H | H | HCl |
| 29 | $SCH_2CH_2F$ | 2-H | 4-H | 5-H | 6-H | 3 | 0 | H | H | 0 | $^t$BuOCO | H | — |
| 30 | $SCH_2CH_2F$ | 2-H | 4-H | 5-H | 6-H | 3 | 0 | H | H | 0 | H | H | HCl |
| 31 | $SCH_2CH{=}CH_2$ | 2-H | 4-H | 5-H | 6-H | 3 | 0 | H | H | 0 | $^t$BuOCO | H | HBr |
| 32 | $SCH_2CH{=}CH_2$ | 2-H | 4-H | 5-H | 6-H | 3 | 0 | H | H | 0 | H | H | HCl |
| 33 | $NHNO_2$ | 2-H | 4-H | 5-H | 6-H | 3 | 0 | H | H | 0 | $^t$BuOCO | H | — |
| 34 | $NHNO_2$ | 2-H | 4-H | 5-H | 6-H | 3 | 0 | H | H | 0 | H | H | — |
| 35 | $NH_2$ | 2-H | 4-H | 5-H | 6-H | 3 | 0 | H | H | 0 | $^t$BuOCO | H | HCOOH |
| 36 | $NH_2$ | 2-H | 4-H | 5-H | 6-H | 3 | 0 | H | H | 0 | H | H | HCl |
| 39 | $NHNO_2$ | 2-H | 4-H | 5-H | 6-H | 3 | 0 | H | H | 0 | Me | Me | $CH_2COOH$ |
| 41 | SMe | 2-H | 4-H | 5-H | 6-H | 3 | 0 | H | H | 0 | Me | Me | $HNO_3$, HCl |
| 46 | SEt | 2-H | 4-H | 5-H | 6-H | 3 | 0 | H | H | 0 | $^t$BuOCO | Me | HI |
| 47 | SEt | 2-H | 4-H | 5-H | 6-H | 3 | 0 | H | H | 0 | H | Me | HCl |
| 51 | SMe | 2-H | 3-H | 5-H | 6-H | 4 | 0 | H | H | 1 | $^t$BuOCO | H | HI |
| 52 | SMe | 2-H | 3-H | 5-H | 6-H | 4 | 0 | H | H | 1 | H | H | HCl |

*Numeral represents the position of substitution on the benzene ring.

★

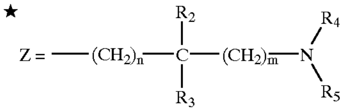

TABLE 29

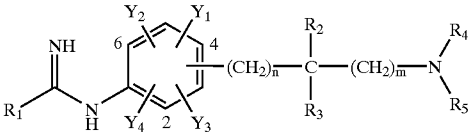

acid

| Example No. | $R_1$ | $Y_1$* | $Y_2$* | $Y_3$* | $Y_4$* | Z★ position | n | $R_2$ | $R_3$ | m | $R_4$ | $R_5$ | Acid |
|---|---|---|---|---|---|---|---|---|---|---|---|---|---|
| 53 | $NHNO_2$ | 2-H | 3-H | 5-H | 6-H | 4 | 0 | H | H | 1 | $^t$BuOCO | H | — |
| 54 | $NHNO_2$ | 2-H | 3-H | 5-H | 6-H | 4 | 0 | H | H | 1 | H | H | — |
| 59 | SMe | 2-H | 4-H | 5-H | 6-H | 3 | 0 | H | H | 1 | $^t$BuOCO | H | HI |
| 60 | SMe | 2-H | 4-H | 5-H | 6-H | 3 | 0 | H | H | 1 | H | H | HCl |
| 61 | $NHNO_2$ | 2-H | 4-H | 5-H | 6-H | 3 | 0 | H | H | 1 | $^t$BuOCO | H | — |
| 62 | $NHNO_2$ | 2-H | 4-H | 5-H | 6-H | 3 | 0 | H | H | 1 | H | H | HCl |
| 67 | SMe | 2-H | 3-H | 5-H | 6-H | 4 | 1 | COOMe | H | 0 | $^t$BuOCO | H | HI |
| 68 | SMe | 2-H | 3-H | 5-H | 6-H | 4 | 1 | COOMe | H | 0 | H | H | HCl |
| 69 | $NHNO_2$ | 2-H | 3-H | 5-H | 6-H | 4 | 1 | COOMe | H | 0 | $^t$BuOCO | H | — |
| 70 | $NHNO_2$ | 2-H | 3-H | 5-H | 6-H | 4 | 1 | COOMe | H | 0 | H | H | — |
| 74 | SMe | 2-H | 3-H | 5-H | 6-H | 4 | 1 | COO'Bu | H | 0 | $^t$BuOCO | H | HI |
| 75 | SMe | 2-H | 3-H | 5-H | 6-H | 4 | 1 | COOH | H | 0 | H | H | HCl |
| 76 | $NHNO_2$ | 2-H | 3-H | 5-H | 6-H | 4 | 1 | COO'Bu | H | 0 | $^t$BuOCO | H | — |
| 77 | $NHNO_2$ | 2-H | 3-H | 5-H | 6-H | 4 | 1 | COOH | H | 0 | H | H | HCl |
| 80 | SMe | 2-H | 3-H | 5-H | 6-H | 4 | 0 | COOMe | H | 0 | $^t$BuOCO | H | HI |

*Numeral represents the position of substitution on the benzene ring.

★

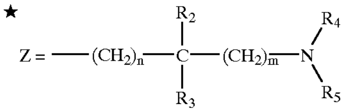

TABLE 30

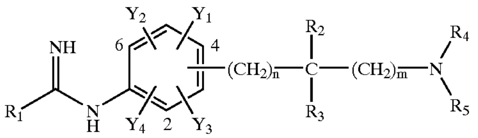

acid

| Example No. | $R_1$ | $Y_1$* | $Y_2$* | $Y_3$* | $Y_4$* | Z★ position | n | $R_2$ | $R_3$ | m | $R_4$ | $R_5$ | Acid |
|---|---|---|---|---|---|---|---|---|---|---|---|---|---|
| 81 | SMe | 2-H | 3-H | 5-H | 6-H | 4 | 0 | COOMe | H | 0 | H | H | HCl |
| 83 | NH$^c$Pr | 2-H | 3-H | 5-H | 6-H | 4 | 0 | H | H | 0 | $^t$BuOCO | H | — |
| 84 | NH$^c$Pr | 2-H | 3-H | 5-H | 6-H | 4 | 0 | H | H | 0 | H | H | — |
| 85 | $NHNO_2$ | 2-H | 3-H | 5-H | 6-H | 4 | 0 | H | H | 0 | $^t$BuOCO | H | — |
| 86 | $NHNO_2$ | 2-H | 3-H | 5-H | 6-H | 4 | 0 | H | H | 0 | H | H | — |
| 87 | NH$^c$Pr | 2-H | 4-H | 5-H | 6-H | 3 | 0 | H | H | 0 | $^t$BuOCO | H | — |
| 88 | NH$^c$Pr | 2-H | 4-H | 5-H | 6-H | 3 | 0 | H | H | 0 | H | H | — |
| 89 | $NHNO_2$ | 2-H | 4-H | 5-H | 6-H | 3 | 0 | H | H | 0 | C(=NH)NH$^c$Pr | H | — |
| 90 | $NHNO_2$ | 2-H | 4-H | 5-H | 6-H | 3 | 0 | H | H | 0 | C(=NH)$NHNO_2$ | H | — |
| 91 | S$^c$Pr | 2-H | 4-H | 5-H | 6-H | 3 | 0 | H | H | 0 | $^t$BuOCO | H | — |
| 92 | S$^c$Pr | 2-H | 4-H | 5-H | 6-H | 3 | 0 | H | H | 0 | H | H | HCl |
| 93 | S$^c$Bu | 2-H | 4-H | 5-H | 6-H | 3 | 0 | H | H | 0 | $^t$BuOCO | H | — |
| 94 | S$^c$Bu | 2-H | 4-H | 5-H | 6-H | 3 | 0 | H | H | 0 | H | H | HCl |
| 95 | SEt | 2-H | 4-H | 5-H | 6-H | 3 | 0 | Me | Me | 0 | $^t$BuOCO | H | — |
| 96 | SEt | 2-H | 4-H | 5-H | 6-H | 3 | 0 | Me | Me | 0 | H | H | HCl |

*Numeral represents the position of substitution on the benzene ring.

★

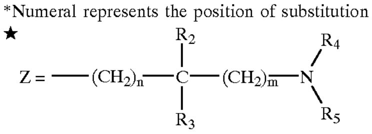

TABLE 31

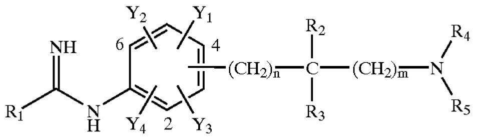

acid

| Example No. | $R_1$ | $Y_1$* | $Y_2$* | $Y_3$* | $Y_4$* | Z★ position | n | $R_2$ | $R_3$ | m | $R_4$ | $R_5$ | Acid |
|---|---|---|---|---|---|---|---|---|---|---|---|---|---|
| 99 | $NHNO_2$ | 2-H | 3-H | 5-H | 6-H | 4 | 1 | H | H | 0 | Me | Me | — |
| 101 | SMe | 2-H | 3-H | 5-H | 6-H | 4 | 1 | H | H | 0 | Me | Me | $HNO_3$, HCl |
| 102 | SEt | 2-H | 3-H | 5-H | 6-H | 4 | 1 | H | H | 0 | Me | Me | $HNO_3$, HCl |
| 103 | SEt | 2-H | 3-H | 5-H | 6-H | 4 | 1 | H | H | 0 | $^t$BuOCO | H | — |
| 104 | SEt | 2-H | 3-H | 5-H | 6-H | 4 | 1 | H | H | 0 | H | H | HCl |
| 109 | SMe | 2-H | 4-H | 5-H | 6-H | 3 | 0 | Me | H | 0 | $^t$BuOCO | Me | HI |
| 110 | SMe | 2-H | 4-H | 5-H | 6-H | 3 | 0 | Me | H | 0 | H | Me | HCl |
| 111 | SEt | 2-H | 4-H | 5-H | 6-H | 3 | 0 | Me | H | 0 | $^t$BuOCO | Me | HI |
| 112 | SEt | 2-H | 4-H | 5-H | 6-H | 3 | 0 | Me | H | 0 | H | Me | HCl |
| 113 | $NHNO_2$ | 2-H | 4-H | 5-H | 6-H | 3 | 0 | Me | H | 0 | $^t$BuOCO | Me | — |
| 114 | $NHNO_2$ | 2-H | 4-H | 5-H | 6-H | 3 | 0 | Me | H | 0 | H | Me | — |
| 115 | SMe | 2-H | 4-H | 5-H | 6-H | 3 | 0 | H | H | 0 | $^t$BuOCO | Me | HI |
| 116 | SMe | 2-H | 4-H | 5-H | 6-H | 3 | 0 | H | H | 0 | H | Me | HCl |
| 121 | SEt | 2-H | 4-OMe | 5-H | 6-H | 3 | 0 | H | H | 0 | $^t$BuOCO | H | HI |
| 122 | SEt | 2-H | 4-OMe | 5-H | 6-H | 3 | 0 | H | H | 0 | H | H | HCl |

*Numeral represents the position of substitution on the benzene ring.

★

Z = 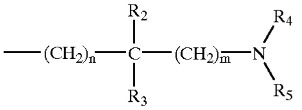

TABLE 32

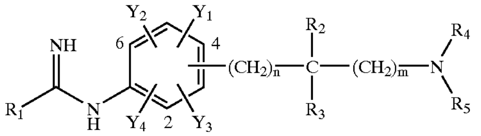

acid

| Example No. | $R_1$ | $Y_1$* | $Y_2$* | $Y_3$* | $Y_4$* | Z★ position | n | $R_2$ | $R_3$ | m | $R_4$ | $R_5$ | Acid |
|---|---|---|---|---|---|---|---|---|---|---|---|---|---|
| 126 | SEt | 2-H | 4-H | 5-H | 6-H | 3 | 0 | H | H | 0 | $CH_3CO$ | H | HI |
| 130 | SEt | 2-Me | 4-H | 5-H | 6-H | 3 | 0 | H | H | 0 | $^t$BuOCO | H | HI |
| 131 | SEt | 2-Me | 4-H | 5-H | 6-H | 3 | 0 | H | H | 0 | H | H | HCl |
| 136 | SEt | 2-Cl | 4-H | 5-H | 6-H | 3 | 0 | H | H | 0 | $^t$BuOCO | $^t$BuOCO | HI |
| 137 | SEt | 2-Cl | 4-H | 5-H | 6-H | 3 | 0 | H | H | 0 | H | H | HCl |
| 141 | SMe | 2-H | 4-H | 5-H | 6-H | 3 | 0 | $—(CH_2)_5—$ | | 0 | $^t$BuOCO | H | — |
| 142 | SMe | 2-H | 4-H | 5-H | 6-H | 3 | 0 | $—(CH_2)_5—$ | | 0 | H | H | HCl |
| 143 | SEt | 2-H | 4-H | 5-H | 6-H | 3 | 0 | $—(CH_2)_5—$ | | 0 | $^t$BuOCO | H | — |
| 144 | SEt | 2-H | 4-H | 5-H | 6-H | 3 | 0 | $—(CH_2)_5—$ | | 0 | H | H | HCl |
| 145 | S$^c$Pr | 2-H | 4-H | 5-H | 6-H | 3 | 0 | $—(CH_2)_5—$ | | 0 | $^t$BuOCO | H | — |
| 146 | S$^c$Pr | 2-H | 4-H | 5-H | 6-H | 3 | 0 | $—(CH_2)_5—$ | | 0 | H | H | HCl |
| 150 | SMe | 2-H | 4-H | 5-H | 6-H | 3 | 0 | $—(CH_2)_4—$ | | 0 | $^t$BuOCO | H | — |
| 151 | SMe | 2-H | 4-H | 5-H | 6-H | 3 | 0 | $—(CH_2)_4—$ | | 0 | H | H | HCl |
| 152 | SEt | 2-H | 4-H | 5-H | 6-H | 3 | 0 | $—(CH_2)_4—$ | | 0 | $^t$BuOCO | H | — |
| 153 | SEt | 2-H | 4-H | 5-H | 6-H | 3 | 0 | $—(CH_2)_4—$ | | 0 | H | H | HCl |

*Numeral represents the position of substitution on the benzene ring.

★

Z = 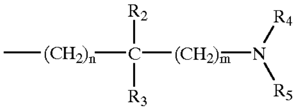

TABLE 33

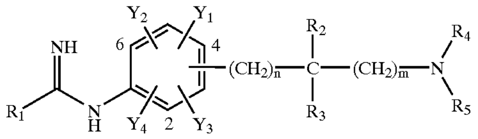

acid

| Example No. | $R_1$ | $Y_1$* | $Y_2$* | $Y_3$* | $Y_4$* | Z★ position | n | $R_2$ | $R_3$ | m | $R_4$ | $R_5$ | Acid |
|---|---|---|---|---|---|---|---|---|---|---|---|---|---|
| 154 | $S^cPr$ | 2-H | 4-H | 5-H | 6-H | 3 | 0 | $-(CH_2)_4-$ | | 0 | $^t$BuOCO | H | — |
| 155 | $S^cPr$ | 2-H | 4-H | 5-H | 6-H | 3 | 0 | $-(CH_2)_4-$ | | 0 | H | H | HCl |
| 159 | SMe | 2-H | 4-H | 5-H | 6-H | 3 | 0 | $-(CH_2)_3-$ | | 0 | $^t$BuOCO | H | — |
| 160 | SMe | 2-H | 4-H | 5-H | 6-H | 3 | 0 | $-(CH_2)_3-$ | | 0 | H | H | HCl |
| 161 | SEt | 2-H | 4-H | 5-H | 6-H | 3 | 0 | $-(CH_2)_3-$ | | 0 | $^t$BuOCO | H | — |
| 162 | SEt | 2-H | 4-H | 5-H | 6-H | 3 | 0 | $-(CH_2)_3-$ | | 0 | H | H | HCl |
| 166 | SEt | 2-H | 4-H | 5-H | 6-H | 3 | 0 | $-(CH_2)_2-$ | | 0 | $^t$BuOCO | H | — |
| 167 | SEt | 2-H | 4-H | 5-H | 6-H | 3 | 0 | $-(CH_2)_2-$ | | 0 | H | H | HCl |
| 168 | $NHNO_2$ | 2-H | 4-H | 5-H | 6-H | 3 | 0 | $-(CH_2)_3-$ | | 0 | $^t$BuOCO | H | — |
| 169 | $NHNO_2$ | 2-H | 4-H | 5-H | 6-H | 3 | 0 | $-(CH_2)_3-$ | | 0 | H | H | HCl |
| 170 | $NHNO_2$ | 2-H | 4-H | 5-H | 6-H | 3 | 0 | $-(CH_2)_4-$ | | 0 | $^t$BuOCO | H | — |
| 171 | $NHNO_2$ | 2-H | 4-H | 5-H | 6-H | 3 | 0 | $-(CH_2)_3-$ | | 0 | H | H | HCl |
| 172 | $NHNO_2$ | 2-H | 4-H | 5-H | 6-H | 3 | 0 | $-(CH_2)_3-$ | | 0 | $^t$BuOCO | H | — |
| 173 | $NHNO_2$ | 2-H | 4-H | 5-H | 6-H | 3 | 0 | $-(CH_2)_3-$ | | 0 | H | H | HCl |
| 174 | SEt | 2-H | 4-H | 5-H | 6-H | 3 | 0 | Me | H | 0 | $^t$BuOCO | H | — |

*Numeral represents the position of substitution on the benzene ring.

★

Z =

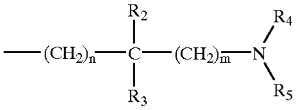

TABLE 34

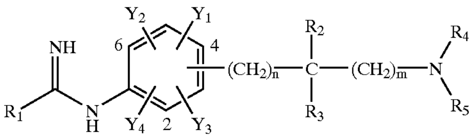

acid

| Example No. | $R_1$ | $Y_1$* | $Y_2$* | $Y_3$* | $Y_4$* | Z★ position | n | $R_2$ | $R_3$ | m | $R_4$ | $R_5$ | Acid |
|---|---|---|---|---|---|---|---|---|---|---|---|---|---|
| 175 | SEt | 2-H | 4-H | 5-H | 6-H | 3 | 0 | Me | H | 0 | H | H | HCl |
| 176 | SEt | 2-H | 4-H | 5-H | 6-H | 3 | 0 | Et | H | 0 | $^t$BuOCO | H | — |
| 177 | SEt | 2-H | 4-H | 5-H | 6-H | 3 | 0 | Et | H | 0 | H | H | HCl |
| 184 | SEt | 2-H | 3-H | 5-H | 6-H | 4 | 0 | Me | Me | 1 | $^t$BuOCO | H | — |
| 185 | SEt | 2-H | 3-H | 5-H | 6-H | 4 | 0 | Me | Me | 1 | H | H | HCl |
| 186 | $NHNO_2$ | 2-H | 3-H | 5-H | 6-H | 4 | 0 | Me | Me | 1 | $^t$BuOCO | H | — |
| 187 | $NHNO_2$ | 2-H | 3-H | 5-H | 6-H | 4 | 0 | Me | Me | 1 | H | H | HCl |
| 192 | SEt | 2-H | 3-H | 5-H | 6-H | 4 | 1 | Me | Me | 0 | $^t$BuOCO | H | — |
| 193 | SEt | 2-H | 3-H | 5-H | 6-H | 4 | 1 | Me | Me | 0 | H | H | HCl |
| 194 | $NHNO_2$ | 2-H | 3-H | 5-H | 6-H | 4 | 1 | Me | Me | 0 | $^t$BuOCO | H | — |
| 195 | $NHNO_2$ | 2-H | 3-H | 5-H | 6-H | 4 | 1 | Me | Me | 0 | H | H | HCl |
| 201 | SEt | 2-H | 4-H | 5-H | 6-OMe | 3 | 0 | H | H | 0 | $^t$BuOCO | H | HI |
| 202 | SEt | 2-H | 4-H | 5-H | 6-OMe | 3 | 0 | H | H | 0 | H | H | HCl |
| 208 | SEt | 2-H | 4-H | 5-H | 6-Cl | 3 | 0 | H | H | 0 | $^t$BuOCO | H | HI |
| 209 | SEt | 2-H | 4-H | 5-H | 6-Cl | 3 | 0 | H | H | 0 | H | H | HCl |

*Numeral represents the position of substitution on the benzene ring.

★

Z =

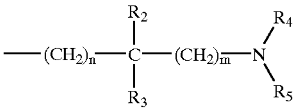

TABLE 35

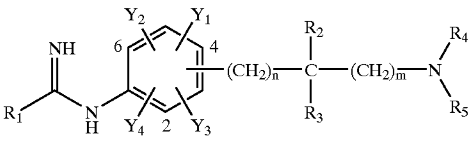

acid

| Example No. | $R_1$ | $Y_1$* | $Y_2$* | $Y_3$* | $Y_4$* | Z★ position | n | $R_2$ | $R_3$ | m | $R_4$ | $R_5$ | Acid |
|---|---|---|---|---|---|---|---|---|---|---|---|---|---|
| 211 | SMe | 2-H | 4-H | 5-H | 6-H | 3 | 0 | COOMe | H | 0 | $^t$BuOCO | H | — |
| 212 | SMe | 2-H | 4-H | 5-H | 6-H | 3 | 0 | COOMe | H | 0 | H | H | HCl |
| 216 | SMe | 2-H | 4-H | 5-H | 6-H | 3 | 1 | COOMe | H | 0 | $^t$BuOCO | H | — |
| 217 | SMe | 2-H | 4-H | 5-H | 6-H | 3 | 1 | COOMe | H | 0 | H | H | HCl |
| 220 | $NHNO_2$ | 2-H | 3-H | 5-H | 6-H | 4 | 0 | COOMe | H | 1 | $^t$BuOCO | H | — |
| 221 | $NHNO_2$ | 2-H | 3-H | 5-H | 6-H | 4 | 0 | COOMe | H | 1 | H | H | HCl |
| 222 | $NHNO_2$ | 2-H | 3-H | 5-H | 6-H | 4 | 0 | COOH | H | 1 | $^t$BuOCO | H | — |
| 223 | $NHNO_2$ | 2-H | 3-H | 5-H | 6-H | 4 | 0 | COOH | H | 1 | H | H | HCl |
| 225 | SEt | 2-H | 3-H | 5-H | 6-H | 4 | 0 | COOMe | H | 1 | $^t$BuOCO | H | — |
| 226 | SEt | 2-H | 3-H | 5-H | 6-H | 4 | 0 | COOMe | H | 1 | H | H | HCl |
| 231 | SEt | 3-H | 4-H | 5-H | 6-H | 2 | 0 | H | H | 0 | $^t$BuOCO | H | HI |
| 232 | SEt | 3-H | 4-H | 5-H | 6-H | 2 | 0 | H | H | 0 | H | H | HCl |
| 234 | NHEt | 2-H | 4-H | 5-H | 6-H | 3 | 0 | $—(CH_2)_3—$ | | 0 | H | H | HCl |
| 236 | NHEt | 2-H | 4-H | 5-H | 6-H | 3 | 0 | $—(CH_2)_4—$ | | 0 | H | H | HCl |
| 238 | NHEt | 2-H | 4-H | 5-H | 6-H | 3 | 0 | $—(CH_2)_3—$ | | 0 | H | H | HCl |

*Numeral represents the position of substitution on the benzene ring.

★

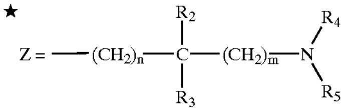

TABLE 36

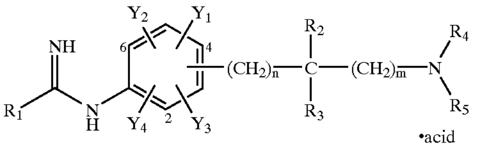

•acid

| Example No. | $R_1$ | $Y_1$* | $Y_2$* | $Y_3$* | $Y_4$* | Z★ position | n | $R_2$ | $R_3$ | m | $R_4$ | $R_5$ | Acid |
|---|---|---|---|---|---|---|---|---|---|---|---|---|---|
| 244 | SEt | 2-H | 4-H | $5-CF_3$ | 6-H | 3 | 0 | H | H | 0 | $^1$BuOCO | $^1$BuOCO | — |
| 245 | SEt | 2-H | 4-H | $5-CF_3$ | 6-H | 3 | 0 | H | H | 0 | H | H | HCl |
| 246 | $NHNO_2$ | 2-H | 4-H | $5-CF_3$ | 6-H | 3 | 0 | H | H | 0 | $^1$ BuOCO | $^1$BuOCO | — |
| 247 | $NHNO_2$ | 2-H | 4-H | $5-CF_3$ | 6-H | 3 | 0 | H | H | 0 | H | H | HCl |
| 255 | SEt | 2-H | 3-F | 5-H | 6-H | 4 | 1 | H | H | 0 | $^1$BuOCO | H | — |
| 256 | SEt | 2-H | 3-F | 5-H | 6-H | 4 | 1 | H | H | 0 | H | H | HCl |
| 258 | NHEt | 2-H | 3-F | 5-H | 6-H | 4 | 1 | H | H | 0 | H | H | HCl |
| 259 | $NHNO_2$ | 2-H | 3-F | 5-H | 6-H | 4 | 1 | H | H | 0 | $^1$BuOCO | H | — |
| 260 | $NHNO_2$ | 2-H | 3-F | 5-H | 6-H | 4 | 1 | H | H | 0 | H | H | HCl |
| 267 | NHEt | 2-H | $4-NMe_2$ | 5-H | 6-H | 3 | 0 | H | H | 0 | H | H | HCl |
| 269 | SEt | 2-H | $4-NMe_2$ | 5-H | 6-H | 3 | 0 | H | H | 0 | $^1$BuOCO | $^1$BuOCO | — |
| 270 | SEt | 2-H | $4-NMe_2$ | 5-H | 6-H | 3 | 0 | H | H | 0 | H | H | HCl |
| 271 | $NHNO_2$ | 2-H | 4-OMe | 5-H | 6-H | 3 | 0 | H | H | 0 | $^1$BuOCO | H | — |
| 272 | $NHNO_2$ | 2-H | 4-OMe | 5-H | 6-H | 3 | 0 | H | H | 0 | H | H | HCl |
| 274 | NHEt | 2-H | 4-OMe | 5-H | 6-H | 3 | 0 | H | H | 0 | H | H | HCl |

*: Numeral represents the position of substitution on the benzene ring.

★:

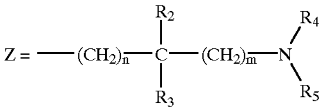

TABLE 37

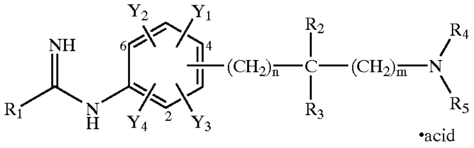

| Example No. | $R_1$ | $Y_1$* | $Y_2$* | $Y_3$* | $Y_4$* | Z★ position | n | $R_2$ | $R_3$ | m | $R_4$ | $R_5$ | Acid |
|---|---|---|---|---|---|---|---|---|---|---|---|---|---|
| 275 | NHMe | 2-H | 4-OMe | 5-H | 6-H | 3 | 0 | H | H | 0 | $^{1}$BuOCO | H | — |
| 276 | NHMe | 2-H | 4-OMe | 5-H | 6-H | 3 | 0 | H | H | 0 | H | H | HCl |
| 278 | NH*Pr | 2-H | 4-OMe | 5-H | 6-H | 3 | 0 | H | H | 0 | $^{1}$BuOCO | H | — |
| 279 | NH*Pr | 2-H | 4-OMe | 5-H | 6-H | 3 | 0 | H | H | 0 | H | H | HCl |
| 280 | $NHNO_3$ | 2-H | 4-$NMe_3$ | 5-H | 6-H | 3 | 0 | H | H | 0 | $^{1}$BuOCO | $^{1}$BuOCO | — |
| 281 | $NHNO_3$ | 2-H | 4-$NMe_3$ | 5-H | 6-H | 3 | 0 | H | n | 0 | H | H | HCl |
| 285 | NHEt | 2-H | 4-NMeEt | 5-H | 6-H | 3 | 0 | H | H | 0 | H | H | HCl |
| 287 | SEt | 2-H | 4-NMeEt | 5-H | 6-H | 3 | 0 | H | H | 0 | $^{1}$BuOCO | $^{1}$BuOCO | — |
| 288 | SEt | 2-H | 4-NMeEt | 5-H | 6-H | 3 | 0 | H | H | 0 | H | H | HCl |
| 291 | NHOMe | 2-H | 3-H | 5-H | 6-H | 4 | 1 | H | H | 0 | H | H | HCl |
| 297 | SEt | 2-OMe | 4-OMe | 5-H | 6-H | 3 | 0 | H | H | 0 | $^{1}$BuOCO | $^{1}$BuOCO | — |
| 298 | SEt | 2-OMe | 4-OMe | 5-H | 6-H | 3 | 0 | H | H | 0 | H | H | HCl |
| 300 | NHEt | 2-H | 4-H | 5-H | 6-H | 3 | 0 | Me | Me | 0 | H | H | HCl |
| 302 | $NMe_2$ | 2-H | 4-H | 5-H | 6-H | 3 | 0 | H | H | 0 | $^{1}$BuOCO | $^{1}$BuOCO | — |
| 303 | $NMe_2$ | 2-H | 4-H | 5-H | 6-H | 3 | 0 | H | H | 0 | H | H | HCl |

*: Numeral represents the position of substitution on the benzene ring.

★: Z =

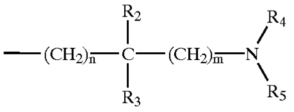

TABLE 38

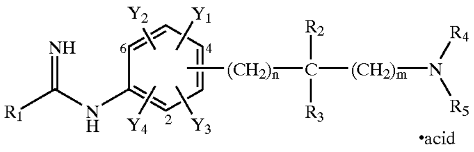

| Example No. | $R_1$ | $Y_1$* | $Y_2$* | $Y_3$* | $Y_4$* | Z★ position | n | $R_2$ | $R_3$ | m | $R_4$ | $R_5$ | Acid |
|---|---|---|---|---|---|---|---|---|---|---|---|---|---|
| 304 | NMeEt | 2-H | 4-H | 5-H | 6-H | 3 | 0 | H | H | 0 | $^{1}$BuOCO | $^{1}$BuOCO | — |
| 305 | NMeEt | 2-H | 4-H | 5-H | 6-H | 3 | 0 | H | H | 0 | H | H | HCl |
| 306 | $NHCH_2C{\equiv}CH$ | 2-H | 4-H | 5-H | 6-H | 3 | 0 | H | H | 0 | $^{1}$BuOCO | $^{1}$BuOCO | — |
| 307 | $NHCH_2C{\equiv}CH$ | 2-H | 4-H | 5-H | 6-H | 3 | 0 | H | H | 0 | H | H | HCl |
| 312 | SEt | 3-H | 4-H | 5-H | 6-H | 2 | 1 | H | H | 0 | $^{1}$BuOCO | H | — |
| 313 | SEt | 3-H | 4-H | 5-H | 6-H | 2 | 1 | H | H | 0 | H | H | HCl |
| 316 | SEt | 2-H | 4-F | 5-H | 6-H | 3 | 0 | H | H | 0 | $^{1}$BuOCO | H | — |
| 317 | SEt | 2-H | 4-F | 5-H | 6-H | 3 | 0 | H | H | 0 | H | H | HCl |
| 323 | SEt | 2-H | 4-OEt | 5-H | 6-H | 3 | 0 | H | H | 0 | $^{1}$BuOCO | H | HI |
| 324 | SEt | 2-H | 4-OEt | 5-H | 6-H | 3 | 0 | H | H | 0 | H | H | HCl |
| 326 | NHEt | 2-H | 4-OEt | 5-H | 6-H | 3 | 0 | H | H | 0 | H | H | HCl |
| 327 | $NHNO_3$ | 2-H | 4-OEt | 5-H | 6-H | 3 | 0 | H | H | 0 | $^{1}$BuOCO | H | — |
| 328 | $NHNO_3$ | 2-H | 4-OEt | 5-H | 6-H | 3 | 0 | H | H | 0 | H | H | HCl |
| 336 | SEt | 2-H | 4-OBn | 5-H | 6-H | 3 | 0 | H | H | 0 | $^{1}$BuOCO | H | — |
| 337 | SEt | 2-H | 4-OBn | 5-H | 6-H | 3 | 0 | H | H | 0 | H | H | HCl |

*: Numeral represents the position of substitution on the benzene ring.

★: Z =

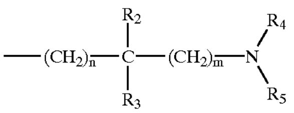

TABLE 39

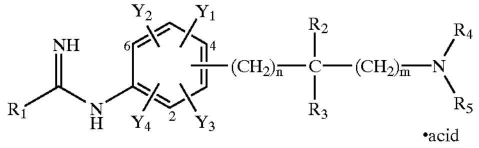

| Example No. | $R_1$ | $Y_1$* | $Y_2$* | $Y_3$* | $Y_4$* | Z★ position | n | $R_2$ | $R_3$ | m | $R_4$ | $R_5$ | Acid |
|---|---|---|---|---|---|---|---|---|---|---|---|---|---|
| 339 | NHEt | 2-H | 4-OBn | 5-H | 6-H | 3 | 0 | H | H | 0 | H | H | HCl |
| 340 | $NHNO_2$ | 2-H | 4-OBn | 5-H | 6-H | 3 | 0 | H | H | 0 | $^{1}$BuOCO | H | — |
| 341 | $NHNO_2$ | 2-H | 4-OBn | 5-H | 6-H | 3 | 0 | H | H | 0 | H | H | HCl |
| 342 | SEt | 2-H | 4-OMe | 5-H | 6-H | 3 | 0 | Me | Me | 0 | $^{1}$BuOCO | H | HI |
| 350 | SEt | 2-H | 4-OMe | 5-H | 6-H | 3 | 0 | Me | Me | 0 | H | H | HCl |
| 354 | SEt | 2-H | 4-H | 5-H | 6-H | 3 | 0 | H | H | 0 | $^{1}$BuOCO | $^{1}$BuOCONH | HI |
| 355 | SEt | 2-H | 4-H | 5-H | 6-H | 3 | 0 | H | H | 0 | H | $NH_2$ | HCl |
| 356 | $NHNO_2$ | 2-H | 4-H | 5-H | 6-H | 3 | 0 | H | H | 0 | $^{1}$BuOCO | $^{1}$BuOCONH | — |
| 357 | $NHNO_2$ | 2-H | 4-H | 5-H | 6-H | 3 | 0 | H | H | 0 | H | $NH_2$ | HCl |
| 360 | $NHNO_2$ | 2-H | 3-H | 5-H | 6-H | 4 | 1 | H | H | 1 | $^{1}$BuOCO | H | — |
| 361 | $NHNO_2$ | 2-H | 3-H | 5-H | 6-H | 4 | 1 | H | H | 1 | H | H | HCl |
| 365 | SMe | 2-H | 4-H | 5-H | 6-H | 3 | 0 | H | H | 0 | $^{1}$BuOCO | $^{1}$BuOCO | HI |
| 366 | NHMe | 2-H | 4-H | 5-H | 6-H | 3 | 0 | H | H | 0 | $^{1}$BuOCO | $^{1}$BuOCO | — |
| 367 | NHMe | 2-H | 4-H | 5-H | 6-H | 3 | 0 | H | H | 0 | H | H | HCl |
| 368 | NHEt | 2-H | 4-H | 5-H | 6-H | 3 | 0 | H | H | 0 | $^{1}$BuOCO | $^{1}$BuOCO | — |

*: Numeral represents the position of substitution on the benzene ring.

★: Z = 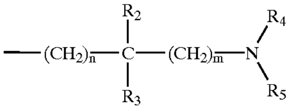

TABLE 40

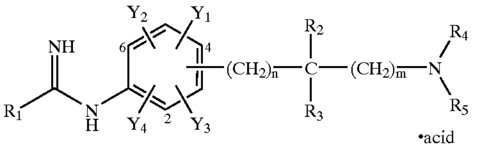

| Example No. | $R_1$ | $Y_1$* | $Y_2$* | $Y_3$* | $Y_4$* | Z★ position | n | $R_2$ | $R_3$ | m | $R_4$ | $R_5$ | Acid |
|---|---|---|---|---|---|---|---|---|---|---|---|---|---|
| 369 | NHEt | 2-H | 4-H | 5-H | 6-H | 3 | 0 | H | H | 0 | H | H | HCl |
| 370 | NH*Pr | 2-H | 4-H | 5-H | 6-H | 3 | 0 | H | H | 0 | $^{1}$BuOCO | $^{1}$BuOCO | — |
| 371 | NH*Pr | 2-H | 4-H | 5-H | 6-H | 3 | 0 | H | H | 0 | H | H | HCl |
| 372 | SEt | 2-H | 4-H | 5-H | 6-H | 3 | 0 | H | H | 0 | Me | Me | — |
| 374 | NHEt | 2-H | 4-H | 5-H | 6-H | 3 | 0 | H | H | 0 | Me | Me | HCl |
| 376 | NHEt | 2-H | 4-H | 5-H | 6-H | 3 | 0 | H | H | 0 | Me | H | HCl |
| 380 | SEt | 2-H | 4-H | 5-H | 6-H | 3 | 0 | H | H | 0 | Bn | Me | HCl |
| 382 | NHEt | 2-H | 4-H | 5-H | 6-H | 3 | 0 | H | H | 0 | Bn | Me | HCl |
| 387 | SEt | 2-H | 4-H | 5-H | 6-H | 3 | 0 | H | H | 0 | $^{1}$BuOCO | Et | HI |
| 388 | SEt | 2-H | 4-H | 5-H | 6-H | 3 | 0 | H | H | 0 | H | Et | HCl |
| 392 | NHEt | 2-H | 4-OMe | 5-H | 6-H | 3 | 0 | H | H | 0 | Me | H | HCl |
| 394 | SEt | 2-H | 4-OMe | 5-H | 6-H | 3 | 0 | H | H | 0 | $^{1}$BuOCO | Me | HI |
| 395 | SEt | 2-H | 4-OMe | 5-H | 6-H | 3 | 0 | H | H | 0 | H | Me | HCl |
| 399 | NHEt | 2-H | 4-OMe | 5-H | 6-H | 3 | 0 | H | H | 0 | Me | Me | HCl |
| 401 | SEt | 2-H | 4-OMe | 5-H | 6-H | 3 | 0 | H | H | 0 | Me | Me | HCl |

*: Numeral represents the position of substitution on the benzene ring.

★: Z = 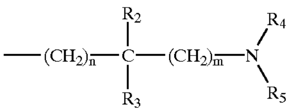

TABLE 41

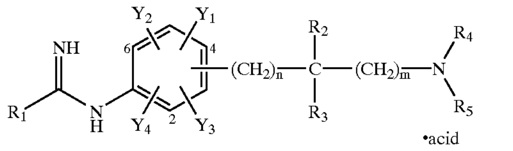

| Example No. | $R_1$ | $Y_1$* | $Y_2$* | $Y_3$* | $Y_4$* | Z★ position | n | $R_2$ | $R_3$ | m | $R_4$ | $R_5$ | Acid |
|---|---|---|---|---|---|---|---|---|---|---|---|---|---|
| 405 | SEt | 2-H | 4-H | 5-H | 6-H | 3 | 0 | H | H | 0 | $^{1}$BuOCO | Bn | HI |
| 406 | SEt | 2-H | 4-H | 5-H | 6-H | 3 | 0 | H | H | 0 | H | Bn | HCl |
| 410 | SEt | 2-Me | 4-H | 5-H | 6-H | 3 | 0 | H | H | 0 | $^{1}$BuOCO | Me | HI |
| 411 | SEt | 2-Me | 4-H | 5-H | 6-H | 3 | 0 | H | H | 0 | H | Me | HCl |
| 413 | NHEt | 2-Me | 4-H | 5-H | 6-H | 3 | 0 | H | H | 0 | H | Me | HCl |
| 415 | SEt | 2-Me | 4-H | 5-H | 6-H | 3 | 0 | H | H | 0 | Me | Me | HCl |
| 417 | NHEt | 2-Me | 4-H | 5-H | 6-H | 3 | 0 | H | H | 0 | Me | Me | HCl |
| 423 | SEt | 2-OMe | 4-H | 5-H | 6-H | 3 | 0 | H | H | 0 | $^{1}$BuOCO | H | — |
| 424 | SEt | 2-OMe | 4-H | 5-H | 6-H | 3 | 0 | H | H | 0 | H | H | HCl |
| 426 | NHEt | 2-OMe | 4-H | 5-H | 6-H | 3 | 0 | H | H | 0 | H | H | HCl |
| 430 | SEt | 2-H | 4-H | 5-Me | 6-H | 3 | 0 | H | H | 0 | $^{1}$BuOCO | H | — |
| 431 | SEt | 2-H | 4-H | 5-Me | 6-H | 3 | 0 | H | H | 0 | H | H | HCl |
| 433 | NHEt | 2-H | 4-H | 5-Me | 6-H | 3 | 0 | H | H | 0 | H | H | HCl |
| 437 | SEt | 2-H | 4-NHBn | 5-H | 6-H | 3 | 0 | H | H | 0 | $^{1}$BuOCO | H | — |
| 438 | SEt | 2-H | 4-NHBn | 5-H | 6-H | 3 | 0 | H | H | 0 | H | H | HCl |

*: Numeral represents the position of substitution on the benzene ring.

★: Z =

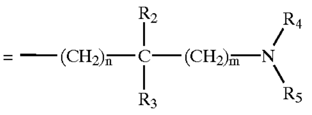

TABLE 42

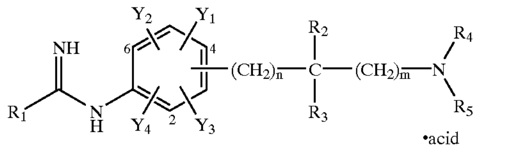

| Example No. | $R_1$ | $Y_1$* | $Y_2$* | $Y_3$* | $Y_4$* | Z★ position | n | $R_2$ | $R_3$ | m | $R_4$ | $R_5$ | Acid |
|---|---|---|---|---|---|---|---|---|---|---|---|---|---|
| 440 | NHEt | 2-H | 4-NHBn | 5-H | 6-H | 3 | 0 | H | H | 0 | H | H | HCl |
| 442 | NHEt | 3-H | 4-H | 5-H | 6-H | 2 | 1 | H | H | 0 | $^{1}$BuOCO | H | — |
| 443 | NHEt | 3-H | 3-H | 5-H | 6-H | 2 | 1 | H | H | 0 | H | H | HCl |
| 445 | NHEt | 2-H | 4-F | 5-H | 6-H | 3 | 0 | H | H | 0 | H | H | HCl |
| 449 | NHEt | 2-H | 4-NHMe | 5-H | 6-H | 3 | 0 | H | H | 0 | H | H | HCl |
| 451 | SEt | 2-H | 4-NHMe | 5-H | 6-H | 3 | 0 | H | H | 0 | $^{1}$BuOCO | $^{1}$BuOCO | — |
| 452 | SEt | 2-H | 4-NHMe | 5-H | 6-H | 3 | 0 | H | H | 0 | H | H | HCl |
| 456 | NHEt | 2-H | 4-NHEt | 5-H | 6-H | 3 | 0 | H | H | 0 | H | H | HCl |
| 458 | SEt | 2-H | 4-NHEt | 5-H | 6-H | 3 | 0 | H | H | 0 | $^{1}$BuOCO | $^{1}$BuOCO | — |
| 459 | SEt | 2-H | 4-NHEt | 5-H | 6-H | 3 | 0 | H | H | 0 | H | H | HCl |
| 463 | SEt | 2-H | 4-Et | 5-H | 6-H | 3 | 0 | H | H | 0 | $^{1}$BuOCO | $^{1}$BuOCO | — |
| 464 | SEt | 2-H | 4-Et | 5-H | 6-H | 3 | 0 | H | H | 0 | H | H | HCl |
| 466 | NHEt | 2-H | 4-Et | 5-H | 6-H | 3 | 0 | H | H | 0 | H | H | HCl |
| 470 | SEt | 2-H | 4-Me | 5-H | 6-H | 3 | 0 | H | H | 0 | $^{1}$BuOCO | $^{1}$BuOCO | — |
| 471 | SEt | 2-H | 4-Me | 5-H | 6-H | 3 | 0 | H | H | 0 | H | H | HCl |

*: Numeral represents the position of substitution on the benzene ring.

★: Z =

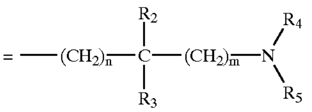

TABLE 43

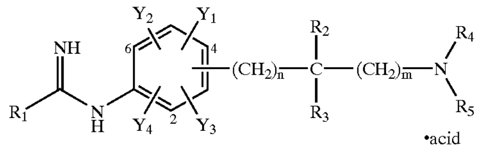

| Example No. | $R_1$ | $Y_1$* | $Y_2$* | $Y_3$* | $Y_4$* | Z★ position | n | $R_2$ | $R_3$ | m | $R_4$ | $R_5$ | Acid |
|---|---|---|---|---|---|---|---|---|---|---|---|---|---|
| 473 | NHEt | 2-H | 4-Me | 5-H | 6-H | 3 | 0 | H | H | 0 | H | H | HCl |
| 481 | SEt | 2-H | 3-OMe | 5-H | 6-H | 4 | 1 | H | H | 0 | $^{1}$BuOCO | H | — |
| 482 | SEt | 2-H | 3-OMe | 5-H | 6-H | 4 | 1 | H | H | 0 | H | H | HCl |
| 484 | NHEt | 2-H | 3-OMe | 5-H | 6-H | 4 | 1 | H | H | 0 | H | H | HCl |
| 492 | SEt | 2-OMe | 3-H | 5-H | 6-H | 4 | 1 | H | H | 0 | $^{1}$BuOCO | H | — |
| 493 | SEt | 2-OMe | 3-H | 5-H | 6-H | 4 | 1 | H | H | 0 | H | H | HCl |
| 497 | SEt | 2-Cl | 3-H | 5-H | 6-H | 4 | 1 | H | H | 0 | $^{1}$BuOCO | H | — |
| 498 | SEt | 2-Cl | 3-H | 5-H | 6-H | 4 | 1 | H | H | 0 | H | H | HCl |
| 506 | SEt | 2-F | 3-H | 5-H | 6-H | 4 | 1 | H | H | 0 | $^{1}$BuOCO | H | |
| 507 | SEt | 2-F | 3-H | 5-H | 6-H | 4 | 1 | H | H | 0 | H | H | HCl |
| 512 | SEt | 3-H | 4-OMe | 5-H | 6-H | 2 | 1 | H | H | 0 | $^{1}$BuOCO | H | — |
| 513 | SEt | 3-H | 4-OMe | 5-H | 6-H | 2 | 1 | H | H | 0 | H | H | HCl |
| 514 | $NHNO_2$ | 3-H | 4-OMe | 5-H | 6-H | 2 | 1 | H | H | 0 | $^{1}$BuOCO | H | — |
| 515 | $NHNO_2$ | 3-H | 4-OMe | 5-H | 6-H | 2 | 1 | H | H | 0 | H | H | HCl |
| 517 | NHEt | 3-H | 4-OMe | 5-H | 6-H | 2 | 1 | H | H | 0 | H | H | HCl |

*: Numeral represents the position of substitution on the benzene ring.

★: Z =

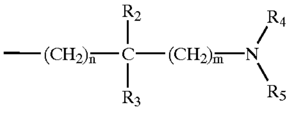

TABLE 44

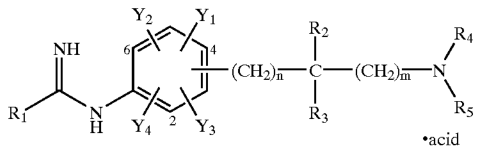

| Example No. | $R_1$ | $Y_1$* | $Y_2$* | $Y_3$* | $Y_4$* | Z★ position | n | $R_2$ | $R_3$ | m | $R_4$ | $R_5$ | Acid |
|---|---|---|---|---|---|---|---|---|---|---|---|---|---|
| 525 | SEt | 2-Me | 3-H | 5-H | 6-H | 4 | 1 | H | H | 0 | $^{1}$BuOCO | H | — |
| 526 | SEt | 2-Me | 3-H | 5-H | 6-H | 4 | 1 | H | H | 0 | H | H | HCl |
| 528 | NHEt | 2-H | 3-H | 5-H | 6-H | 4 | 1 | H | H | 0 | H | H | HCl |
| 532 | NHEt | 2-Me | 4-H | 5-H | 6-H | 3 | 0 | H | H | 0 | $^{1}$BuOCO | $^{1}$BuOCO | — |
| 533 | NHEt | 2-Me | 4-H | 5-H | 6-H | 3 | 0 | H | H | 0 | H | H | HCl |
| 534 | NMeEt | 2-Me | 4-H | 5-H | 6-H | 3 | 0 | H | H | 0 | $^{1}$BuOCO | $^{1}$BuOCO | — |
| 535 | NMeEt | 2-Me | 4-H | 5-H | 6-H | 3 | 0 | H | H | 0 | H | H | HCl |
| 537 | NMeEt | 2-Cl | 4-H | 5-H | 6-H | 3 | 0 | H | H | 0 | $^{1}$BuOCO | $^{1}$BuOCO | — |
| 538 | NHEt | 2-Cl | 4-H | 5-H | 6-H | 3 | 0 | H | H | 0 | H | H | HCl |
| 539 | NMeEt | 2-Cl | 4-H | 5-H | 6-H | 3 | 0 | H | H | 0 | $^{1}$BuOCO | $^{1}$BuOCO | — |
| 540 | NMeEt | 2-Cl | 4-H | 5-H | 6-H | 3 | 0 | H | H | 0 | H | H | HCl |
| 542 | NHEt | 2-H | 4-H | 5-H | 6-H | 3 | 1 | H | H | 0 | $^{1}$BuOCO | H | — |
| 543 | NHEt | 2-H | 4-H | 5-H | 6-H | 3 | 1 | H | H | 0 | H | H | HCl |
| 544 | NMeEt | 2-H | 4-H | 5-H | 6-H | 3 | 1 | H | H | 0 | $^{1}$BuOCO | H | — |
| 545 | NMeEt | 2-H | 4-H | 5-H | 6-H | 3 | 1 | H | H | 0 | H | H | HCl |

*: Numeral represents the position of substitution on the benzene ring.

★: Z =

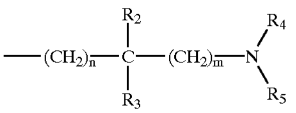

TABLE 45

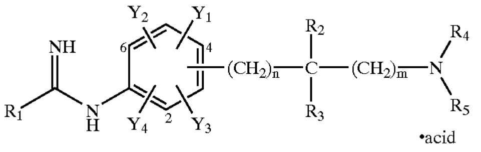

| Example No. | $R_1$ | $Y_1$* | $Y_2$* | $Y_3$* | $Y_4$* | Z★ position | n | $R_2$ | $R_3$ | m | $R_4$ | $R_5$ | Acid |
|---|---|---|---|---|---|---|---|---|---|---|---|---|---|
| 549 | SEt | 2-H | 4-pipelidino | 5-H | 6-H | 3 | 0 | H | H | 0 | $^1$BuOCO | $^1$BuOCO | — |
| 550 | SEt | 2-H | 4-pipelidino | 5-H | 6-H | 3 | 0 | H | H | 0 | H | H | HCl |
| 552 | NHEt | 2-H | 4-pipelidino | 5-H | 6-H | 3 | 0 | H | H | 0 | $^1$BuOCO | $^1$BuOCO | — |
| 553 | NHEt | 2-H | 4-pipelidino | 5-H | 6-H | 3 | 0 | H | H | 0 | H | H | HCl |
| 557 | SEt | 2-H | 4-Cl | 5-H | 6-H | 3 | 0 | H | H | 0 | $^1$BuOCO | H | — |
| 558 | SEt | 2-H | 4-Cl | 5-H | 6-H | 3 | 0 | H | H | 0 | H | H | HCl |
| 560 | NHEt | 2-H | 4-Cl | 5-H | 6-H | 3 | 0 | H | H | 0 | H | H | HCl |
| 567 | $NHNO_2$ | 2-H | 4-OBn | 5-H | 6-H | 3 | 0 | Me | Me | 0 | $^1$BuOCO | H | — |
| 568 | $NHNO_2$ | 2-H | 4-OBn | 5-H | 6-H | 3 | 0 | Me | Me | 0 | H | H | — |
| 570 | NHEt | 2-H | 4-OBn | 5-H | 6-H | 3 | 0 | Me | Me | 0 | H | H | — |
| 572 | SEt | 2-H | 4-OBn | 5-H | 6-H | 3 | 0 | Me | Me | 0 | $^1$BuOCO | H | — |
| 573 | SEt | 2-H | 4-OBn | 5-H | 6-H | 3 | 0 | Me | Me | 0 | H | H | — |
| 580 | NHEt | 2-OBn | 4-H | 5-H | 6-H | 3 | 0 | Me | Me | 0 | H | H | — |
| 582 | SEt | 2-OBn | 4-H | 5-H | 6-H | 3 | 0 | Me | Me | 0 | $^1$BuOCO | H | — |
| 583 | SEt | 2-OBn | 4-H | 5-H | 6-H | 3 | 0 | Me | Me | 0 | H | H | — |

*: Numeral represents the position of substitution on the benzene ring.

★: Z =

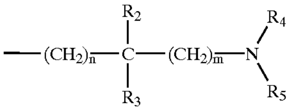

TABLE 46

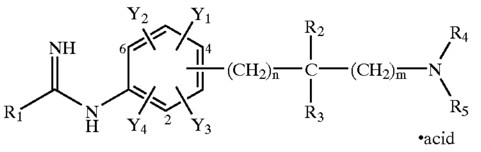

| Example No. | $R_1$ | $Y_1$* | $Y_2$* | $Y_3$* | $Y_4$* | Z★ position | n | $R_2$ | $R_3$ | m | $R_4$ | $R_5$ | Acid |
|---|---|---|---|---|---|---|---|---|---|---|---|---|---|
| 587 | SEt | 2-H | 4-pyrrolidinyl | 5-H | 6-H | 3 | 0 | H | H | 0 | $^1$BuOCO | $^1$BuOCO | — |
| 588 | SEt | 2-H | 4-pyrrolidinyl | 5-H | 6-H | 3 | 0 | H | H | 0 | H | H | HCl |
| 590 | NHEt | 2-H | 4-pyrrolidinyl | 5-H | 6-H | 3 | 0 | H | H | 0 | H | H | HCl |
| 592 | NHEt | 2-OMe | 3-H | 5-H | 6-H | 4 | 1 | H | H | 0 | H | H | HCl |
| 594 | NHEt | 2-Cl | 3-H | 5-H | 6-H | 4 | 1 | H | H | 0 | H | H | HCl |
| 596 | NHEt | 2-F | 3-H | 5-H | 6-H | 4 | 1 | H | H | 0 | H | H | HCl |
| 598 | NHEt | 2-H | 4-H | 5-H | 6-H | 3 | 0 | Me | H | 0 | H | H | HCl |
| 600 | NHEt | 2-Me | 3-H | 5-H | 6-H | 4 | 1 | H | H | 0 | H | H | HCl |
| 607 | SEt | 2-H | 3-Cl | 5-H | 6-H | 4 | 1 | H | H | 0 | $^1$BuOCO | H | — |
| 608 | SEt | 2-H | 3-Cl | 5-H | 6-H | 4 | 1 | H | H | 0 | H | H | HCl |
| 610 | NHEt | 2-H | 3-Cl | 5-H | 6-H | 4 | 1 | H | H | 0 | H | H | HCl |
| 614 | SEt | 2-H | 4-NMeBn | 5-H | 6-H | 3 | 0 | H | H | 0 | H | H | HCl |
| 616 | NHEt | 2-H | 4-NMeBn | 5-H | 6-H | 3 | 0 | H | H | 0 | H | H | HCl |
| 621 | SEt | 2-Me | 4-H | 5-H | 6-H | 3 | 0 | Me | H | 0 | $^1$BuOCO | H | — |
| 622 | SEt | 2-Me | 4-H | 5-H | 6-H | 3 | 0 | Me | H | 0 | H | H | HCl |

*: Numeral represents the position of substitution on the benzene ring.

★: Z =

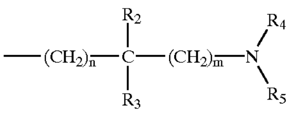

TABLE 47

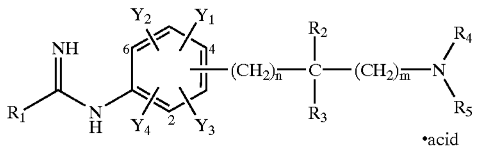

| Example No. | $R_1$ | $Y_1$* | $Y_2$* | $Y_3$* | $Y_4$* | Z★ position | n | $R_2$ | $R_3$ | m | $R_4$ | $R_5$ | Acid |
|---|---|---|---|---|---|---|---|---|---|---|---|---|---|
| 624 | NHEt | 2-Me | 4-H | 5-H | 6-H | 3 | 0 | Me | H | 0 | H | H | HCl |
| 626 | SEt | 2-H | 3-H | 5-H | 6-H | 4 | 0 | H | H | 0 | PhCO | H | — |
| 628 | NHEt | 2-H | 3-H | 5-H | 6-H | 4 | 0 | H | H | 0 | PhCO | H | — |
| 631 | SEt | 2-H | 4-H | 5-H | 6-H | 3 | 0 | H | H | 0 | PhCO | H | — |
| 633 | NHEt | 2-H | 4-H | 5-H | 6-H | 3 | 0 | H | H | 0 | PhCO | H | HCl |
| 638 | SEt | 2-H | 4-OMe | 5-H | 6-H | 3 | 0 | Me | H | 0 | $^{1}$BuOCO | H | — |
| 639 | SEt | 2-H | 4-OMe | 5-H | 6-H | 3 | 0 | Me | H | 0 | H | H | HCl |
| 641 | NHEt | 2-H | 4-OMe | 5-H | 6-H | 3 | 0 | Me | H | 0 | H | H | HCl |
| 645 | SEt | 2-H | 4-NMeAc | 5-H | 6-H | 3 | 0 | H | H | 0 | $^{1}$BuOCO | $^{1}$BuOCO | — |
| 646 | SEt | 2-H | 4-NMeAc | 5-H | 6-H | 3 | 0 | H | H | 0 | H | H | HCl |
| 648 | NHEt | 2-H | 4-NMeAc | 5-H | 6-H | 3 | 0 | H | H | 0 | H | H | HCl |
| 654 | NHEt | 2-$NMe_2$ | 4-H | 5-H | 6-H | 3 | 0 | H | H | 0 | H | H | HCl |
| 656 | NHEt | 2-H | 4-OH | 5-H | 6-H | 3 | 0 | H | H | 0 | H | H | HCl |
| 657 | SEt | 2-H | 4-NHAc | 5-H | 6-H | 3 | 0 | H | H | 0 | H | H | — |
| 658 | NHEt | 2-H | 4-NHAc | 5-H | 6-H | 3 | 0 | H | H | 0 | H | H | — |

*: Numeral represents the position of substitution on the benzene ring.

★: Z =

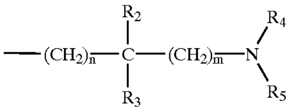

TABLE 48

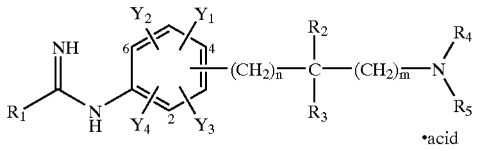

| Example No. | $R_1$ | $Y_2$* | $Y_2$* | $Y_3$* | $Y_4$* | Z★ position | n | $R_2$ | $R_3$ | m | $R_4$ | $R_5$ | Acid |
|---|---|---|---|---|---|---|---|---|---|---|---|---|---|
| 659 | SEt | 2-H | 4-NHBz | 5-H | 6-H | 3 | 0 | H | H | 0 | H | H | — |
| 660 | NHEt | 2-H | 4-NHBz | 5-H | 6-H | 3 | 0 | H | H | 0 | H | H | — |
| 661 | SEt | 3-H | 4-NMeBz | 5-H | 6-H | 3 | 0 | H | H | 0 | H | H | — |
| 662 | NHEt | 3-H | 4-NMeBz | 5-H | 6-H | 3 | 0 | H | H | 0 | H | H | — |
| 663 | SEt | 2-F | 4-H | 5-H | 6-H | 3 | 0 | H | H | 0 | H | H | — |
| 664 | NHEt | 2-F | 4-H | 5-H | 6-H | 3 | 0 | H | H | 0 | H | H | — |

*: Numeral represents the position of substitution on the benzene ring.

★: Z =

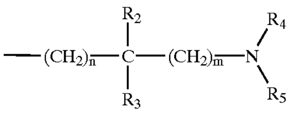

Example 1

Synthesis of N-(1-methyl-1-(3-nitrophenyl)ethyl) carbamic acid t-butyl ester

Example 1a

A solution of 3-nitrophenylacetic acid t-butyl ester (1.56 g) in dimethylformamide (30 ml) was added dropwise to a mixture of sodium hydride (content=60%; 631 mg) and dimethylformamide (45 ml) at 0° C. After the reaction mixture was stirred for 10 min, methyl iodide (2 eq., 0.9 ml) was added dropwise at 0 ° C., and stirred for 30 min and stirred for 16 h at room temperature. The reaction mixture was concentrated under reduced pressure and water was added to the resulting residue and the mixture was extracted with ethyl acetate. The organic layer was washed with a saturated aqueous sodium chloride solution, dried with anhydrous sodium sulfate and concentrated under reduced pressure. The resulting residue was purified by silica gel column chromatography (eluent, n-hexane:ethyl acetate=

97:3) to give 367 mg of 2-methyl-2-(3-nitrophenyl) propionic acid t-butyl ester (yield, 28%).

$^1$H-NMR($CDCl_3$) δ: 1.39(9H,s), 1.59(6H,s), 7.46–7.69 (2H,m), 8.08–8.25(2H,m)

Example 1b

A mixture of the dimethyl compound (1.1 g) obtained in the above reaction and trifluoroacetic acid (25 ml) was stirred at room temperature for 2 h. The reaction mixture was concentrated under reduced pressure and the resulting residue was purified by silica gel column chromatography (eluent, n-hexane:ethyl acetate=4:6) to give 0.87 g of 2-methyl-2-(3-nitrophenyl)propionic acid quantitatively. $^1$H-NMR($CDCl_3$) δ: 1.67(6H,s), 7.52–7.76(2H,m), 8.12–8.29(2H,m)

Example 1c

A mixture of 2-methyl-2-(3-nitrophenyl)-propionic acid (866 mg) obtained in Example 1b, diphenylphosphorylazide (0.89 ml), triethylamine (0.58 ml) and t-butanol (15 ml) was refluxed for 16 h and concentrated under reduced pressure. The residue was dissolved in benzene and washed successively with a 5% aqueous citric acid solution, water, a saturated aqueous sodium chloride solution and a saturated aqueous sodium bicarbonate solution; the organic layer was dried with anhydrous sodium sulfate and concentrated under reduced pressure. The resulting residue was purified by silica gel column chromatography (eluent, n-hexane:ethyl acetate=85:15) to yield 649 mg of the titled compound (yield, 56%).

$^1$H-NMR($CDCl_3$) δ: 1.38(9H,s), 1.65(6H,s), 5.08(1H, brs), 7.46–7.75(2H,m), 8.07–8.28(2H,m)

MS(m/z) 280($M^+$)

Example 2

Synthesis of N-(1-methyl-1-(3-aminophenyl)ethyl) carbamic acid t-butyl ester

A mixture of the compound (649 mg) obtained in Example 1, 10% palladium-carbon (300 mg) and ethanol (100 ml) was stirred in a hydrogen atmosphere at room temperature for 16 h. The reaction mixture was filtered and the filtrate was concentrated under reduced pressure; the resulting residue was purified by silica gel column chromatography (eluent, n-hexane:ethyl acetate=7:3) to give 439 mg of the titled compound (yield, 76%).

H-NMR($CDCl_3$) δ: 1.37(9H,s), 1.60(6H,s), 3.62(2H,brs), 4.87(1H, brs), 6.53–6.81(3H,m), 7.07–7.13(1H,m)

MS(m/z)250($M^+$)

Example 3

Synthesis of N-(1-methyl-1-(3-thioureidophenyl) ethyl)carbamic acid t-butyl ester Thiophosgene (0.12 ml) and a solution of the compound (284 mg) obtained in Example 2 in methylene chloride (10 ml) were added dropwise to a suspension of calcium carbonate (319 mg) in water (5 ml) at room temperature and stirred at room temperature for 5 h; thereafter, a 28% aqueous ammonia solution (5 ml) was added to the reaction mixture and stirred at room temperature for 16 h. After neutralization with 2 N HCl, the reaction mixture was extracted with ethyl acetate and the organic layer was washed with a saturated aqueous sodium chloride solution, dried with anhydrous sodium sulfate and concentrated under reduced pressure. The resulting residue was purified by silica gel column chromatography (eluent, n-hexane:ethyl acetate=6:4) to yield 351 mg of the titled compound (yield, 89%).

$^1$H-NMR($CDCl_3$) δ: 1.36(9H,s), 1.60(6H,s), 5.04(1H, brs), 6.21(2H,brs), 7.05–7.42(4H,m), 8.07(1H,brs)

MS(m/z)309($M^+$)

Example 4

Synthesis of N-(1-methyl-1-(3-(S-methylisothioureido)phenyl)ethyl)carbamic acid t-butyl ester hydroiodide To a mixture of the compound (164 mg) obtained in Example 3 and acetonitrile (15 ml) was added methyl iodide (0.1 ml) and the reaction mixture was heated under reflux for 2 h. The reaction mixture was concentrated under reduced pressure and the resulting residue was purified by silica gel column chromatography (eluent, chloroform methanol=95:5) to give 130 mg of the titled compound (yield, 54%).

$^1$H-NMR($CDCl_3$) δ: 1.37(9H,s), 1.60(6H,s), 2.47(3H,s), 4.93(1H,brs), 6.77–7.29(4H,m)

Example 5

Syntheis of N-(1-methyl-1-(3-(S-methylisothioureido)phenyl)ethyl)amine dihydrochloride A mixture of the compound (130 mg) obtained in Example 4 and trifluoroacetic acid (15 ml) was stirred at room temperature for 2 h, and concentrated under reduced pressure. The residue was dissolved in ethanol (5 ml) and, thereafter, a solution of hydrogen chloride in 1,4-dioxane (4N, 0.29 ml) was added at room temperature and the reaction mixture was concentrated under reduced pressure. The residue was dissolved in water, washed with ethyl acetate and freeze-dried to give 100 mg of the titled compound (yield, 84%).

$^1$H-NMR($D_2O$) δ: 1.77(6H,s), 2.70(3H,s), 7.40–7.68(4H, m)

MS(m/z) 223($M^+$)

Example 6

Synthesis of N-(1-methyl-1-(3-(N'-nitroguanidino) phenyl)ethyl)carbamic acid t-butyl ester A mixture of the compound (145 mg) obtained in Example 2, acetonitrile (10 ml), N-methyl-N'-nitro-N-nitrosoguanidine (85 mg), triethylamine (0.08 ml) and acetic acid (0.03 ml) was stirred at room temperature for 16 h. The reaction mixture was concentrated under reduced pressure and the resulting residue was purified by silica gel column chromatography (eluent, n-hexane:ethyl acetate=1:1) to give 106 mg of the titled compound (yield, 54%).

$^1$H-NMR($CDCl_3$) δ: 1.36(9H,s), 1.62(6H,s), 5.06(1H, brs), 7.16–7.47(4H,m), 9.73(1H,brs)

FAB-MS(m/z) 338($M^+$+1)

Example 7

Synthesis of N-(1-methyl-1-(3-(N'-nitroguanidino) phenyl)ethyl)amine hydrochloride Using the compound obtained in Example 6 as a starting material, the same procedure of Example 5 gave 66 mg of the titled compound (yield, 77%).

$^1$H-NMR($D_2O$) δ: 1.76(6H,s), 7.37–7.62(4H,m)

FAB-MS(m/z) 238($M^+$+1)

Example 8

Synthesis of N-(1-(3-nitrophenyl)ethyl)carbamic acid t-butyl ester

Example 8a

Using 3-nitrophenylacetic acid t-butyl ester as a starting material and methyl iodide (1 eq.) as a reagent, the same procedures of Examples 1a and 1b gave 2-(3-nitrophenyl) propionic acid.

$^1$H-NMR($CDCl_3$) δ: 1.59(3H,d, J=7.3 Hz), 3.88(1H,q, J=7.3 Hz), 7.49–7.68(2H,m), 8.13–8.21(2H,m)

Example 8b

Using 2-(3-nitrophenyl)propionic acid as a starting material, the same procedure of Example 1c gave 183 mg of the titled compound (yield, 67%).

$^1$H-NMR($CDCl_3$) δ: 1.41(9H,s), 1.48(3H,d, J=6.6 Hz), 4.68–5.06(2H,m), 7.47–7.66(2H,m), 8.10–8.17(2H,m)

MS(m/z) 266($M^+$)

Example 9

Synthesis of N-(1-(3-aminophenyl)ethyl)carbamic acid t-butyl ester

Using the compound obtained in Example 8 as a starting material, the same procedure of Example 2 gave 496 mg of the titled compound (yield, 78%).

$^1$H-NMR($CDCl_3$) δ: 1.40–1.42(12H,m), 3.66(2H,brs), 4.58–4.86(2H,m), 6.55–6.70(3H,m), 7.08–7.14(1H,m)

Example 10

Synthesis of N-(1-(3-thioureidophenyl)ethyl) carbamic acid t-butyl ester

Using the compound obtained in Example 9 as a starting material, the same procedure of Example 3 gave 246 mg of the titled compound (yield, 89%).

$^1$H-NMR($CDCl_3$) δ: 1.41(9H,s), 1.43(3H,d J=6.9 Hz), 4.67–4.79(1H,m) 4.80–4.98(1H,m), 6.14(2H,brs), 7.09–7.43(4H,m), 7.97(1H,brs)

Example 11

Synthesis of N-(1-(3-(S-methylisothioureido) phenyl)ethyl)carbamic acid t-butyl ester hydroiodide Using the compound obtained in Example 10 as a starting material, the same procedure of Example 4 gave 318 mg of the titled compound (yield, 87%).

$^1$H-NMR($CDCl_3$) δ: 1.42–1.45(12H,m), 2.60(3H,s), 4.68–4.91(2H,m), 7.03–7.37(4H,m)

Example 12

Synthesis of N-(1-(3-(S-methylisothioureido) phenyl)ethyl)amine dihydrochloride

Using the compound obtained in Example 11 as a starting material, the same procedure of Example 5 gave 192 mg of the titled compound quantitatively.

$^1$H-NMR($D_2O$) δ: 1.67(3H,d, J=6.9 Hz), 2.70(3H,s), 4.61 (1H,q, J=6.9 Hz), 7.42–7.67(4H,m)

MS(m/z) 209($M^+$)

Example 13

Synthesis of N-(1-(3-(N'-nitroguanidino)phenyl) ethyl)carbamic acid t-butyl ester Using the compound obtained in Example 9 as a starting material, the same procedure of Example 6 gave 123 mg of the titled compound (yield, 40%).

$^1$H-NMR($CDCl_3$) δ: 1.41(9H,s), 1.46(3H,d, J=6.9 Hz), 4.72–4.80(1H,m), 4.89(1H,d, J=6.3 Hz), 7.17–7.49(4H,m), 9.25(1H,brs)

FAB-MS(m/z) 324($M^+$+1)

Example 14

Synthesis of N-(1-(3-(N'-nitroguanidino)phenyl) ethyl)amine hydrochloride

Using the compound obtained in Example 13 as a starting material, the same procedure of Example 7 gave 92 mg of the titled compound (yield, 84%).

$^1$H-NMR($D_2O$) δ: 1.66(3H,d, J=6.9 Hz), 4.58(1H,q, J=6.9 Hz), 7.38–7.61(4H,m)

FAB-MS(m/z) 224($M^+$+1)

Example 15

Synthesis of N-(1-(3-nitrophenyl)propyl)carbamic acid t-butyl ester

Example 15a

Using 3-nitrophenylacetic acid t-butyl ester as a starting material and also using ethyl iodide (1 eq.) as a reagent, the same procedures of Examples 1a and 1b gave 2-(3-nitrophenyl)butyric acid.

$^1$H-NMR($CDCl_3$) δ: 0.94(3H,t, J=7.3 Hz), 1.79–1.95(1H, m), 2.10–2.26(1H,m), 3.60(1H,t, J=7.6 Hz), 7.49–7.78(2H, m), 8.13–8.28(2H,m)

Example 15b

Using 2-(3-nitrophenyl)butyric acid as a starting material, the same procedure of Example 1c gave 1.0 g of the titled compound (yield, 96%).

$^1$H-NMR($CDCl_3$) δ: 0.93(3H,t, J=7.3 Hz), 1.42(9H,s), 1.73–1.84(2H,m), 4.51–4.71(1H,m), 4.78–4.98(1H,m), 7.47–7.67(2H,m), 8.10–8.13 (2H,m)

Example 16

Synthesis of N-(1-(3-aminophenyl)propyl)carbamic acid t-butyl ester

Using the compound obtained in Example 15 as a starting material, the same procedure of Example 2 gave 701 mg of the titled compound (yield, 79%).

$^1$H-NMR($CDCl_3$) δ: 0.87(3H,t, J=7.3 Hz), 1.41(9H,s), 1.68–1.85(2H,m), 3.64(2H, brs), 4.30–4.50(1H,m), 4.62–4.86(1H,m), 6.55–6.66(3H,m), 7.07–7.13(1H,m)

Example 17

Synthesis of N-(1-(3-thioureidophenyl)propyl) carbamic acid t-butyl ester

Using the compound obtained in Example 16 as a starting material, the same procedure of Example 3 gave 371 mg of the titled compound (yield, 97%).

$^1$H-NMR($CDCl_3$) δ: 0.92(3H,t, J=7.3 Hz), 1.40(9H,s), 1.69–1.80(2H,m), 4.40–4.60(1H,m), 4.80–5.00(1H,m), 6.15 (2H,brs), 7.09–7.42 (4H,m), 7.97(1H,brs)

Example 18

Synthesis of N-(1-(3-(S-methylisothioureido) phenyl)propyl)carbamic acid t-butyl ester hydroiodide Using the compound obtained in Example 17 as a starting material, the same procedure of Example 4 gave 443 mg of the titled compound (yield, 82%).

$^1$H-NMR($CDCl_3$) δ: 0.90(3H,t, J=7.3 Hz), 1.41(9H,s), 1.70–1.80(2H,m), 2.59(3H,s), 4.39–4.61(1H,m), 4.85(1H,d, J=7.6 Hz), 7.01–7.36(4H,m)

Example 19

Synthesis of N-(1-(3-(S-methylisothioureido) phenyl)propyl)amine dihydrochloride Using the compound obtained in Example 18 as a starting material, the same procedure of Example 5 gave 267 mg of the titled compound (yield, 93%).

$^1$H-NMR($D_2O$) δ: 0.89(3H,t, J=7.3 Hz), 1.91–2.16(2H, m), 2.70(3H,s), 4.30–4.36(1H,m), 7.43–7.70(4H,m)

MS(m/z) 223($M^+$)

Example 20

Synthesis of N-(1-(3-(N'-nitroguanidino)phenyl) propyl)carbamic acid t-butyl ester Using the compound obtained in Example 16 as a starting material, the same procedure of Example 6 gave 406 mg of the titled compound (yield, 87%).

$^1$H-NMR($CDCl_3$) δ: 0.94(3H,t, J=7.3 Hz), 1.40(9H,s), 1.72–1.83(2H,m), 4.43–4.58(1H,m), 4.84–5.01(1H,m), 7.19–7.48(4H,m), 9.56(1H,brs)

FAB-MS(m/z) 338($M^+$+1)

Example 21

Synthesis of N-(1-(3-(N'-nitroguanidino)phenyl) propyl)amine hydrochloride

Using the compound obtained in Example 20 as a starting material, the same procedure of Example 5 gave 270 mg of the titled compound (yield, 83%). $^1$H-NMR($D_2O$) δ: 0.89 (3H,t, J=7.3 Hz), 1.93–2.12(2H,m), 4.30(1H,t, J=8.6 Hz), 7.39–7.61(4H,m)

FAB-MS(m/z) 238($M^+$+1)

Example 22

Synthesis of N-(3-nitrophenylmethyl)carbamic acid t-butyl ester

Triethylamine (2.8 ml) and di-t-butyl dicarbonate (2.3 g) were added to a solution of 3-nitrobenzylamine hydrochloride (1.5 g) in dimethylformamide (30 ml) and stirred at room temperature for 16 h. Water and 2 N HCl were added to the reaction mixture for pH adjustment to 3; following extraction with ethyl acetate, the organic layer was successively washed with a saturated aqueous sodium chloride solution, a saturated aqueous sodium bicarbonate solution and a saturated aqueous sodium chloride solution, dried with anhydrous sodium sulfate, and concentrated under reduced pressure. The resulting residue was purified by silica gel column chromatography (eluent, n-hexane:ethyl acetate=6:4) to give 1.9 g of the titled compound (yield, 94%).

$^1$H-NMR($CDCl_3$) δ: 1.47(9H,s), 4.42(2H,d, J=6.3 Hz), 4.92–5.10(1H,m), 7.48–7.65(2H,m), 8.11–8.15(2H,m)

Example 23

Synthesis of N-(3-aminophenylmethyl)carbamic acid t-butyl ester

Using the compound obtained in Example 22 as a starting material, the same procedure of Example 2 gave 1.1 g of the titled compound quantitatively.

$^1$H-NMR($CDCl_3$) δ: 1.46(9H,s), 3.66(2H,brs), 4.21(2H,d, J=5.9 Hz), 4.73–4.87(1H,m), 6.56–6.67(3H,m), 7.07–7.13 (1H,m)

Example 24

Synthesis of N-(3-thioureidophenylmethyl)carbamic acid t-butyl ester

Using the compound obtained in Example 23 as a starting material, the same procedure of Example 3 gave 382 mg of the titled compound (yield, 81%).

$^1$H-NMR($CDCl_3$) δ: 1.45(9H,s), 4.32(2H,d, J=5.9 Hz), 4.97–5.11(1H,m), 6.22(2H,brs), 7.12–7.27(3H,m), 7.36–7.42(1H,m), 8.19(1H,brs)

FAB-MS(m/z) 282($M^+$+1)

Example 25

Synthesis of N-(3-(S-methylisothioureido) phenylmethyl)carbamic acid t-butyl ester hydroiodide Using the compound obtained in Example 24 as a starting material, the same procedure of Example 4 gave 489 mg of the titled compound (yield, 85%).

$^1$H-NMR($CDCl_3$) δ: 1.46(9H,s), 2.46(3H,s), 4.28(2H,d, J=5.6 Hz), 4.75–4.89(1H,m), 6.81–6.97(3H,m), 7.24–7.29 (1H,m)

FAB-MS(m/z) 296($M^+$+1)

Example 26

Synthesis of N-(3-(S-methylisothioureido) phenylmethyl)amine dihydrochloride Using the compound obtained in Example 25 as a starting material, the same procedure of Example 5 gave 150 mg of the titled compound (yield, 94%).

$^1$H-NMR($D_2O$) δ: 2.70(3H,s), 4.25(2H,s), 7.31–7.66(4H, m)

FAB-MS(m/z) 196($M^+$+1)

Example 27

Synthesis of N-(3-(S-ethylisothioureido) phenylmethyl)carbamic acid t-butyl ester hydroiodide Using the compound obtained in Example 24 as a starting material and also using ethyl iodide as a reagent, the same procedure of Example 4 gave 178 mg of the titled compound (yield, 68%).

$^1$H-NMR($CDCl_3$) δ: 1.37(3H,t, J=7.3 Hz), 1.46(9H,s), 3.06(2H,q, J=7.3 Hz), 4.29(2H, d, J=5.9 Hz), 4.78–4.92(1H, m), 6.87–7.31(4H,m)

Example 28

Synthesis of N-(3-(S-ethylisothioureido) phenylmethyl)amine dihydrochloride

Using the compound obtained in Example 27 as a starting material, the same procedure of Example 5 gave 105 mg of the titled compound (yield, 92%).

$^1$H-NMR($D_2O$) δ: 1.43(3H,t, J=7.3 Hz), 3.25(2H,q, J=7.3 Hz), 4.25(2H,s), 7.43–7.66(4H,m)

MS(m/z) 209($M^+$)

Example 29

Synthesis of N-(3-(S-(2-fluoroethyl)isothioureido) phenylmethyl)carbamic acid t-butyl ester To a mixture of the compound (500 mg) obtained in Example 24 and acetonitrile (20 ml) was added 1-bromo-2-fluoroethane (0.26 ml) and the reaction mixture was heated under reflux for 2 h. The reaction mixture was distilled under reduced pressure and the resulting residue was dissolved in ethyl acetate and washed successively with a saturated aqueous sodium bicarbonate solution and a saturated aqueous sodium chloride solution and the organic layer was dried with anhydrous sodium sulfate and then concentrated under reduced pressure. The resulting residue was purified by silica gel column chromatography (eluent, n-hexane:ethyl acetate=6:4) to give 50 mg of the titled compound (yield, 9%).

$^1$H-NMR($CDCl_3$) δ: 1.46(9H,s), 3.36(2H, destorted dt, J=22.1, 5.9 Hz), 4.27(2H, d, J=5.6 Hz), 4.66(2H, destorted dt, J=47.2, 5.9 Hz), 4.80–4.94(1H,m), 6.77–6.97(3H,m), 7.24–7.29(1H,m)

Example 30

Synthesis of N-(3-(S-(2-fluoroethyl)isothioureido) phenylmethyl)amine dihydrochloride Using the compound obtained in Example 29 as a starting material, the same procedure of Example 5 gave 36 mg of the titled compound (yield, 79%).

$^1$H-NMR($D_2O$) δ: 3.61(2H, destorted dt, J=25.4, 5.3 Hz), 4.24(2H,s), 4.82(2H,destorted dt, J=46.5, 5.3 Hz), 7.41–7.71 (4H,m)

Example 31

Synthesis of N-(3-(S-(2-propenyl)isothioureido) phenylmethyl)carbamic acid t-butyl ester hydrobromide Using the compound obtained in Example 24 as a starting material and also using allyl bromide as a reagent, the same procedure of Example 4 gave 118 mg of the titled compound (yield, 34%).

$^1$H-NMR($CDCl_3$) δ: 1.46(9H,s), 3.85(2H,d, J=6.6 Hz), 4.30(2H, d, J=5.9 Hz), 4.93–5.05(1H,m), 5.28(1H,d, J=9.9 Hz), 5.44(1H,d, J=16.8 Hz), 5.83–5.98(1H,m), 7.03–7.36 (4H,m)

MS(m/z) 321($M^+$)

Example 32

Synthesis of N-(3-(S-(2-propenyl)isothioureido) phenylmethyl)amine dihydrochloride Using the compound obtained in Example 31 as a starting material, the same procedure of Example 5 gave 73 mg of the titled compound (yield, 85%).

$^1$H-NMR($D_2O$) δ: 3.91(2H,d, J=6.6 Hz), 4.24(2H,s), 5.36 (1H,d, J=10.2 Hz), 5.44(1H,d, J=16.8 Hz), 5.93–6.08(1H, m), 7.42–7.66(4H,m)

MS(m/z) 221($M^+$)

Example 33

Synthesis of N-(3-(N'-nitroguanidino)phenylmethyl) carbamic acid t-butyl ester

Using the compound obtained in Example 23 as a starting material, the same procedure of Example 6 gave 201 mg of the titled compound (yield, 70%).

$^1$H-NMR($CDCl_3$) δ: 1.45(9H,s), 4.33(2H,d, J=6.3 Hz), 4.86–5.00(1H,m), 6.55(1H,brs), 7.17–7.47(4H,m), 9.03(1H, brs)

FAB-MS(m/z) 310($M^+$+1)

Example 34

Synthesis of N-(3-(N'-nitroguanidino)phenylmethyl) amine

A mixture of the compound (230 mg) obtained in Example 33, methylene chloride (3 ml) and trifluoroacetic acid (1.15 ml) was stirred at room temperature for 3 h. The reaction mixture was concentrated under reduced pressure and 25% aqueous ammonia solution was added to the resulting residue, and the reaction mixture was extracted with chloroform. The organic layer was washed with a saturated aqueous sodium chloride solution and dried with anhydrous sodium sulfate, and the solvent was distilled off under reduced pressure. The residue was purified by silica gel column chromatography (eluent; methanol) to give 117 mg of the titled compound (yield, 75%).

$^1$H-NMR($CDCl_3$) δ: 4.14(2H,s), 7.30–7.34(2H,m), 7.45 (1H,d, J=7.9 Hz), 7.56(1H,s)

Example 35

Synthesis of N-(3-guanidinophenylmethyl)carbamic acid t-butyl ester formate

A solution of the compound (190 mg) obtained in Example 33 in 4.4% formic acid-methanol (10 ml) was added dropwise to a suspension of palladium-black (200 mg) in 4.4% formic acid-methanol (10 ml) at room temperature and stirred at room temperature for 16 h. The reaction mixture was filtered and the filtrate was concentrated under reduced pressure; the resulting residue was purified by silica gel column chromatography (eluent, chloroform methanol=8:2) to give 71 mg of the titled compound (yield, 37%).

$^1$H-NMR($CDCl_3$) δ: 1.39(9H,s), 4.22(2H, d, J=5.9 Hz), 5.59–5.76(1H,m), 7.05–7.36(4H,m), 9.72(1H,brs)

FAB-MS(m/z) 265($M^+$+1)

Example 36

Synthesis of N-(3-guanidinophenylmethyl)amine dihydrochloride

Using the compound obtained in Example 35 as a starting material, the same procedure of Example 5 gave 57 mg of the titled compound quantitatively.

$^1$H-NMR($D_2O$) δ: 4.22(2H,s), 7.35–7.60(4H,m)

FAB-MS(m/z) 165($M^+$+1)

Example 37

Synthesis of N-(3-nitrophenylmethyl)dimethylamine

A solution of m-nitro-α-bromotoluene (3.2 g) in dimethylformamide (50 ml) was added dropwise to a solution of dimethylamine hydrochloride (1.45 g) and triethylamine (4.36 ml) in dimethylformamide (50 ml). The reaction mixture was stirred at room temperature for 1 h and then its temperature was raised to 50° C., at which it was stirred for 3 h. The reaction mixture was distilled under reduced pressure, water was added to the residue, and the mixture was extracted with ethyl acetate. The organic layer was washed with a saturated aqueous sodium chloride solution, dried with anhydrous magnesium sulfate and the solvent was distilled off under reduced pressure. The resulting residue was purified by silica gel column chromatography (eluent, n-hexane:ethyl acetate=2:1) to give 2.56 g of the titled compound (yield, 96%).

$^1$H-NMR($CDCl_3$) δ: 2.26(6H,s), 3.15(2H,s), 7.49(1H,dd, J=7.9, 7.6 Hz), 7.67(1H,d, J=7.6 Hz), 8.12(1H,d, J=7.9 Hz), 8.19(1H,s)

Example 38

Synthesis of N-(3-aminophenylmethyl)dimethylamine

Using the compound obtained in Example 37 as a starting material, the same procedure of Example 2 gave 1.6 g of the titled compound (yield, 99%).

$^1$H-NMR($CDCl_3$) δ: 2.24(6H,s), 3.37(2H,s), 3.45(2H, brs), 6.58(1H,d, J=6.6 Hz), 6.66–6.69(2H,m), 7.10(1H, dd, J=7.6, 6.6 Hz)

Example 39

Synthesis of N-(3-(N'-nitroguanidino)phenylmethyl)dimethylamine acetate

Using the compound obtained in Example 38 as a starting material, the same procedure of Example 6 gave 0.11 g of the titled compound (yield, 42%).

$^1$H-NMR(DMSO-$d_6$) δ: 2.13(3H,s), 2.16(6H,s), 3.37(2H, s), 7.08(1H, d, J=7.3 Hz), 7.22–7.30(3H,m), 8.26–8.80(1H, m)

MS(m/z) 191($M^+$–46)

Example 40

Synthesis of N-(3-thioureidophenylmethyl)dimethylamine

Benzoyl chloride (0.18 ml) was added to a solution of ammonium thiocyanate (0.12 g) in acetone (7 ml) and heated under reflux for 5 min. Subsequently, a solution of the compound (0.21 g) obtained in Example 38 in acetone (6 ml) was added. The reaction mixture was stirred at room temperature for 20 min and then water was added to give a yellow precipitate, which was separated off by filtration. To the recovered product, 10% aqueous sodium hydroxide solution (20 ml) was added and heated under reflux for 5 min. The reaction mixture was made acidic with 35% HCl, then weakly alkaline with 28% aqueous ammonia solution, and concentrated to 20 ml under reduced pressure. The resulting precipitate was filtered off and the filtrate was extracted with chloroform; the organic layer was dried with anhydrous magnesium sulfate and the solvent was concentrated under reduced pressure. The residue was purified by silica gel column chromatography (eluent, chloroform methanol=5:1) to give 0.1 g of the titled compound (yield, 35%).

$^1$H-NMR(DMSO-$d_6$) δ: 2.22(6H,s), 3.49(2H,s), 6.72(2H, brs), 7.15–7.36(4H,m), 9.12(1H,brs)

MS(m/z) 209($M^+$)

Example 41

Synthesis of N-(3-(S-methylisothioureido)phenylmethyl)dimethylamine mononitrate monohydrochloride To a mixture of the compound (42.7 mg) obtained in Example 40 and tetrahydrofuran (2 ml), 60% nitric acid (0.1 ml) was added and the resulting mixture was concentrated under reduced pressure to form a nitrate, which was subjected to the same reaction as in Example 4; the residue was dissolved in ethanol (1 ml) and a solution of hydrogen chloride in 1,4-dioxane (4N, 1 ml) was added at room temperature; then, the reaction mixture was concentrated under reduced pressure. The residue was dissolved in water, washed with ethyl acetate and freeze-dried to give 46.9 mg of the titled compound (yield, 71%).

$^1$H-NMR(DMSO-$d_6$) δ: 2.34(6H,s), 2.42(3H,s), 3.54(2H, s), 4.45(3H,br), 6.86(1H,d, J=7.9 Hz), 6.92(1H,s), 6.99(1H, d, J=7.6 Hz), 7.25(1H, dd, J=7.9, 7.6 Hz), 7.69(1H,s)

MS(m/z) 223($M^+$)

Example 42

Synthesis of N-(3-nitrophenylmethyl)methylamine

To a mixture of sodium cyanoborohydride (2.52 g), triethylamine (18.7 ml), methylamine hydrochloride (5.42 g) and methanol (660 ml), m-nitrobenzaldehyde (10.10 g) was added dropwise over 20 minutes at room temperature and the resulting mixture was stirred at room temperature for 20 h. The pH of the reaction mixture was adjusted to 2 by addition of 10% HCl and the methanol was distilled off under reduced pressure. The residue was washed with chloroform and a 10% aqueous potassium hydroxide solution was added to the aqueous layer for pH adjustment to 12, and the mixture was extracted with chloroform. The organic layer was washed with a saturated aqueous sodium chloride solution, dried with anhydrous magnesium sulfate and concentrated under reduced pressure. The resulting residue was purified by silica gel column chromatography (eluent, chloroform:methanol=95:5) to give 3.0 g of the titled compound (yield, 27%).

$^1$H-NMR($CDCl_3$) δ: 1.52(1H,brs), 2.47(3H,s), 3.87(2H, s), 7.50(1H,dd, J=7.8, 7.8 Hz), 7.68(1H,d J=7.8 Hz), 8.20 (1H,d, J=7.8 Hz), 8.44(1H,s)

Example 43

Synthesis of N-(3-nitrophenylmethyl)methylcarbamic acid t-butyl ester

Using the compound obtained in Example 42 as a starting material, the same procedure of Example 22 gave 4.1 g of the titled compound (yield, 85%).

$^1$H-NMR($CDCl_3$) δ: 1.49(9H,s), 2.87(3H,s), 4.51(2H,s), 7.49–7.56(2H,m), 8.11–8.15(2H,m)

Example 44

Synthesis of N-(3-aminophenylmethyl)methylcarbamic acid t-butyl ester

Using the compound obtained in Example 43 as a starting material, the same procedure of Example 2 gave 2.96 g of the titled compound (yield, 81%).

$^1H$-NMR($CDCl_3$) δ: 1.48(9H,s), 2.80(3H,s), 3.40(2H,br), 4.33(2H,s), 6.44–6.64(3H,m), 7.10(1H, dd, J=7.8, 7.8 Hz)

FAB-MS(m/z) 236($M^+$)

Example 45

Synthesis of N-(3-thioureidophenylmethyl) methylcarbamic acid t-butyl ester

Using the compound obtained in Example 44 as a starting material, the same procedure of Example 3 gave 2.21 g of the titled compound (yield, 86%).

$^1H$-NMR($CDCl_3$) δ: 1.47(9H,s), 2.84(3H,s), 4.42(2H,s), 6.36(2H,brs), 7.10–7.18(3H,m), 7.39(1H, dd, J=7.8, 7.8 Hz), 8.56(1H,s)

FAB-MS(m/z) 296($M^+$+1)

Example 46

Synthesis of N-(3-(S-ethylisothioureido) phenylmethyl)methylcarbamic acid t-butyl ester hydroiodide Using the compound obtained in Example 45 as a starting material, the same procedure of Example 27 gave 0.27 g of the titled compound (yield, 69%).

$^1H$-NMR($CDCl_3$) δ: 1.35(3H, t, J=7.3 Hz), 1.48(9H,s), 2.81(3H,s), 3.01(2H, q, J=7.3 Hz), 4.38(2H,s), 4.55(1H,brs), 6.78–6.82 (2H,m), 6.89(1H, d, J=7.6 Hz), 7.25(1H, dd, J=7.6, 7.6 Hz)

FAB-MS(m/z) 324($M^+$+1)

Example 47

Synthesis of N-(3-(S-ethylisothioureido) phenylmethyl)methylamine dihydrochloride Using the compound obtained in Example 46 as a starting material, the same procedure of Example 5 gave 85.5 mg of the titled compound (yield, 87%).

$^1H$-NMR($D_2O$) δ: 1.43(3H, t, J=7.3 Hz), 2.78(3H,s), 3.27(2H, q, J=7.3 Hz), 4.37(2H,s), 7.47–7.51(2H,m), 7.56 (1H, d, J=7.6 Hz), 7.66(1H, dd, J=7.6, 7.3 Hz)

Example 48

Synthesis of N-(4-nitrophenylethyl)carbamic acid t-butyl ester

Using N-(4-nitrophenylethyl)amine hydrochloride as a starting material, the same procedure of Example 22 gave the titled compound quantitatively.

$^1H$-NMR($CDCl_3$) δ: 1.41(9H,s), 2.72–3.02(2H,m), 3.19–3.50(2H,m), 7.23(2H,d,J=9.0 Hz), 8.05(2H, d, J=9.0 Hz)

FAB-MS(m/z) 267($M^+$+1)

Example 49

Synthesis of N-(4-aminophenylethyl)carbamic acid t-butyl ester

Using the compound obtained in Example 48 as a starting material, the same procedure of Example 2 gave the titled compound (yield, 78%).

$^1H$-NMR($CDCl_3$) δ: 1.43(9H,s), 2.62–2.69(2H,m), 3.22–3.36(2H,m), 3.57(2H,brs), 4.56–4.72(1H,m), 6.61(2H, d, J=8.3 Hz), 6.95(2H, d, J=8.3 Hz)

MS(m/z) 236($M^+$)

Example 50

Synthesis of N-(4-thioureidophenylethyl)carbamic acid t-butyl ester

Using the compound obtained in Example 49 as a starting material, the same procedure of Example 3 gave the titled compound (yield, 71%).

$^1H$-NMR(DMSO-$d_6$) δ: 1.39(9H,s), 2.57–2.71(2H,m), 3.10–3.21(2H,m), 6.70–6.84(1H,m), 7.13(2H, d, J=8.3 Hz), 7.30(2H, d, J=8.3 Hz), 9.59(1H,s)

MS(m/z) 295($M^+$)

Example 51

Synthesis of N-(4-(S-methylisothioureido) phenylethyl)carbamic acid t-butyl ester hydroiodide Using the compound obtained in Example 50 as a starting material, the same procedure of Example 4 gave the titled compound quantitatively.

$^1H$-NMR($CDCl_3$) δ: 1.42(9H,s), 2.71(3H,s), 2.99(2H,t, J=6.9 Hz), 3.26–3.38(2H,m), 4.80–4.92(1H,m), 6.75–7.08 (2H,m), 7.18–7.27(4H,m)

MS(m/z) 309($M^+$)

Example 52

Synthesis of N-(4-(S-methylisothioureido) phenylethyl)amine dihydrochloride

Using the compound obtained in Example 51 as a starting material, the same procedure of Example 5 gave the titled compound quantitatively.

$^1H$-NMR($D_2O$) δ: 2.71(3H,s), 3.08(2H,t, J=7.3 Hz), 3.30–3.36(2H,m), 7.35–7.52(4H,m)

FAB-MS(m/z) 210($M^+$+1)

Example 53

Synthesis of N-(4-(N'-nitroguanidino)phenylethyl) carbamic acid t-butyl ester

Using the compound obtained in Example 49 as a starting material, the same procedure of Example 6 gave the titled compound (yield, 35%).

$^1H$-NMR(DMSO-$d_6$) δ: 1.38(9H,s), 2.66–2.72(2H,m), 3.10–3.18(2H,m), 6.82(1H,brs), 7.20(4H,s), 8.13(1H,brs), 9.52(1H,s)

FAB-MS(m/z) 324($M^+$+1)

Example 54

Synthesis of N-(4-(N'-nitroguanidino)phenylethyl) amine

Using the compound obtained in Example 53 as a starting material, reaction was performed as in Example 5 and the product was purified by basic silica gel column chromatography (eluent, methylene chloride:methanol=95:5) and recrystallized from a mixture of ethanol and diethyl ether to give the titled compound (yield, 57%).

$^1H$-NMR(DMSO-$d_6$) δ: 2.60–2.65(2H,m), 2.77(2H, t, J=6.9 Hz), 5.75(2H,br), 7.20(4H,s), 8.27–8.30(2H,m)

FAB-MS(m/z) 224($M^+$+1)

Example 55

Synthesis of 3-(2-bromoethyl)nitrobenzene

Carbon tetrabromide (2.48 g) and triphenylphosphine (2.35 g) were added to a mixture of 3-nitrophenethyl alcohol (1.0 g) and methylene chloride (20 ml) under cooling with ice and stirred for 30 min under cooling with ice. The reaction mixture was distilled under reduced pressure and the resulting residue was purified by silica gel column chromatography (eluent, n-hexane:ethyl acetate=4:1) to give 1.58 g of the titled compound quantitatively.

$^1$H-NMR($CDCl_3$) δ: 3.29(2H, t, J=6.9 Hz), 3.65(2H, t, J=6.9 Hz), 7.48–7.61(2H,m), 8.08–8.10(2H,m)

MS(m/z) 230($M^+$)

Example 56

Synthesis of N-(3-nitrophenylethyl)carbamic acid t-butyl ester

To a mixture of the compound (1.58 g) obtained in Example 55 and dimethyl sulfoxide (30 ml) was added 28% aqueous ammonia solution (15 ml) and the resulting mixture was stirred at room temperature for 2.5 h. The unreacted 28% aqueous ammonia solution was distilled off under reduced pressure and di-t-butyl dicarbonate (6.5 g) and triethylamine (1.3 ml) were added to the resulting residue, and reaction was performed at room temperature for 18 h. The reaction solution was diluted with ethyl acetate and washed successively with 2 N HCl and water; the organic layer was dried with anhydrous sodium sulfate and the solvent was distilled off under reduced pressure. The resulting residue was purified by silica gel column chromatography (eluent, n-hexane:ethyl acetate=4:1) to give 1.22 g of the titled compound (yield, 77%).

$^1$H-NMR($CDCl_3$) δ: 1.42(9H,s), 2.91–2.97(2H,m), 3.41–3.46(2H,m), 4.98–5.13(1H,m), 7.45–7.58(2H,m), 8.05–8.08(2H,m)

MS(m/z) 266($M^+$)

Example 57

Synthesis of N-(3-aminophenylethyl)carbamic acid t-butyl ester

Using the compound obtained in Example 56 as a starting material, the same procedure of Example 2 gave the titled compound (yield, 69%).

$^1$H-NMR($CDCl_3$) δ: 1.44(9H,s), 2.70(2H, t, J=6.9 Hz), 3.34–3.48(2H,m), 4.48–4.60(1H,m), 6.53–6.60(3H,m), 7.80 (1H, t, J=7.6 Hz)

MS(m/z) 236($M^+$)

Example 58

Synthesis of N-(3-thioureidophenylethyl)carbamic acid t-butyl ester

Using the compound obtained in Example 57 as a starting material, the same procedure of Example 3 gave the titled compound (yield, 82%).

$^1$H-NMR($CDCl_3$) δ: 1.29(9H,s), 2.76–2.81(2H,m), 3.35–3.49(2H,m), 4.53–4.68(1H,m), 6.46(2H,brs), 7.02–7.35(4H,m), 8.09(1H,brs)

MS(m/z) 295($M^+$)

Example 59

Synthesis of N-(3-(S-methylisothioureido)phenylethyl)carbamic acid t-butyl ester hydroiodide Using the compound obtained in Example 58 as a starting material, the same procedure of Example 4 gave the titled compound (yield, 94%).

$^1$H-NMR($CDCl_3$) δ: 1.39(9H,s), 2.76(3H,s), 2.81(2H, t, J=6.9 Hz), 3.35–3.38(2H,m), 4.75–4.87(1H,m), 7.15–7.19 (3H,m), 7.30–7.38(1H,m), 7.72(2H,br)

MS(m/z) 309($M^+$)

Example 60

Synthesis of N-(3-(S-methylisothioureido)phenylethyl)amine dihydrochloride

Using the compound obtained in Example 59 as a starting material, the same procedure of Example 5 gave the titled compound quantitatively.

$^1$H-NMR($D_2O$) δ: 2.72(3H,s), 3.05–3.11(2H,m), 3.34(2H, t, J=7.3 Hz), 7.31–7.59(4H,m)

MS(m/z) 209($M^+$)

Example 61

Synthesis of N-(3-(N'-nitroguanidino)phenylethyl)carbamic acid t-butyl ester Using the compound obtained in Example 57 as a starting material, the same procedure of Example 6 gave the titled compound (yield, 59%).

$^1$H-NMR($CDCl_3$) δ: 1.29(9H,s), 2,79(2H, t, J=6.3 Hz), 3.38–3.43(2H,m), 4.91–5.03(1H,m), 7.11–7.36(4H,m), 9.76 (1H,brs)

FAB-MS(m/z) 324($M^+$+1)

Example 62

Synthesis of N-(3-(N'-nitroguanidino)phenylethyl)amine hydrochloride

Using the compound obtained in Example 61 as a starting material, the same procedure of Example 5 gave the titled compound (yield, 44%).

$^1$H-NMR($D_2O$) δ: 3.04(2H, t, J=7.3 Hz), 3.31(2H, t, J=7.3 Hz), 7.26–7.55(4H,m)

Example 63

Synthesis of 2-t-butoxycarbonylamino-3-(4-nitrophenyl)propionic acid

A 2 N aqueous sodium hydroxide solution (12.3 ml) and di-t-butyl dicarbonate (6.36 g) were added to a mixture of 4-nitrophenylalanine (5.35 g), 1,4-dioxane (80 ml) and water (40 ml) under cooling with ice and stirred at room temperature for 1 h. The reaction mixture was concentrated under reduced pressure and the resulting residue was diluted with ethyl acetate and washed successively with 2 N HCl and water; the organic layer was dried with anhydrous sodium sulfate and the solvent was concentrated under reduced pressure. The resulting residue was recrystallized from a mixture of ethyl acetate and n-hexane to give the titled compound quantitatively.

$^1$H-NMR($CDCl_3$) δ: 1.36(9H,s), 3.06–3.25(2H,m), 4.01–4.78(1H,m), 7.45(2H, d, J=9.0 Hz), 8.08(2H, d, J=9.0 Hz)

MS(m/z) 310($M^+$)

Example 64

Synthesis of 2-t-butoxycarbonylamino-3-(4-nitrophenyl)propionic acid methyl ester To a mixture of the compound (1.15 g) obtained in Example 63, diethyl ether (6 ml) and methanol (14 ml), a solution of trimethylsilyldiazomethane in n-hexane (2.0 M, 7.4 ml) was added and the resulting mixture was stirred at room temperature for 16 h. The reaction solution was concentrated under reduced pressure to give the titled compound quantitatively.

$^1$H-NMR($CDCl_3$) δ: 1.45(9H,s), 3.08–3.31(2H,m), 3.75 (3H,s), 4.38–4.78(1H,m), 4.95–5.42(1H,m), 7.28(2H, d, J=9.0 Hz), 8.09(2H, d, J=9.0 Hz)

MS(m/z) 324($M^+$)

Example 65

Synthesis of 2-t-butoxycarbonylamino-3-(4-aminophenyl)propionic acid methyl ester Using the compound obtained in Example 64 as a starting material, the same procedure of Example 2 gave the titled compound (yield, 87%).

$^1$H-NMR($CDCl_3$) δ: 1.41(9H,s), 2.95(2H, d, J=5.8 Hz), 3.61(2H,brs), 3.68(3H,s), 4.40–4.58(1H,m), 5.04–5.08(1H, m), 6.58(2H, d, J=8.3 Hz), 6.88(2H, d, J=8.3 Hz)

MS(m/z) 294($M^+$)

Example 66

Synthesis of 2-t-butoxycarbonylamino-3-(4-thioureidophenyl)propionic acid methyl ester Using the compound obtained in Example 65 as a starting material, the same procedure of Example 3 gave the titled compound (yield, 73%).

$^1$H-NMR($CDCl_3$) δ: 1.41(9H,s), 2.97–3.19(2H,m), 3.74 (3H,s), 4.56–4.60(1H,m), 5.11(1H, d, J=7.9 Hz), 6.28(2H, brs), 7.18(2H, d, J=5.9 Hz), 7.21(2H, d, J=5.9 Hz), 8.36(1H, s)

FAB-MS(m/z) 354($M^+$+1)

Example 67

Synthesis of 2-t-butoxycarbonylamino-3-(4-(S-methylisothioureido)phenyl)propionic acid methyl ester hydroiodide Using the compound obtained in Example 66 as a starting material, the same procedure of Example 4 gave the titled compound (yield, 80%).

$^1$H-NMR($CDCl_3$) δ: 1.42(9H,s), 2.64(3H,s), 2.99–3.17 (2H,m), 3.72(3H,s), 4.48–4.53(1H,m), 5.04(1H, d, J=7.9 Hz), 6.25–6.53(2H,m), 7.13(2H, d, J=8.6 Hz), 7.17(2H, d, J=8.6 Hz)

FAB-MS(m/z) 368($M^{++}$1)

Example 68

Synthesis of 2-amino-3-(4-(S-methylisothioureido)phenyl)propionic acid methyl ester dihydrochloride Using the compound obtained in Example 67 as a starting material, the same procedure of Example 5 gave the titled compound quantitatively.

$^1$H-NMR($D_2O$) δ: 2.70(3H,s), 3.28–3.47(2H,m), 3.85 (3H,s), 4.45–4.52(1H,m), 7.39(2H, d, J=8.6 Hz), 7.45(2H, d, J=8.6 Hz)

FAB-MS(m/z) 268($M^+$+1)

Example 69

Synthesis of 2-t-butoxycarbonylamino-3-(4-(N'-nitroguanidino)phenyl)propionic acid methyl ester Using the compound obtained in Example 65 as a starting material, the same procedure of Example 6 gave the titled compound (yield, 74%).

$^1$H-NMR($CDCl_3$) δ: 1.41(9H,s), 3.00–3.20(2H,m), 3.73 (3H,s), 4.50–4.36(1H,m), 5.20(1H,d, J=7.6 Hz), 7.20–7.28 (4H,m)

FAB-MS(m/z) 382($M^+$+1)

Example 70

Synthesis of 2-amino-3-(4-(N'-nitroguanidino)phenyl)propionic acid methyl ester

Using the compound obtained in Example 69 as a starting material, the same procedure of Example 54 gave the titled compound (yield, 65%).

$^1$H-NMR($CDCl_3$) δ: 2.80–2.91(1H,m), 3.07–3.17(1H,m), 3.74(3H,s), 3.70–3.82(1H,m), 7.24–7.34(4H,m)

FAB-MS(m/z) 282($M^+$+1)

Example 71

Synthesis of 2-t-butoxycarbonylamino-3-(4-nitrophenyl)propionic acid t-butyl ester To a mixture of the compound (6.9 g) obtained in Example 63 and methylene chloride (70 ml) were added t-butanol (20 ml), N,N-dimethylaminopyridine (2.63 g) and 1-ethyl-3-(3-dimethylaminopropyl)carbodiimide hydrochloride (4.9 g) and the resulting mixture was stirred at room temperature for 4 days. The reaction mixture was diluted with ethyl acetate and washed successively with 2 N HCl and a saturated aqueous sodium chloride solution; the organic layer was dried with anhydrous sodium sulfate and the solvent was distilled off under reduced pressure. The resulting residue was purified by silica gel column chromatography (eluent, n-hexane:ethyl acetate=3:1) to give 7.64 g of the titled compound (yield, 97%).

$^1$H-NMR($CDCl_3$) δ: 1.417(9H,s), 1.419(9H,s), 3.08–3.30 (2H,m), 4.45–4.53(1H,m), 5.02–5.11(1H,m), 7.36(2H, d, J=8.6 Hz), 8.16(2H, d, J=8.6 Hz)

FAB-MS(m/z) 367($M^+$+1)

Example 72

Synthesis of 2-t-butoxycarbonylamino-3-(4-aminophenyl)propionic acid t-butyl ester Using the compound obtained in Example 71 as a starting material, the same procedure of Example 2 gave the titled compound (yield, 84%).

$^1$H-NMR(DMSO-$d_6$) δ: 1.36(18H,s), 2.51–2.80(2H,m), 3.88–3.94(1H,m), 4.58–4.80(2H,m), 6.48(2H, d, J=7.9 Hz), 6.86(2H, d, J=7.9 Hz)

FAB-MS(m/z) 337($M^+$+1)

Example 73

Synthesis of 2-t-butoxycarbonylamino-3-(4-thioureidophenyl)propionic acid t-butyl ester Using the compound obtained in Example 72 as a starting material, the same procedure of Example 3 gave the titled compound quantitatively.

$^1$H-NMR($CDCl_3$) δ: 1.41(9H,s), 1.42(9H,s), 2.96–3.14 (2H,m), 4.22–4.46(1H,m), 5.16(1H, d, J=7.3 Hz), 6.40(2H, brs), 7.18(2H, d, J=8.3 Hz), 7.24(2H, d, J=8.3 Hz), 8.70(1H, brs)

FAB-MS(m/z) 396($M^+$+1)

Example 74

Synthesis of 2-t-butoxycarbonylamino-3-(4-(S-methylisothioureido)phenyl)propionic acid t-butyl ester hydroiodide Using the compound obtained in Example 73 as a starting material, the same procedure of Example 4 gave the titled compound (yield, 99%).

$^1$H-NMR($CDCl_3$) δ: 1.42(18H,s), 2.76(3H,s), 2.99–3.16 (2H,m), 4.42–4.45(1H,m), 5.07(1H, d, J=7.9 Hz), 7.26(4H, s), 8.55(2H,br)

FAB-MS(m/z) 410($M^+$+1)

Example 75

Synthesis of 2-amino-3-(4-(S-methylisothioureido) phenyl)propionic acid dihydrochloride Using the compound obtained in Example 74 as a starting material, the same procedure of Example 5 gave the titled compound (yield, 91%).

$^1$H-NMR($D_2O$) δ: 2.69(3H,s), 3.23–3.36(2H,m), 4.21–4.26(1H,m), 7.37(2H, d, J=8.6 Hz), 7.46(2H, d, J=8.6 Hz)

MS(m/z) 253($M^+$)

Example 76

Synthesis of 2-t-butoxycarbonylamino-3-(4-(N'-nitroguanidino)phenyl)propionic acid t-butyl ester Using the compound obtained in Example 72 as a starting material, the same procedure of Example 6 gave the titled compound (yield, 67%).

$^1$H-NMR(DMSO-$d_6$) δ: 1.36(9H,s), 1.39(9H,s), 2.80–2.98(2H,m), 4.02–4.07(1H,m), 7.10(1H, d, J=7.9 Hz), 7.19–7.26(4H,m), 8.14(1H,brs), 9.49(1H,s)

FAB-MS(m/z) 424($M^+$+1)

Example 77

Synthesis of 2-amino-3-(4-(N'-nitroguanidino) phenyl)propionic acid hydrochloride Using the compound obtained in Example 76 as a starting material, the same procedure of Example 5 gave the titled compound quantitatively.

$^1$H-NMR(DMSO-$d_6$+$D_2O$) δ: 3.05–3.22(2H,m), 4.12–4.17(1H,m), 7.25–7.33(4H,m)

FAB-MS(m/z) 268($M^+$+1)

Example 78

Synthesis of 2-t-butoxycarbonylamino-2-(4-aminophenyl)acetic acid methyl ester

To a mixture of 4-nitrophenylacetic acid (2.0 g), benzene (40 ml) and N-bromosuccinimide (3.3 g), 2,2'-azobis(2-methylpropionitrile)(0.16 g) was added and heated under reflux for 22 h. The reaction mixture was diluted with ethyl acetate and washed successively with 2 N HCl and water; the organic layer was dried with anhydrous sodium sulfate and the solvent was distilled off under reduced pressure. The residue was purified by silica gel column chromatography (eluent, n-hexane:ethyl acetate:acetic acid=75:25:1) to give 2-bromo-2-(4-nitrophenyl)acetic acid. The resulting bromo compound was mixed with 28% aqueous ammonia solution (5 ml) and stirred at room temperature for 2 h. The reaction mixture was concentrated under reduced pressure; to the resulting residue, 1 N aqueous sodium hydroxide solution (20 ml), 1,4-dioxane (10 ml) and di-t-butyl dicarbonate (7.2 g) were added and stirred at room temperature for 2 h. The reaction mixture was concentrated under reduced pressure and the resulting residue was dissolved in a mixture of methanol (20 ml) and diethyl ether (10 ml); a solution of trimethylsilyldiazomethane (2.0 M) in n-hexane was added until the reaction mixture no longer foamed; the reaction mixture was then concentrated under reduced pressure. The residue was purified by silica gel column chromatography (eluent, n-hexane:ethyl acetate=3:1) to give 2-t-butoxycarbonylamino-2-(4-nitrophenyl)acetic acid methyl ester. The resulting methyl ester compound was worked up as in Example 2 to give 0.77 g of the titled compound (yield, 25%).

$^1$H-NMR($CDCl_3$) δ: 1.42(9H,s), 3.68(3H,s), 3.75(2H, brs), 5.16(1H, d, J=6.9 Hz), 5.45–5.56(1H,m), 6.60(2H, d, J=8.6 Hz), 7.10(2H, d, J=8.6 Hz)

MS(m/z) 280($M^+$)

Example 79

Synthesis of 2-t-butoxycarbonylamino-2-(4-thioureidophenyl)acetic acid methyl ester Using the compound obtained in Example 78 as a starting material, the same procedure of Example 3 gave the titled compound (yield, 43%).

$^1$H-NMR($CDCl_3$) δ: 1.42(9H,s), 3.73(3H,s), 5.25–5.38 (1H,m), 5.73–5.90(1H,m), 6.41(2H,brs), 7.23(2H, d, J=8.3 Hz), 7.42(2H, d, J=8.3 Hz), 8.70(1H,brs)

MS(m/z) 339($M^+$)

Example 80

Synthesis of 2-t-butoxycarbonylamino-2-(4-(S-methylisothioureido)phenyl)acetic acid methyl ester hydroiodide Using the compound obtained in Example 79 as a starting material, the same procedure of Example 4 gave the titled compound (yield, 52%).

$^1$H-NMR($CDCl_3$) δ: 1.43(9H,s), 2.70(3H,s), 3.73(3H,s), 5.30–5.34(1H,m), 5.73–5.77(1H,m), 7.27(2H, d, J=8.3 Hz), 7.38–7.60(4H,m)

MS(m/z) 353($M^+$)

Example 81

Synthesis of 2-amino-2-(4-(S-methylisothioureido) phenyl)acetic acid methyl ester dihydrochloride Using the compound obtained in Example 80 as a starting material, the same procedure of Example 5 gave the titled compound (yield, 88%).

$^1$H-NMR($D_2O$) δ: 2.71(3H,s), 3.85(3H,s), 5.40(1H,s), 7.52(2H, d, J=8.6 Hz), 7.64(2H, d, J=8.6 Hz)

MS(m/z) 253($M^+$)

Example 82

Synthesis of N-(4-aminophenylmethyl)carbamic acid t-butyl ester

Sodium hydroxide (1.77 g) was added to a mixture of N-(4-aminophenylmethyl)amine (3.0 g) and water (30 ml) under cooling with ice and stirred for 5 min under cooling with ice; thereafter, di-t-butyl dicarbonate (4.88 g) was added to the reaction mixture under cooling with ice and stirred for 10 h at room temperature. The precipitate that occurred during the reaction was collected by filtration to give 5.83 g of the titled compound (yield, 92%).

$^1$H-NMR($CDCl_3$) δ: 1.45(9H,s), 3.64(2H,brs), 4.18(2H, d, J=5.5 Hz), 6.64(2H, d, J=8.5 Hz), 7.07(2H, d, J=8.5 Hz)

Example 83

Synthesis of N-(4-(N'-cyclopropylguanidino) phenylmethyl)carbamic acid t-butyl ester The compound (0.946 g) obtained in Example 82 was added to a mixture of N-cyclopropyl-S-methylisothiourea hydroiodide (1.0 g) and pyridine (10 ml) and heated under reflux for 2 days. The reaction mixture was concentrated under reduced pressure and the residue was purified by silica gel column chromatography (eluent, n-hexane:ethyl acetate=2:1) to give 0.131 g of the titled compound (yield, 12%).

$^1$H-NMR($CD_3OD$) δ: 0.61–0.65(2H,m), 0.76–0.86(2H, m), 1.44(9H,s), 2.72–2.86(1H,m), 4.18–4.24(2H,m), 7.23–7.34(4H,m)

Example 84

Synthesis of N-(4-(N'-cyclopropylguanidino) phenylmethyl)amine

Using the compound obtained in Example 83 as a starting material, the same procedure of Example 34 gave the titled compound (yield, 53%).

$^1$H-NMR($CD_3OD$) δ: 0.58–0.65(2H,m), 0.73–0.86(2H, m), 2.72–2.88(1H,m), 3.76(2H,s), 7.30(2H, d, J=8.6 Hz), 7.35(2H, d, J=8.6 Hz)

Example 85

Synthesis of N-(4-(N'-nitroguanidino)phenylmethyl) carbamic acid t-butyl ester

Using the compound obtained in Example 82 as a starting material, the same procedure of Example 6 gave the titled compound (yield, 56%).

$^1$H-NMR($CD_3OD$) δ: 1.44(9H,s), 4.22(2H,s), 7.27(2H, d, J=8.5 Hz), 7.34(2H, d, J=8.5 Hz)

Example 86

Synthesis of N-(4-(N'-nitroguanidino)phenylmethyl) amine

Using the compound obtained in Example 85 as a starting material, the same procedure of Example 34 gave the titled compound (yield, 75%).

$^1$H-NMR ($CD_3OD$) δ: 4.12(2H,s), 7.41(2H, d, J=8.6 Hz), 7.49(2H, d, J=8.6 Hz)

Example 87

Synthesis of N-(3-(N'-cyclopropylguanidino) phenylmethyl)carbamic acid t-butyl ester Using the compound obtained in Example 23 as a starting material, the same procedure of Example 83 gave the titled compound (yield, 8.8%).

$^1$H-NMR($CDCl_3$) δ: 0.62–0.76(2H,m), 0.80–0.95(2H,m), 1.46(9H,s), 2.73–2.92(1H,m), 4.30(2H, d, J=5.5 Hz), 4.93–5.07(1H,m), 6.52(1H,brs), 7.12–7.39(4H,m), 7.98(1H, brs)

Example 88

Synthesis of N-(3-(N'-cyclopropylguanidino) phenylmethyl)amine

Using the compound obtained in Example 87 as a starting material, the same procedure of Example 34 gave the titled compound (yield, 51%).

$^1$H-NMR($CD_3OD$) δ: 0.61–0.69(2H,m), 0.80–0.87(2H, m), 2.72–2.90(1H,m), 3.77(2H,s), 7.13–7.35(4H,m)

Example 89

Synthesis of N-(3-(N'-cyclopropylguanidinomethyl) phenyl)N'-nitroguanidine

Using the compound obtained in Example 34 as a starting material, the same procedure of Example 83 gave the titled compound (yield, 22%).

$^1$H-NMR($CD_3OD$) δ: 0.57–0.62(2H,m), 0.78–0.84(2H, m), 2.52–2.68(1H,m), 4.86(2H,s), 7.18–7.40(4H,m)

Example 90

Synthesis of N-(3-(N'-nitroguanidinomethyl) phenyl)-N'-nitroguanidine

Using the compound obtained in Example 34 as a starting material and also using N-methyl-N'-nitro-N-nitrosoguanidine as a reagent, reaction was performed as in Example 83 to give the titled compound (yield, 25%).

$^1$H-NMR($CD_3OD$) δ: 4.50(2H,s), 7.20–7.22(1H,m), 7.32–7.43(3H,m)

Example 91

Synthesis of N-(3-(S-n-propylisothioureido) phenylmethyl)carbamic acid t-butyl ester Using the compound obtained in Example 24 as a starting material and also using n-propyl iodide as a reagent, reaction was performed as in Example 29 to give 227 mg of the titled compound (yield, 99%).

$^1$H-NMR($CDCl_3$) δ: 1.04(3H, t, J=7.3 Hz), 1.46(9H,s), 1.68–1.81(2H,m), 3.10(2H, t, J=7.3 Hz), 4.31(2H, d, J=5.6 Hz), 4.84–4.98(1H,m), 6.98–7.35(4H,m)

FAB-MS(m/z) 324($M^+$+1)

Example 92

Synthesis of N-(3-(S-n-propylisothioureido) phenylmethyl)amine dihydrochloride

Using the compound obtained in Example 91 as a starting material, the same procedure of Example 5 gave 173 mg of the titled compound (yield, 83%).

$^1$H-NMR($D_2O$) δ: 1.05(3H, t, J=7.3 Hz), 1.73–1.87(2H, m), 3.22(2H, t, J=7.3 Hz), 4.25(2H,s), 7.43–7.66(4H,m)

FAB-MS(m/z) 224($M^+$+1)

Example 93

Synthesis of N-(3-(S-n-butylisothioureido) phenylmethyl)carbamic acid t-butyl ester Using the compound obtained in Example 24 as a starting material and also using n-butyl iodide as a reagent, reaction was performed as in Example 29 to give 220 mg of the titled compound (yield, 92%).

$^1$H-NMR($CDCl_3$) δ: 0.94(3H, t, J=7.3 Hz), 1.39–1.53(2H, m), 1.46(9H,s), 1.64–1.75(2H,m), 3.14(2H, t, J=7.3 Hz), 4.31(2H, d, J=5.6 Hz), 4.82–4.98(1H,m), 7.02–7.36(4H,m)

FAB-MS(m/z) 338($M^+$+1)

Example 94

Synthesis of N-(3-(S-n-butylisothioureido) phenylmethyl)amine dihydrochloride

Using the compound obtained in Example 93 as a starting material, the same procedure of Example 5 gave 194 mg of the titled compound (yield, 96%).

$^1$H-NMR($D_2O$) δ: 0.93(3H, t, J=7.3 Hz), 1.40–1.53(2H, m), 1.70–1.80(2H,m), 3.23(2H, t, J=7.3 Hz), 4.24(2H,s), 7.43–7.65(4H,m)

FAB-MS(m/z) 238($M^+$+1)

Example 95

Synthesis of N-(1-methyl-1-(3-(S-ethylisothioureido)phenyl)ethyl)carbamic acid t-butyl ester Using the compound obtained in Example 3 as a starting material and also using ethyl iodide as a reagent, reaction was performed as in Example 29 to give 110 mg of the titled compound (yield, 97%).

$^1$H-NMR($CDCl_3$) δ: 1.37(9H,s), 1.37(3H, t, J=7.3 Hz), 1.60(6H,s), 3.04(2H, q, J=7.3 Hz), 4.92(1H,brs), 6.77–7.28 (4H,m)

MS(m/z) 337($M^+$)

Example 96

Synthesis of N-(1-methyl-1-(3-(S-ethylisothioureido)phenyl)ethyl)amine dihydrochloride Using the compound obtained in Example 95 as a starting material, the same procedure of Example 5 gave 72 mg of the titled compound (yield, 71%).

$^1$H-NMR($D_2O$) δ: 1.42(3H, t, J=7.3 Hz), 1.77(6H,s), 3.24(2H, q, J=7.3 Hz), 7.37–7.68(4H,m)

MS(m/z) 237($M^+$)

Example 97

Synthesis of N-(4-nitrophenylethyl)dimethylamine

Using the p-nitrophenethyl bromide as a starting material and also using sodium bicarbonate as a base, the same procedure of Example 37 gave 2.3 g of the titled compound (yield, 54%).

$^1$H-NMR($CDCl_3$) δ: 2.30(6H,s), 2.56(2H, t, J=7.3 Hz), 2.89(2H, t, J=7.3 Hz), 7.37(2H, d, J=8.9 Hz), 8.14(2H, d, J=8.9 Hz),

MS(m/z) 194($M^+$)

Example 98

Synthesis of N-(4-aminophenylethyl)dimethylamine dihydrochloride

Using the compound obtained in Example 97 as a starting material and after adding a solution of hydrogen chloride (4N) in 1,4-dioxane, the same procedure of Example 2 gave 2.37 g of the titled compound (yield, 85%).

$^1$H-NMR($CDCl_3$) δ: 2.27(6H,s), 2.55(2H, t, J=6.9 Hz), 2.80(2H, t, J=6.9 Hz), 7.23(2H, d, J=8.3 Hz), 7.31(2H, d, J=8.3 Hz),

MS(m/z) 164($M^+$)

Example 99

Synthesis of N-(4-(N'-nitroguanidino)phenylethyl)dimethylamine

Using the compound obtained in Example 98 as a starting material and after dissolving it in a solvent system consisting of acetonitrile and methanol, the same procedure of Example 6 gave 45 mg of the titled compound (yield, 30%).

$^1$H-NMR($CDCl_3$) δ: 2.28(6H,s), 2.43–2.49(2H,m), 2.64–2.69(2H,m), 6.61(2H, d, J=8.2 Hz), 6.98(2H, d, J=8.2 Hz)

MS(m/z) 219($M^+$−32)

Example 100

Synthesis of N-(4-thioureidophenylethyl)dimethylamine

Using the compound obtained in Example 98 as a starting material, the same procedure of Example 3 gave 1.46 g of the titled compound (yield, 99%).

$^1$H-NMR($CDCl_3$) δ: 2.29(6H,s), 2.54(2H, t, J=6.9 Hz), 2.80(2H, t, J=6.9 Hz), 6.04(2H,brs), 7.15(2H, d, J=8.6 Hz), 7.28(2H, d, J=8.6 Hz), 7.85(1H,brs)

MS(m/z) 223($M^+$)

Example 101

Synthesis of N-(4-(S-methylisothioureido)phenylethyl)dimethylamine monohydrochloride mononitrate Using the compound obtained in Example 100 as a starting material, the same procedure of Example 41 gave 0.18 g of the titled compound (yield, 99%).

$^1$H-NMR(DMSO-$d_6$) δ: 2.68(3H,s), 2.86(6H,s), 2.99–3.05(2H,m), 3.17–3.44(2H,m), 7.31(2H, d, J=8.3 Hz), 7.43(2H, d, J=8.3 Hz), 9.27(1H,brs), 9.69(1H,brs), 11.22 (1H,brs)

MS(m/z) 237($M^+$)

Example 102

Synthesis of N-(4-(S-ethylthioureido)phenylethyl)dimethylamine monohydrochloride mononitrate Using the compound obtained in Example 100 as a starting material and also using ethyl iodide as a reagent, the same procedure of Example 41 gave 107 mg of the titled compound (yield, 48%).

$^1$H-NMR(DMSO-$d_6$) δ: 1.22(3H, t, J=7.3 Hz), 2.27(6H, s), 2.50–2.60(2H,m), 2.64–2.85(2H,m), 2.89(2H, q, J=7.3 Hz), 6.74(2H, d, J=7.9 Hz), 7.07(2H, d, J=7.9 Hz)

MS(m/z) 251($M^+$)

Example 103

Synthesis of N-(4-(S-ethylisothioureido)phenylethyl)carbamic acid t-butyl ester

Using the compound obtained in Example 50 as a starting material and also using ethyl iodide as a reagent, the same procedure of Example 29 gave the titled compound (yield, 85%).

$^1$H-NMR(DMSO-$d_6$) δ: 1.22(3H, t, J=7.3 Hz), 1.38(9H, s), 2.58–2.65(2H,m), 2.90(2H, q, J=7.3 Hz), 3.06–3.15(2H, m), 6.21–6.58(1H,brs), 6.68–6.84(2H,m), 7.05(2H, d, J=8.3 Hz)

MS(m/z) 323($M^+$)

Example 104

Synthesis of N-(4-(S-ethylisothioureido)phenylethyl)amine dihydrochloride

Using the compound obtained in Example 103 as a starting material, the same procedure of Example 5 gave the titled compound (yield, 93%).

$^1$H-NMR($D_2O$) δ: 1.41(3H, t, J=7.3 Hz), 3.02–3.10(2H, m), 3.18–3.34(4H,m), 7.36(2H, d, J=8.3 Hz), 7.47(2H, d, J=8.3 Hz)

FAB-MS(m/z) 224($M^+$+1)

Example 105

Synthesis of N-(1-(3-nitrophenyl)ethyl)methylamine

Using 3'-nitroacetophenone as a starting material, the same procedure of Example 42 gave 4.14 g of the titled compound (yield, 80%).

$^1$H-NMR($CDCl_3$) δ: 1.38(3H, d, J=6.8 Hz), 2.32(3H,s), 3.79(1H, q, J=6.8 Hz), 7.51(1H, dd, J=7.8,7.8 Hz), 7.69–7.74(1H,m), 8.03–8.14(1H,m), 8.17–8.26(1H,m)

Example 106

Synthesis of N-(1-(3-nitrophenyl)ethyl) methylcarbamic acid t-butyl ester

Using the compound obtained in Example 105 as a starting material, the same procedure of Example 22 gave the titled compound quantitatively.

$^1$H-NMR($CDCl_3$) δ: 1.49(9H,s), 1.55(3H, d, J=5.8 Hz), 2.64(3H,s), 5.34–5.71(1H,m), 7.43–7.69(2H,m), 8.07–8.20 (2H,m)

Example 107

Synthesis of N-(1-(3-aminophenyl)ethyl) methylcarbamic acid t-butyl ester

Using the compound obtained in Example 106 as a starting material, the same procedure of Example 2 gave the titled compound (yield, 86%).

$^1$H-NMR ($CDCl_3$) δ: 1.44(3H, d, J=6.9 Hz), 1.49(9H,s), 2.58(3H,s), 3.53–3.75(2H,m), 5.37–5.59(1H,m), 6.55–6.87 (3H,m), 7.11(1H, dd, J=8.2, 7.6 Hz)

Example 108

Synthesis of N-(1-(3-thioureidophenyl)ethyl) methylcarbamic acid t-butyl ester

Using the compound obtained in Example 107 as a starting material, the same procedure of Example 3 gave the titled compound quantitatively.

$^1$H-NMR($CDCl_3$) δ: 1.39–1.55(12H,m), 2.61(3H,s), 5.30–5.50(1H,m), 6.32(2H,brs), 7.11–7.22(3H,m), 7.38(1H, dd, J=8.2, 7.9 Hz), 8.72(1H,brs)

MS(m/z) 309($M^+$)

Example 109

Synthesis of N-(1-(3-(S-methylisothioureido) phenyl)ethyl)methylcarbamic acid t-butyl ester hydroiodide Using the compound obtained in Example 108 as a starting material, the same procedure of Example 4 gave the titled compound (yield, 87%).

$^1$H-NMR($CDCl_3$) δ: 1.44–1.53(12H,m), 2.61(3H,s), 2.77 (3H,s), 5.26–5.57(1H,m), 7.14–7.57(4H,m), 8.51(2H,br)

Example 110

Synthesis of N-(1-(3-(S-methylisothioureido) phenyl)ethyl)methylamine dihydrochloride Using the compound obtained in Example 109 as a starting material, the same procedure of Example 5 gave the titled compound quantitatively.

$^1$H-NMR($D_2O$) δ: 1.71(3H, d, J=6.8 Hz), 2.63(3H,s), 2.72(3H,s), 4.45(1H, q, J=6.8 Hz), 7.34–7.84(4H,m)

MS(m/z) 223($M^+$)

Example 111

Synthesis of N-(1-(3-(S-ethylisothioureido)phenyl) ethyl)methylcarbamic acid t-butyl ester hydroiodide Using the compound obtained in Example 108 as a starting material, the same procedure of Example 27 gave the titled compound (yield, 83%).

$^1$H-NMR($CDCl_3$) δ: 1.40(3H, t, J=7.3 Hz), 1.43–1.61 (12H,m), 2.62(3H,s),3.35(2H, q, J=7.3 Hz), 5.29–5.56(1H, m), 7.16–7.28(2H,m), 7.28–7.34(1H,m), 7.35–7.43(1H,m), 8.17(2H,br)

Example 112

Synthesis of N-(1-(3-(S-ethylisothiourido)phenyl) ethyl)methylamine dihydrochloride Using the compound obtained in Example 111 as a starting material, the same procedure of Example 5 gave the titled compound (yield, 98%).

$^1$H-NMR($D_2O$) δ: 1.43(3H, t, J=7.3 Hz), 1.70(3H, d, J=6.8 Hz), 2.63(3H,s), 3.25(2H, q, J=7.3 Hz), 4.44(1H, q, J=6.8 Hz), 7.40–7.74(4H,m)

MS(m/z) 237($M^+$)

Example 113

Synthesis of N-(1-(3-(N'-nitroguanidino)phenyl) ethyl)methylcarbamic acid t-butyl ester Using the compound obtained in Example 107 as a starting material, the same procedure of Example 6 gave the titled compound (yield, 61%).

$^1$H-NMR($CDCl_3$) δ: 1.43–1.48(12H,m), 2.56(3H,s), 3.52–3.82(1H,m), 6.52–6.68(3H,m), 7.10(1H, dd, J=8.2, 7.6 Hz)

Example 114

Synthesis of N-(1-(3-(N'-nitroguanidino)phenyl) ethyl)methylamine

Using the compound obtained in Example 113 as a starting material, the same procedure of Example 55 gave the title compound (yield, 29%).

$^1$H-NMR($CDCl_3$) δ: 1.33(3H, d, J=6.8 Hz), 2.31(3H,s), 3.54(1H, q, J=6.8 Hz), 6.49–6.73(3H,m), 7.11(1H, dd, J=7.8, 7.3 Hz)

MS(m/z) 237($M^+$)

Example 115

Synthesis of N-(3-(S-methylisothioureido) phenylmethyl)methylcarbamic acid t-butyl ester hydroiodide Using the compound obtained in Example 45 as a starting material, the same procedure of Example 4 gave the titled compound (yield, 56%).

$^1$H-NMR($CDCl_3$) δ: 1.47(9H,s), 2.44(3H,s), 2.81(3H,s), 4.38(2H,s), 6.79–6.83(2H,m), 6.90(1H,d,J=7.6 Hz), 7.25 (1H, dd, J=8.6, 7.6 Hz)

Example 116

Synthesis of N-(3-(S-methylisothioureido) phenylmethyl)methylamine dihydrochloride Using the compound obtained in Example 115 as a starting material, the same procedure of Example 5 gave the titled compound (yield, 56%).

$^1$H-NMR($D_2O$) δ: 2.70(3H,s), 2.75(3H,s), 4.28(2H,s), 7.40–7.71(4H,m)

Example 117

Synthesis of N-(2-methoxy-5-nitrophenylmethyl) phthalimide

Potassium phthalimide (836 mg) was added to a solution of 2-methoxy-5-nitrobenzyl bromide (1.01 g) in dimethylformamide (41 ml) and stirred at room temperature for 10 minutes. Water and 2 N HCl were added to the reaction mixture and extraction was performed with ethyl acetate; then, the organic layer was washed successively with a saturated aqueous sodium bicarbonate solution and a saturated aqueous sodium chloride solution, dried with anhydrous sodium sulfate and concentrated under reduced pressure. The resulting residue was washed successively with ethyl acetate and hexane to give 1.2 g of the titled compound (yield, 94%).

$^1$H-NMR(DMSO-$d_6$) δ: 3.97(3H,s), 4.80(2H,s), 7.26(1H, d, J=9.3 Hz), 7.82–7.93(4H,m), 7.99(1H, d, J=2.9 Hz), 8.40(1H, dd, J=9.3, 2.9 Hz)

Example 118

Synthesis of N-(2-methoxy-5-nitrophenylmethyl) carbamic acid t-butyl ester

To a mixture of the compound (357 mg) obtained in Example 117 and methanol (10 ml), hydrazine monohydrate (0.06 ml) was added and stirred at room temperature for 3 h. The reaction mixture was made acidic by addition of 2 N HCl and washed with ethyl acetate. The aqueous layer was made alkaline by addition of a 2 N aqueous sodium hydroxide solution and extracted with ethyl acetate; then, the organic layer was washed successively with water and a saturated aqueous sodium chloride solution, dried with anhydrous sodium sulfate and concentrated under reduced pressure. To a solution of the resulting residue in dimethylformamide (10 ml), di-t-butyl dicarbonate (274 mg) and triethylamine (0.17 ml) were added and stirred at room temperature for 3 h. Water and 2 N HCl were added to the reaction mixture and extraction was performed with ethyl acetate; then, the organic layer was washed successively with water and a saturated aqueous sodium chloride solution, dried with anhydrous sodium sulfate and concentrated under reduced pressure. The resulting residue was purified by silica gel column chromatography (eluent, n-hexane:ethyl acetate=1:1) to give 62 mg of the titled compound (yield, 20%).

$^1$H-NMR($CDCl_3$) δ: 1.47(9H,s), 3.96(3H,s), 4.23–4.40 (2H,m), 4.80–5.09(1H,m), 6.92(1H, d, J=9.3 Hz), 8.16–8.20 (2H,m)

Example 119

Synthesis of N-(5-amino-2-methoxyphenylmethyl) carbamic acid t-butyl ester

Using the compound obtained in Example 118 as a starting material, the same procedure of Example 2 gave the titled compound (yield, 95%)

$^1$H-NMR($CDCl_3$) δ: 1.44(9H,s), 3.34(2H,br), 3.76(3H,s), 4.22(2H, d, J=5.9 Hz), 4.80–5.19(1H,m), 6.57(1H, dd, J=8.6, 3.0 Hz), 6.64–6.82(2H,m)

Example 120

Synthesis of N-(2-methoxy-5-thioureidophenylmethyl)carbamic acid t-butyl ester

To a mixture of the compound (52 mg) obtained in Example 119 and N,N-dimethylaminopyridine (53 mg) in methylene chloride (5 ml), thiophosgene (0.02 ml) was added dropwise and stirred at room temperature for 15 min. To the reaction mixture, 28% aqueous ammonia solution (5 ml) was added and stirred at room temperature for 1.5 h. After neutralization with 2 N HCl, the reaction mixture was extracted with methylene chloride and the organic layer was washed successively with water and a saturated aqueous sodium chloride solution, dried with anhydrous sodium sulfate and concentrated under reduced pressure. The resulting residue was purified by silica gel column chromatography (eluent, ethyl acetate) to give 58 mg of the titled compound (yield, 91%).

$^1$H-NMR($CDCl_3$) δ: 1.44(9H,s), 3.86(3H,s), 4.27(2H, d, J=6.3 Hz), 4.90–5.05(1H,m), 5.95(2H,brs), 6.88(1H, d, J=8.6 Hz), 7.09–7.16(2H,m), 7.66(1H,brs)

Example 121

Synthesis of N-(5-(S-ethylisothioureido)-2-methoxyphenylmethyl)carbamic acid t-butyl ester hydroiodide Using the compound obtained in Example 120 as a starting material, the same procedure of Example 27 gave the titled compound (yield, 90%).

$^1$H-NMR($CDCl_3$) δ: 1.38(3H, t, J=7.3 Hz), 1.45(9H,s), 3.30(2H, q, J=7.3 Hz), 3.86(3H,s), 4.18–4.31(2H,m), 5.00–5.15(1H,m), 6.89(1H, d, J=9.3 Hz), 7.14–7.26(2H,m)

MS(m/z) 339 ($M^+$)

Example 122

Synthesis of N-(5-(S-ethylisothioureido)-2-methoxyphenylmethyl)amine dihydrochloride Using the compound obtained in Example 121 as a starting material, the same procedure of Example 5 gave the titled compound quantitatively.

$^1$H-NMR($D_2O$) δ: 1.41(3H, t, J=7.3 Hz), 3.23(2H, q, J=7.3 Hz), 3.95(3H,s), 4.22(2H,s), 7.22(1H, d, J=8.9 Hz), 7.35(1H, d, J=2.6 Hz), 7.44(1H, dd, J=8.9, 2.6 Hz)

MS(m/z) 178 ($M^+$−61)

Example 123

Synthesis of N-(3-nitrophenylmethyl acetamide

Acetic anhydride (0.08 ml) was added dropwise to a solution of 3-nitrobenzylamine hydrochloride (139 mg) and triethylamine (0.22 ml) in methylene chloride (10 ml) and stirred at room temperature for 2 h. To the reaction mixture, 2 N HCl was added and extraction was performed with methylene chloride; then, the organic layer was washed successively with water and a saturated aqueous sodium chloride solution, dried with anhydrous sodium sulfate and concentrated under reduced pressure. The resulting residue was purified by silica gel column chromatography (eluent: ethyl acetate) to give 102 mg of the titled compound (yield, 71%).

$^1$H-NMR($CDCl_3$) δ: 2.03(3H,s), 4.51(2H, d, J=5.8 Hz), 6.43–6.86(1H,m), 7.48(1H, dd, J=7.8, 6.8 Hz), 7.63(1H, d, J=7.8 Hz), 8.07–8.11(1H,m)

Example 124

Synthesis of N-(3-aminophenylmethyl)acetamide

Using the compound obtained in Example 123 as a starting material, the same procedure of Example 2 gave the titled compound (yield, 69%).

$^1$H-NMR($CDCl_3$) δ: 1.97(3H,s), 3.70(2H,brs), 4.28(2H, d, J=5.9 Hz), 6.00–6.28(1H,m), 6.48–6.68(3H,m), 7.00–7.14(1H,m)

Example 125

Synthesis of N-(3-thioureidophenylmethyl) acetamide

Using the compound obtained in Example 124 as a starting material, the same procedure of Example 120 gave the titled compound quantitatively.

$^1$H-NMR($CDCl_3$) δ: 1.98(3H,s), 4.33(2H, d, J=5.8 Hz), 6.94(2H,brs), 7.00–7.14(1H,m), 7.20–7.37(3H,m), 7.71–7.91(1H,m), 9.49(1H,brs)

Example 126

Synthesis of N-(3-(S-ethylisothioureido) phenylmethyl)acetamide hydroiodide

Using the compound obtained in Example 124 as a starting material, the same procedure of Example 27 gave the titled compound (yield, 67%).

$^1$H-NMR(DMSO-$d_6$) δ: 1.33(3H, t, J=7.3 Hz), 1.89(3H, s), 3.31(2H, q, J=7.3 Hz), 4.30(2H, d, J=5.9 Hz), 7.19–7.22 (2H,m), 7.29(1H, d, J=7.6 Hz), 7.46(1H, dd, J=7.6, 7.6 Hz), 8.30–8.50(1H,m), 9.33(2H,br)

MS(m/z) 251($M^+$)

Example 127

Synthesis of N-(2-methyl-3-nitrophenylmethyl) iminodicarboxylic acid di-t-butyl ester A solution of 2-methyl-3-nitrobenzyl chloride (1.07 g) in dimethylformamide (30 ml) was added dropwise to a solution of di-t-butyl iminodicarboxylate (1.38 g) and sodium hydride (content, 60%; 0.30 g) in dimethylformamide (30 ml) at 0° C. Following 1-h stirring at room temperature, the temperature of the mixture was raised to 80° C. and stirred for 1 h. The reaction mixture was concentrated under reduced pressure, water was added to the residue, and the mixture was extracted with ethyl acetate. The organic layer was washed with a saturated aqueous sodium chloride solution, dried with anhydrous sodium sulfate and concentrated under reduced pressure. The resulting residue was purified by silica gel column chromatography (eluent, n-hexane:ethyl acetate=10:1) to give 1.49 g of the titled compound (yield, 96%).

$^1$H-NMR($CDCl_3$) δ: 1.46(9H,s), 1.48(9H,s), 2.43(3H,s), 4.37–4.41(2H,m), 7.30(1H, dd, J=8.1, 8.0 Hz), 7.51(1H, d, J=8.0 Hz), 7.69(1H, d, J=8.1 Hz)

Example 128

Synthesis of N-(3-amino-2-methylphenylmethyl) carbamic acid t-butyl ester

Using the compound obtained in Example 127 as a starting material, the same procedure of Example 2 gave the titled compound (yield, 74%).

$^1$H-NMR($CDCl_3$) δ1.46(9H,s), 2.11(3H,s), 3.62(2H,brs), 4.29(2H, d, J=5.3 Hz), 4.55–4.78(1H,m), 6.63–6.71(2H,m), 6.99(1H, dd, J=7.9, 7.6 Hz)

MS(m/z) 236($M^+$)

Example 129

Synthesis of N-(2-methyl-3-thioureidophenylmethyl)carbamic acid t-butyl ester Using the compound obtained in Example 128 as a starting material, the same procedure of Example 120 gave the titled compound (yield, 88%).

$^1$H-NMR($CDCl_3$) δ: 1.46(9H,s), 2.27(3H,s), 4.34(2H, d, J=5.6 Hz), 4.71–4.94(1H,m), 5.83(2H,br), 7.15–7.30(5H, m), 7.71(1H,brs)

Example 130

Synthesis of N-(3-(S-ethylisothioureido)-2-methylphenylmethyl)carbamic acid t-butyl ester hydroiodide Using the compound obtained in Example 129 as a starting material, the same procedure of Example 27 gave the titled compound (yield, 89%).

$^1$H-NMR($CDCl_3$) δ: 1.40(3H, t, J=7.8 Hz), 1.47(9H,s), 2.32(3H,s), 3.27(2H, q, J=7.8 Hz), 4.36(2H, d, J=5.7 Hz), 4.66–4.86(1H,m), 7.19–7.37(3H,m)

Example 131

Synthesis of N-(3-(S-ethylisothioureido)-2-methylphenylmethyl)amine dihydrochloride Using the compound obtained in Example 130 as a starting material, the same procedure of Example 5 gave the titled compound (yield, 66%).

$^1$H-NMR($D_2O$) δ: 1.43(3H, t, J=7.6 Hz), 2.29(3H,s), 3.25(2H, q, J=7.6 Hz), 4.31(2H,s), 7.37–7.54(3H,m)

MS(m/z) 223($M^+$)

Example 132

Synthesis of (2-chloro-3-nitrophenyl)methanol

A borane-tetrahydrofuran complex (1.0 M, 20 ml) was added dropwise to a solution of 2-chloro-3-nitrobenzoic acid (5.0 g) in anhydrous tetrahydrofuran (30 ml) in a nitrogen atmosphere and the mixture was heated under reflux for 16 h. Water was added to the reaction mixture which was extracted with ethyl acetate; the organic layer was washed successively with a saturated aqueous sodium bicarbonate solution and a saturated aqueous sodium chloride solution, dried with anhydrous-sodium sulfate and concentrated under reduced pressure. The resulting residue was purified by silica gel column chromatography (eluent, n-hexane:ethyl acetate=5:2) to give 3.5 g of the titled compound (yield, 84%).

$^1$H-NMR($CDCl_3$) δ: 2.04(1H, t, J=5.9 Hz), 4.88(2H, d, J=5.9 Hz), 7.45(1H, dd, J=7.9, 7.9 Hz), 7.72–7.82(2H,m)

Example 133

Synthesis of N-(2-chloro-3-nitrophenylmethyl) iminodicarboxylic acid di-t-butyl ester A mixture of the compound (1.01 g) obtained in Example 132 and thionyl chloride (50 ml) was heated under reflux for 48 h. The reaction mixture was concentrated under reduced pressure; the resulting residue was dissolved in dimethylformamide (25 ml) and added dropwise to a solution of sodium hydride (content, 60%; 0.24 g) and di-t-butyl iminodicarboxylate (1.29 g) in dimethylformamide (25 ml) at 0° C. The reaction mixture was stirred at room temperature for 1 h and stirred at 80° C. for 2 h. Water and 2 N HCl were added to the reaction mixture and extraction was performed with ethyl acetate; then, the organic layer was washed successively with water and a saturated aqueous sodium chloride solution, dried with anhydrous sodium sulfate and concentrated under reduced pressure. The resulting residue was purified by silica gel column chromatography (eluent, n-hexane:ethyl acetate=5:1) to give 1.70 g of the titled compound (yield, 82%).

$^1$H-NMR($CDCl_3$) δ: 1.47(9H,s), 1.48(9H,s), 4.97(2H,s), 7.32–7.42(2H,m), 7.66–7.72(1H,m)

Example 134

Synthesis of N-(3-amino-2-chlorophenylmethyl) iminodicarboxylic acid di-t-butyl ester Using the compound obtained in Example 133 as a starting material, the same procedure of Example 2 gave the titled compound (yield, 67%).

$^1$H-NMR($CDCl_3$) δ: 1.44(9H,s), 1.48(9H,s), 4.10(2H, brs), 4.86(2H,s), 6.53–6.66(2H,m), 7.06(1H, dd, J=8.3, 7.8 Hz)

MS(m/z) 356($M^+$)

Example 135

Synthesis of N-(2-chloro-3-thioureidophenylmethyl) iminodicarboxylic acid di-t-butyl ester Using the compound obtained in Example 134 as a starting material, the same procedure of Example 120 gave the titled compound (yield, 82%).

$^1$H-NMR($CDCl_3$) δ: 1.46(9H,s), 1.47(9H,s), 4.90(2H,s), 6.35(2H,brs), 7.11–7.13(1H,m), 7.31–7.43(2H,m), 8.05(1H, brs)

Example 136

Synthesis of N-(2-chloro-3-(S-ethylisothioureido) phenylmethy)iminodicarboxylic acid di-t-butyl ester hydroiodide Using the compound obtained in Example 135 as a starting material, the same procedure of Example 27 gave the titled compound (yield, 38%).

$^1$H-NMR($CDCl_3$) δ: 1.40(3H, t, J=7.3 Hz), 1.45(18H,s), 3.34(2H, q, J=7.3 Hz), 4.92(2H,s), 7.22–7.36(3H,m)

Example 137

Synthesis of N-(2-chloro-3-(S-ethylisothioureido) phenylmethyl)amine dihydrochloride Using the compound obtained in Example 136 as a starting material, the same procedure of Example 5 gave the titled compound (yield, 97%).

$^1$H-NMR($D_2O$) δ: 1.44(3H, t, J=7.3 Hz), 3.26(2H, q, J=7.3 Hz), 4.42(2H,s), 7.53–7.70(3H,m)

MS(m/z) 243($M^+$)

Example 138

Synthesis of N-(1-(3-nitrophenyl)cyclohexyl) carbamic acid t-butyl ester

Example 138a

Using 3-nitrophenylacetic acid t-butyl ester as a starting material and also using 1,5-diboromopentane (1 eq.) as a reagent, the same procedures of Examples 1a and 1b gave 1-(3-nitrophenyl)cyclohexanecarboxylic acid.

$^1$H-NMR($CDCl_3$) δ: 1.19–1.86(8H,m), 2.49–2.54(2H,m), 7.49–7.81(2H,m), 8.10–8.33(2H,m)

Example 138b

Using 1-(3-nitrophenyl)cyclohexanecarboxylic acid as a starting material, the same procedure of Example 1c gave 110 mg of the titled compound (yield, 28%).

$^1$H-NMR($CDCl_3$) δ: 1.39(9H,s), 1.52–1.82(8H,m), 2.21–2.25(2H,m), 4.94(1H,brs), 7.46–7.77(2H,m), 8.06–8.29(2H,m)

Example 139

Synthesis of N-(1-(3-aminophenyl)cyclohexyl) carbamic acid t-butyl ester

Using the compound obtained in Example 138 as a starting material, the same procedure of Example 2 gave 877 mg of the titled compound (yield, 65%).

$^1$H-NMR($CDCl_3$) δ: 1.38(9H,s), 1.48–1.78(8H,m), 2.08–2.30(2H,m), 3.59(2H,brs), 4.75(1H,brs), 6.52–6.82 (3H,m), 7.06–7.12(1H,m)

Example 140

Synthesis of N-(1-(3-thioureidophenyl)cyclohexyl) carbamic acid t-butyl ester

Using the compound obtained in Example 139 as a starting material, the same procedure of Example 120 gave 224 mg of the titled compound (yield, 93%).

$^1$H-NMR($CDCl_3$) δ: 1.35(9H,s), 1.50–1.81(8H,m), 2.06–2.17(2H,m), 4.93(1H,brs), 6.21(2H,brs), 7.03–7.42 (4H,m), 8.03(1H,brs)

Example 141

Synthesis of N-(1-(3-(S-methylisothioureido) phenyl)cyclohexyl)carbamic acid t-butyl ester Using the compound obtained in Example 140 as a starting material and also using methyl iodide as a reagent, reaction was performed as in Example 29 to give 85 mg of the titled compound (yield, 70%).

$^1$H-NMR($CDCl_3$) δ: 1.36(9H,s), 1.49–1.83(8H,m), 2.15–2.20(2H,m), 2.46(3H,s), 4.55(1H,brs), 4.81(1H,brs), 6.75–7.26(4H,m)

Example 142

Synthesis of N-(1-(3-(S-methylisothioureido) phenyl)cyclohexyl)amine dihydrochloride Using the compound obtained in Example 141 as a starting material, the same procedure of Example 5 gave 74 mg of the titled compound (yield, 94%).

$^1$H-NMR($D_2O$) δ: 1.43–2.02(8H,m), 2.48–2.52(2H,m), 2.69(3H,s), 7.44–7.78(4H,m)

FAB-MS(m/z) 264($M^+$+1)

Example 143

Synthesis of N-(1-(3-(S-ethylisothioureido)phenyl) cyclohexyl)carbamic acid t-butyl ester Using the compound obtained in Example 140 as a starting material, the same procedure of Example 95 gave 108 mg of the titled compound (yield, 93%).

$^1$H-NMR($CDCl_3$) δ: 1.34–1.39(3H,m), 1.37(9H,s), 1.49–1.82(8H,m), 2.15–2.20(2H,m), 2.92–3.20(2H,m), 4.52 (1H,brs), 4.80(1H,brs), 6.75–7.28(4H,m)

Example 144

Synthesis of N-(1-(3-(S-ethylisothioureido)phenyl) cyclohexyl)amine dihydrochloride Using the compound obtained in Example 143 as a starting material, the same procedure of Example 5 gave 79 mg of the titled compound (yield, 87%).

$^1$H-NMR($D_2O$) δ: 1.32–2.08(8H,m), 1.41(3H, t, J=7.3 Hz), 2.47–2.52(2H,m), 3.23(2H, q, J=7.3 Hz), 7.43–7.74 (4H,m)

FAB-MS(m/z) 278($M^+$+1)

Example 145

Synthesis of N-(1-(3-(S-n-propylisothioureido) phenyl)cyclohexyl)carbamic acid t-butyl ester Using the compound obtained in Example 140 as a starting material, the same procedure of Example 91 gave 78 mg of the titled compound (yield, 69%).

$^1$H-NMR($CDCl_3$) δ: 1.02(3H, t, J=7.3 Hz), 1.36(9H,s), 1.49–1.82(10H,m), 2.15–2.20(2H,m), 2.90–3.14(2H,m), 4.52(1H,brs), 4.80(1H,brs), 6.73–7.28(4H,m)

Example 146

Synthesis of N-(1-(3-(S-n-propylisothioureido) phenyl)cyclohexyl)amine dihydrochloride Using the compound obtained in Example 145 as a starting material, the same procedure of Example 5 gave 64 mg of the titled compound (yield, 98%).

$^1$H-NMR($D_2O$) δ: 1.04(3H, t, J=7.3 Hz), 1.39–2.05(10H, m), 2.47–2.52 (2H,m), 3.20(2H, t, J=7.3 Hz), 7.43–7.74(4H, m)

FAB-MS(m/z) 292($M^+$+1)

Example 147

Synthesis of N-(1-(3-nitrophenyl)cyclopentyl) carbamic acid t-butyl ester

Example 147a

Using 3-nitrophenylacetic acid t-butyl ester as a starting material and also using 1,4-dibromobutane (1 eq.) as a reagent, the same procedures of Examples 1a and 1b gave 1-(3-nitrophenyl)cyclopentanecarboxylic acid.

$^1$H-NMR($CDCl_3$) δ: 78–2.05(6H,m), 2.68–2.74(2H,m), 7.46–7.74(2H,m), 8.10–8.25(2H,m)

Example 147b

Using the 1-(3-nitrophenyl)cyclopentanecarboxylic acid as a starting material, the same procedure of Example 1c gave 211 mg of the titled compound (yield, 54%).

$^1$H-NMR($CDCl_3$) δ: 1.37(9H,s), 1.86–2.23(8H,m), 4.97 (1H,brs), 7.45–7.78(2H,m), 8.06–8.27(2H,m)

Example 148

Synthesis of N-(1-(3-aminophenyl)cyclopentyl) carbamic acid t-butyl ester

Using the compound obtained in Example 147 as a starting material, the same procedure of Example 2 gave 1.81 g of the titled compound (yield, 96%).

$^1$H-NMR($CDCl_3$) δ: 1.35(9H,s), 1.72–2.18(8H,m), 3.60 (2H,brs), 4.83(1H,brs), 6.51–7.11(4H,m)

Example 149

Synthesis of N-(1-(3-thioureidophenyl)cyclopentyl) carbamic acid t-butyl ester

Using the compound obtained in Example 148 as a starting material, the same procedure of Example 120 gave 296 mg of the titled compound quantitatively.

$^1$H-NMR($CDCl_3$) δ: 1.33(9H,s), 1.84–2.21(8H,m), 4.91 (1H,brs), 6.24 (2H,brs), 6.87–7.40(4H,m), 7.90(1H,brs)

Example 150

Synthesis of N-(1-(3-(S-methylisothioureido) phenyl)cyclopentyl)carbamic acid t-butyl ester Using the compound obtained in Example 149 as a starting material and also using methyl iodide as a reagent, reaction was performed as in Example 29 to give 82 mg of the titled compound (yield, 94%).

$^1$H-NMR($CDCl_3$) δ: 1.34(9H,s), 1.80–2.18(8H,m), 2.47 (3H,s), 4.57(1H,brs), 4.84(1H,brs), 6.78–7.27(4H,m)

Example 151

Synthesis of N-(1-(3-(S-methylisothioureido) phenyl)cyclopentyl)amine dihydrochloride Using the compound obtained in Example 150 as a starting material, the same procedure of Example 5 gave 72 mg of the titled compound (yield, 95%).

$^1$H-NMR($D_2O$) δ: 1.87–1.97(4H,m), 2.30–2.35(4H,m), 2.70(3H,s), 7.39–7.67(4H,m)

FAB-MS(m/z) 250($M^+$+1)

Example 152

Synthesis of N-(1-(3-(S-ethylisothioureido)phenyl) cyclopentyl)carbamic acid t-butyl ester Using the compound obtained in Example 149 as a starting material, the same procedure of Example 95 gave 97 mg of the titled compound (yield, 97%).

$^1$H-NMR($CDCl_3$) δ: 1.26–1.39(12H,m), 1.80–2.30(8H, m), 2.95–3.20(2H,m), 4.55(1H,brs), 4.86(1H,brs), 6.77–7.24(4H,m)

Example 153

Synthesis of N-(1-(3-(S-ethylisothioureido)phenyl) cyclopentyl)amine dihydrochloride Using the compound obtained in Example 152 as a starting material, the same procedure of Example 5 gave 79 mg of the titled compound (yield, 88%).

$^1$H-NMR($D_2O$) δ: 1.42(3H, t, J=7.3 Hz), 1.88–1.98(4H, m), 2.30–2.35(4H,m), 3.24(2H, q, J=7.3 Hz), 7.39–7.68(4H, m)

FAB-MS(m/z) 264($M^+$+1)

Example 154

Synthesis of N-(1-(3-(S-n-propylisothioureido) phenyl)cyclopentyl)carbamic acid t-butyl ester Using the compound obtained in Example 149 as a starting material, the same procedure of Example 91 gave 94 mg of the titled compound (yield, 98%).

$^1$H-NMR($CDCl_3$) δ: 1.03(3H, t, J=7.3 Hz), 1.34(9H,s), 1.70–2.17(10H,m), 2.95–3.15(2H,m), 4.54(1H,brs), 4.85 (1H,brs), 6.76–7.25(4H,m)

Example 155

Synthesis of N-(1-(3-(S-n-propylisothioureido) phenyl)cyclopentyl)amine dihydrochloride Using the compound obtained in Example 154 as a starting material, the same procedure of Example 5 gave 83 mg of the titled compound quantitatively.

$^1$H-NMR($D_2O$) δ: 1.04(3H, t, J=7.3 Hz), 1.73–1.97(6H, m), 2.29–2.35(4H,m), 3.20(2H, t, J=7.3 Hz), 7.40–7.64(4H, m)

FAB-MS(m/z) 278($M^+$+1)

Example 156

Synthesis of N-(1-(3-nitrophenyl)cyclobutyl) carbamic acid t-butyl ester

Example 156a

Using 3-nitrophenylacetic acid t-butyl ester as a starting material and also using 1,3-dibromopropane (1 eq.) as a reagent, the same procedures of Examples 1a and 1b gave 1-(3-nitrophenyl)cyclobutanecarboxylic acid.

$^1$H-NMR($CDCl_3$) δ: 1.86–2.27(2H,m), 2.50–2.62(2H,m), 2.88–2.97(2H,m), 7.48–7.64(2H,m), 8.10–8.17(2H,m)

Example 156b

Using the 1-(3-nitrophenyl)cyclobutanecarboxylic acid as a starting material, the same procedure of Example 1c gave 2.0 g of the titled compound (yield, 89%).

$^1$H-NMR($CDCl_3$) δ: 1.36(9H,s), 1.85–2.26(2H,m), 2.46–2.62(4H,m), 5.28(1H,brs), 7.51–8.28(4H,m)

Example 157

Synthesis of N-(1-(3-aminophenyl)cyclobutyl) carbamic acid t-butyl ester

Using the compound obtained in Example 156 as a starting material, the same procedure of Example 2 gave 1.2 g of the titled compound (yield, 62%).

$^1$H-NMR($CDCl_3$) δ: 1.36(9H,s), 1.72–2.12(2H,m), 2.48–2.53(4H,m), 3.64(2H,brs), 4.99(1H,brs), 6.54–7.15 (4H,m)

Example 158

Synthesis of N-(1-(3-thioureidophenyl)cyclobutyl) carbamic acid t-butyl ester

Using the compound obtained in Example 157 as a starting material, the same procedure of Example 120 gave 302 mg of the titled compound quantitatively.

$^1$H-NMR($CDCl_3$) δ: 1.34(9H,s), 1.80–2.24(2H,m), 2.37–2.59(4H,m), 5.24(1H,brs), 6.34(2H,brs), 7.04–7.45 (4H,m), 8.24(1H,s)

Example 159

Synthesis of N-(1-(3-(S-methylisothioureido) phenyl)cyclobutyl)carbamic acid t-butyl ester Using the compound obtained in Example 158 as a starting material and also using methyl iodide as a reagent, reaction was performed as in Example 29 to give 150 mg of the titled compound (yield, 96%).

$^1$H-NMR($CDCl_3$) δ: 1.35(9H,s), 1.76–2.20(2H,m), 2.46–2.72(7H,m), 4.56 (1H,brs), 5.07(1H,brs), 6.78–7.25 (4H,m)

Example 160

Synthesis of N-(1-(3-(S-methylisothioureido) phenyl)cyclobutyl)amine dihydrochloride Using the compound obtained in Example 159 as a starting material, the same procedure of Example 5 gave 110 mg of the titled compound (yield, 86%).

$^1$H-NMR($D_2O$) δ: 1.88–2.29(2H,m), 2.60–2.84(7H,m), 7.42–7.69(4H,m)

Example 161

Synthesis of N-(1-(3-(S-ethylisothioureido)phenyl) cyclobutyl)carbamic acid t-butyl ester Using the compound obtained in Example 158 as a starting material, the same procedure of Example 95 gave 150 mg of the titled compound (yield, 91%).

$^1$H-NMR($CDCl_3$) δ: 1.26–1.43(12H,m), 1.79–2.16(2H, m), 2.48–2.54(4H,m), 2.90–3.14(2H,m), 4.54(1H,brs), 5.07 (1H,brs), 6.78–7.24(4H,m)

Example 162

Synthesis of N-(1-(3-(S-ethylisothioureido)phenyl) cyclobutyl)amine dihydrochloride Using the compound obtained in Example 161 as a starting material, the same procedure of Example 5 gave 100 mg of the titled compound (yield, 83%).

$^1$H-NMR($D_2O$) δ: 1.42(3H, t, J=7.3 Hz), 1.94–2.23(2H, m), 2.60–2.84(4H,m), 3.24(2H, q, J=7.3 Hz), 7.42–7.69(4H, m)

Example 163

Synthesis of N-(1-(3-nitrophenyl)cyclopropyl) carbamic acid t-butyl ester

Example 163a

Using 3-nitrophenylacetic acid t-butyl ester as a starting material and also using 1,2-dibromoethane (1 eq.) as a reagent, the same procedures of Examples 1a and 1b gave 1-(3-nitrophenyl)cyclopropanecarboxylic acid.

$^1$H-NMR($CDCl_3$) δ: 1.34(2H, dd, J=7.3, 4.3 Hz), 3.56 (2H, dd, J=7.3, 4.3 Hz), 7.46–7.71(2H,m), 8.13–8.21(2H,m)

Example 163b

Using the 1-(3-nitrohenyl)cyclopropanecarboxylic acid as a starting material, the same procedure of Example 1c gave 162 mg of the titled compound (yield, 78%).

$^1$H-NMR($CDCl_3$) δ: 1.31–1.45(13H,m), 5.34(1H,brs), 7.43–7.48(2H,m), 8.03–8.08(2H,m)

Example 164

Synthesis of N-(1-(3-aminophenyl)cyclopropyl) carbamic acid t-butyl ester

Using the compound obtained in Example 163 as a starting material, the same procedure of Example 2 gave 18.7 mg of the titled compound (yield, 2%).

$^1$H-NMR($CDCl_3$) δ: 1.18–1.28(4H,m), 1.43(9H,s), 3.61 (2H,brs), 5.24 (1H,brs), 6.49–6.61(2H,m), 7.03–7.09(2H,m)

Example 165

Synthesis of N-(1-(3-thioureidophenyl)cyclopropyl) carbamic acid t-butyl ester

Using the compound obtained in Example 164 as a starting material, the same procedure of Example 120 gave 20 mg of the titled compound (yield, 87%).

$^1$H-NMR($CDCl_3$) δ: 1.24–1.35(4H,m), 1.43(9H,s), 5.31 (1H,brs), 6.21 (2H,brs), 7.03–7.37(4H,m), 8.10(1H,brs)

Example 166

Synthesis of N-(1-(3-(S-ethylisothioureido)phenyl) cyclopropyl)carbamic acid t-butyl ester Using the compound obtained in Example 165 as a starting material, the same procedure of Example 95 gave 20 mg of the titled compound (yield, 92%).

$^1$H-NMR($CDCl_3$) δ: 1.21–1.25(4H,m), 1.35(3H, t, J=7.3 Hz), 1.43(9H,s), 2.95–3.10(2H,m), 5.29(1H,brs), 6.73–6.88 (2H,m), 7.18–7.27(2H,m)

Example 167

Synthesis of N-(1-(3-(S-ethylisothioureido)phenyl) cyclopropyl)amine dihydrochloride Using the compound obtained in Example 166 as a starting material, the same procedure of Example 5 gave 21 mg of the titled compound quantitatively.

$^1$H-NMR($D_2O$) δ: 1.31–1.49(7H,m), 3.23(2H, q, J=7.3 Hz), 7.39–7.44(2H,m), 7.59–7.61(2H,m)

Example 168

Synthesis of N-(1-(3-(N'-nitroguanidino)phenyl) cyclohexyl)carbamic acid t-butyl ester Using the compound obtained in Example 139 as a starting material, the same procedure of Example 6 gave 63 mg of the titled compound (yield, 32%).

$^1$H-NMR($CDCl_3$) δ: 1.35(9H,s), 1.51–1.86(8H,m), 2.14–2.19(2H,m), 4.95(1H,brs), 7.15–7.47(4H,m), 9.66(1H, brs)

Example 169

Synthesis of N-(1-(3-(N'-nitroguanidino)phenyl) cyclohexyl)amine hydrochloride

Using the compound obtained in Example 168 as a starting material, the same procedure of Example 5 gave 51 mg of the titled compound (yield, 97%).

$^1$H-NMR($D_2O$) δ: 1.43–2.07(8H,m), 2.48–2.53(2H,m), 7.37–7.62(4H,m)

Example 170

Synthesis of N-(1-(3-(N'-nitroguanidino)phenyl) cyclopentyl)carbamic acid t-butyl ester Using the compound obtained in Example 148 as a starting material, the same procedure of Example 6 gave 121 mg of the titled compound (yield, 61%).

$^1$H-NMR($CDCl_3$) δ: 1.34(9H,s), 1.87–2.24(8H,m), 4.94 (1H,brs), 7.14–7.45(4H,m), 9.67(1H,brs)

Example 171

Synthesis of N-(1-(3-(N'-nitroguanidino)phenyl) cyclopentyl)amine hydrochloride

Using the compound obtained in Example 170 as a starting material, the same procedure of Example 5 gave 78 mg of the titled compound (yield, 98%).

$^1$H-NMR($D_2O$) δ: 1.90–1.97(4H,m), 2.29–2.32(4H,m), 7.37–7.61(4H,m)

Example 172

Synthesis of N-(1-(3-(N'-nitroguanidino)phenyl) cyclobutyl)carbamic acid t-butyl ester Using the compound obtained in Example 157 as a starting material, the same procedure of Example 6 gave 106 mg of the titled compound (yield, 53%).

$^1$H-NMR($CDCl_3$) δ: 1.35(9H,s), 1.87–2.28(2H,m), 2.38–2.63(4H,m), 5.26(1H,brs), 7.15–7.48(4H,m), 9.69(1H, brs)

Example 173

Synthesis of N-(1-(3-(N'-nitroguanidino)phenyl) cyclobutyl)amine hydrochoride

Using the compound obtained in Example 172 as a starting material, the same procedure of Example 5 gave 72 mg of the titled compound (yield, 98%).

$^1$H-NMR($D_2O$) δ: 1.90–2.28(2H,m), 2.59–2.84(4H,m), 7.38–7.63(4H,m)

Example 174

Synthesis of N-(1-(3-(S-ethylisothioureido)phenyl) ethyl)carbamic acid t-butyl ester Using the compound obtained in Example 10 as a starting material, the same procedure of Example 95 gave 71 mg of the titled compound (yield, 74%).

$^1$H-NMR($CDCl_3$) δ: 1.34–1.44(15H,m), 2.90–3.12(2H, m), 4.42–4.54(1H,m), 4.76(1H,brs), 6.82–7.29(4H,m)

Example 175

Synthesis of N-(1-(3-(S-ethylisothioureido)phenyl) ethyl)amine dihydrochloride

Using the compound obtained in Example 174 as a starting material, the same procedure of Example 5 gave 53 mg of the titled compound (yield, 97%).

$^1$H-NMR($D_2O$) δ: 1.42(3H, t, J=7.6 Hz), 1.67(3H, d, J=6.9 Hz), 3.25 (2H, q, J=7.6 Hz), 4.60(1H, q, J=6.9 Hz), 7.42–7.67(4H,m)

Example 176

Synthesis of N-(1-(3-(S-ethylisothioureido)phenyl) propyl)carbamic acid t-butyl ester Using the compound obtained in Example 17 as a starting material, the same procedure of Example 95 gave 820 mg of the titled compound (yield, 91%).

$^1$H-NMR($CDCl_3$) δ: 0.88(3H, t, J=7.3 Hz), 1.30–1.50 (12H,m), 1.72–1.78(2H,m), 3.00–3.17(2H,m), 4.40–4.58 (2H,m), 4.78 (1H,brs), 6.80–6.94(2H,m), 7.22–7.28(2H,m)

Example 177

Synthesis of N-(1-(3-(S-ethylisothioureido)phenyl) propyl)amine dihydrochloride

Using the compound obtained in Example 176 as a starting material, the same procedure of Example 5 gave 653 mg of the titled compound (yield, 82%).

$^1$H-NMR($D_2O$) δ: 0.89(3H, t, J=7.3 Hz), 1.42(3H, t, J=7.3 Hz), 1.94–2.13(2H,m), 3.24(2H, q, J=7.3 Hz), 4.33(1H, t, J=7.3 Hz), 7.44–7.68(4H,m)

Example 178

Synthesis of 2-methyl-2-(4-nitrophenyl)propanol

Example 178a

Using 4-nitrophenylacetic acid diphenylmethyl ester as a starting material and also using methyl iodide (2 eq.) as a reagent, the same procedures of Examples 1a and 1b gave 2-methyl-2-(4-nitrophenyl)propionic acid.

$^1$H-NMR($CDCl_3$) δ: 1.65(6H,s), 7.57(2H, d, J=8.9 Hz), 8.20(2H, d, J=8.9 Hz)

Example 178b

Using the 2-methyl-2-(4-nitrophenyl)propionic acid as a starting material, the same procedure of Examaple 132 gave 172 mg of the titled compound (yield, 88%).

$^1$H-NMR($CDCl_3$) δ: 1.38(6H,s), 3.69(2H,s), 7.56(2H, d, J=8.9 Hz), 8.18(2H, d, J=8.9 Hz)

Example 179

Synthesis of N-(2-methyl-2-(4-nitrophenyl)propyl) phthalimide

A solution of the compound (152 mg) obtained in Example 178 in anhydrous tetrahydrofuran (10 ml) was added drowise to a mixture of triphenylphosphine (484 mg), diethyl azodicarboxylate (0.29 ml) and anhydrous tetrahydrofuran (20 ml) at 0° C. in a nitrogen atmosphere. Then, a solution of phthalimide (272 mg) in anhydrous tetrahydrofuran (10 ml) was added dropwise to the reaction mixture at 0° C., stirred for 10 min and stirred for 4 h at room temperature. The reaction mixture was concentrated under reduced pressure and the resulting residue was purified by silica gel column chromatography (eluent, n-hexane ethyl acetate=8:2) to give 439 mg of the titled compound (yield, 88%).

$^1$H-NMR($CDCl_3$) δ: 1.46(6H,s), 3.84(2H,s), 7.72(2H, d, J=8.9 Hz), 7.75–7.83(4H,m), 8.17(2H, d, J=8.9 Hz)

Example 180

Synthesis of N-(2-methyl-2-(4-nitrophenyl)propyl) amine

To a mixture of the compound (152 mg) obtained in Example 179, methanol (10 ml) and chloroform (10 ml), hydrazine monohydrate (0.05 ml) was added and heated under reflux for 24 h. The reaction mixture was filtered and the filtrate was concentrated under reduced pressure; following addition of 2 N HCl, the mixture was washed with ethyl acetate. Then, the aqueous layer was made alkaline with a 2 N aqueous sodium hydroxide solution and extracted with ethyl acetate. The organic layer was washed with a saturated aqueous sodium chloride solution, dried with anhydrous sodium sulfate and concentrated under reduced pressure to give 71 mg of the titled compound (yield, 78%).

$^1$H-NMR($CDCl_3$) δ: 1.36(6H,s), 2.87(2H,s), 7.52(2H, d, J=8.9 Hz), 8.18(2H, d, J=8.9 Hz)

Example 181

Synthesis of N-(2-methyl-2-(4-nitrophenyl)propyl) carbamic acid t-butyl ester

Using the compound obtained in Example 180 as a starting material, the same procedure of Example 22 gave 77 mg of the titled compound (yield, 86%).

$^1$H-NMR($CDCl_3$) δ: 1.37(6H,s), 1.38(9H,s), 3.36(2H, d, J=6.3 Hz), 4.30–4.40(1H,m), 7.53(2H, d, J=8.9 Hz), 8.18 (2H, d, J=8.9 Hz)

Example 182

Synthesis of N-(2-(4-aminophenyl)-2-methylpropyl) carbamic acid t-butyl ester

Using the compound obtained in Example 181 as a starting material, the same procedure of Example 2 gave 796 mg of the titled compound (yield, 65%).

$^1$H-NMR($CDCl_3$) δ: 1.26(6H,s), 1.40(9H,s), 3.26(2H, d, J=5.9 Hz), 3.60(2H,brs), 4.20–4.38(1H,m), 6.66(2H, d, J=8.6 Hz), 7.12(2H, d, J=8.6 Hz)

Example 183

Synthesis of N-(2-methyl-2-(4-thioureidophenyl) propyl)carbamic acid t-butyl ester Using the compound obtained in Example 182 as a starting material, the same procedure of Example 120 gave 240 mg of the titled compound (yield, 98%).

$^1$H-NMR($CDCl_3$) δ: 1.32(6H,s), 1.38(9H,s), 3.30(2H, d, J=6.3 Hz), 4.38–4.50(1H,m), 6.20(2H,brs), 7.20(2H, d, J=8.3 Hz), 7.42(2H, d, J=8.3 Hz), 8.19(1H,brs)

Example 184

Synthesis of N-(2-(4-(S-ethylisothioureido)phenyl)-2-methylpropyl)carbamic acid t-butyl ester Using the compound obtained in Example 183 as a starting material, the same procedure of Example 95 gave 120 mg of the titled compound (yield, 91%).

$^1$H-NMR($CDCl_3$) δ: 1.30(6H,s), 1.34–1.40(12H,m), 3.00–3.18(2H,m), 3.29(2H, d, J=6.3 Hz), 4.20(1H,brs), 4.40–4.60(1H,m), 6.80–6.95(2H,m), 7.28(2H, d, J=7.6 Hz)

Example 185

Synthesis of N-(2-(4-(S-ethylisothioureido)phenyl)-2-methylpropyl)amine dihydrochloride Using the compound obtained in Example 184 as a starting material, the same procedure of Example 5 gave 110 mg of the titled compound quantitatively.

$^1$H-NMR($D_2O$) δ: 1.39–1.46(9H,m), 3.19–3.29(4H,m), 7.40(2H, d, J=8.6 Hz), 7.63(2H, d, J=8.6 Hz)

Example 186

Synthesis of N-(2-methyl-2-(4-(N'-nitroguanidino) phenyl)propyl)carbamic acid t-butyl ester Using the compound obtained in Example 182 as a starting material, the same procedure of Example 6 gave 163 mg of the titled compound (yield, 82%).

$^1$H-NMR($CDCl_3$) δ: 1.34(6H,s), 1.39(9H,s), 3.32(2H, d, J=6.3 Hz), 4.18–4.28(1H,m), 7.29(2H, d, J=8.3 Hz), 7.48 (2H, d, J=8.3 Hz), 9.85(1H,brs)

Example 187

Synthesis of N-(2-methyl-2-(4-(N'-nitroguanidino) phenyl)propyl)amine hydrochloride Using the compound obtained in Example 186 as a starting material, the same procedure of Example 5 gave 90 mg of the titled compound (yield, 92%).

$^1$H-NMR($D_2O$) δ: 1.45(6H,s), 3.27(2H,s), 7.38(2H, d, J=8.6 Hz), 7.58(2H, d, J=8.6 Hz)

Example 188

Synthesis of N-(1,1-dimethyl-2-(4-nitrophenyl) ethyl)amine

A solution of phentermine (1.0 g) in chloroform (20 ml) was added dropwise to sulfuric acid (3.57 ml) at 0° C.; then fuming nitric acid (specific gravity=1.52; 2.8 ml) was added dropwise at 0° C. The reaction mixture was stirred at 0° C. for 2 h, made alkaline with water and a 2 N aqueous sodium hydroxide solution and extracted with ethyl acetate. The organic layer was washed with a saturated aqueous sodium chloride solution, dried with anhydrous sodium sulfate and concentrated under reduced pressure. The resulting residue was purified by silica gel column chromatography (eluent, chloroform:methanol=9:1) to give 367 mg of the titled compound (yield, 28%).

$^1$H-NMR($CDCl_3$) δ: 1.15(6H,s), 2.78(2H,s), 7.37(2H, d, J=8.6 Hz), 8.16(2H, d, J=8.6 Hz)

Example 189

Synthesis of N-(1,1-dimethyl-2-(4-nitrophenyl) ethyl)carbamic acid t-butyl ester Using the compound obtained in Example 188 as a starting material, the same procedure of Example 22 gave 473 mg of the titled compound (yield, 89%).

$^1$H-NMR($CDCl_3$) δ: 1.28(6H,s), 1.48(9H,s), 3.15(2H,s), 4.24(1H,brs), 7.31(2H, d, J=8.6 Hz), 8.07(2H, d, J=8.6 Hz)

Example 190

Synthesis of N-(2-(4-aminophenyl)-1,1-dimethylethyl)carbamic acid t-butyl ester

Using the compound obtained in Example 189 as a starting material, the same procedure of Example 2 gave 350 mg of the titled compound (yield, 87%).

$^1$H-NMR($CDCl_3$) δ: 1.24(6H,s), 1.46(9H,s), 2.84(2H,s), 3.58(2H,brs), 4.27(1H,brs), 6.61(2H, d, J=8.2 Hz), 6.94(2H, d, J=8.2 Hz)

Example 191

Synthesis of N-(1,1-dimethyl-2-(4-thioureidophenyl)ethyl)carbamic acid t-butyl ester Using the compound obtained in Example 190 as a starting material, the same procedure of Example 120 gave 152 mg of the titled compound (yield, 93%).

$^1$H-NMR($CDCl_3$) δ: 1.26(6H,s), 1.47(9H,s), 3.02(2H,s), 4.26(1H,brs), 6.06(2H,brs), 7.14(2H, d, J=8.3 Hz), 7.23(2H, d, J=8.3 Hz), 7.85(1H,brs)

Example 192

Synthesis of N-(1,1-dimethyl-2-(4-(S-ethylisothioureido)phenyl)ethyl)carbamic acid t-butyl ester Using the compound obtained in Example 191 as a starting material, the same procedure of Example 95 gave 150 mg of the titled compound (yield, 91%).

$^1$H-NMR($CDCl_3$) δ: 1.25(6H,s), 1.37(3H, t, J=7.3 Hz), 1.46(9H,s), 2.92(2H,s), 2.98–3.18(2H,m), 4.25(1H,brs), 4.49(1H,brs), 6.78–6.90(2H,m), 7.09(2H, d, J=7.9 Hz)

Example 193

Synthesis of N-(1,1-dimethyl-2-(4-(S-ethylisothioureido)phenyl)ethyl)amine dihydrochloride Using the compound obtained in Example 192 as a starting material, the same procedure of Example 5 gave 140 mg of the titled compound quantitatively.

$^1$H-NMR($D_2O$) δ: 1.37(6H,s), 1.41(3H, t, J=7.6 Hz), 3.02(2H,s), 3.23(2H, q, J=7.6 Hz), 7.37(2H, d, J=8.3 Hz), 7.44(2H, d, J=8.3 Hz)

Example 194

Synthesis of N-(1,1-dimethyl-2-(4-(N'-nitroguanidino)phenyl)ethyl)carbamic acid t-butyl ester Using the compound obtained in Example 190 as a starting material, the same procedure of Example 6 gave 70 mg of the titled compound (yield, 43%).

$^1$H-NMR($CDCl_3$) δ: 1.28(6H,s), 1.48(9H,s), 3.05(2H,s), 4.30(1H,brs), 7.23(2H, d, J=8.6 Hz), 7.28(2H, d, J=8.6 Hz), 9.73(1H,brs)

Example 195

Synthesis of N-(1,1-dimethyl-2-(4-(N'-nitroguanidino)phenyl)ethyl)amine hydrochloride Using the compound obtained in Example 194 as a starting material, the same procedure of Example 5 gave 56 mg of the titled compound (yield, 97%).

$^1$H-NMR($D_2O$) δ: 1.37(6H,s), 3.00(2H,s), 7.34–7.44(4H, m)

Example 196

Synthesis of (4-methoxy-3-nitrophenyl)methanol

Using 4-methoxy-3-nitrobenzoic acid as a starting material, the same procedure of Example 132 gave 5.4 g of the titled compound (yield, 98%).

$^1$H-NMR($CDCl_3$) δ: 1.87(1H, t, J=5.9 Hz), 3.96(3H,s), 4.69(2H, d, J=5.9 Hz), 7.08(1H, d, J=8.6 Hz), 7.55(1H, dd, J=8.6, 2.3 Hz), 7.85(1H, d, J=2.3 Hz)

Example 197

Synthesis of N-(4-methoxy-3-nitrophenylmethyl) phthalimide

Using the compound obtained in Example 196 as a starting material, the same procedure of Example 179 gave 2.74 g of the titled compound (yield, 59%).

$^1$H-NMR($CDCl_3$) δ: 3.93(3H,s), 4.82(2H,s), 7.03(1H, d, J=8.8 Hz), 7.65(1H, dd, J=8.8, 2.4 Hz), 7.70–7.75(2H,m), 7.84–7.89(2H,m), 7.92(1H,d, J=2.4 Hz)

Example 198

Synthesis of N-(4-methoxy-3-nitrophenylmethyl) carbamic acid t-butyl ester

Using the compound obtained in Example 197 as a starting material, reaction was performed as in Example 118 to give 1.47 g of the titled compound (yield, 92%).

$^1$H-NMR($CDCl_3$) δ: 1.46(9H,s), 3.95(3H,s) 4.29(2H, d, J=5.4 Hz), 4.93(1H,br), 7.05(1H, d, J=8.8 Hz), 7.49(1H, dd, J=8.8, 2.4 Hz), 7.77(1H, d, J=2.4 Hz)

Example 199

Synthesis of N-(3-amino-4-methoxyphenylmethyl) carbamic acid t-butyl ester

Using the compound obtained in Example 198 as a starting material, the same procedure of Example 2 gave 1.24 g of the titled compound (yield, 96%).

$^1$H-NMR($CDCl_3$) δ: 1.46(9H,s), 3.79(2H,br), 3.83(3H,s), 4.16(2H, d, J=5.6 Hz), 4.71(1H,br), 6.60–6.65(2H,m), 6.72 (1H, d, J=8.3 Hz)

Example 200

Synthesis of N-(4-methoxy-3-thioureidophenylmethyl)carbamic acid t-butyl ester

Using the compound obtained in Example 199 as a starting material, reaction was performed as in Example 120 to give 605 mg of the titled compound (yield, 97%).

$^1$H-NMR(DMSO-$d_6$) δ: 1.39(9H,s), 3.79(3H,s), 4.03(1H, d, J=5.9 Hz), 6.92–7.03(2H,m), 7.23–7.27(1H,m), 7.30(2H, br), 7.61(1H,s), 8.96(1H,s)

Example 201

Synthesis of N-(3-(S-ethylisothioureido)-4-methoxyphenylmethyl)carbamic acid t-butyl ester hydroiodide Using the compound obtained in Example 200 as a starting material, the same procedure of Example 27 gave 591 mg of the titled compound (yield, 89%).

$^1$H-NMR($CDCl_3$) δ: 1.39(3H, t, J=7.3 Hz), 1.46(9H,s), 3.30(2H, q, J=7.3 Hz), 3.86(3H,s), 4.25(2H, d, J=5.6 Hz), 4.93(1H,br), 6.93(1H, d, J=8.4 Hz), 7.22–7.30(3H,m)

Example 202

Synthesis of N-(3-(S-ethylisothioureido)-4-methoxyphenylmethyl)amine dihydrochloride Using the compound obtained in Example 201 as a starting material, the same procedure of Example 5 gave 102 mg of the titled compound quantitatively.

$^1$H-NMR(DMSO-$d_6$) δ: 1.33(3H, t, J=7.3 Hz), 3.29(2H, q, J=7.3 Hz), 3.86(3H,s), 3.97–4.01(2H,m), 7.24(1H, d, J=8.6 Hz), 7.44(1H, d, J=2.0 Hz), 7.56(1H, dd, J=8.6, 2.0 Hz), 8.45(3H,br), 9.53(1H,br), 11.28(1H,br)

Example 203

Synthesis of (4-chloro-3-nitrophenyl)methanol

Using 4-chloro-3-nitrobenzoic acid as a starting material, the same procedure of Example 132 gave 1.53 g of the titled compound (yield, 82%).

$^1$H-NMR($CDCl_3$) δ: 1.96(1H, t, J=5.4 Hz), 4.78(2H, d, J=5.4 Hz), 7.48–7.57(2H,m), 7.90(1H,s)

Example 204

Synthesis of N-(4-chloro-3-nitrophenylmethyl)phthalimide

Using the compound obtained in Example 203 as a starting material, the same procedure of Example 179 gave 1.65 g of the titled compound (yield, 87%).

$^1$H-NMR($CDCl_3$) δ: 4.87(2H,s), 7.50(1H, d, J=8.3 Hz), 7.60(1H, dd, J=8.3, 2.0 Hz), 7.73–7.80(2H,m), 7.83–7.91 (2H,m), 7.93(1H, d, J=2.0 Hz)

Example 205

Synthesis of N-(4-chloro-3-nitrophenylmethyl)carbamic acid t-butyl ester

Using the compound obtained in Example 204 as a starting material, the same procedure of Example 118 gave 626 mg of the titled compound (yield, 78%).

$^1$H-NMR($CDCl_3$) δ: 1.46(9H,s), 4.33–4.37(2H,m), 5.01 (1H,br), 7.41–7.54(2H,m), 7.79(1H, d, J=1.5 Hz)

Example 206

Synthesis of N-(3-amino-4-chlorophenylmethyl)carbamic acid t-butyl ester

Using the compound obtained in Example 205 as a starting material, the same procedure of Example 2 gave 376 mg of the titled compound (yield, 87%).

$^1$H-NMR($CDCl_3$) δ: 1.47(9H,s), 4.18–4.22(2H,m), 4.79 (1H,br), 6.59(1H, dd, J=8.3, 1.5 Hz), 6.69(1H, d, J=1.5 Hz), 7.17(1H, d, J=8.3 Hz)

Example 207

Synthesis of N-(4-chloro-3-thioureidophenylmethyl)carbamic acid t-butyl ester

Using the compound obtained in Example 206 as a starting material, the same procedure of Example 120 gave 100 mg of the titled compound (yield, 81%).

$^1$H-NMR($CDCl_3$) δ: 1.44(9H,s), 4.28(2H, d, J=5.9 Hz), 5.26(1H,br), 6.49 (2H,br), 7.14(1H, dd, J=8.3, 1.5 Hz), 7.37–7.42(2H,m), 8.15(1H,br)

Example 208

Synthesis of N-(4-chloro-3-(S-ethylisothioureido)phenylmethyl)carbamic acid t-butyl ester hydroiodide Using the compound obtained in Example 207 as a starting material, the same procedure of Example 27 gave 113 mg of the titled compound (yield, 75%).

$^1$H-NMR($CDCl_3$) δ: 1.40(3H, t, J=7.3 Hz), 1.46(9H,s), 3.20(2H, q, J=7.3 Hz), 4.28(2H, d, J=6.3 Hz), 4.94(1H,br), 7.10–7.14(2H,m), 7.40(1H, d, J=9.3 Hz)

Example 209

Synthesis of N-(4-chloro-3-(S-ethylisothioureido)phenylmethyl)amine dihydrochloride Using the compound obtained in Example 208 as a starting material, the same procedure of Example 5 gave 97 mg of the titled compound quantitatively.

$^1$H-NMR(DMSO-$d_6$) δ: 1.34(3H, t, J=7.3 Hz), 3.32(2H, q, J=7.3 Hz), 4.01–4.08(2H,m), 7.56–7.63(2H,m), 7.71(1H, d, J=8.3 Hz), 8.61(3H,br), 9.41(2H,br), 11.90(1H,br)

Example 210

Synthesis of 2-(3-aminophenyl)-2-t-butoxycarbonylaminoacetic acid methyl ester

Using 3-nitrophenylacetic acid as a starting material, the same procedure of Example 78 gave 2.09 g of the titled compound (yield, 27%).

$^1$H-NMR($CDCl_3$) δ: 1.43(9H,s), 3.81(3H,s), 5.20(1H, d, J=7.3 Hz), 5.51–5.66(1H,m), 6.61–6.74(3H,m), 7.09–7.15 (1H,m)

MS(m/z) 280($M^+$)

Example 211

Synthesis of 2-t-butoxycarbonylamino-2-(3-(S-methylisothioureido)phenyl)acetic acid methyl ester Using the compound obtained in Example 210 as a starting material, the same procedure of Example 40 gave 2-t-butoxycarbonylamino-2-(3-thioureido)acetic acid. The resulting compound was dissolved in a mixture of methanol (10 ml) and diethylether (5 ml) and a solution of trimethylsilyldiazomethane (2.0 M) in n-hexane was added at room temperature until the reaction mixture no longer foamed. The reaction mixture was concentrated under reduced pressure and the residue was purified by silica gel column chromatography (eluent, n-hexane:ethyl acetate=3:1) to give 0.15 g of the titled compound (yield, 21%).

$^1$H-NMR($CDCl_3$) δ: 1.42(9H,s), 2.44(3H,s), 3.71(3H,s), 4.61(2H,brs), 5.27(1H, d, J=7.6 Hz), 5.56–5.67(1H,m), 6.86–6.92(2H,m), 7.02(1H,d, J=7.9 Hz), 7.24–7.37(1H,m)

FAB-MS(m/z) 354($M^+$+1)

Example 212

Synthesis of 2-amino-2-(3-(S-methylisothioureido) phenyl)acetic acid methyl ester dihydrochloride Using the compound obtained in Example 211 as a starting material, the same procedure of Example 5 gave 123 mg of the titled compound (yield, 90%).

$^1$H-NMR($D_2O$) δ: 2.70(3H,s), 3.84(3H,s), 5.37(1H,s), 7.30–7.57(3H,m), 7.65–7.71(1H,m)

FAB-MS(m/z) 254($M^+$+1)

Example 213

Synthesis of 2-t-butoxycarbonylamino-3-(3-nitrophenyl)propionic acid

Using 3-nitrophenylalanine as a starting material, the same procedure of Example 63 gave 2.54 g of the titled compound quantitatively.

$^1$H-NMR($CDCl_3$) δ: 1.41(9H,s), 3.01–3.22(1H,m), 3.25–3.45(1H,m), 4.60–4.73(1H,m), 5.02–5.11(1H,m), 7.45–7.56(2H,m), 8.07–8.14(2H,m)

FAB-MS(m/z) 311($M^+$+1)

Example 214

Synthesis of 2-t-butoxycarbonylamino-3-(3-nitrophenyl)propionic acid methyl ester Using the compound obtained in Example 213 as a starting material, the same procedure of Example 64 gave 2.7 g of the titled compound quantitatively.

$^1$H-NMR($CDCl_3$) δ: 1.41(9H,s), 3.12(1H, dd, J=13.9, 6.3 Hz), 3.30(1H, dd, J=13.9, 5.6 Hz), 3.76(3H,s), 4.57–4.68 (1H,m), 5.10–5.17(1H,m), 7.46–7.53(2H,m), 7.99–8.04(1H, m), 8.08–8.17(1H,m)

Example 215

Synthesis of 3-(3-aminophenyl)-2-t-butoxcyarbonylaminopropionic acid methyl ester Using the compound obtained in Example 214 as a starting material, the same procedure of Example 2 gave 1.84 of the titled compound (yield, 81%).

$^1$H-NMR($CDCl_3$) δ: 1.42(9H,s), 2.90–3.02(2H,m), 3.62 (2H,brs), 3.71(3H,s), 4.47–4.61(1H,m), 4.92–5.00(1H,m), 6.45–6.58(3H,m), 7.04–7.10(1H,m)

Example 216

Synthesis of 2-t-butoxycarbonylamino-3-(3-(S-methylisothioureido)phenyl)propionic acid methyl ester Using the compound obtained in Example 215 as a starting material, the same procedure of Example 211 gave 0.10 g of the titled compound (yield, 4%).

$^1$H-NMR($CDCl_3$) δ: 1.36(9H,s), 2.46(3H,s), 2.85–2.93 (1H,m), 3.08–3.15(1H,m), 3.73(3H,s), 4.57–4.69(2H,m), 4.98–5.01(1H,m), 6.72–6.80(3H,m), 7.19–7.27(1H,m)

Example 217

Synthesis of 2-amino-3-(3-(S-methylisothioureido) phenyl)propionic acid methyl ester dihydrochloride Using the compound obtained in Example 216 as a starting material, the same procedure of Example 5 gave 33 mg of the titled compound (yield, 81%).

$^1$H-NMR($D_2O$) δ: 2.69(3H,s), 3.30(1H, dd, J=14.5, 7.3 Hz), 3.40(1H, dd, J=14.5, 6.3 Hz), 3.84(3H,s), 4.45–4.50 (1H,m), 7.28–7.40(3H,m), 7.54–7.59(1H,m)

Example 218

Synthesis of 3-t-butoxycarbonylamino-2-(4-nitrophenyl)propionic acid methyl ester Using monomethyl 3-phenylsuccinate as a starting material, the same procedure of Example 1c gave 4.2 g of the titled compound (yield, 40%).

$^1$H-NMR($CDCl_3$) δ: 1.42(9H,s), 3.53–3.68(2H,m), 3.72 (3H,s), 4.00–4.12(1H,m), 4.85–4.95(1H,m), 7.45(2H, d, J=8.6 Hz), 8.20(2H, d, J=8.6 Hz)

Example 219

Synthesis of 2-(4-aminophenyl)-3-t-butoxycarbonylaminopropionic acid methyl ester Using the compound obtained in Example 218 as a starting material, the same procedure of Example 2 gave 3.1 g of the titled compound (yield, 81%).

$^1$H-NMR($CDCl_3$) δ: 1.48(9H,s), 3.47–3.82(5H,m), 3.72 (3H,s), 4.87–4.95(1H,m), 6.68(2H, d, J=8.5 Hz), 7.09(2H, d, J=8.5 Hz)

Example 220

Synthesis of 3-t-butoxycarbonylamino-2-(4-(N'-nitroguanidino)phenyl)propionic acid methyl ester Using the compound obtained in Example 219 as a starting material, the same procedure of Example 6 gave 0.86 g of the titled compound (yield, 68%).

$^1$H-NMR($CDCl_3$) δ: 1.42(9H,s), 3.39–3.89(3H,m), 3.66 (3H,s), 4.80–4.92(1H,m), 6.23(2H, d, J=8.3 Hz), 7.03(2H, d, J=8.3 Hz)

Example 221

Synthesis of 3-amino-2-(4-(N'-nitroguanidino) phenyl)propionic acid methyl ester hydrochloride Using the compound obtained in Example 220 as a starting material, the same procedure of Example 5 gave 348 mg of the titled compound quantitatively.

$^1$H-NMR($D_2O$) δ: 3.44(1H, dd, J=13.2, 6.9 Hz), 3.63–3.80(1H,m), 3.76(3H,s), 4.22–4.28(1H,m), 7.48(2H, d, J=8.9 Hz), 7.53(2H, d, J=8.9 Hz)

Example 222

Synthesis of 3-t-butoxycarbonylamino-2-(4-(N'-nitroguanidino)phenyl)propionic acid A mixture of the compound (0.42 g) obtained in Example 220, 2 N aqueous sodium hydroxide solution (0.6 ml) and methanol (10 ml) was stirred at room temperature for 5 h. The reaction mixture was concentrated under reduced pressure and a 5% aqueous citric acid solution and ethyl acetate were added to the residue. The organic layer was washed with water, dried and concentrated under reduced pressure. The resulting residue was purified by silica gel column chromatography (eluent, methanol:methylene chloride=5:95) to give 0.34 g of the titled compound (yield, 84%).

$^1$H-NMR(DMSO-$d_6$) δ: 1.35(9H,s), 3.05–3.18(1H,m), 3.32–3.41(3H,m), 3.52–3.58(1H,m), 6.50(2H, d, J=8.6 Hz), 6.88(2H, d, J=8.6 Hz)

Example 223

Synthesis of 3-amino-2-(4-(N'-nitroguanidino)phenyl)propionic acid hydrochloride Using the compound obtained in Example 222 as a starting material, the same procedure of Example 5 gave 287 mg of the titled compound quantitatively.

$^1$H-NMR($D_2O$) δ: 3.40(1H, dd, J=13.2, 6.9 Hz), 3.67(1H, dd, J=13.2, 7.9 Hz), 4.18(1H, dd, J=7.9, 6.9 Hz), 7.48(2H, d, J=8.9 Hz), 7.55(2H, d, J=8.9 Hz)

Example 224

Synthesis of 3-t-butoxycarbonylamino-2-(4-thioureidophenyl)propionic acid methyl ester Using the compound obtained in Example 219 as a starting material, the same procedure of Example 120 gave 1.10 g of the titled compound (yield, 94%).

$^1$H-NMR($CDCl_3$) δ: 1.41(9H,s), 3.38–3.70(2H,m), 3.69 (3H,s), 3.82–3.97(1H,m), 5.04–5.16(1H,m), 6.57(2H,brs), 7.22(2H, d, J=8.3 Hz), 7.30(2H, d, J=8.3 Hz), 9.00(1H,brs)

MS(m/z) 353($M^+$)

Example 225

Synthesis of 3-t-butoxycarbonylamino-2-(4-(S-ethylisothioureido)phenyl)propionic acid methyl ester Using the compound obtained in Example 224 as a starting material and also using ethyl iodide as a reagent, the same procedure of Example 29 gave 0.55 g of the titled compound (yield, 96%).

$^1$H-NMR($CDCl_3$) δ: 1.34(3H, t, J=7.3 Hz), 1.42(9H,s), 2.92–3.08(2H,m), 3.40–3.72(2H,m), 3.67(3H,s), 3.78–3.90 (1H,m), 4.67(1H,br), 4.90–5.06(1H,m), 6.78(2H, d, J=7.9 Hz), 7.17(2H, d, J=7.9 Hz)

FAB-MS(m/z) 382($M^+$+1)

Example 226

Synthesis of 3-amino-2-(4-(S-ethylisothioureido)phenyl)propionic acid methyl ester dihydrochloride Using the compound obtained in Example 225 as a starting material, the same procedure of Example 5 gave 0.199 g of the titled compound (yield, 83%).

$^1$H-NMR($D_2O$) δ: 1.41(3H, t, J=7.3 Hz), 3.24(2H, q, J=7.3 Hz), 3.44(1H, dd, J=13.2, 6.9 Hz), 3.69–3.74(1H,m), 3.76(3H,s), 4.21–4.27(1H,m), 7.44(2H, d, J=8.9 Hz), 7.52 (2H, d, J=8.9 Hz)

FAB-MS(m/z) 282($M^+$+1)

Example 227

Synthesis of N-(2-nitrophenylmethyl)phthalimide

Using 2-nitrophenylmethyl bromide as a starting material, the same procedure of Example 117 gave 6.24 g of the titled compound (yield, 96%).

$^1$H-NMR($CDCl_3$) δ: 5.31(2H,s), 7.25–7.27(1H,m), 7.45 (1H, t, J=7.6 Hz), 7.55(1H, t, J=7.6 Hz), 7.75–7.94(4H,m), 8.11(1H, d, J=7.9 Hz)

MS(m/z) 282($M^+$)

Example 228

Synthesis of N-(2-nitrophenylmethyl)carbamic acid t-butyl ester

Using the compound obtained in Example 227 as a starting material, the same procedure of Example 118 gave 7.59 g of the titled compound quantitatively.

$^1$H-NMR($CDCl_3$) δ: 1.43(9H,s), 4.57(2H, d, J=6.6 Hz), 5.30–5.43(1H,m), 7.38–7.50(1H,m), 7.62–7.64(2H,m), 8.05 (1H, d, J=7.9 Hz)

Exmaple 229

Synthesis of N-(2-aminophenylmethyl)carbamic acid t-butyl ester

Using the compound obtained in Example 228 as a starting material, the same procedure of Example 2 gave 4.54 g of the titled compound (yield, 92%).

$^1$H-NMR($CDCl_3$) δ: 1.42(9H,s), 4.18(2H, d, J=6.4 Hz), 6.40–6.79(1H,m), 6.85–7.23(2H,m), 7.80(1H, d, J=8.0 Hz)

MS(m/z) 222($M^+$)

Example 230

Synthesis of N-(2-thioureidophenylmethyl)carbamic acid t-butyl ester

Using the compound obtained in Example 229 as a starting material, the same procedure of Example 120 gave 525 mg of the titled compound (yield, 26%).

$^1$H-NMR($CDCl_3$) δ: 1.40(9H,s), 4.26(2H, d, J=5.9 Hz), 5.38–5.57(1H,m), 6.42(2H,brs), 7.28–7.38(4H,m), 9.27(1H, brs)

MS(m/z) 281($M^+$)

Example 231

Synthesis of N-(2-(S-ethylisothioureido)phenylmethyl)carbamic acid t-butyl ester hydroiodide Using the compound obtained in Example 230 as a starting material, the same procedure of Example 27 gave 0.60 g of the titled compound quantitatively.

$^1$H-NMR($CDCl_3$) δ: 1.34(3H, t, J=7.3 Hz), 1.43(9H,s), 2.88–3.06(2H,m), 4.15(2H, d, J=4.4 Hz), 4.80(2H,brs), 5.25–5.38(1H,m), 6.80(1H, d, J=7.8 Hz), 6.98(1H, t, J=7.8 Hz), 7.13–7.34(2H,m)

MS(m/z) 309($M^+$)

Example 232

Synthesis of N-(2-(S-ethylisothioureido)phenylmethyl)amine dihydrochloride

Using the compound obtained in Example 231 as a starting material, the same procedure of Example 5 gave 451 mg of the titled compound (yield, 86%).

$^1$H-NMR $D_2O$) δ: 1.40(3H, t, J=7.3 Hz), 3.24(2H, q, J=7.3 Hz), 4.23(2H,s), 7.47–7.64(4H,m)

FAB-MS(m/z) 210($M^+$+1)

Example 233

Synthesis of N-(1-(3-(N'-t-butoxycarbonyl-N'-ethylguanidino)phenyl)cyclohexyl)carbamic acid t-butyl ester To a mixture of the compound (100 mg) obtained in Example 139, N-ethyl-N'-t-butoxycarbonylthiourea (85 mg) and dimethylformamide (5 ml) was added 1-ethyl-3-(3-dimethylaminopropyl)carbodiimide hydrochloride (79 mg) at room temperature and the mixture was stirred at room temperature for 16 h. The reaction mixture was diluted with ethyl acetate and washed with a saturated aqueous sodium chloride solution; the organic layer was then dried with anhydrous sodium sulfate and concentrated under reduced pressure. The resulting residue was purified by silica gel column chromatography (eluent, chloroform:methanol=98:2) to give 156 mg of the titled compound (yield, 98%).

$^1$H-NMR($CDCl_3$) δ: 1.00–1.08(3H,m), 1.27–1.82(8H,m), 1.53(9H,s), 1.62(9H,s), 2.07–2.30(2H,m), 3.32–3.48(2H,m), 4.84 (1H,brs), 6.98–7.40(4H,m), 8.02(1H,s)

Example 234

Synthesis of N-(1-(3-(N'-ethylguanidino)phenyl)cyclohexyl)amine dihydrochloride

Using the compound obtained in Example 233 as a starting material, the same procedure of Example 5 gave 85 mg of the titled compound (yield, 78%).

$^1$H-NMR($D_2O$) δ: 1.23(3H, t, J=7.3 Hz), 1.31–1.64(4H, m), 1.64–1.86(2H,m), 1.90–2.06(2H,m), 2.40–2.60(2H,m), 3.33(2H, q, J=7.3 Hz), 7.30–7.77(4H,m)

Example 235

Synthesis of N-(1-(3-(N'-t-butoxycarbonyl-N''-ethylguanidino)phenyl)cyclopentyl)carbamic acid t-butyl ester Using the compound obtained in Example 148 as a starting material, the same procedure of Example 233 gave 160 mg of the titled compound (yield, 99%).

$^1$H-NMR($CDCl_3$) δ: 1.00–1.20(3H,m), 1.34(9H,s), 1.53 (9H,s), 1.72–1.92(4H,m), 1.93–2.10(2H,m), 2.12–2.35(2H, m), 3.30–3.50(2H,m), 4.82(1H, brs), 6.90–7.20(4H,m), 8.02 (1H,s)

Example 236

Synthesis of N-(1-(3-(N'-ethylguanidino)phenyl)cyclopentyl)amine dihydrochloride Using the compound obtained in Example 235 as a starting material, the same procedure of Example 5 gave 88 mg of the titled compound (yield, 79%).

$^1$H-NMR($D_2O$) δ: 1.23(3H, t, J=7.3 Hz), 1.82–2.06(4H, m), 2.22–2.40(4H,m), 3.33(2H, q, J=7.3 Hz), 7.34–7.61(4H, m)

Example 237

Synthesis of N-(1-(3-(N'-t-butoxycarbonyl-N''-ethylguanidino)phenyl)cyclobutyl)carbamic acid t-butyl ester Using the compound obtained in Example 157 as a starting material, the same procedure of Example 233 gave 171 mg of the titled compound quantitatively.

$^1$H-NMR($CDCl_3$) δ: 1.00–1.21(3H,m), 1.36(9H,s), 1.53 (9H,s), 1.65–1.98(1H,m), 2.01–2.22(1H,m), 2.26–2.60(4H, m), 3.35–3.50(2H,m), 5.17(1H,brs), 6.95–7.20(4H,m), 8.01 (1H,s)

Example 238

Synthesis of N-(1-(3-(N'-ethylguanidino)phenyl)cyclobutyl)amine dihydrochloride

Using the compound obtained in Example 237 as a starting material, the same procedure of Example 5 gave 85 mg of the titled compound (yield, 73%).

$^1$H-NMR($D_2O$) δ: 1.24(3H, t, J=7.3 Hz), 1.94–2.04(1H, m), 2.19–2.24(1H,m), 2.60–2.84(4H,m), 3.33(2H, q, J=7.3 Hz), 7.35–7.63(4H,m)

Example 239

Synthesis of (3-nitro-5-trifluoromethylphenyl)methanol

Using 3-nitro-5-trifluoromethylbenzoic acid as a starting material, the same procedure of Example 132 gave 4.6 g of the titled compound (yield, 98%)

$^1$H-NMR($CDCl_3$) δ: 2.21(1H, t, J=5.6 Hz), 4.92(2H, d, J=5.6 Hz), 7.99(1H,s), 8.41(1H,s), 8.44(1H,s)

Example 240

Synthesis of 3-bromomethyl-5-trifluoromethylnitrobenzene

Using the compound obtained in Example 239 as a starting material, the same procedure of Example 55 gave 7.72 g of the titled compound quantitatively.

$^1$H-NMR($CDCl_3$) δ: 4.58(2H,s), 7.99(1H,s), 8.44(1H,s), 8.46(1H,s)

Example 241

Synthesis of N-(3-nitro-5-trifluoromethylphenylmethyl)iminodicarboxylic acid di-t-butyl ester Using the compound obtained in Example 240 as a starting material, the same procedure of Example 127 gave 2.6 g of the titled compound (yield, 59%).

$^1$H-NMR($CDCl_3$) δ: 1.51(18H,s), 4.92(2H,s), 7.93(1H,s), 8.41(2H,s)

Example 242

Synthesis of N-(3-amino-5-trifluoromethylphenylmethyl)iminodicarboxylic acid di-t-butyl ester Using the compound obtained in Example 241 as a starting material, the same procedure of Example 2 gave 2.19 g of the titled compound (yield, 99%).

$^1$H-NMR($CDCl_3$) δ: 1.46(18H,s), 4.71(2H,s), 6.76–6.90 (3H,m)

Example 243

Synthesis of N-(3-thioureido-5-trifluoromethylphenylmethyl)iminodicarboxylic acid di-t-butyl ester Using the compound obtained in Example 242 as a starting material, the same procedure of Example 120 gave 1.02 g of the titled compound quantitatively.

$^1$H-NMR($CDCl_3$) δ: 1.48(18H,s), 4.82(2H,s), 6.26(2H, brs), 7.45–7.50(3H,m), 8.32(1H,s)

Example 244

Synthesis of N-(3-(S-ethylisothioureido)-5-trifluoromethylphenylmethyl)iminodicarboxylic acid di-t-butyl ester Using the compound obtained in Example 243 as a starting material, the same procedure of Example 95 gave 99 mg of the titled compound (yield, 59%).

$^1$H-NMR($CDCl_3$) δ: 1.36(3H, t, J=7.3 Hz), 1.47(18H,s), 2.90–3.12(2H,m), 4.78(2H,s), 7.00–7.22(3H,m)

Example 245

Synthesis of N-(3-(S-ethylisothioureido)-5-trifluoromethylphenylmethyl)amine dihydrochloride Using the compound obtained in Example 244 as a starting material, the same procedure of Example 5 gave 81 mg of the titled compound (yield, 88%).

$^1$H-NMR($D_2O$) δ: 1.42(3H, t, J=7.3 Hz), 3.26(2H, q, J=7.3 Hz), 4.33(2H,s), 7.72(1H,s), 7.83(1H,s), 7.89(1H,s)

Example 246

Synthesis of N-(3-(N'-nitroguanidino)-5-trifluoromethylphenylmethyl)iminodicarboxylic acid di-t-butyl ester Using the compound obtained in Example 242 as a starting material, the same procedure of Example 6 gave 17.2 mg of the titled compound (yield, 5.6%).

$^1$H-NMR($CDCl_3$) δ: 1.48(18H,s), 4.84(2H,s), 7.50–7.60 (3H,m), 9.79(1H,s)

Example 247

Synthesis of N-(3-(N'-nitroguanidino)-5-trifluoromethylphenylmethyl)amine hydrochloride Using the compound obtained in Example 246 as a starting material, the same procedure of Example 5 gave 81 mg of the titled compound (yield, 88%).

$^1$H-NMR($D_2O$) δ: 4.29(2H,s), 7.68–7.78(3H,m)

Example 248

Synthesis of N-(3-fluoro-4-methylphenyl) phthalimide

A mixture of 3-fluoro-4-methylaniline (12.5 g), phthalic anhydride (17.8 g), triethylamine (27.9 ml) and chloroform (100 ml) was heated under reflux for 6 days and concentrated under reduced pressure. The residue was dissolved in ethyl acetate and washed successively with 2 N HCl and a saturated aqueous sodium chloride solution; the organic layer was then dried with anhydrous sodium sulfate and concentrated under reduced pressure. Subsequently, chloroform was added to the resulting residue and the insoluble matter was filtered off whereas the filtrate was concentrated under reduced pressure. The resulting residue was purified by silica gel column chromatography (eluent, chloroform methanol=98:2) to give 18.7 g of the titled compound (yield, 73%).

$^1$H-NMR($CDCl_3$) δ: 2.33(3H,s), 7.14(1H,s), 7.18(1H,s), 7.28–7.34(1H,m), 7.79–7.82(2H,m), 7.94–7.98(2H,m)

Example 249

Synthesis of N-(4-bromomethyl-3-fluorophenyl) phthalimide

A mixture of the compound (1.0 g) obtained in Example 248, N-bromosuccinimide (698 mg), α,α'-azobis (isobutyronitrile) (catalytic amount) and carbon tetrachloride (20 ml) was heated under reflux for 16 h. The reaction mixture was concentrated under reduced pressure and the resulting residue was purified by silica gel column chromatography (eluent, n-hexane:ethyl acetate=8:2) to give 605 mg of the titled compound (yield, 46%).

$^1$H-NMR($CDCl_3$) δ: 4.55(2H,s), 7.28–7.33(2H,m), 7.50–7.56(1H,m), 7.80–7.84(2H,m), 7.96–7.99(2H,m)

Example 250

Synthesis of N-(4-cyanomethyl-3-fluorophenyl) phthalimide

To a solution of sodium cyanide (99 mg) in dimethyl sulfoxide (5 ml), a solution of the compound (605 mg) obtained in Example 249 in dimethyl sulfoxide (10 ml) was added dropwise at 60° C. and stirred at 60° C. for 40 minutes. The reaction mixture was diluted with water and extracted with ethyl acetate-diethyl ether (1:1); thereafter, the organic layer was washed with a saturated aqueous sodium chloride solution, dried with anhydrous sodium sulfate and concentrated under reduced pressure. The resulting residue was purified by silica gel column chromatography (eluent, n-hexane:ethyl acetate=6:4) to give 164 mg of the titled compound (yield, 32%).

$^1$H-NMR($CDCl_3$) δ: 3.83(2H,s), 7.33–7.41(2H,m), 7.57–7.63(1H,m), 7.81–7.84(2H,m), 7.96–8.00(2H,m)

Example 251

Synthesis of 4-cyanomethyl-3-fluoroaniline

To a solution of the compound (164 mg) obtained in Example 250 in methanol (5 ml), hydrazine monohydrate (0.057 ml) was added and heated under reflux for 3 h. The reaction mixture was concentrated under reduced pressure and the resulting residue was purified by silica gel column chromatography (eluent, n-hexane:ethyl acetate=6:4) to give 67 mg of the titled compound (yield, 76%).

$^1$H-NMR($CDCl_3$) δ: 3.62(2H,s), 3.84(2H,brs), 6.37–6.47 (2H,m), 7.09–7.16(1H,m)

Example 252

Synthesis of 4-(2-aminoethyl)-3-fluoroaniline

To a suspension of aluminum lithium hydride (76 mg) in diethyl ether (5 ml), conc. sulfuric acid (0.053 ml) was added under ice cooling and stirred at room temperature for 1 h. Subsequently, a solution of the compound (100 mg) obtained in Example 251 in diethyl ether (15 ml) was added dropwise at room temperature and heated under reflux for 18 h. To the reaction mixture, water (1 ml) and 2 N aqueous sodium hydroxide solution (10 ml) were added under ice cooling and the mixture was extracted with diethyl ether; the organic layer was dried with anhydrous sodium sulfate and concentrated under reduced pressure to give 110 mg of the titled compound quantitatively.

$^1$H-NMR($CDCl_3$) δ: 2.65(2H, t, J=6.9 Hz), 2.88(2H, t, J=6.9 Hz), 3.70(2H, brs), 6.34–6.42(2H,m), 6.91–6.98(1H, m)

Example 253

Synthesis of N-(2-(4-amino-2-fluorophenyl)ethyl) carbamic acid t-butyl ester

To a solution of the compound (110 mg) obtained in Example 252 in methylene chloride (10 ml), di-t-butyl dicarbonate (113 mg) was added under ice cooling and stirred for 1 h under ice cooling. The reaction mixture was concentrated under reduced pressure and the resulting residue was purified by silica gel column chromatography (eluent, n-hexane:ethyl acetate=6:4) to give 51 mg of the titled compound (yield, 39%)

$^1$H-NMR($CDCl_3$) δ: 1.43(9H,s), 2.70(2H, t, J=6.9 Hz), 3.22–3.38(2H,m) 3.70(2H,brs), 4.58(1H,brs), 6.34–6.40 (2H,m), 6.90–6.96(1H,m)

Example 254

Synthesis of N-(2-(2-fluoro-4-thioureidophenyl) ethyl)carbamic acid t-butyl ester Using the compound obtained in Example 253 as a starting material, the same procedure of Example 120 gave 172 mg of the titled compound quantitatively.

$^1$H-NMR($CDCl_3$) δ: 1.42(9H,s), 2.84(2H, t, J=6.9 Hz), 3.30–3.44(2H,m), 4.63(1H,brs), 6.19(2H,brs), 6.95–6.99 (2H,m), 7.20–7.35(1H,m), 8.10(1H,brs)

Example 255

Synthesis of N-(2-(4-(S-ethylisothioureido)-2-fluorophenyl)ethyl)carbamic acid t-butyl ester Using the compound obtained in Example 254 as a starting material, the same procedure of Example 95 gave 151 mg of the titled compound (yield, 92%).

$^1$H-NMR($CDCl_3$) δ: 1.36(3H, t, J=7.3 Hz), 1.43(9H,s), 2.78(2H, t, J=6.9 Hz), 2.92–3.15(2H,m), 3.28–3.40(2H,m), 4.58(1H,brs), 6.60–6.70(2H,m), 7.07–7.13(1H,m)

Example 256

Synthesis of N-(2-(4-(S-ethylisothioureido)-2-fluorophenyl)ethyl)amine dihydrochloride Using the compound obtained in Example 255 as a starting material, the same procedure of Example 5 gave 141 mg of the titled compound quantitatively.

$^1$H-NMR($D_2O$) δ: 1.41(3H, t, J=7.3 Hz), 3.09(2H, t, J=7.3 Hz), 3.23(2H, q, J=7.3 Hz), 3.29(2H, t, J=7.3 Hz), 7.19–7.24 (2H,m), 7.45–7.52(1H,m)

Example 257

Synthesis of N-(2-(4-(N'-t-butoxycarbonyl-N"-ethylguanidino)-2-fluorophenyl)ethyl)carbamic acid t-butyl ester Using the compound obtained in Example 253 as a starting material, the same procedure of Example 233 gave 167 mg of the titled compound (yield, 76%).

$^1$H-NMR($CDCl_3$) δ: 1.19(3H, t, J=7.3 Hz), 1.43(9H,s), 1.48(9H,s), 2.70–2.86(2H,m), 3.22–3.48(4H,m), 5.94(1H, brs), 6.50–7.22 (3H,m), 8.02(1H,s)

Example 258

Synthesis of N-(2-(4-(N'-ethylguanidino)-2-fluorophenyl)ethyl)amine dihydrochloride Using the compound obtained in Example 257 as a starting material, the same procedure of Example 5 gave 75 mg of the titled compound (yield, 67%).

$^1$H-NMR($D_2O$) δ: 1.23(3H, t, J=7.3 Hz), 3.07(2H, t, J=7.3 Hz), 3,27–3.36(4H,m), 7.11–7.45(3H,m)

Example 259

Synthesis of N-(2-(2-fluoro-4-(N'-nitroguanidino) phenyl)ethyl)carbamic acid t-butyl ester Using the compound obtained in Example 253 as a starting material, the same procedure of Example 6 gave 65 mg of the titled compound (yield, 48%).

$^1$H-NMR($CDCl_3$) δ: 1.42(9H,s), 2.87(2H, t, J=6.6 Hz), 3.30–3.46(2H,m), 4.69(1H,brs), 7.00–7.12(2H,m), 7.28–7.40(1H,m), 9.84(1H,s)

Example 260

Synthesis of N-(2-(2-fluoro-4-(N'-nitroguanidino) phenyl)ethyl)amine hydrochloride Using the compound obtained in Example 259 as a starting material, the same procedure of Example 5 gave 28 mg of the titled compound (yield, 57%).

$^1$H-NMR($D_2O$) δ: 3.07(2H, t, J=7.3 Hz), 3.30(2H, t, J=7.3 Hz), 7.15–7.45(3H,m)

Example 261

Synthesis of 2-fluoro-5-nitrobenzyl alcohol

Using 2-fluoro-5-nitrobenzoic acid as a starting material, the same procedure of Example 132 gave the titled compound (yield, 95%).

$^1$H-NMR($CDCl_3$) δ: 2.10(1H, t, J=5.9 Hz), 4.86(2H, d, J=5.9 Hz), 7.16–7.24(1H,m), 8.15–8.25(1H,m), 8.40–8.47 (1H,m)

Example 262

Synthesis of 2-fluoro-5-nitrobenzyl bromide

Using the compound obtained in Example 261 as a starting material, the same procedure of Example 55 gave the titled compound (yield, 98%).

$^1$H-NMR($CDCl_3$) δ: 4.53(2H,s), 7.22–7.30(1H,m), 8.18–8.27(1H,m), 8.40–8.47(1H,m)

MS(m/Z) 234($M^+$)

Example 263

Synthesis of N-(2-fluoro-5-nitrophenylmethyl) iminodicarboxylic acid di-t-butyl ester Using the compound obtained in Example 262 as a starting material, the same procedure of Example 127 gave the titled compound (yield, 99%).

$^1$H-NMR($CDCl_3$) δ: 1.50(18H,s), 4.91(2H,s), 7.15–7.22 (1H,m), 8.12–8.21(2H,m)

Example 264

Synthesis of N-(2-dimethylamino-5-nitrophenylmethyl)iminodicarboxylic acid di-t-butyl ester A mixture of the compound (1.0 g) obtained in Example 263, dimethylamine hydrochloride (485 mg), triethylamine (0.8 ml) and dimethylformamide (10 ml) was heated at 80° C. for 5.5 h. The reaction mixture was distilled under reduced pressure and water and 2 N HCl were added to the residue; after extraction with ethyl acetate, the organic layer was washed with a saturated aqueous sodium chloride solution, dried with anhydrous magnesium sulfate and concentrated under reduced pressure. The resulting residue was purified by silica gel column chromatography (eluent, n-hexane:ethyl acetate=3:1) to give 1.1 g of the titled compound quantitatively.

$^1$H-NMR($CDCl_3$) δ: 1.39(18H,s), 2.78(6H,s), 4.78(2H,s), 6.97(1H, d, J=8.6 Hz), 7.95–8.02(2H,m)

Example 265

Synthesis of N-(5-amino-2-dimethylaminophenylmethyl)iminodicarboxylic acid di-t-butyl ester Using the compound obtained in Example 264 as a starting material, the same procedure of Example 2 gave the titled compound (yield, 99%).

$^1$H-NMR($CDCl_3$) δ: 1.42(18H,s), 2.58(6H,s), 3.48(2H, brs), 4.85(2H,s), 6.43–6.54(2H,m), 6.94(1H, d, J=8.3 Hz)

MS(m/z) 365($M^+$+1)

Example 266

Synthesis of N-(5-(N'-t-butoxycarbonyl-N"-ethylguanidino)2-dimethylaminophenylmethyl) iminodicarboxylic acid di-t-butyl ester Using the compound obtained in Example 265 as a starting material, the same procedure of Example 233 gave the titled compound (yield, 73%).

$^1$H-NMR ($CDCl_3$) δ: 1.08–1.12(3H,m), 1.43(18H,s), 1.53 (9H,s), 2.68(6H,s), 3.10–3.48(2H,m), 4.85(2H,s), 6.84–7.12 (3H,m)

MS(m/z) 535($M^+$)

Example 267

Synthesis of N-(2-dimethylamino-5-(N'-ethylguanidino)phenylmethyl)amine trihydrochloride Using the compound obtained in Example 266 as a starting material, the same procedure of Example 5 gave the titled compound (yield, 67%).

$^1$H-NMR($D_2O$) δ: 1.24(3H, t, J=7.3 Hz), 3.24(6H,s), 3.35(2H, q, J=7.3 Hz), 4.41(2H,s), 7.49–7.58(2H,m), 7.82 (1H, d, J=8.9 Hz)

MS(m/z) 235($M^+$)

Example 268

Synthesis of N-(2-dimethylamino-5-thioureidophenylmethyl)iminodicarboxylic acid di-t-butyl ester Using the compound obtained in Example 265 as a starting material, the same procedure of Example 120 gave the titled compound (yield, 91%).

$^1$H-NMR($CDCl_3$) δ: 1.44(18H,s), 2.68(6H,s), 4.84(2H,s), 6.22(2H,brs), 6.92–7.00(1H,m), 7.04–7.16(2H,m), 8.25(1H, brs)

MS(m/z) 424($M^+$)

Example 269

Synthesis of N-(2-dimethylamino-5-(S-ethylisothioureido)phenylmethyl)iminodicarboxylic acid di-t-butyl ester Using the compound obtained in Example 268 as a starting material, the same procedure of Example 95 gave the titled compound (yield, 92%).

$^1$H-NMR($CDCl_3$) δ1.34(3H, t, J=7.3 Hz), 1.42(18H,s), 2.63(6H,s), 2.83–3.13(2H,m), 4.87(2H,s), 6.69–7.06(3H,m)

MS(m/z) 452($M^+$)

Example 270

Synthesis of N-(2-dimethylamino-5-(S-ethylisothioureido)phenylmethyl)amine trihydrochloride Using the compound obtained in Example 269 as a starting material, the same procedure of Example 5 gave the titled compound (yield, 67%).

$^1$H-NMR($D_2O$) δ: 1.43(3H, t, J=7.3 Hz), 3.27(2H, q, J=7.3 Hz), 3.33(6H,s), 4.48(2H,s), 7.66(1H, d,J=2.3 Hz), 7.72(1H, dd, J=8.6, 2.3 Hz), 7.97(1H, d, J=8.6 Hz)

MS(m/z) 252($M^+$)

Example 271

Synthesis of N-(2-methoxy-5-(N'-nitroguanidino) phenylmethyl)carbamic acid t-butyl ester A mixture of the compound (130 mg) obtained in Example 119, triethylamine (0.09 ml), S-methyl-N-nitroisothiourea (84 mg), acetonitrile (3 ml) and methanol (1 ml) was heated under reflux for 20 h. The reaction mixture was distilled under reduced pressure and the residue was purified by silica gel column chromatography (eluent, chloroform:ethyl acetate=1:1) to give 57.2 mg of the titled compound (yield, 33%).

$^1$H-NMR($CDCl_3$) δ: 1.43(9H,s), 3.87(3H,s), 4.28(2H, d, J=5.9 Hz), 5.20(1H,brs), 6.91(1H, d, J=9.3 Hz), 7.19–7.28 (2H,m), 9.28(1H,brs)

Example 272

Synthesis of N-(2-methoxy-5-(N'-nitroguanidino) phenylmethyl)amine hydrochloride Using the compound obtained in Example 271 as a starting material, the same procedure of Example 5 gave 41 mg of the titled compound (yield, 90%).

$^1$H-NMR($D_2O$) δ: 3.95(3H,s), 4.20(2H,s), 7.18(1H, d, J=8.9 Hz), 7.34(1H, d, J=2.6 Hz), 7.41(1H, dd, J=8.9, 2.6 Hz)

Example 273

Synthesis of N-(5-(N'-t-butoxycarbonyl-N-ethylguanidino)-2-methoxyphenylmethyl)carbamic acid t-butyl ester Using the compound obtained in Example 119 as a starting material, the same procedure of Example 233 gave the titled compound (yield, 61%).

$^1$H-NMR($CDCl_3$) δ: 1.00–1.20(3H,m), 1.44(9H,s), 1.53 (9H,s), 3.30–3.50(2H,m), 3.85(3H,s), 4.28(2H,brs), 5.00 (1H,brs), 6.80–7.20(3H,m)

Example 274

Synthesis of N-(5-(N'-ethylguanidino)-2-methoxyphenylmethyl)amine dihydrochloride Using the compound obtained in Example 273 as a starting material, the same procedure of Example 5 gave the titled compound (yield, 95%).

$^1$H-NMR($D_2O$) δ: 1.21(3H, t, J=7.3 Hz), 3.29(2H, q, J=7.3 Hz), 3.93(3H,s), 4.17(2H,s), 7.16(1H, d, J=8.9 Hz), 7.28(1H, d, J=2.6 Hz), 7.38(1H, dd, J=8.9, 2.6 Hz)

MS(m/z) 222($M^+$)

Example 275

Synthesis of N-(2-methoxy-5-(N'-methylguanidino) phenylmethyl)carbamic acid t-butyl ester The compound obtained in Example 121 was dissolved in ethyl acetate and the solution was washed with a saturated aqueous sodium bicarbonate solution, dried with anhydrous magnesium sulfate and concentrated under reduced pressure. A mixture of the resulting residue (150 mg), methylamine hydrochloride (33 mg), triethylamine (0.13 ml) and dimethylformamide (6 ml) was stirred at 80° C. for 5 h. The reaction mixture was concentrated under reduced pressure and the resulting residue was purified by silica gel column chromatography (eluent, chloroform:methanol=6:1) to give 106.1 mg of the titled compound (yield, 78%).

$^1$H-NMR($CDCl_3$) δ: 1.40(9H,s), 2.96(3H, d, J=3.9 Hz), 3.83(3H,s), 4.20(2H, d, J=5.9 Hz), 5.50(1H, brs), 6.85(1H, d, J=9.3 Hz), 7.00–7.20(2H,m), 9.54(1H,brs)

MS(m/z) 308($M^+$)

Example 276

Synthesis of N-(2-methoxy-5-(N'-methylguanidino) phenylmethyl)amine dihydrochloride Using the compound obtained in Example 275 as a starting material, the same procedure of Example 5 gave the titled compound (yield, 55%).

$^1$H-NMR($D_2O$) δ: 2.88(3H,s), 3.93(3H,s), 4.17(2H,s), 7.16(1H, d, J=8.9 Hz), 7.28(1H, d, J=2.6 Hz), 7.38(1H, dd, J=8.9, 2.6 Hz)

MS(m/z) 208($M^+$)

Example 277

Synthesis of N-(3-(t-butoxycarbonylaminomethyl)-4-methoxyphenyl)amidinosulfonic acid To a mixture of the compound (327 mg) obtained in Example 120, sodium molybdate dehydrate (25 mg), methanol (10 ml) and water (10 ml), aqueous hydrogen peroxide (0.3 ml) was added dropwise at 0° C. The reaction mixture was stirred at room temperature for 1.5 h, and methanol was distilled off under reduced pressure. The resulting suspension was collected by filtration, washed with water and dried under reduced pressure to give 335 mg of the titled compound (yield, 93%).

$^1$H-NMR(DMSO-$d_6$) δ: 1.40(9H,s), 3.83(3H,s), 4.12(2H, d, J=5.9 Hz), 7.03–7.19(3H,m), 8.98(1H,brs), 9.50(1H,brs), 11.30(1H,brs)

Example 278

Synthesis of N-(2-methoxy-5-(N'-n-propylguanidino)phenylmethyl)carbamic acid t-butyl ester To a solution of the compound (160 mg) obtained in Example 277 in acetonitrile (5 ml), n-propylamine (0.05 ml) was added dropwise and stirred at room temperature for 1.5 h. The reaction mixture was concentrated under reduced pressure and 2 N aqueous sodium hydroxide solution was added to the resulting residue and the mixture was extracted with ethyl acetate. The organic layer was washed successively with water and a saturated aqueous sodium chloride solution, dried with anhydrous magnesium sulfate and concentrated under reduced pressure. The resulting residue was purified by basic silica gel column chromatography (eluent, n-hexane:ethyl acetate=1:2) to give 160 mg of the titled compound quantitatively.

$^1$H-NMR($CDCl_3$) δ: 0.93(3H, t, J=7.3 Hz), 1.42(9H,s), 1.49–1.59(2H,m), 3.15(2H, t, J=7.3 Hz), 3.80(3H,s), 4.22 (2H,brs), 4.92(1H,brs), 6.75–6.86(3H,m)

MS(m/z) 336($M^+$)

Example 279

Synthesis of N-(2-methoxy-5-(N'-n-propylguanidino)phenylmethyl)amine dihydrochloride Using the compound obtained in Example 278 as a starting material, the same procedure of Example 5 gave the titled compound (yield, 71%).

$^1$H-NMR($D_2O$) δ: 0.93(3H, t, J=7.3 Hz), 1.55–1.68(2H, m), 3.22(2H, t, J=7.3 Hz), 3.93(3H,s), 4.17(2H,s), 7.16(1H, d, J=8.6 Hz), 7.28(1H, d, J=2.6 Hz), 7.38(1H, dd, J=8.6, 2.6 Hz)

MS(m/z) 236($M^+$)

Example 280

Synthesis of N-(2-dimethylamino-5-(N'-nitroguanidino)phenylmethyl)iminodicarboxylic acid di-t-butyl ester Using the compound obtained in Example 265 as a starting material, the same procedure of Example 6 gave the titled compound (yield, 52%). 1H-NMR($CDCl_3$) δ: 1.43 (18H,s), 2.71(6H,s), 4.86(2H,s), 7.02–7.16(3H,m), 9.82(1H, brs)

Example 281

Synthesis of N-(2-dimethylamino-5-(N'-nitroguanidino)phenylmethyl)amine dihydrochloride Using the compound obtained in Example 280 as a starting material, the same procedure of Example 5 gave the titled compound (yield, 83%).

$^1$H-NMR($D_2O$) δ: 3.13(6H,s), 4.38(2H,s), 7.51–7.55(2H, m), 7.73(1H, dd, J=7.9, 1.3 Hz)

Example 282

Synthesis of N-(2-(N-ethyl-N-methylamino)-5-nitrophenylmethyl)iminodicarboxylic acid di-t-butyl ester Using the compound obtained in Example 263 as a starting material and also using ethylmethylamine as a reagent, the same procedure of Example 264 gave the titled compound (yield, 42%).

$^1$H-NMR($CDCl_3$) δ: 1.18(3H, t, J=7.2 Hz), 1.45(18H,s), 2.81(3H,s), 3.05(2H, q, J=7.2 Hz), 4.82(2H,s), 7.06(1H, d, J=8.2 Hz), 8.04–8.15(2H,m)

Example 283

Synthesis of N-(5-amino-2-(N-ethyl-N-methylamino)phenylmethyl)iminodicarboxylic acid di-t-butyl ester Using the compound obtained in Example 282 as a starting material, the same procedure of Example 2 gave the titled compound (yield, 58%).

$^1$H-NMR($CDCl_3$) δ: 1.04(3H, t, J=7.0 Hz), 1.42(18H,s), 2.56(3H,s), 2.79(2H, q, J=7.0 Hz), 3.55(2H, brs), 4.84(2H, s), 6.43–6.56(3H,m)

MS(m/z) 379($M^+$)

Example 284

Synthesis of N-(5-(N'-t-butoxycarbonyl-N"-ethylguanidino)-2-(N-ethyl-N-methylamino) phenylmethyl)iminodicarboxylic acid di-t-butyl ester Using the compound obtained in Example 283 as a starting material, the same procedure of Example 233 gave the titled compound (yield, 77%).

$^1$H-NMR($CDCl_3$) δ: 1.09(3H, t, J=7.2 Hz), 1.29–2.66 (21H,m), 2.65(3H,s), 2.86(2H, q, J=7.2 Hz), 3.30–3.50(2H, m), 4.84(2H,s), 6.80–7.11(3H,m)

MS(m/z) 549($M^+$)

Example 285

Synthesis of N-(5-(N'-ethylguanidino)-2-(N-ethyl-N-methyl-amino)phenylmethyl)amine trihydrochloride Using the compound obtained in Example 284 as a starting material, the same procedure of Example 5 gave the titled compound (yield, 83%).

$^1$H-NMR($D_2O$) δ: 1.15–1.26(6H,m), 3.21(3H,s), 3.26–3.38(2H,m), 3.54–3.65(2H,m), 4.39(2H,s), 7.35–7.57 (2H,m), 7.75(1H, d, J=8.6 Hz)

Example 286

Synthesis of N-(2-(N-ethyl-N-methylamino)-5-thioureidophenylmethyl)iminodicarboxylic acid di-t-butyl ester Using the compound obtained in Example 283 as a starting material, the same procedure of Example 120 gave the titled compound (yield, 77%).

$^1$H-NMR($CDCl_3$) δ: 1.14(3H, t, J=7.1 Hz), 1.45(18H,s), 2.66(3H,s), 2.89(2H, q, J=7.1 Hz), 4.83(2H, s), 6.15(2H, brs), 6.94–7.14(3H,m), 8.00(1H,brs)

MS(m/z) 439($M^+$+1)

Example 287

Synthesis of N-(5-(S-ethylisothioureido)-2-(N-ethyl-N-methylamino)phenylmethyl)iminodicarboxylic acid di-t-butyl ester Using the compound obtained in Example 286 as a starting material, the same procedure of Example 95 gave the titled compound (yield, 66%).

$^1$H-NMR($CDCl_3$) δ: 1.04(3H, t, J=7.2 Hz), 1.31–1.45 (21H,m), 2.61(3H,s), 2.83(2H, q, J=7.2 Hz), 3.00–3.20(2H, m), 4.47(1H,brs), 4.86(2H,s), 6.60–6.85(2H,m), 7.05(1H, d, J=8.2 Hz)

MS(m/z) 466($M^+$)

Example 288

Synthesis of N-(5-(S-ethylisothioureido)-2-(N-ethyl-N-methylamino)phenylmethyl)amine trihydrochloride Using the compound obtained in Example 287 as a starting material, the same procedure of Example 5 gave the titled compound (yield, 95%).

$^1$H-NMR($D_2O$) δ: 1.24(3H, t, J=7.3 Hz), 1.43(3H, t, J=7.3 Hz), 3.27(2H, q, J=7.3 Hz), 3.37(3H,s), 3.72(2H, q, J=7.3 Hz), 4.51(2H,s), 7.69(1H, d, J=2.3 Hz), 7.74(1H, dd, J=8.6, 2.3 Hz), 7.94(1H, d, J=8.6 Hz)

MS(m/z) 266($M^+$)

Example 289

Synthesis of N-(2-(4-(N'-t-butoxycarbonyl-S-methylisothioureido)phenyl)ethyl)carbamic acid t-butyl ester To a mixture of the compound (280 mg) obtained in Example 51, sodium bicarbonate (87 mg) and methylene chloride (5 ml), di-t-butyl dicarbonate (227 mg) was added and stirred at room temperature for 15 h; thereafter, methylene chloride and water were added. The organic layer was dried with anhydrous magnesium sulfate and concentrated under reduced pressure. The resulting residue was purified by silica gel column chromatography (eluent, n-hexane:ethyl acetate=3:1) to give 303 mg of the titled compound (yield, 81%).

$^1$H-NMR ($CDCl_3$) δ: 1.26–1.56(18H,m), 2.40(3H,s), 2.77–2.80(2H,m), 3.35–3.38(2H,m), 4.69(1H,brs), 7.20(4H, s), 11.28(1H,brs)

Example 290

Synthesis of N-(2-(4-(N'-t-butoxycarbonyl-N"-methoxyguanidino)phenyl)ethyl)carbamic acid t-butyl ester To a mixture of the compound (190 mg) obtained in Example 289, triethylamine (0.14 ml), O-methylhydroxylamine hydrochloride (84 mg) and acetonitrile (5 ml), a solution of silver nitrate (90 mg) in acetonitrile (2 ml) was added and stirred at 0° C. for 15 min. The reaction mixture was filtered through Celite and the filtrate was concentrated under reduced pressure. The resulting residue was purified by silica gel column chromatography (eluent, chloroform:ethyl acetate=3:1) to give the 75 mg of titled compound (yield, 38%).

$^1$H-NMR($CDCl_3$) δ: 1.43(9H,s), 1.51(9H,s), 2.72(2H, t, J=6.9 Hz), 3.32–3.35(2H,m), 3.80(3H,s), 4.53(1H,brs), 7.08 (2H, d, J=8.5 Hz), 7.40(2H, d, J=8.5 Hz), 7.85(1H,brs), 8.88(1H,brs)

MS(m/z) 408($M^+$)

Example 291

Synthesis of N-(2-(4-(N'-methoxyguanidino)phenyl)ethyl)amine dihydrochloride

Using the compound obtained in Example 290 as a starting material, the same procedure of Example 5 gave the titled compound quantitatively.

$^1$H-NMR($D_2O$) δ: 3.04(2H, t, J=7.2 Hz), 3.29(2H, t, J=7.2 Hz), 3.81(3H,s), 7.30(2H, d, J=8.6 Hz), 7.42(2H, d, J=8.6 Hz)

MS(m/z) 208($M^+$)

Example 292

Synthesis of (2,6-dimethoxy-3-nitrophenyl)methanol

Using 2,6-dimethoxy-3-nitrobenzoic acid as a starting material, the same procedure of Example 132 gave the titled compound (yield, 39%).

$^1$H-NMR($CDCl_3$) δ: 3.98(6H,s), 4.79(2H,s), 6.75(1H, d, J=9.2 Hz), 7.99(1H, d, J=9.2 Hz)

Example 293

Synthesis of 2,6-dimethoxy-3-nitrobenzyl bromide

Using the compound obtained in Example 292 as a starting material, the same procedure of Example 55 gave the titled compound (yield, 98%).

$^1$H-NMR($CDCl_3$) δ: 4.00(3H,s), 4.02(3H,s), 4.62(2H,s), 6.74(1H, d, J=9.2 Hz), 8.02(1H, d, J=9.2 Hz)

MS(m/z) 276($M^+$)

Example 294

Synthesis of N-(2,6-dimethoxy-3-nitrophenylmethyl)iminodicarboxylic acid di-t-butyl ester Using the compound obtained in Example 293 as a starting material, the same procedure of Example 127 gave the titled compound (yield, 71%).

$^1$H-NMR($CDCl_3$) δ: 1.44–1.48(18H,m), 3.86(3H,s), 3.88 (3H,s), 4.94(2H,s), 6.68(1H, d, J=9.2 Hz), 7.93(1H, d, J=9.2 Hz)

Example 295

Synthesis of N-(3-amino-2,6-dimethoxyphenylmethyl)iminodicarboxylic acid di-t-butyl ester Using the compound obtained in Example 294 as a starting material, the same procedure of Example 2 gave the titled compound (yield, 45%).

$^1$H-NMR($CDCl_3$) δ: 1.42(18H,s), 3.50(2H,brs), 3.70(6H, s), 4.91(2H,s), 6.56(1H, d, J=8.3 Hz), 6.63(1H, d, J=8.3 Hz)

MS(m/z) 382($M^+$)

Example 296

Synthesis of N-(2,6-dimethoxy-3-thioureidophenylmethyl)iminodicarboxylic acid di-t-butyl ester Using the compound obtained in Example 295 as a starting material, the same procedure of Example 120 gave the titled compound (yield, 46%).

$^1$H-NMR($CDCl_3$) δ: 1.44(18H,s), 3.79(3H,s), 3.81(3H,s), 4.89(2H,s), 6.11(2H,brs), 6.66(1H, d, J=8.9 Hz), 7.12(1H, d, J=8.9 Hz), 7.63(1H,brs)

MS(m/z) 441($M^+$)

Example 297

Synthesis of N-(2,6-dimethoxy-3-(S-ethylisothioureido)phenylmethyl)iminodicarboxylic acid di-t-butyl ester Using the compound obtained in Example 296 as a starting material, the same procedure of Example 95 gave the titled compound (yield, 71%).

$^1$H-NMR($CDCl_3$) δ: 1.35–1.51(21H,m), 3.00–3.12(2H, m), 3.70(3H,s), 3.76(3H,s), 4.58(1H,brs), 4.91(2H,s), 6.58 (1H, d, J=8.9 Hz), 6.75–6.78(1H,m)

MS(m/z) 469($M^+$)

Example 298

Synthesis of N-(2,6-dimethoxy-3-(S-ethylisothioureido)phenylmethyl)amine dihydrochloride Using the compound obtained in Example 297 as a starting material, the same procedure of Example 5 gave the titled compound quantitatively.

$^1$H-NMR($D_2O$) δ: 1.43(3H, t, J=7.3 Hz), 3.34(2H, q, J=7.3 Hz), 3.63(3H,s), 3.66(3H,s), 4.28(2H,s), 7.01(1H, d, J=8.9 Hz), 7.42(1H, d, J=8.9 Hz)

MS(m/z) 269($M^+$)

Example 299

Synthesis of N-(1-(3-(N'-t-butoxycarbonyl-N"-ethylguanidino)phenyl)-1-methylethyl)carbamic acid t-butyl ester Using the compound obtained in Example 2 as a starting material, the same procedure of Example 233 gave the titled compound (yield, 81%).

$^1$H-NMR($CDCl_3$) δ: 1.11–1.60(27H,m), 3.30–3.40(2H, m), 5.00(2H,s), 7.00–7.34(4H,m)

MS(m/z) 420($M^+$)

Example 300

Synthesis of N-(1-(3-(N'-ethylguanidino)phenyl)-1-methylethyl) amine dihydrochloride Using the compound obtained in Example 299 as a starting material, the same procedure of Example 5 gave the titled compound quantitatively.

$^1$H-NMR($D_2O$) δ: 1.24(3H, t, J=7.3 Hz), 1.77(6H,s), 3.33(2H, q, J=7.3 Hz), 7.36–7.68(4H,m)

MS(m/z) 220($M^+$)

Example 301

Synthesis of N-(3-(di-(t-butoxycarbonyl)aminomethyl)phenyl)amidinosulfonic acid

Using N-(3-thioureidophenylmethyl)iminodicarboxylic acid di-t-butyl ester as a starting material, the same procedure of Example 277 gave the titled compound (yield, 98%).

$^1$H-NMR(DMSO-$d_6$) δ: 1.42(18H,s), 4.71(2H,s), 7.15–7.24(3H,m), 7.43–7.49(1H,m), 9.61(1H,brs), 11.50 (1H,brs)

Example 302

Synthesis of N-(3-(N',N'-dimethylguanidino)phenylmethyl)iminodicarboxylic acid di-t-butyl ester Using the compound obtained in Example 301 as a starting material and also using dimethylamine hydrochloride and triethylamine as reagents, the same procedure of Example 278 gave the titled compound (yield, 50%).

$^1$H-NMR($CDCl_3$) δ: 1.45(18H,s), 2.98(6H,s), 4.73(2H,s), 6.75–6.87(3H,m), 7.16–7.19(1H,m)

MS(m/z) 392($M^+$)

Example 303

Synthesis of N-(3-(N',N'-dimethylguanidino)phenylmethyl)amine dihydrochloride

Using the compound obtained in Example 302 as a starting material, the same procedure of Example 5 gave the titled compound (yield, 96%).

$^1$H-NMR($D_2O$) δ: 3.14(6H,s), 4.19(2H,s), 7.31–7.57(4H, m)

MS(m/z) 192($M^+$)

Example 304

Synthesis of N-(3-(N'-ethyl-N'-methylguanidino)phenylmethyl)iminodicarboxylic acid di-t-butyl ester Using the compound obtained in Example 301 as a starting material and also using ethylmethylamine as a reagent, the same procedure of Example 278 gave the titled compound (yield, 27%).

$^1$H-NMR($CDCl_3$) δ: 1.17(3H, t, J=7.3 Hz), 1.45(18H,s), 2.95(3H,s), 3.38(2H, q, J=7.3 Hz), 4.73(2H,s), 6.75–7.19 (4H,m)

MS(m/z) 406($M^+$)

Example 305

Synthesis of N-(3-(N'-ethyl-N'-methylguanidino)phenylmethyl)amine dihydrochloride Using the compound obtained in Example 304 as a starting material, the same procedure of Example 5 gave the titled compound quantitatively.

$^1$H-NMR($D_2O$) δ: 1.28(3H, t, J=7.3 Hz), 3.12(3H,s), 3.53(2H, q, J=7.3 Hz), 4.23(2H,s), 7.30–7.70(4H,m)

MS(m/z) 206($M^+$)

Example 306

Synthesis of N-(3-(N'-(2-propynyl)guanidino) phenylmethyl)iminodicarboxylic acid di-t-butyl ester Using the compound obtained in Example 301 as a starting material and also using propargylamine as reagent, the same procedure of Example 278 gave the titled compound (yield, 55%).

$^1$H-NMR($CDCl_3$) δ: 1.45(18H,s), 2.26(1H,s), 4.04(2H,s), 4.73(2H,s), 6.78–6.90(3H,m), 7.21(1H, dd, J=7.6, 7.6 Hz)

MS(m/z) 402($M^+$)

Example 307

Synthesis of N-(3-(N'-(2-propynyl)guanidino) phenylmethyl)amine dihydrochloride

Using the compound obtained in Example 306 as a starting material, the same procedure of Example 5 gave the titled compound quantitatively.

$^1$H-NMR($D_2O$) δ: 2.81(1H, t, J=2.6 Hz), 4.15(2H, d, J=2.6 Hz), 4.24(2H,s), 7.28–7.41(2H,m), 7.47(1H, d, J=7.9 Hz), 7.58(1H, dd, J=7.9, 7.9 Hz)

MS(m/z) 202($M^+$)

Example 308

Synthesis of N-(2-nitrophenylethyl)phthalimide

Using 2-nitrophenethyl alcohol as a starting material, the same procedure of Example 179 gave the titled compound (yield, 97%).

$^1$H-NMR($CDCl_3$) δ: 3.31(2H, t, J=6.9 Hz), 4.10(2H, t, J=6.9 Hz), 7.28–7.50(3H,m), 7.68–7.74(2H,m), 7.77–7.84 (2H,m), 7.96–8.20(1H,m)

Example 309

Synthesis of N-(2-nitrophenylethyl)carbamic acid t-butyl ester

Using the compound (2.18 g) obtained in Example 308 as a starting material, the same procedure of Example 180 gave 2-nitrophenylethylamine. A two-layered mixture consisting of the resulting amine compound, di-t-butyl dicarbonate (1.77 g), methylene chloride (120 ml) and 2 N aqueous sodium hydroxide solution (30 ml) was stirred at room temperature for 14 h. The organic layer was dried with anhydrous sodium sulfate and distilled under reduced pressure. The resulting residue was purified by silica gel column chromatography (eluent, n-hexane:ethyl acetate=3:1) to give 1.95 g of the titled compound (yield, 99%).

$^1$H-NMR($CDCl_3$) δ: 1.42(9H,s), 3.09(2H, t, J=6.6 Hz), 3.46(2H, dt, J=6.6, 6.6 Hz), 4.70(1H,brs), 7.34–7.43(2H,m), 7.50–7.59(1H,m), 7.91–7.97(1H,m)

MS(m/z) 266($M^+$)

Example 310

Synthesis of N-(2-aminophenylethyl)carbamic acid t-butyl ester

Using the compound obtained in Example 309 as a starting material, the same procedure of Example 2 gave the titled compound (yield, 94%).

$^1$H-NMR($CDCl_3$) δ: 1.45(9H,s), 2.70(2H, t, J=6.9 Hz), 3.28(2H, dt, J=6.9, 6.9 Hz), 3.93(2H,brs), 4.87(1H,brs), 6.64–6.74(2H,m), 6.96–7.09(2H,m)

MS(m/z) 236($M^+$)

Example 311

Synthesis of N-(2-thioureidophenylethyl)carbamic acid t-butyl ester

Using the compound obtained in Example 310 as a starting material, the same procedure of Example 120 gave the titled compound (yield, 98%).

$^1$H-NMR($CDCl_3$) δ: 1.35(9H,s), 2.80(2H, t, J=6.9 Hz), 3.32(2H, dt, J=6.9, 6.9 Hz), 4.80(1H,brs), 6.28(2H,brs), 7.20–7.28(4H,m)

MS(m/z) 295($M^+$)

Example 312

Synthesis of N-(2-(S-ethylisothioureido) phenylethyl)carbamic acid t-butyl ester Using the compound obtained in Example 311 as a starting material, the same procedure of Example 95 gave the titled compound (yield, 81%).

$^1$H-NMR($CDCl_3$) δ: 1.33–1.40(3H,m), 1.39(9H,s), 2.69 (2H, t, J=6.3 Hz), 3.00–3.20(2H,m), 3.32(2H, dt, J=6.3, 6.3 Hz), 4.56(2H,brs), 5.27(1H,brs), 6.80–6.88(1H,m), 6.95–7.05(1H,m), 7.12–7.24(2H,m)

MS(m/z) 323($M^+$)

Example 313

Synthesis of N-(2-(S-ethylisothioureido) phenylethyl)amine dihydrochloride

Using the compound obtained in Example 312 as a starting material, the same procedure of Example 5 gave the titled compound (yield, 81%).

$^1$H-NMR($D_2O$) δ: 1.35–1.50(3H,m), 2.99(2H, t, J=7.3 Hz), 3.20–3.33(4H,m), 7.36–7.42(1H,m), 7.44–7.60(3H,m)

Example 314

Synthesis of N-(5-amino-2-fluorophenylmethyl) iminodicarboxylic acid di-t-butyl ester Using the compound obtained in Example 263 as a starting material, the same procedure of Example 2 gave the titled compound (yield, 87%).

$^1$H-NMR($CDCl_3$) δ: 1.45(18H,s), 3.50(2H,brs), 4.78(2H, s), 6.47–6.54(2H,m), 6.77–6.85(1H,m)

Example 315

Synthesis of N-(2-fluoro-5-thioureidophenylmethyl) iminodicarboxylic acid di-t-butyl ester Using the compound obtained in Example 314 as a starting material, the same procedure of Example 120 gave the titled compound (yield, 99%).

$^1$H-NMR($CDCl_3$) δ: 1.48(18H,s), 4.84(2H,s), 6.11(2H, brs), 7.09–7.14(3H,m), 8.06(1H,brs)

Example 316

Synthesis of N-(5-(S-ethylisothioureido)-2-fluorophenylmethyl)carbamic acid t-butyl ester Using the compound obtained in Example 315 as a starting material, the same procedure of Example 95 gave the titled compound (yield, 53%).

$^1$H-NMR($CDCl_3$) δ: 1.33–1.39(3H,m), 1.45(9H,s), 3.00–3.17(2H,m), 4.32(2H, d, J=5.6 Hz), 4.49(1H,brs), 4.85 (1H,brs), 6.71–7.01(4H,m)

MS(m/z) 327($M^+$)

Example 317

Synthesis of N-(5-(S-ethylisothioureido)-2-fluorophenylmethyl)amine dihydrochloride Using the compound obtained in Example 316 as a starting material, the same procedure of Example 5 gave the titled compound (yield, 83%).

$^1$H-NMR($D_2O$) δ: 1.41(3H, t, J=7.3 Hz), 3.20–3.28(2H, m), 4.29(2H,s), 7.39–7.53(3H,m)

MS(m/z) 227($M^+$)

Example 318

Synthesis of N-(2-hydroxy-5-nitrophenylmethyl) phthalimide

To a solution of the compound (937 mg) obtained in Example 117 in anhydrous methylene chloride (30 ml), a solution of boron tribromide in methylene chloride (1.0 M, 9 ml) was added dropwise at −78° C. in a nitrogen atmosphere and the mixture was stirred at −78° C. for 1 h, then stirred at room temperature for 21 h. Water was added to the reaction mixture, which was extracted with chloroform. The organic layer was washed with a saturated aqueous sodium chloride solution, dried with anhydrous sodium sulfate and concentrated under reduced pressure. The resulting residue was purified by silica gel column chromatography (eluent, n-hexane:ethyl acetate=1:1) to give 743 mg of the titled compound (yield, 83%).

$^1$H-NMR($CDCl_3$) δ: 4.84(2H,s), 6.99(1H, d, J=9.2 Hz), 7.85–7.92(4H,m), 7.95(1H, dd, J=9.2, 2.6 Hz), 8.06(1H, dd, J=9.2, 2.6 Hz), 11.4(1H,s)

MS(m/z) 298($M^+$)

Example 319

Synthesis of N-(2-ethoxy-5-nitrophenylmethyl) phthalimide

To a mixture of sodium hydride (content, 60%; 36 mg) and anhydrous dimethylformamide (5 ml), a solution of the compound (224 mg) obtained in Example 318 in anhydrous dimethylformamide (3 ml) and ethyl iodide (0.072 ml) were successively added dropwise at 0° C. in a nitrogen atmosphere and stirred at room temperature for 24 h. Water was added to the reaction mixture, which was distilled under reduced pressure; thereafter, ethyl acetate and water were added to the resulting residue. The organic layer was washed with a saturated aqueous sodium chloride solution, dried with anhydrous sodium sulfate and distilled under reduced pressure. The resulting residue was purified by silica gel column chromatography (eluent, n-hexane ethyl acetate=1:1) to give 213 mg of the titled compound (yield, 87%).

$^1$H-NMR($CDCl_3$) δ: 1.47(3H, t, J=7.3 Hz), 4.17(2H, q, J=7.3 Hz), 4.93(2H,s), 6.90(1H, d, J=9.2 Hz), 7.74–7.91(4H, m), 8.05(1H, d, J=2.6 Hz), 8.17(1H, dd, J=9.2, 2.6 Hz)

MS(m/z) 326($M^+$)

Example 320

Synthesis of N-(2-ethoxy-5-nitrophenylmethyl) carbamic acid t-butyl ester

Using the compound obtained in Example 319 as a starting material, the same procedure of Example 309 gave the titled compound (yield, 95%).

$^1$H-NMR($CDCl_3$) δ: 1.45(9H,s), 1.49(3H, t, J=7.3 Hz), 4.17(2H, q, J=7.3 Hz), 4.36(2H, d, J=5.9 Hz), 4.98(1H,brs), 6.86–6.91(1H,m), 8.14–8.17(2H,m)

Example 321

Synthesis of N-(5-amino-2-ethoxyphenylmethyl) carbamic acid t-butyl ester

Using the compound obtained in Example 320 as a starting material, the same procedure of Example 2 gave the titled compound (yield, 75%).

$^1$H-NMR($CDCl_3$) δ: 1.38(3H, t, J=6.9 Hz), 1.44(9H,s), 3.41(2H,brs), 3.97(2H, q, J=6.9 Hz), 4.23(2H, d, J=5.9 Hz), 5.00(1H,brs), 6.55(1H, dd, J=8.6, 3.0 Hz), 6.66–6.69(2H,m)

Example 322

Synthesis of N-(2-ethoxy-5-thioureidophenylmethyl)carbamic acid t-butyl ester

Using the compound obtained in Example 321 as a starting material, the same procedure of Example 120 gave the titled compound quantitatively.

$^1$H-NMR($CDCl_3$) δ: 1.44(3H, t, J=7.3 Hz), 1.44(9H,s), 4.07(2H, q, J=7.3 Hz), 4.28(2H, d, J=6.3 Hz), 5.03(1H,brs), 6.04(2H,brs), 6.85(1H, d, J=8.6 Hz), 7.07–7.16(2H,m), 7.85 (1H,brs)

MS(m/z) 325($M^+$)

Example 323

Synthesis of N-(2-ethoxy-5-(S-ethylisothioureido) phenylmethyl)carbamic acid t-butyl ester hydroiodide Using the compound obtained in Example 322 as a starting material, the same procedure of Example 27 gave the titled compound (yield, 90%).

$^1$H-NMR($CDCl_3$) δ: 1.38(6H, t, J=7.6 Hz), 1.45(9H,s), 3.22(2H, q, J=7.6 Hz), 4.07(2H, q, J=7.6 Hz), 4.28–4.29 (2H,m), 5.02(1H,brs), 6.84(1H, d, J=8.6 Hz), 7.06–7.10(2H, m)

MS(m/z) 353($M^+$)

Example 324

Synthesis of N-(2-ethoxy-5-(S-ethylisothioureido) phenylmethyl) amine dihydrochloride Using the compound obtained in Example 323 as a starting material, the same procedure of Example 5 gave the titled compound quantitatively.

$^1$H-NMR($D_2O$) δ: 1.41(3H, t, J=6.9 Hz), 1.43(3H, t, J=6.9 Hz), 3.15–3.30(2H,m), 4.16–4.31(4H,m), 7.20(1H, d, J=8.9 Hz), 7.34(1H, d, J=2.6 Hz), 7.42(1H, dd, J=8.9, 2.6 Hz)

MS(m/z) 253($M^+$)

Example 325

Synthesis of N-(5-(N'-t-butoxycarbonyl-N''-ethylguanidino)-2-ethoxyphenylmethyl)carbamic acid t-butyl ester Using the compound obtained in Example 321 as a starting material, the same procedure of Example 233 gave the titled compound (yield, 90%).

$^1$H-NMR($CDCl_3$) δ: 1.06(3H, t, J=7.3 Hz), 1.40–1.47(3H, m), 1.45(9H,s), 1.53(9H,s), 3.33–3.43(2H,m), 4.06(2H, q,

J=7.3 Hz), 4.16(2H, d, J=5.9 Hz), 4.97(1H,brs), 6.83(1H, d, J=8.3 Hz), 7.04–7.12(2H,m)

Example 326

Synthesis of N-(2-ethoxy-5-(N'-ethylguanidino) phenylmethyl)amine dihydrochloride Using the compound obtained in Example 325 as a starting material, the same procedure of Example 5 gave the titled compound quantitatively.

$^1$H-NMR($D_2O$) δ: 1.21(3H, t, J=7.3 Hz), 1.43(3H, t, J=6.9 Hz), 3.29(2H, q, J=7.3 Hz), 4.17–4.28(4H,m), 7.16(1H, d, J=8.9 Hz), 7.29(1H, d, J=2.6 Hz), 7.36(1H, dd, J=8.9, 2.6 Hz)

MS(m/z) 236($M^+$)

Example 327

Synthesis of N-(2-ethoxy-5-(N'-nitroguanidino) phenylmethyl)carbamic acid t-butyl ester Using the compound obtained in Example 321 as a starting material, the same procedure of Example 6 gave the titled compound quantitatively.

$^1$H-NMR($CDCl_3$) δ: 1.44(9H,s), 1.44–1.48(3H,m), 4.05–4.11(2H,m), 4.30(2H, d, J=3.0 Hz), 5.08(1H,brs), 6.88–6.93(1H,m), 7.16–7.27(2H,m), 9.63(1H,brs)

MS(m/z) 353($M^+$)

Example 328

Synthesis of N-(2-ethoxy-5-(N'-nitroguanidino) phenylmethyl)amine hydrochloride

Using the compound obtained in Example 327 as a starting material, the same procedure of Example 5 gave the titled compound (yield, 95%).

$^1$H-NMR($D_2O$) δ: 1.43(3H, t, J=6.9 Hz), 4.19–4.29(4H, m), 7.17(1H, d, J=8.6 Hz), 7.34(1H, d, J=2.6 Hz), 7.39(1H, dd, J=8.6, 2.6 Hz)

Example 329

Synthesis of N-(5-amino-2-methoxyphenylmethyl) phthalimide

Using the compound obtained in Example 117 as a starting material, the same procedure of Example 2 gave the titled compound (yield, 91%).

$^1$H-NMR($CDCl_3$) δ: 3.36(2H,brs), 3.79(3H,s), 4.85(2H, s), 6.52–6.59(2H,m), 6.70(6H, d, J=2.3 Hz), 7.68–7.76(2H, m), 7.82–7.90(2H,m)

Example 330

Synthesis of N-(2-methoxy-5-(N'-trifluoroacetoxyamino)phenylmethyl)phthalimide

To a solution of the compound (150 mg) obtained in Example 329 and pyridine (0.13 ml) in anhydrous methylene chloride (5 ml), trifluoroacetic anhydride (0.165 ml) was added dropwise at room temperature and stirred at room temperature for 1 h. Water was added to the reaction mixture, which was extracted with methylene chloride. The organic layer was washed with a saturated aqueous sodium chloride solution, dried with anhydrous sodium sulfate and distilled under reduced pressure. The resulting residue was washed with chloroform to give 176 mg of the titled compound (yield, 88%).

$^1$H-NMR($CDCl_3$) δ: 3.86(3H,s), 4.89(2H,s), 6.87(1H, d, J=8.9 Hz), 7.17(1H, d, J=2.3 Hz), 7.66(1H, dd, J=8.9, 2.3 Hz), 7.71–7.74(2H,m), 7.83–7.87(2H,m)

MS(m/z) 378($M^+$)

Example 331

Synthesis of N-(2-hydroxy-5-(N'-trifluoroacetoxyamino)phenylmethyl)phthalimide

Using the compound obtained in Example 330 as a starting material, the same procedure of Example 318 gave the titled compound (yield, 93%).

$^1$H-NMR(DMSO-$d_6$) δ: 4.71(2H,s), 6.84(1H, d, J=8.9 Hz), 7.16(1H, d, J=2.3 Hz), 7.52(1H, dd, J=8.9, 2.3 Hz), 7.86–7.97(4H,m), 9.88(1H,s), 10.88(1H,s)

MS(m/z) 364($M^+$)

Example 332

Synthesis of N-(2-benzyloxy-5-(N'-trifluoroacetoxyamino)phenylmethyl)phthalimide Using the compound obtained in Example 331 as a starting material and also using potassium carbonate and benzyl bromide as a base and a reagent, respectively, the same procedure of Example 319 gave the titled compound (yield, 53%).

$^1$H-NMR(DMSO-$d_6$) δ: 4.80(2H,s), 5.19(2H,s), 7.00–7.18(2H,m), 7.27–7.52(5H,m), 7.68(1H, dd, J=8.9, 2.6 Hz), 7.85–7.98(4H,m), 10.99(1H,brs)

MS(m/z) 454($M^+$)

Example 333

Synthesis of N-(5-amino-2-benzyloxyphenylmethyl) amine

Using the compound (684 mg) obtained in Example 332 as a starting material, the same procedure of Example 180 gave N-(3-aminomethyl-4-benzyloxyphenyl)-2,2,2-trifluoroacetamide. To a solution of the resulting amino compound in 6% hydrous methanol (10.6 ml), potassium carbonate (265 mg) was added and heated under reflux for 2 h. The reaction mixture was distilled under reduced pressure and ethyl acetate and water were added to the resulting residue. The organic layer was washed with a saturated aqueous sodium chloride solution, dried with anhydrous sodium sulfate and distilled under reduced pressure, thereby giving 339 mg of the titled compound (yield, 98%).

$^1$H-NMR($CDCl_3$) δ: 3.79(2H,s), 5.02(2H,s), 6.54(1H, dd, J=8.6, 3.0 Hz), 6.65(1H, d, J=3.0 Hz), 6.76(1H, d, J=8.6 Hz), 7.30–7.43(5H,m)

MS(m/z) 228($M^+$)

Example 334

Synthesis of N-(5-amino-2-benzyloxyphenylmethyl) carbamic acid t-butyl ester

Using the compound obtained in Example 333 as a starting material, the same procedure of Example 253 gave the titled compound (yield, 78%).

$^1$H-NMR($CDCl_3$) δ: 1.44(9H,s), 4.26(2H, d, J=5.9 Hz), 4,98(1H,brs), 5.01(2H,s), 6.55(1H, dd, J=8.3, 2.6 Hz), 6.67 (1H, d, J=2.6 Hz), 6.76(1H, d, J=8.3 Hz), 7.31–7.40(5H,m)

MS(m/z) 328($M^+$)

Example 335

Synthesis of N-(2-benzyloxy-5-thioureidophenylmethyl)carbamic acid t-butyl ester Using the compound obtained in Example 334 as a starting material, the same procedure of Example 120 gave the titled compound (yield, 81%).

$^1$H-NMR(DMSO-$d_6$) δ: 1.40(9H,s), 4.17(2H, d, J=5.9 Hz), 5,13(2H,s), 7.00(1H, d, J=8.6 Hz), 7.07(1H, d, J=2.3 Hz), 7.11–7.22(2H,m), 7.26–7.50(4H,m), 9.51(1H,brs)

Example 336

Synthesis of N-(2-benzyloxy-5-(S-ethylisothioureido)phenylmethyl)carbamic acid t-butyl ester Using the compound obtained in Example 335 as a starting material, the same procedure of Example 95 gave the titled compound (yield, 93%).

$^1$H-NMR($CDCl_3$) δ: 1.36(3H, t, J=7.3 Hz), 1.43(9H,s), 3.00–3.07(2H,m), 4.32(2H, d, J=5.6 Hz), 4.50(1H,brs), 4.97 (1H,brs), 5.07(2H,s), 6.72–6.90(3H,m), 7.32–7.42(5H,m)

MS(m/z) 415M$^{30}$ )

Example 337

Synthesis of N-(2-benzyloxy-5-(S-ethylisothioureido)phenylmethyl)amine dihydrochloride Using the compound obtained in Example 336 as a starting material, the same procedure of Example 5 gave the titled compound (yield, 94%).

$^1$H-NMR($D_2O$) δ: 1.42(3H, t, J=7.3 Hz), 3.23(2H, q, J=7.3 Hz), 4.24(2H,s), 5.34(2H,s), 7.24–7.60(8H,m)

Example 338

Synthesis of N-(2-benzyloxy-5-(N'-t-butoxycarbonyl-N"-ethylguanidino)phenylmethyl) carbamic acid t-butyl ester Using the compound obtained in Example 334 as a starting material, the same procedure of Example 233 gave the titled compound (yield, 70%).

$^1$H-MR($CDCl_3$) δ: 1.07(3H, t, J=6.9 Hz), 1.44(9H,s), 1.53(9H,s), 3.36–3.41(2H,m), 4.33(2H, d, J=5.6 Hz), 4.98 (1H,brs), 5.10(2H,s), 6.92(1H, d, J=8.6 Hz), 7.01–7.19(2H, m), 7.30–7.45(5H,m)

Example 339

Synthesis of N-(2-benzyloxy-5-(N'-ethylguanidino) phenylmethyl)amine dihydrochloride Using the compound obtained in Example 338 as a starting material, the same procedure of Example 5 gave the titled compound (yield, 94%).

$^1$H-NMR($D_2O$) δ: 1.21(3H, t, J=7.3 Hz), 3.29(2H, q, J=7.3 Hz), 4.22(2H,s), 5.32(2H,s), 7.20–7.58(8H,m)

MS(m/z) 298($M^+$)

Example 340

Synthesis of N-(2-benzyloxy-5-(N'-nitroguanidino) phenylmethyl)carbamic acid t-butyl ester Using the compound obtained in Example 334 as a starting material, the same procedure of Example 6 gave the titled compound (yield, 87%).

$^1$H-NMR (DMSO-$d_6$) δ: 1.40(9H,s ), 4.19(2H, d, J=4.0 Hz), 5.15(2H,s), 7.02–7.20(4H,m), 7.28–7.51(5H,m), 8.30 (1H,s)

Example 341

Synthesis of N-(2-benzyloxy-5-(N'-nitroguanidino) phenylmethyl)amine hydrochloride Using the compound obtained in Example 340 as a starting material, the same procedure of Example 5 gave the titled compound (yield, 32%).

$^1$H-NMR($D_2O$) δ: 4.22(2H,s), 5.31(2H,s), 7.20–7.24(1H, m), 7.32–7.39(2H,m), 7.40–7.57(5H,m)

Example 342

Synthesis of 2-methoxy-5-nitrophenylacetic acid diphenylmethyl ester

Using 2-methoxyphenylacetic acid (5.00 g) as a starting material, the same procedure of Example 188 gave 2-methoxy-5-nitrophenylacetic acid. To a solution of the resulting nitro compound in methylene chloride (140 ml), a solution of diphenyldiazomethane in methylene chloride was added at room temperature until the reaction mixture turned purple and then acetic acid was added until the purple color of the reaction mixture disappeared. The reaction mixture was washed successively with a saturated aqueous sodium bicarbonate solution and a saturated aqueous sodium chloride solution, dried with anhydrous sodium sulfate and distilled under reduced pressure. The resulting residue was purified by silica gel column chromatography (eluent, n-hexane:ethyl acetate=3:1) to give 2.34 g of the titled compound (yield, 21%).

$^1$H-NMR($CDCl_3$) δ: 3.73(3H,s), 3.77(2H,s), 6.88(1H, d, J=8.9 Hz), 6.91(1H,s), 7.20–7.39(10H,m), 8.12(1H, d, J=2.6 Hz), 8.20(1H, dd, J=8.6, 2.6 Hz)

Example 343

Synthesis of 2-(2-methoxy-5-nitrophenyl)propionic acid diphenylmethyl ester

Using the compound obtained in Example 342 as a starting material and also using methyl iodide (1 eq.) as a reagent, the same procedure of Example 1a gave the titled compound (yield, 46%).

$^1$H-NMR($CDCl_3$) δ: 1.55(3H, d, J=7.3 Hz), 3.63(3H,s), 4.08(1H, q, J=7.3 Hz), 6.84(1H, d, J=8.9 Hz), 6.91(1H,s), 7.15–7.38(10H,m), 8.12(1H, d, J=2.6 Hz), 8.19(1H, dd, J=8.9, 2.6 Hz)

Example 344

Synthesis of 2-(2-methoxy-5-nitrophenyl)-2-methyl-propionic acid diphenylmethyl ester Using the compound obtained in Example 343 as a starting material, the same procedure of Example 343 gave the titled compound (yield, 82%).

$^1$H-NMR($CDCl_3$) δ: 1.60(6H,s), 3.26(3H,s), 6.73(1H, d, J=8.9 Hz), 6.94(1H,s), 7.12–7.31(10H,m), 8.19(1H, dd, J=8.9, 2.6 Hz), 8.26(1H, d, J=2.6 Hz)

Example 345

Synthesis of 2-(2-methoxy-5-nitrophenyl)-2-methylpropionic acid

Using the compound obtained in Example 344 as a starting material, the same procedure of Example 1b gave the titled compound (yield, 88%).

$^1$H-NMR($CDCl_3$) δ: 1.60(6H,s), 3.92(3H,s), 6.95(1H, d, J=9.2 Hz), 8.18–8.23(2H,m)

MS(m/z) 239($M^+$)

Example 346

Synthesis of N-(1-(2-methoxy-5-nitrophenyl)-1-methyl-ethyl)carbamic acid t-butyl ester Using the compound obtained in Example 345 as a starting material, the same procedure of Example 1c gave the titled compound (yield, 40%).

$^1$H-NMR($CDCl_3$) δ: 1.33(9H,brs), 1.70(6H,s), 3.95(3H, s), 5.06(1H,brs), 6.94(1H, d, J=8.9 Hz), 8.15(1H, dd, J=8.9, 2.6 Hz), 8.26(1H, d, J=2.6 Hz)

Example 347

Synthesis of N-(1-(5-amino-2-methoxyphenyl)-1-methyl-ethyl)carbamic acid t-butyl ester Using the compound obtained in Example 346 as a starting material, the same procedure of Example 2 gave the titled compound (yield, 87%).

$^1$H-NMR($CDCl_3$) δ: 1.33(9H,brs), 1.65(6H,s), 3.77(3H, s), 5.21(1H,brs), 6.54(1H, dd, J=8.6, 3.0 Hz), 6.70–6.74(2H, m)

MS(m/z) 280($M^+$)

Example 348

Synthesis of N-(1-(2-methoxy-5-thioureidophenyl)-1-methylethyl)carbamic acid t-butyl ester Using the compound obtained in Example 347 as a starting material, the same procedure of Example 120 gave the titled compound quantitatively.

$^1$H-NMR($CDCl_3$) δ: 1.35(9H,s), 1.66(6H,s), 3.85(3H,s), 5.08(1H,brs), 6.14(2H,brs), 6.90(1H, d, J=8.9 Hz), 7.07(1H, dd, J=8.9, 2.0 Hz), 7.23(1H, d, J=2.0 Hz), 7.80(1H,brs)

MS(m/z) 339($M^+$)

Example 349

Synthesis of N-(1-(5-(S-ethylisothioureido)-2-methoxy-phenyl)-1-methylethyl)carbamic acid t-butyl ester hydroiodide Using the compound obtained in Example 348 as a starting material, the same procedure of Example 27 gave the titled compound (yield, 70%). 1H-NMR($CDCl_3$) δ: 1.34(9H,s), 1.36(3H, t, J=7.6 Hz), 1.66(6H,s), 3.03(2H, q, J=7.6 Hz), 3.81(3H,s), 5.16(1H,brs), 6.80–6.91(3H,m)

MS(m/z) 367($M^+$)

Example 350

Synthesis of N-(1-(5-(S-ethylisothioureido)-2-methoxyphenyl)-1-methylethyl)amine Using the compound (111 mg) obtained in Example 349 as a starting material, reaction was performed as in Example 5 and the resulting residue was purified by basic silica gel column chromatography (eluent, n-hexane chloroform=1:3) to give 24.9 mg of the titled compound (yield, 42%).

$^1$H-NMR($CDCl_3$) δ: 1.34–1.41(3H,m), 1.51(6H,s), 3.01–3.15(2H,m), 3.85(3H,s), 4.50(1H,brs), 6.69–6.92(3H, m)

MS(m/z) 267($M^+$)

Example 351

Synthesis of N,N'-di-(t-butoxycarbonyl)-N-(3-nitrophenylmethyl)hydrazine

To a solution of triphenylphosphine (2.06 g) in tetrahydrofuran (20 ml), a solution of di-t-butyl azodicarboxylate (1.80 g) in tetrahydrofuran (15 ml) was added dropwise under ice cooling and stirred for 15 min. To the reaction mixture, a solution of m-nitrobenzyl alcohol (1.0 g) in tetrahydrofuran (15 ml) was added dropwise and stirred at room temperature for 63 h. The reaction mixture was concentrated under reduced pressure and the resulting residue was purified by silica gel column chromatography (eluent, n-hexane:ethyl acetate=1:1) to give 2.25 g of the titled compound (yield, 94%).

$^1$H-NMR(CDCl3) δ: 1.47(9H,s), 1.49(9H,s), 4.72(2H,s), 6.30(1H,brs), 7.51(1H, t, J=7.3 Hz), 7.65(1H, d, J=7.3 Hz), 8.15(1H, d, J=7.3 Hz), 8.16(1H,s)

Example 352

Synthesis of N-(3-aminophenylmethyl)-N,N'-di-(t-butoxy-carbonyl)hydrazine

Using the compound obtained in Example 351 as a starting material, the same procedure of Example 2 gave 985 mg of the titled compound (yield, 62%).

$^1$H-NMR($CDCl_3$) δ: 1.44(9H,s), 1.48(9H,s), 4.56(2H,s), 6.25(1H,brs), 6.59(1H, d, J=6.9 Hz), 6.65(1H, d, J=6.9 Hz), 6.81–6.98(2H,m)

Example 353

Synthesis of N,N'-di-(t-butoxycarbonyl)-N-(3-thioureidophenylmethyl)hydrazine

Using the compound obtained in Example 352 as a starting material, the same procedure of Example 120 gave 173 mg of the titled compound (yield, 74%).

$^1$H-NMR($CDCl_3$) δ: 1.35(9H,s), 1.48(9H,s), 4.60(2H,s), 6.44(1H,brs), 6.57(2H,brs), 7.08–7.21(2H,m), 7.26–7.40 (2H,m), 8.27(1H,m)

Example 354

Synthesis of N,N'-di-(t-butoxycarbonyl)-N-(3-(S-ethylisothioureido)phenylmethyl)hydrazine hydroiodide Using the compound obtained in Example 353 as a starting material, the same procedure of Example 27 gave 143 mg of the titled compound (yield, 79%).

$^1$H-NMR($CDCl_3$) δ: 1.41(3H, t, J=7.3 Hz), 1.44(9H,s), 1.48(9H,s), 3.31(2H, q, J=7.3 Hz), 4.64(2H,s), 6.40(1H,brs), 7.23–7.41(4H,m)

Example 355

Synthesis of 3-(S-ethylisothioureido) phenylmethylhydrazine trihydrochloride

Using the compound obtained in Example 354 as a starting material, the same procedure of Example 5 gave 62 mg of the titled compound (yield, 79%).

$^1$H-NMR(DMSO-$d_6$) δ: 1.34(3H, t, J=7.3 Hz), 3.28–3.40 (2H,m), 4.08(2H,s), 7.30(1H, d, J=7.6 Hz), 7.41(1H,s), 7.42(1H, d, J=7.6 Hz), 7.53(1H, t, J=7.6 Hz), 9.26(1H,brs), 9.61(1H,brs), 11.51(1H,brs)

MS(m/z) 224($M^+$)

Example 356

Synthesis of N,N'-di-(t-butoxycarbonyl)-N-(3-(N'-nitroguanidino)phenylmethyl)hydrazine Using the compound obtained in Example 352 as a starting material, the same procedure of Example 6 gave 22 mg of the titled compound (yield, 18%).

$^1$H-NMR($CDCl_3$) δ: 1.32(9H,s), 1.48(9H,s), 4.62(2H,s), 6.48(1H,brs), 7.15–7.25(2H,m), 7.38(1H, t, J=7.3 Hz), 7.49 (1H,s) 9.54(1H,brs)

MS(m/z) 224($M^+$−200)

Example 357

Synthesis of 3-(N'-nitroguanidino)phenylmethylhydrazine dihydrochloride

Using the compound obtained in Example 356 as a starting material, the same procedure of Example 5 gave 15 mg of the titled compound (yield, 74%).

$^1$H-NMR(DMSO-$d_6$) δ: 3.75(2H,s), 7.08–7.40(6H,m), 8.26(2H,brs)

MS(m/z) 208($M^+$−16)

Example 358

Synthesis of N-(4-nitrophenylpropyl)carbamic acid t-butyl ester

Using 4-(4-nirophenyl)butylic acid as a starting material, the same procedure of Example 1c gave 400 mg of the titled compound (yield, 30%).

$^1$H-NMR($CDCl_3$) δ: 1.44(9H,s), 1.84(2H, quin, J=7.3 Hz), 2.75(2H, t, J=7.3 Hz), 3.10–3.26(2H,m), 4.57(1H,brs), 7.34(2H, d, J=8.8 Hz), 8.15(2H, d, J=8.8 Hz)

MS(m/z) 281($M^+$+1)

Example 359

Synthesis of N-(4-aminophenylpropyl)carbamic acid t-butyl ester

Using the compound obtained in Example 358 as a starting material, the same procedure of Example 2 gave 170 mg of the titled compound (yield, 48%).

$^1$H-NMR($CDCl_3$) δ: 1.45(9H,s), 1.75(2H, quin, J=7.3 Hz), 2.53(2H, t, J=7.3 Hz), 3.04–3.18(2H,m), 3.53(2H,brs), 4.48(1H,brs), 6.62(2H, d, J=8.3 Hz), 6.95(2H, d, J=8.3 Hz)

Example 360

Synthesis of N-(4-(N'-nitroguanidino)phenylpropyl)carbamic acid t-butyl ester

Using the compound obtained in Example 359 as a starting material, the same procedure of Example 6 gave 42 mg of the titled compound (yield, 37%).

$^1$H-NMR($CDCl_3$) δ: 1.42(9H,s), 1.82(2H, quin, J=7.3 Hz), 2.70(2H, t, J=7.3 Hz), 3.16(2H, dt, J=7.3, 7.3 Hz), 4.54(1H,brs), 7.24(2H, d, J=8.3 Hz), 7.31(2H, d, J=8.3 Hz), 9.60(1H,brs)

Example 361

Synthesis of N-(4-(N'-nitroguanidino)phenylpropyl)amine hydrochloride

Using the compound obtained in Example 360 as a starting material, the same procedure of Example 5 gave 35.5 mg of the titled compound quantitatively.

$^1$H-NMR(DMSO-$d_6$) δ: 1.94(2H, quin, J=7.5 Hz), 2.67 (2H, t, J=7.5 Hz), 2.74–2.86(2H,m), 7.20(2H, d, J=8.6 Hz), 7.26(2H, d, J=8.6 Hz), 8.16(1H, brs), 9.58(1H,s)

MS(m/z) 237($M^+$)

Example 362

Synthesis of N-(3-nitrophenylmethyl)iminodicarboxylic acid di-t-butyl ester

Using m-nitrobenzyl bromide as a starting material, the same procedure of Example 127 gave 11.7 g of the titled compound quantitatively.

$^1$H-NMR($CDCl_3$) δ: 1.48(18H,s), 4.86(2H,s), 7.49(1H, dd, J=7.9, 7.5 Hz), 7.65(1H, d, J=7.5 Hz), 8.13(1H, d, J=7.9 Hz), 8.19(1H,s)

Example 363

Synthesis of N-(3-aminophenylmethyl)iminodicarboxylic acid di-t-butyl ester

Using the compound obtained in Example 362 as a starting material, the same procedure of Example 2 gave 5.45 g of the titled compound (yield, 41%).

$^1$H-NMR($CDCl_3$) δ: 1.45(18H,s), 3.60(2H,brs), 4.68(2H, s), 6.53–6.58(1H,m), 6.60(1H,s), 6.66(1H, d, J=7.6 Hz), 7.07(1H, dd, J=7.9, 7.6 Hz)

Example 364

Synthesis of N-(3-thioureidophenylmethyl)iminodicarboxylic acid di-t-butyl ester Using the compound obtained in Example 363 as a starting material, the same procedure of Example 120 gave 2.1 g of the titled compound quantitatively.

$^1$H-NMR($CDCl_3$) δ: 1.47(18H,s), 4.78(2H,s), 6.12(2H, brs), 7.10–7.42(4H,m), 7.96(1H,brs)

Example 365

Synthesis of N-(3-(S-methylisothioureido)phenylmethyl)iminodicarboxylic acid di-t-butyl ester hydroiodide Using the compound obtained in Example 364 as a starting material, the same procedure of Example 4 gave 1.81 g of the titled compound (yield, 70%).

$^1$H-NMR($CDCl_3$) δ: 1.46(18H,s), 2.46(3H,s), 4.49(1H, brs), 4.75(2H,s), 6.76–6.88(2H,m), 6.95(1H, d, J=7.6 Hz), 7.20–7.28(1H,m)

Example 366

Synthesis of N-(3-(N'-methylguanidino)phenylmethyl)iminodicarboxylic acid di-t-butyl ester A mixture of the compound (158 mg) obtained in Example 365, methylamine hydrochloride (31 mg), triethylamine (156 mg) and dimethylformamide (3 ml) was heated at 80° C. for 4 h. The reaction mixture was concentrated under reduced pressure and the resulting residue was purified by basic silica gel column chromatography (eluent, methylene chloride:methanol=20:1) to give 60 mg of the titled compound (yield, 72%).

$^1$H-NMR($CDCl_3$) δ: 1.45(18H,s), 2.85(3H,s), 4.73(2H,s), 6.81(1H, d, J=7.9 Hz), 6.85(1H,s), 6.89(1H, d, J=7.6 Hz), 7.21(1H, dd, J=7.9, 7.6 Hz)

Example 367

Synthesis of N-(3-(N'-methylguanidino)phenylmethyl)amine dihydrochloride

Using the compound obtained in Example 366 as a starting material, the same procedure of Example 5 gave 49 mg of the titled compound quantitatively.

$^1$H-NMR(DMSO-$d_6$) δ: 2.84(3H, d, J=4.3 Hz), 4.03(2H, s), 7.22(1H, d, J=7.3 Hz), 7.44–7.51(1H,m), 7.69–7.86(2H, m), 9.82(1H,brs)

MS(m/z) 178(M$^+$)

Example 368

Synthesis of N-(3-(N'-ethylguanidino)phenylmethyl)iminodicarboxylic acid di-t-butyl ester Using the compound obtained in Example 365 as a starting material and also using ethylamine hydrochloride as a reagent, the same procedure of Example 366 gave 59 mg of the titled compound (yield, 61%).

$^1$H-NMR(CDCl$_3$) δ: 1.19(3H, t, J=7.3 Hz), 1.45(18H,s), 3.23(2H, q, J=7.3 Hz), 4.73(2H,s), 6.80(1H, d, J=7.9 Hz), 6.85(1H,s), 6.88(1H, d, J=7.5 Hz), 7.21(1H, dd, J=7.9, 7.5 Hz)

Example 369

Synthesis of N-(3-(N'-ethylguanidino)phenylmethyl)amine dihydrochloride

Using the compound obtained in Example 368 as a starting material, the same procedure of Example 5 gave 28.6 mg of the titled compound (yield, 71%).

$^1$H-NMR(DMSO-$d_6$) δ: 1.16(3H, t, J=6.9 Hz), 3.26–3.38 (2H,m), 4.03(2H, d, J=5.6 Hz), 7.21(1H, d, J=7.6 Hz), 7.36(1H, d, J=7.9 Hz), 7.39(1H,s), 7.48(1H, dd, J=7.9, 7.6 Hz), 7.77(1H,brs), 7.96–8.02(1H,m), 8.47(2H,brs), 9.92(1H, brs)

MS(m/z) 192(M$^+$)

Example 370

Synthesis of N-(3-(N'-n-propylguanidino)phenylmethyl)iminodicarboxylic acid di-t-butyl ester Using the compound obtained in Example 365 as a starting material and also using n-propylamine as a reagent, the same procedure of Example 366 gave 15 mg of the titled compound (yield, 64%).

$^1$H-NMR(CDCl$_3$) δ: 0.96(3H, t, J=7.6 Hz), 1.45(18H,s), 1.54–1.66(2H,m), 3.15(2H, t, J=7.3 Hz), 4.73(2H,s), 6.84–6.97(3H,m), 7.21(1H, d, J=7.9 Hz)

Example 371

Synthesis of N-(3-(N'-n-propylguanidino)phenylmethyl)amine dihydrochloride

Using the compound obtained in Example 370 as a starting material, the same procedure of Example 5 gave 10.7 mg of the titled compound quantitatively.

$^1$H-NMR(DMSO-$d_6$) δ: 0.92(3H, t, J=7.3 Hz), 1.50–1.62 (2H,m), 3.20(2H, dt, J=6.6, 6.3 Hz), 4.04(2H, d, J=5.6 Hz), 7.23(1H, d, J=7.9 Hz), 7.34(1H,s), 7.35(1H, d, J=7.6 Hz), 7.48(1H, dd, J=7.9, 7.6 Hz), 7.67–7.73(1H,m), 7.90–7.96 (1H,m), 9.73(1H,brs)

MS(m/z) 206(M$^+$)

Example 372

Synthesis of N-(3-(S-ethylisothioureido)phenylmethyl)dimethylamine

To a solution of the compound (43.5 mg) obtained in Example 40 in acetonitrile (5 ml), a solution of hydrogen chloride in 1,4-dioxane (4N, 0.1 ml) and ethyl iodide (50 mg) were added and heated under reflux for 5 h. The reaction mixture was concentrated under reduced pressure and the resulting residue was purified by basic silica gel column chromatography (eluent, methylene chloride methanol=5:1) to give 9.2 mg of the titled compound (yield, 19%).

$^1$H-NMR(CDCl$_3$) δ: 1.23(3H, t, J=7.3 Hz), 2.14(6H,s), 2.89(2H, q, J=7.3 Hz), 3.31(2H,s), 6.16(2H,brs), 6.60–6.64 (2H,m), 6,84(1H, d, J=7.3 Hz), 7.16(1H, dd, J=7.6, 7.3 Hz)

Example 373

Synthesis of N-(3-(N'-t-butoxycarbonyl-N"-ethylguanidino)phenylmethyl)dimethylamine Using the compound obtained in Example 38 as a starting material, the same procedure of Example 233 gave 104 mg of the titled compound (yield, 61%).

$^1$H-NMR(CDCl$_3$) δ: 1.05–1.10(3H,m), 1.51(9H,s), 2.25 (6H,s), 3.39–3.42(4H,m), 7.16–7.33(4H,m)

MS(m/z) 320(M$^+$)

Example 374

Synthesis of N-(3-(N'-ethylguanidino)phenylmethyl)dimethylamine dihydrochloride

Using the compound obtained in Example 373 as a starting material, the same procedure of Example 5 gave 48.2 mg of the titled compound quantitatively.

$^1$H-NMR(DMSO-$d_6$) δ: 1.15(3H, t, J=6.8 Hz), 2.70(3H, d, J=5.0 Hz), 3.29(2H, q, J=6.8 Hz), 4.27(2H, d, J=4.9 Hz), 7.28(1H, d, J=7.6 Hz), 7.42–7.56(2H,m), 7.80(1H,brs), 8.00–8.08(1H,m), 9.92(1H,s), 10.92(1H,brs)

MS(m/z) 220(M$^+$)

Example 375

Synthesis of N-(3-(N'-t-butoxycarbonyl-N"-ethylguanidino)phenylmethyl)methylcarbamic acid t-butyl ester Using the compound obtained in Example 44 as a starting material, the same procedure of Example 233 gave 107 mg of the titled compound (yield, 69%).

$^1$H-NMR(CDCl$_3$) δ: 1.06–1.18(3H,m), 1.48(18H,s), 2.83 (3H,s), 3.38(2H, q, J=7.0 Hz), 4.42(2H,s), 7.06–7.34(4H,m), 10.58(1H,brs)

Example 376

Synthesis of N-(3-(N'-ethylguanidino)phenylmethyl)methylamine dihydrochloride

Using the compound obtained in Example 375 as a starting material, the same procedure of Example 5 gave 57.6 mg of the titled compound quantitatively.

$^1$H-NMR(DMSO-$d_6$) δ: 1.16(3H, t, J=6.9 Hz), 2.55(3H, t, J=5.3 Hz), 3.25–3.35(2H,m), 4.12(2H, t, J=5.3 Hz), 7.25 (1H, d, J=7.9 Hz), 7.40(1H, d, J=7.9 Hz), 7.41(1H,brs), 7.49(1H, t, J=7.9 Hz), 7.75(1H,brs), 7.94(1H, t, J=5.3 Hz), 9.22(1H,brs), 9.78(1H,brs)

MS(m/z) 206($M^+$)

Example 377

Synthesis of N-(3-nitrophenylmethyl) benzylmethylamine

To a solution of the compound (630 mg) obtained in Example 42 and triethylamine (768 mg) in acetonitrile (20 ml), benzyl bromide (778 mg) was added dropwise at room temperature. The reaction mixture was stirred at room temperature for 1 h and, after addition of water, extracted with ethyl acetate. The organic layer was washed with a saturated aqueous sodium chloride solution, dried with anhydrous sodium sulfate and concentrated under reduced pressure. The resulting residue was purified by silica gel column chromatography (eluent, n-hexane:ethyl acetate= 4:1) to give 925 mg of the titled compound (yield, 95%).

$^1$H-NMR($CDCl_3$) δ: 2.21(3H,s), 3.57(2H,s), 3.60(2H,s), 7.26–7.40(5H,m) 7.48(1H, dd, J=8.3, 7.6 Hz), 7.70(1H, d, J=7.6 Hz), 8.10(1H, d, J=8.3 Hz), 8.24(1H,s)

Example 378

Synthesis of N-(3-aminophenylmethyl) benzylmethylamine

Using the compound obtained in Example 377 as a starting material and also using 5% palladium-carbon and ethyl acetate as a catalyst and a solvent, respectively, reaction was performed as in Example 2 to give 487 mg of the titled compound (yield, 61%).

$^1$H-NMR($CDCl_3$) δ: 2.18(3H,s), 3.43(2H,s), 3.51(2H,s), 3.64(2H,brs), 6.58(1H, d, J=8.6 Hz), 6.73(s,1H), 6.75(1H, d, J=7.6 Hz), 7.10(1H, dd, J=8.6, 7.6 Hz), 7.21–7.39(5H,m)

Example 379

Synthesis of N-(3-thioureidophenylmethyl) benzylmethylamine

Using the compound obtained in Example 378 as a starting material, the same procedure of Example 40 gave 153 mg of the titled compound (yield, 32%).

$^1$H-NMR ($CDCl_3$) δ: 2.19(3H,s), 3.54(4H,s), 6.15(2H, brs), 6.60(s, 1H), 6.75–6.79(1H,m), 7.10–7.20(1H,m), 7.26–7.36(6H,m), 8.01–8.18(1H,brs)

Example 380

Synthesis of N-(3-(S-ethylisothioureido) phenylmethyl)benzylmethylamine dihydrochloride Using the compound obtained in Example 379 as a starting material, the same procedure of Example 372 gave N-(3-(S-ethylisothioureido)phenylmethyl) benzylmethylamine. To this compound, a solution of hydrogen chloride in 1,4-dioxane (4 N, 0.1 ml) was added and the mixture was concentrated under reduced pressure to give 9.3 mg of the titled compound (yield, 6%).

$^1$H-NMR(DMSO-$d_6$) δ: 1.34(3H, t, J=7.3 Hz), 2.54(3H, d, J=3.6 Hz), 3.30–3.40(2H,m), 4.20–4.31(2H,m), 4.38–4.49 (2H,m), 7.40–7.50(4H,m), 7.55–7.68(5H,m), 9.43(1H,brs), 9.72(1H,brs), 11.24(1H,brs), 11.66(1H,brs)

Example 381

Synthesis of N-(3-(N'-t-butoxycarbonyl-N"-ethylguanidino)phenylmethyl)benzylmethylamine Using the compound obtained in Example 378 as a starting material, the same procedure of Example 233 gave 96 mg of the titled compound (yield, 62%).

$^1$H-NMR($CDCl_3$) δ: 1.01–1.18(3H,m), 1.52(9H,s), 2.18 (3H,s), 3.36–3.41(2H,m), 3.49(2H,s), 3.54(2H,s), 4.71(1H, brs), 7.08(1H,brs), 7.26–7.35(9H,m), 10.70(1H,brs)

Example 382

Synthesis of N-(3-(N'-ethylguanidino)phenylmethyl) benzylmethylamine dihydrochloride Using the compound obtained in Example 381 as a starting material, the same procedure of Example 5 gave 133 mg of the titled compound quantitatively.

$^1$H-NMR(DMSO-$d_6$) δ: 1.16(3H, t, J=6.9 Hz), 2.56(3H, s), 3.27–3.33(2H,m), 4.17–4.27(2H,m), 4.36–4.47(2H,m), 7.29(1H, d, J=6.9 Hz), 7.48–7.60(8H,m), 7.73–7.80(1H,m), 7.93–7.99(2H,m), 9.75(1H,brs), 10.87(1H,brs)

MS(m/z) 296($M^+$)

Example 383

Synthesis of N-(3-nitrophenylmethyl)ethylamine

Using m-nitrobenzaldehyde as a starting material and also using ethylamine hydrochloride as a reagent, the same procedure of Example 42 gave 2.8 g of the titled compound (yield, 47%).

$^1$H-NMR($CDCl_3$) δ: 1.15(3H, t, J=7.3 Hz), 2.69(2H, q, J=7.3 Hz), 3.91(2H,s), 7.49(1H, dd, J=7.9, 7.6 Hz), 7.68(1H, d, J=7.6 Hz), 8.11(1H, d, J=7.9 Hz), 8.21(1H,s)

Example 384

Synthesis of N-(3-nitrophenylmethyl)ethylcarbamic acid t-butyl ester

Using the compound obtained in Example 383 as a starting material, the same procedure of Example 22 gave 1.94 g of the titled compound (yield, 99%).

$^1$H-NMR($CDCl_3$) δ: 1.11(3H, t, J=7.3 Hz), 1.48(9H,s), 3.20–3.40(2H,m), 4.50(2H,s), 7.50(1H, t, J=8.3 Hz), 7.55–7.60(1H,m), 8.11(1H,s), 8.12(1H, d, J=7.6 Hz)

Example 385

Synthesis of N-(3-aminophenylmethyl) ethylcarbamic acid t-butyl ester

Using the compound obtained in Example 384 as a starting material, the same procedure of Example 2 gave 890 mg of the titled compound quantitatively.

$^1$H-NMR($CDCl_3$) δ: 1.06(3H, t, J=6.9 Hz), 1.47(9H,s), 3.13–3.26(2H,m), 3.64(2H,s), 4.34(2H,s), 6.55–6.65(3H,m), 7.09(1H, t, J=7.9 Hz)

Example 386

Synthesis of N-(3-thioureidophenylmethyl) ethylcarbamic acid t-butyl ester

Using the compound obtained in Example 385 as a starting material, the same procedure of Example 120 gave 460 mg of the titled compound (yield, 78%).

$^1$H-NMR($CDCl_3$) δ: 1.09(3H, t, J=6.9 Hz), 1.47(9H,s), 3.22–3.30(2H,m), 4.42(2H,s), 6.09(2H,brs), 7.11(1H,s), 7.12(1H, d, J=5.9 Hz), 7.19(1H, d, J=7.6 Hz), 7.39(1H, dd, J=7.6, 5.9 Hz), 7.92(1H,brs)

Example 387

Synthesis of N-(3-(S-ethylisothioureido) phenylmethyl)ethylcarbamic acid t-butyl ester hydroiodide Using the compound obtained in Example 386 as a starting material, the same procedure of Example 27 gave 155 mg of the titled compound (yield, 49%).

$^1$H-NMR($CDCl_3$) δ: 1.06(3H, t, J=6.9 Hz), 1.36(3H, t, J=7.3 Hz), 1.47(9H,s), 2.97–3.12(2H,m), 3.12–3.37(2H,m), 4.39(2H,s), 4.48(1H,brs), 6.75–6.86(2H,m), 6.90(1H, d, J=7.3 Hz), 7.25(1H, dd, J=7.9, 7.3 Hz)

Example 388

Synthesis of N-(3-(S-ethylisothioureido) phenylmethyl)ethylamine dihydrochloride Using the compound obtained in Example 387 as a starting material, the same procedure of Example 5 gave 162 mg of the titled compound quantitatively.

$^1$H-NMR(DMSO-$d_6$) δ: 1.26(3H, t, J=6.9 Hz), 1.33(3H, t, J=7.3 Hz), 2.90–3.01(2H,m), 3.35(2H, q, J=7.3 Hz), 4.11 (2H,s), 7.35(1H, d, J=6.9 Hz), 7.50–7.66(3H,m), 9.53(2H, brs), 9.75(1H,brs), 11.79(1H,brs)

MS(m/z) 237($M^+$)

Example 389

Synthesis of N-(2-methoxy-5-nitrophenylmethyl) methylcarbamic acid t-butyl ester To methylamine (as 40% MeOH solution, 50 ml), 5-nitro-2-benzyl bromide (1.04 g) was added under ice cooling and stirred at room temperature for 1 h. The reaction mixture was concentrated under reduced pressure and the resulting residue was worked up as in Example 22 to give the titled compound (yield, 39%).

$^1$H-NMR($CDCl_3$) δ: 1.46(9H,s), 2.92(3H,s), 3.95(3H,s), 4.44(2H,s), 6.92(1H, d, J=9.2 Hz), 7.90–8.19(2H,m)

Example 390

Synthesis of N-(5-amino-2-methoxyphenylmethyl) methylcarbamic acid t-butyl ester Using the compound obtained in Example 389 as a starting material, the same procedure of Example 2 gave 436 mg of the titled compound quantitatively.

$^1$H-NMR($CDCl_3$) δ: 1.46(9H,s), 2.84(3H,s), 3.41(2H,s), 3.75(3H,s), 4.39(2H,s), 6.47–6.53(1H,m), 6.56(1H, dd, J=8.6, 2.3 Hz), 6.70(1H, d, J=8.6 Hz)

Example 391

Synthesis of N-(5-(N'-t-butoxycarbonyl-N"-ethylguanidino)-2-methoxyphenylmethyl) methylcarbamic acid t-butyl ester Using the compound obtained in Example 390 as a starting material, the same procedure of Example 233 gave 75 mg of the titled compound (yield, 65%).

$^1$H-NMR($CDCl_3$) δ: 1.06(3H, t, J=7.3 Hz), 1.47(9H,s), 1.54(9H,s), 2.87(3H,s), 3.38(2H, quin, J=7.3 Hz), 3.84(3H, s), 4.42(2H,s), 6.86(1H, d, J=8.6 Hz), 6.97(1H,s), 7.02–7.13 (1H,m), 10.47(1H,brs)

Example 392

Synthesis of N-(5-(N'-ethylguanidino)-2-methoxyphenylmethyl)methylamine dihydrochloride Using the compound obtained in Example 391 as a starting material, the same procedure of Example 5 gave 42.6 mg of the titled compound (yield, 91%).

$^1$H-NMR(DMSO-$d_6$) δ: 1.15(3H, t, J=6.9 Hz), 2.52–2.58 (3H,m), 3.20–3.38(2H,m), 3.87(3H,s), 4.05–4.17(2H,m), 7.15(1H, d, J=8.3 Hz), 7.27(1H, d, J=8.9 Hz), 7.36(1H,s), 7.42–7.61(1H,m), 7.66–7.81(1H,m), 9.05(1H,brs), 9.60(1H, brs)

MS(m/z) 236($M^+$)

Example 393

Synthesis of N-(2-methoxy-5-thioureidophenylmethyl)methylcarbamic acid t-butyl ester Using the compound obtained in Example 390 as a starting material, the same procedure of Example 120 gave 223 mg of the titled compound (yield, 96%).

$^1$H-NMR($CDCl_3$) δ: 1.47(9H,s), 2.89(3H,s), 3.85(3H,s), 4.41(2H,s), 5.98(2H,brs), 6.88(1H, d, J=8.6 Hz), 7.01(1H,s), 7.05–7.15(1H,m), 7.71(1H,s)

Example 394

Synthesis of N-(5-(S-ethylisothioureido)-2-methoxyphenylmethyl)methylcarbamic acid t-butyl ester hydroiodide Using the compound obtained in Example 393 as a starting material, the same procedure of Example 27 gave 217 mg of the titled compound (yield, 66%).

$^1$H-NMR($CDCl_3$) δ: 1.35(3H, t, J=7.3 Hz), 1.45(9H,s), 2.84(3H,s), 2.92–3.10(2H,m), 3.79(3H,s), 4.41(2H,s), 6.73–6.81(3H,m)

Example 395

Synthesis of N-(5-(S-ethylisothioureido)-2-methoxyphenylmethyl)methylamine dihydrochloride Using the compound obtained in Example 394 as a starting material, the same procedure of Example 5 gave 207.8 mg of the titled compound quantitatively.

$^1$H-NMR(DMSO-$d_6$) δ: 1.33(3H, t, J=7.3 Hz), 2.52–2.59 (3H,m), 3.22–3.36(2H,m), 3.89(3H,s), 4.03–4.18(2H,m), 7.20(1H, d, J=8.6 Hz), 7.37(1H, d, J=8.6 Hz), 7.47(1H,s), 9.08(2H,brs), 9.57(1H,brs), 11.45(1H,brs)

MS(m/z) 253($M^+$)

Example 396

Synthesis of N-(2-methoxy-5-nitrophenylmethyl) dimethylamine

Using 5-nitro-2-benzyl bromide as a starting material, the same procedure of Example 37 gave 3.4 g of the titled compound (yield, 82%).

$^1$H-NMR($CDCl_3$) δ: 2.29(6H,s), 3.47(2H,s), 3.94(3H,s), 6.92(1H, d, J=8.9 Hz), 8.17(1H, dd, J=8.9, 3.0 Hz), 8.23(1H, d, J=3.0 Hz)

Example 397

Synthesis of N-(5-amino-2-methoxyphenylmethyl) dimethylamine

Using the compound obtained in Example 396 as a starting material, the same procedure of Example 2 gave 1.05 g of the titled compound (yield, 37%).

$^1$H-NMR($CDCl_3$) δ: 2.26(6H,s), 3.39(4H,s), 3.76(3H,s), 6.58(1H, dd, J=8.6, 3.0 Hz), 6.71(1H, d, J=8.6 Hz), 6.72(1H, d, J=3.0 Hz)

Example 398

Synthesis of N-(5-(N'-t-butoxycarbonyl-N"-ethylguanidino)-2-methoxyphenylmethyl) dimethylamine Using the compound obtained in Example 397 as a starting material, the same procedure of Example 233 gave 44 mg of the titled compound (yield, 45%).

$^1$H-NMR($CDCl_3$) δ: 1.02–1.15(3H,m), 1.53(9H,s), 2.35 (6H,s), 3.39–3.48(2H,m), 3.49(2H,s), 3.85(3H,s), 6.87(1H, d, J=8.3 Hz), 7.05–7.26(2H,s)

Example 399

Synthesis of N-(5-(N'-ethylguanidino)-2-methoxyphenylmethyl)dimethylamine dihydrochloride Using the compound obtained in Example 398 as a starting material, the same procedure of Example 5 gave 44 mg of the titled compound quantitatively.

$^1$H-NMR(DMSO-$d_6$) δ: 1.15(3H, t, J=6.9 Hz), 2.73(6H, d, J=5.0 Hz), 3.29(2H, quin, J=6.9 Hz), 3.88(3H,s), 4.25(2H, d, J=5.0 Hz), 7.18(1H, d, J=8.9 Hz), 7.31(1H, dd, J=8.9, 1.9 Hz), 7.44(1H, d, J=1.9 Hz), 7.60(1H,brs), 7.78–7.88(1H,m), 9.65(1H,brs), 10.41(1H,brs)

MS(m/z) 250($M^+$)

Example 400

Synthesis of N-(2-methoxy-5-thioureidophenylmethyl)dimethylamine

Using the compound obtained in Example 397 as a starting material, the same procedure of Example 40 gave 410 mg of the titled compound (yield, 62%).

$^1$H-NMR($CDCl_3$) δ: 2.26(6H,s), 3.43(2H,s), 3.85(3H,s), 6.00(2H,brs), 6.88(1H, d, J=8.6 Hz), 7.17(1H, dd, J=8.6, 2.6 Hz), 7.23(1H, d, J=2.6 Hz), 7.77(1H,brs)

Example 401

Synthesis of N-(5-(S-ethylisothioureido)-2-methoxyphenylmethyl)dimethylamine dihydrochloride Using the compound obtained in Example 400 as a starting material, the same procedure of Example 380 gave 69.5 mg of the titled compound (yield, 98%).

$^1$H-NMR(DMSO-$d_6$) δ: 1.33(3H, t, J=7.3 Hz), 2.73(6H, d, J=5.0 Hz), 3.28–3.42(2H,m), 3.89(3H,s), 4.26(2H, d, J=5.0 Hz), 7.24(1H, d, J=8.6 Hz), 7.38–7.44(1H,m), 7.57–7.60 (1H,m), 9.27(1H,brs), 9.65(1H,brs), 10.61(1H,brs), 11.58 (1H,brs)

MS(m/z) 267($M^+$)

Example 402

Synthesis of N-(3-nitrophenylmethyl)benzylamine

To a solution of m-nitrobenzyl bromide (1.0 g) and diisopropylethylamine (1.19 g) in methanol (50 ml), benzyl bromide (495 mg) was added dropwise under ice cooling. The reaction mixture was stirred at room temperature for 3 days and, after addition of water, extracted with ethyl acetate. The organic layer was washed with a saturated aqueous sodium chloride solution, dried with anhydrous sodium sulfate and concentrated under reduced pressure. The resulting residue was purified by silica gel column chromatography (eluent, n-hexane:ethyl acetate=4:1) to give 555 mg of the titled compound (yield, 50%).

$^1$H-NMR($CDCl_3$) δ: 3.83(2H,s), 3.91(2H,s), 7.23–7.38 (5H,m), 7.49(1H, t, J=7.9 Hz), 7.70(1H, d, J=7.9 Hz), 8.07–8.14(1H,m), 8.21(1H,s)

Example 403

Synthesis of N-(3-aminophenylmethyl)benzylcarbamic acid t-butyl ester

Using the compound obtained in Example 402 as a starting material, treatment was performed as in Example 22 and the resulting compound was subsequently subjected to the same reaction as in Example 2 to give 517 mg of the titled compound (yield, 73%).

$^1$H-NMR($CDCl_3$) δ: 1.49(9H,s), 3.65(2H,brs), 4.25–4.43 (4H,m), 6.50–6.63(3H,m), 7.11(1H, t, J=7.9 Hz), 7.20–7.40 (5H,m)

Example 404

Synthesis of N-(3-thioureidophenylmethyl)benzylcarbamic acid t-butyl ester

Using the compound obtained in Example 403 as a starting material, the same procedure of Example 120 gave 223 mg of the titled compound (yield, 97%).

$^1$H-NMR($CDCl_3$) δ: 1.49(9H,s), 4.41(4H,brs), 6.16(2H, brs), 7.02–7.23(5H,m), 7.26–7.41(4H,m), 8.29(1H,brs)

Example 405

Synthesis of N-(3-(S-ethylisothioureido)phenylmethyl)benzylcarbamic acid t-butyl ester hydroiodide Using the compound obtained in Example 404 as a starting material, the same procedure of Example 27 gave 205 mg of the titled compound (yield, 66%).

$^1$H-NMR($CDCl_3$) δ: 1.37(3H, t, J=6.9 Hz), 1.49(9H,s), 3.00–3.12(2H,m), 4.25–4.48(4H,m), 6.75–6.90(2H,m), 7.18–7.38(7H,m)

Example 406

Synthesis of N-(3-(S-ethylisothioureido)phenylmethyl)benzylamine dihydrochloride Using the compound obtained in Example 405 as a starting material, the same procedure of Example 5 gave 176 mg of the titled compound quantitatively.

$^1$H-NMR(DMSO-$d_6$) δ: 1.35(3H, t, J=6.9 Hz), 3.30–3.42 (2H,m), 4.17–4.26(4H,m), 7.38–7.65(9H,m), 9.46(1H,brs), 9.78(1H,brs), 10.02(1H,brs), 11.80(1H,brs)

MS(m/z) 299($M^+$)

Example 407

Synthesis of N-(2-methyl-3-nitrophenylmethyl)methylcarbamic acid t-butyl ester

Using 2-methyl-3-nitrobenzyl bromide as a starting material, the same procedure of Example 389 gave 900 mg of the titled compound (yield, 74%).

$^1$H-NMR($CDCl_3$) δ: 1.47(9H,s), 2.38(3H,s), 2.83(3H,s), 4.51(2H,s), 7.30–7.34(2H,m), 7.65–7.69(1H,m)

Example 408

Synthesis of N-(3-amino-2-methylphenylmethyl)methylcarbamic acid t-butyl ester

Using the compound obtained in Example 407 as a starting material, the same procedure of Example 2 gave 805 mg of the titled compound quantitatively.

$^1$H-NMR($CDCl_3$) δ: 1.48(9H,s), 2.08(3H,s), 2.73(3H,s), 3.62(2H,brs), 4.44(2H,s), 6.59(1H, d, J=7.6 Hz), 6.64(1H, d, J=7.6 Hz), 6.99(1H, t, J=7.6 Hz)

Example 409

Synthesis of N-(2-methyl-3-thioureidophenylmethyl)methylcarbamic acid t-butyl ester Using the compound obtained in Example 408 as a starting material, the same procedure of Example 120 gave 225 mg of the titled compound (yield, 91%).

$^1$H-NMR($CDCl_3$) δ: 1.47(9H,s), 2.23(3H,s), 2.84(3H,s), 4.46(2H,s), 5.79(2H,brs), 7.17(1H, dd, J=6.9, 6.6 Hz), 7.23–7.32(2H,m), 7.56(1H,brs)

Example 410

Synthesis of N-(3-(S-ethylisothioureido)-2-methylphenylmethyl)methylcarbamic acid t-butyl ester hydroiodide Using the compound obtained in Example 409 as a starting material, the same procedure of Example 27 gave 114 mg of the titled compound (yield, 76%).

$^1$H-NMR($CDCl_3$) δ: 1.39(3H, t, J=7.6 Hz), 1.47(9H,s), 2.07(3H,s), 2.78(3H,s), 3.02–3.18(2H,m), 4.35(1H,brs), 4.45(2H,s), 6.75(1H, d, J=7.3 Hz), 6.82(1H, d, J=7.6 Hz), 7.11(1H, dd, J=7.6, 7.3 Hz)

Example 411

Synthesis of N-(3-(S-ethylisothioureido)-2-methylphenylmethyl)methylamine dihydrochloride Using the compound obtained in Example 410 as a starting material, the same procedure of Example 5 gave 128 mg of the titled compound quantitatively.

$^1$H-NMR(DMSO-$d_6$) δ: 1.34(3H, t, J=6.9 Hz), 2.27(3H, s), 2.60–2.65(3H,m), 3.25–3.35(2H,m), 4.20–4.27(2H,m), 7.31(1H, d, J=7.6 Hz), 7.41(1H, dd, J=7.6, 7.3 Hz), 7.60(1H, d, J=7.3 Hz), 9.23(2H,brs), 9.45–9.60(1H,m), 11.46(1H,brs)

MS(m/z) 238($M^+$+1)

Example 412

Synthesis of N-(3-(N'-t-butoxycarbonyl-N"-ethylguanidino)2-methylphenylmethyl) methylcarbamic acid t-butyl ester Using the compound obtained in Example 408 as a starting material, the same procedure of Example 233 gave 43 mg of the titled compound (yield, 53%).

$^1$H-NMR($CDCl_3$) δ: 1.01–1.18(3H,m), 1.48(9H,s), 1.54 (9H,s), 2.18(3H,s), 2.81(3H,s), 3.38–3.42(2H,m), 4.45(1H, s), 7.05–7.26(3H,m), 10.56(1H,brs)

Example 413

Synthesis of N-(3-(N'-ethylguanidino)-2-methylphenylmethyl)methylamine dihydrochloride Using the compound obtained in Example 412 as a starting material, the same procedure of Example 5 gave 30.5 mg of the titled compound quantitatively.

$^1$H-NMR(DMSO-$d_6$) δ: 1.15(3H, t, J=7.3 Hz), 2.28(3H, s), 2.63(3H, t, J=5.0 Hz), 3.22–3.35(2H,m), 4.19(2H, t, J=5.6 Hz), 7.26(1H, d, J=7.6 Hz), 7.35(1H, dd, J=7.6, 7.3 Hz), 7.45(1H,brs), 7.52(1H, d, J=7.3 Hz), 7.61–7.72(1H,m), 9.21(2H,brs), 9.55(1H,brs)

MS(m/z) 220($M^+$)

Example 414

Synthesis of N-(2-methyl-3-thioureidophenylmethyl)dimethylamine

Using N-(3-amino-2-methylphenylmethyl) dimethylamine as a starting material, the same procedure of Example 40 gave 355 mg of the titled compound (yield, 56%).

$^1$H-NMR($CDCl_3$) δ: 2.25(6H,s), 2.32(3H,s), 3.40(2H,s), 5.81(2H,brs), 7.14–7.32(3H,m), 7.53–7.72(1H,m)

Example 415

Synthesis of N-(3-(S-ethylisothioureido)-2-methylphenyl-methyl)dimethylamine dihydrochloride Using the compound obtained in Example 414 as a starting material, the same procedure of Example 380 gave 108 mg of the titled compound (yield, 83%).

$^1$H-NMR(DMSO-$d_6$) δ: 1.34(3H, t, J=7.3 Hz), 2.31(3H, s), 2.77(6H, d, J=4.0 Hz), 3.28–3.40(2H,m), 4.40(2H, d, J=5.3 Hz), 7.35–7.46(2H,m), 7.72(1H, d, J=6.9 Hz), 9.56 (1H, brs), 10.66(1H,brs), 11.49(1H,brs)

MS(m/z) 252($M^+$+1)

Example 416

Synthesis of N-(3-(N'-t-butoxycarbonyl-N"-ethylguanidino)2-methylphenylmethyl) dimethylamine Using N-(3-amino-2-methylphenylmethyl) dimethylamine as a starting material, the same procedure of Example 233 gave 46 mg of the titled compound (yield, 45%).

$^1$H-NMR($CDCl_3$) δ: 1.00–1.08(3H,m), 1.52(9H,s), 2.26 (9H,s), 3.33–3.43(2H,m), 3.42(2H,s), 4.30(1H,brs), 7.02–7.20(3H,m), 10.57(1H,brs)

Example 417

Synthesis of N-(3-(N'-ethylguanidino)-2-methylphenylmethyl)dimethylamine dihydrochloride Using the compound obtained in Example 416 as a starting material, the same procedure of Example 5 gave 37.3 mg of the titled compound (yield, 92%).

$^1$H-NMR(DMSO-$d_6$) δ: 1.15(3H, t, J=7.3 Hz), 2.32(3H, s), 2.77(6H, d, J=4.0 Hz), 3.23–3.35(2H,m), 4.38(2H, d, J=5.3 Hz), 7.29(1H, d, J=7.6 Hz), 7.37(1H, dd, J=7.9, 7.6 Hz), 7.53(1H,brs), 7.64(1H, d, J=7.9 Hz), 7.70–7.86(1H,m), 9.67(1H,brs), 10.71(1H,brs)

MS(m/z) 235($M^+$+1)

Example 418

Synthesis of 2-methoxy-3-nitrobenzyl alcohol

A mixture of 2-methoxy-3-nitrobenzoic acid methyl ester (4.82 g), lithium borohydride (298 mg), trimethyl borate (0.27 ml) and anhydrous tetrahydrofuran (200 ml) was heated under reflux for 5 h. The reaction mixture was distilled under reduced pressure and ethyl acetate and water were added to the resulting residue. The organic layer was washed with a saturated aqueous sodium chloride solution, dried with anhydrous sodium sulfate and distilled under reduced pressure. The resulting residue was purified by silica gel column chromatography (eluent, n-hexane:ethyl acetate=1:1) to give 3.18 g of the titled compound (yield, 76%).

$^1$H-NMR($CDCl_3$) δ: 2.08(1H, t, J=5.6 Hz), 3.94(3H,s), 4.81(2H, d, J=5.6 Hz), 7.23(1H, t, J=7.9 Hz), 7.69(4H, d, J=7.9 Hz), 7.79(4H, d, J=7.9 Hz)

Example 419

Synthesis of 2-methoxy-3-nitrobenzyl bromide

Using the compound obtained in Example 418 as a starting material, the same procedure of Example 55 gave the titled compound quantitatively.

$^1$H-NMR($CDCl_3$) δ: 2.03(3H,s) 4.57(2H,s), 7.21(3H, t, J=7.9 Hz), 7.65(1H, dd, J=7.9, 1.6 Hz), 7.81(1H, dd, J=7.9, 1.6 Hz)

Example 420

Synthesis of N-(2-methoxy-3-nitrohenylmethyl) iminodicarboxylic acid di-t-butyl ester Using the compound obtained in Example 419 as a starting material, the same procedure of Example 127 gave the titled compound (yield, 64%).

$^1$H-NMR($CDCl_3$) δ: 1.46(18H,s), 3.92(3H,s), 4.91(2H,s), 7.19(1H, t, J=7.9 Hz), 7.41(1H, d, J=7.9 Hz), 7.74(1H, d, J=7.9 Hz)

Example 421

Synthesis of N-(3-amino-2-methoxyphenylmethyl) iminodicarboxylic acid di-t-butyl ester Using the compound obtained in Example 420 as a starting material, the same procedure of Example 2 gave the titled compound (yield, 94%).

$^1$H-NMR($CDCl_3$) δ: 1.44(18H,s), 3.75(3H,s), 4.85(2H,s), 6.54(1H, d, J=7.3 Hz), 6.64(1H, d, J=7.3 Hz), 6.87(1H, t, J=7.3 Hz)

Example 422

Synthesis of N-(2-methoxy-3-thioureidophenylmethyl)iminodicarboxylic acid di-t-butyl ester Using the compound obtained in Example 421 as a starting material, the same procedure of Example 120 gave the titled compound (yield, 98%).

$^1$H-NMR($CDCl_3$) δ: 1.46(18H,s), 3.83(3H,s), 4.86(2H,s), 6.29(2H,brs), 7.11–7.20(3H,m), 7.88(1H,brs)

Example 423

Synthesis of N-(3-(S-ethylisothioureido)-2-methoxyphenylmethyl)carbamic acid t-butyl ester Using the compound obtained in Example 422 as a starting material, the same procedure of Example 95 gave the titled compound (yield, 86%).

$^1$H-NMR($CDCl_3$) δ: 1.39(3H, t, J=6.9 Hz), 1.45(9H,s), 3.08–3.18(2H,m), 3.77(3H,s), 4.31–4.32(2H,m), 4.54(2H, brs), 4.98(1H,brs), 6.80–7.01(3H,m)

Example 424

Synthesis of N-(3-(S-ethylisothioureido)-2-methoxyphenylmethyl)amine dihydrochloride Using the compound obtained in Example 423 as a starting material, the same procedure of Example 5 gave the titled compound (yield, 88%).

$^1$H-NMR($D_2O$) δ: 1.43(3H, t, J=7.3 Hz), 3.27(2H, q, J=7.3 Hz), 3.87(3H,s), 4.28(2H,s), 7.35(1H, t, J=7.9 Hz), 7.45(1H, dd, J=7.9, 2.0 Hz), 7.54(1H, dd, J=7.9, 2.0 Hz)

Example 425

Synthesis of N-(3-(N'-t-butoxycarbonyl-N"-ethylquanidino)-2-methoxyphenylmethyl) iminodicarboxylic acid di-t-butyl ester Using the compound obtained in Example 421 as a starting material, the same procedure of Example 233 gave the titled compound (yield, 50%).

$^1$H-NMR($CDCl_3$) δ: 1.45(27H,s), 1.48–1.58(3H,m), 3.38–3.48(2H,m), 3.78(3H,s), 4.86(2H,s), 7.00–7.25(3H,m)

Example 426

Synthesis of N-(3-(N'-ethylguanidino)-2-methoxyphenylmethyl)amine dihydrochloride Using the compound obtained in Example 425 as a starting material, the same procedure of Example 5 gave the titled compound (yield, 93%).

$^1$H-NMR($D_2O$) δ: 1.23(3H, t, J=7.3 Hz), 3.34(2H, q, J=7.3 Hz), 3.87(3H,s), 4.25(2H,s), 7.29(1H, t, J=7.6 Hz), 7.39–7.49(2H,m)

Example 427

Synthesis of N-(3-methyl-5-nitrophenylmethyl) iminodicarboxylic acid di-t-butyl ester Using 3-methyl-5-nitrobenzyl bromide as a starting material, the same procedure of Example 127 gave the titled compound (yield, 92%).

$^1$H-NMR($CDCl_3$) δ: 1.49(18H,s), 2.44(3H,s), 4.82(2H,s), 7.44(1H,s), 7.94(1H,s), 7.98(1H,s)

Example 428

Synthesis of N-(5-amino-3-methylphenylmethyl) iminodicarboxylic acid di-t-butyl ester Using the compound obtained in Example 427 as a starting material, the same procedure of Example 2 gave the titled compound (yield, 89%).

$^1$H-NMR($CDCl_3$) δ: 1.46(18H,s), 2.23(3H,s), 3.56(2H, brs), 4.65(2H,s), 6.39(1H,s), 6.41(1H,s), 6.49(1H,s)

Example 429

Synthesis of N-(3-methyl-5-thioureidophenylmethyl)iminodicarboxylic acid di-t-butyl ester Using the compound obtained in Example 428 as a starting material, the same procedure of Example 120 gave the titled compound quantitatively.

$^1$H-NMR($CDCl_3$) δ: 1.48(18H,s), 2.34(3H,s), 4.74(2H,s), 6.10(2H,brs), 6.91(1H,s), 6.96(1H,s), 7.06(1H,s), 7.84(1H, brs)

Example 430

Synthesis of N-(5-(S-ethylisothioureido)-3-methylphenylmethyl)carbamic acid t-butyl ester Using the compound obtained in Example 429 as a starting material, the same procedure of Example 95 gave the titled compound (yield, 70%).

$^1$H-NMR($CDCl_3$) δ: 1.36(3H, t, J=7.3 Hz), 1.46(9H,s), 2.30(3H,s), 2.95–3.10(2H,m), 4.24(2H, d, J=5.6 Hz), 4.49 (1H,brs), 4.80(1H,brs), 6.64(2H,s), 6.76(1H,s)

Example 431

Synthesis of N-(5-(S-ethylisothioureido)-3-methylphenylmethyl)amine dihydrochloride Using the compound obtained in Example 430 as a starting material, the same procedure of Example 5 gave the titled compound (yield, 70%).

$^1$H-NMR($D_2O$) δ: 1.42(3H, t, J=7.3 Hz), 2.40(3H,s), 3.23(2H, q, J=7.3 Hz), 4.20(2H,s), 7.23(1H,s), 7.28(1H,s), 7.37(1H,s)

Example 432

Synthesis of N-(5-(N'-t-butoxycarbonyl-N"-ethylguanidino)-3-methylphenylmethyl) iminodicarboxylic acid di-t-butyl ester Using the compound obtained in Example 428 as a starting material, the same procedure of Example 233 gave the titled compound (yield, 64%).

$^1$H-NMR($CDCl_3$) b: 1.01–1.15(3H,m), 1.47(27H,s), 2.32 (3H,s), 3.34–3.45(2H,m), 4.72(2H,s), 6.82–7.00(3H,m)

Example 433

Synthesis of N-(5-(N'-ethylguanidino)-3-methylphenylmethyl)amine dihydrochloride Using the compound obtained in Example 432 as a starting material, the same procedure of Example 5 gave the titled compound (yield, 80%).

$^1$H-NMR($D_2O$) δ: 1.22(3H, t, J=7.3 Hz), 2.38(3H,s), 3.32(2H, q, J=7.3 Hz), 4.17(2H,s), 7.15(1H,s), 7.20(1H,s), 7.26(1H,s)

Example 434

Synthesis of N-(2-benzylamino-5-nitrophenylmethyl)iminodicarboxylic acid di-t-butyl ester Using the compound obtained in Example 263 as a starting material and also using benzylamine as a reagent, the same procedure of Example 264 gave the titled compound (yield, 71%).

$^1$H-NMR($CDCl_3$) δ: 1.46(18H,s), 4.45–4.48(2H,m), 4.75 (2H,s), 6.42–6.55(1H,m), 7.13–7.39(5H,m), 7.97–8.09(1H, m), 8.17–8.23(1H,m)

Example 435

Synthesis of N-(5-amino-2-benzylaminophenylmethyl)iminodicarboxylic acid di-t-butyl ester Using the compound obtained in Example 434 as a starting material, the same procedure of Example 2 gave the titled compound (yield, 32%).

$^1$H-NMR($CDCl_3$) δ: 1.44(18H,s), 4.31(2H,s), 4.69(2H,s), 6.43(1H, d, J=8.3 Hz), 6.52(1H, d, J=8.3 Hz), 6.68(1H,s), 7.19–7.40(5H,m)

Example 436

Synthesis of N-(2-benzylamino-5-thioureidophenylmethyl)iminodicarboxylic acid di-t-butyl ester Using the compound obtained in Example 435 as a starting material, the same procedure of Example 120 gave the titled compound (yield, 32%).

$^1$H-NMR($CDCl_3$) δ: 1.45(18H,s), 4.39(2H, d, J=5.6 Hz), 4.70(2H,s), 5.91(2H,brs), 6.10(1H, t, J=5.6 Hz), 6.50(1H, d,J=8.6 Hz), 6.90–6.94(1H,m), 7.13–7.14(1H,m), 7.25–7.34 (5H,m), 7.55(1H,brs)

Example 437

Synthesis of N-(2-benzylamino-5-(S-ethylisothioureido)phenylmethyl)carbamic acid t-butyl ester Using the compound obtained in Example 436 as a starting material, the same procedure of Example 95 gave the titled compound (yield, 48%).

$^1$H-NMR($CDCl_3$) δ: 1.34(3H, t, J=7.3 Hz), 1.40(9H,s), 3.00(2H, q, J=7.3 Hz), 4.25(2H, d, J=6.3 Hz), 4.36(2H,s), 4.83(1H,brs), 5.16(1H,brs), 6.50–6.54(1H,m), 6.60–6.75 (2H,m), 7.20–7.39(5H,m)

Example 438

Synthesis of N-(2-benzylamino-5-(S-ethylisothioureido)phenylmethyl)amine trihydrochloride Using the compound obtained in Example 437 as a starting material, the same procedure of Example 5 gave the titled compound (yield, 99%).

$^1$H-NMR($D_2O$) δ: 1.40(3H, t, J=7.3 Hz), 3.20(2H, q, J=7.3 Hz), 4.21(2H,s), 4.53(2H,s), 6.88(1H, d, J=8.6 Hz), 7.20(1H, dd, J=8.6, 2.6 Hz), 7.26(1H, d, J=2.6 Hz)

Example 439

Synthesis of N-(2-benzylamino-5-(N'-t-butoxycarbonyl-N"-ethylguanidino)phenylmethyl) iminodicarboxylic acid di-t-butyl ester Using the compound obtained in Example 435 as a starting material, the same procedure of Example 233 gave the titled compound (yield, 54%).

$^1$H-NMR($CDCl_3$) δ: 1.04(3H, t, J=7.3 Hz), 1.44(18H,s), 1.52(9H,s), 3.30–3.41(2H,m), 4.38(2H, d, J=4.6 Hz), 4.53 (1H,brs), 4.69(2H,s), 5.87(1H,brs), 6.51(1H, d, J=8.6 Hz), 6.86–6.94(1H,m), 7.08–7.13(1H,m), 7.32–7.35(5H,m)

Example 440

Synthesis of N-(2-benzylamino-5-(N'-ethylguanidino)phenylmethyl)amine trihydrochloride Using the compound obtained in Example 439 as a starting material, the same procedure of Example 5 gave the titled compound (yield, 89%).

$^1$H-NMR($D_2O$) δ: 1.19(3H, t, J=7.3 Hz), 3.28(2H, q, J=7.3 Hz), 4.16(2H, s), 4.52(2H, s), 6.90(1H, d, J=8.6 Hz), 7.16–7.24(2H, m), 7.32–7.48(5H, m)

Example 441

Synthesis of N-(2-(2-t-butoxycarbonylaminoethyl) phenyl)amidinosulfonic acid

Using the compound obtained in Example 331 as a starting material, the same procedure of Example 277 gave the titled compound (yield, 86%).

$^1$H-NMR(DMSO-$d_6$) δ: 1.36(9H, s), 2.64(2H, t, J=6.9 Hz), 3.16(2H, dt, J=5.3, 6.9 Hz), 6.72(1H, t, J=5.3 Hz), 7.12–7.20(1H, m), 7.28–7.40(3H, m), 9.48(1H, brs), 11.29 (1H, brs), Example 442

Synthesis of N-(2-(N'-ethylquanidino)phenylethyl) carbamic acid t-butyl ester

Using the compound obtained in Example 441 as a starting material and also using ethylamine hydrochloride as a reagent, the same procedure of Example 302 gave the titled compound quantitatively.

$^1$H-NMR($CDCl_3$) δ: 1.22(3H, t, J=7.3 Hz), 1.36(9H, s), 2.75(2H, t, J=6.3 Hz), 3.28–3.37(4H, m), 3.99(2H, brs), 5.89(1H, brs), 6.91–7.03(2H, m), 7.13–7.19(2H, m)

Example 443

Synthesis of N-(2-(N'-ethylguanidino)phenylethyl) amine dihydrochloride

Using the compound obtained in Example 442 as a starting material, the same procedure of Example 5 gave the titled compound (yield, 90%).

$^1$H-NMR($D_2O$) δ: 1.21(3H, t, J=7.3 Hz), 3.01(2H, t, J=7.6 Hz), 3.19–3.37(4H, m), 7.32–7.50(4H, m)

Example 444

Synthesis of N-(5-(N'-t-butoxycarbonyl-N"-ethylguanidino)-2-fluorophenylmethyl) iminodicarboxylic acid di-t-butyl ester Using the compound obtained in Example 314 as a starting material, the same procedure of Example 233 gave the titled compound (yield, 70%).

$^1$H-NMR($CDCl_3$) δ: 1.03–1.08(3H, m), 1.47(27H, s), 3.15–3.22(2H, m), 4.83(2H, s),6.99–7.15(3H, m)

Example 445

Synthesis of N-(5-(N'-ethylguanidino)-2-fluorophenylmethyl)amine dihydrochloride Using the compound obtained in Example 444 as a starting material, the same procedure of Example 5 gave the titled compound (yield, 90%).

$^1$H-NMR($D_2O$) δ: 1.22(3H, t, J=7.3 Hz), 3.31(2H, q, J=7.3 Hz), 4.27(2H, s), 7.28–7.46(3H, m)

Example 446

Synthesis of N-(2-methylamino-5-nitrophenylmethyl)iminodicarboxylic acid di-t-butyl ester Using the compound obtained in Example 263 as a starting material and also using methylamine hydrochloride as a reagent, the same procedure of Example 264 gave the titled compound (yield, 99%).

$^1$H-NMR($CDCl_3$) δ: 1.50(18H, s), 2.92(3H, d, J=4.9 Hz), 4.68(2H, s), 6.50(1H, d, J=9.3 Hz), 6.72(1H, brs), 8.08–8.15 (2H, m)

Example 447

Synthesis of N-(5-amino-2-methylaminophenylmethyl)iminodicarboxylic acid di-t-butyl ester Using the compound obtained in Example 446 as a starting material, the same procedure of Example 2 gave the titled compound (yield, 61%).

$^1$H-NMR($CDCl_3$) δ: 1.46(18H, s), 2.78(3H, s), 3.60(2H, brs), 4.63(2H, s), 6.45–6.68(3H, m), MS(m/z)351($M^+$)

Example 448

Synthesis of N-(5-(N'-t-butoxycarbonyl-N"-ethylguanidino)-2-methylaminophenylmethyl) iminodicarboxylic acid di-t-butyl ester Using the compound obtained in Example 447 as a starting material, the same procedure of Example 233 gave the titled compound (yield, 47%).

$^1$H-NMR($CDCl_3$) δ: 1.05(3H, t, J=7.3 Hz), 1.47–1.53 (27H, m), 2.84(3H, s), 3.35–3.39(2H, m), 4.63(2H, s), 5.30(1H, brs), 6.55(1H, d, J=8.6 Hz), 6.99–7.07(2H, m), 10.39(1H, brs)

Example 449

Synthesis of N-(5-(N'-ethylguanidino)-2-methylaminophenylmethyl)amine trihydrochloride Using the compound obtained in Example 448 as a starting material, the same procedure of Example 5 gave the titled compound quantitatively.

$^1$H-NMR($D_2O$) δ: 1.25(3H, t, J=7.3 Hz), 3.10(3H, s), 3.35(2H, q, J=7.3 Hz), 4.36(2H, s), 7.50–7.51(3H, m)

MS(m/z)221($M^+$)

Example 450

Synthesis of N-(2-methylamino-5-thioureidophenylmethyl)iminodicarboxylic acid di-t-butyl ester Using the compound obtained in Example 447 as a starting material, the same procedure of Example 120 gave the titled compound (yield, 61%).

$^1$H-NMR($CDCl_3$) δ: 1.48(18H, s), 2.84(3H, d, J=3.5 Hz), 4.63(2H, s), 5.50(2H, brs), 6.50(1H, d, J=8.6 Hz), 7.04(1H, dd, J=8.6, 2.7 Hz), 7.12(1H, d, J=2.7 Hz), 7.99(1H, brs)

MS(m/z)410($M^+$)

Example 451

Synthesis of N-(5-(S-ethylisothioureido)-2-methylaminophenylmethyl)iminodicarboxylic acid di-t-butyl ester Using the compound obtained in Example 450 as a starting material, the same procedure of Example 95 gave the titled compound (yield, 61%).

$^1$H-NMR($CDCl_3$) δ: 1.31(3H, t, J=7.3 Hz), 1.47(18H, s), 2.82(3H, s), 3.01(2H, q, J=7.3 Hz), 4.64(2H, s), 6.55(1H, d, J=7.6 Hz), 6.81–6.88(2H, m)

MS(m/z)438($M^+$)

Example 452

Synthesis of N-(5-(S-ethylisothioureido)-2-methylaminophenylmethyl)amine trihydrochloride Using the compound obtained in Example 451 as a starting material, the same procedure of Example 5 gave the titled compound quantitatively.

$^1$H-NMR($D_2O$) δ: 1.42(3H, t, J=7.3 Hz), 3.04(3H, s), 3.25(2H, q, J=7.3 Hz), 4.32(2H, s), 7.40(1H, d, J=8.6 Hz), 7.49–7.55(2H, m)

MS(m/z)238($M^+$)

Example 453

Synthesis of N-(2-ethylamino-5-nitrophenylmethyl) iminodicarboxylic acid di-t-butyl ester Using the compound obtained in Example 263 as a starting material and also using ethylamine hydrochloride as a reagent, the same procedure of Example 264 gave the titled compound (yield, 52%).

$^1$H-NMR($CDCl_3$) δ: 1.33(3H, t, J=7.3 Hz), 1.50(18H, s), 3.14–3.34(2H, m), 5.37(2H, s), 6.52(1H, d, J=8.0 Hz), 6.65(1H, brs), 8.05–8.25(2H, m)

MS(m/z)395($M^+$)

Example 454

Synthesis of N-(5-amino-2-ethylaminophenylmethyl)iminodicarboxylic acid di-t-butyl ester Using the compound obtained in Example 453 as a starting material, the same procedure of Example 2 gave the titled compound (yield, 71%).

$^1$H-NMR($CDCl_3$) δ: 1.25(3H, t, J=7.3 Hz), 1.46(18H, s), 3.07(2H, q, J=7.3 Hz), 3.55(2H, brs), 4.64(2H, s), 6.46–6.67 (3H, m)

MS(m/z)365($M^+$)

Example 455

Synthesis of N-(5-(N'-t-butoxycarbonyl-N"-ethylguanidino)-2-ethylaminophenylmethyl) iminodicarboxylic acid di-t-butyl ester Using the compound obtained in Example 454 as a starting material, the same procedure of Example 233 gave the titled compound (yield, 50%).

$^1$H-NMR($CDCl_3$) δ: 1.30(3H, t, J=7.2 Hz), 1.43–1.53 (30H, m), 3.11–3.17(2H, m), 3.34–3.40(2H, m), 4.45(1H, brs), 4.64(2H, s), 5.29(1H, brs), 6.55(1H, d, J=8.5 Hz), 6.98(1H, dd, J=8.5, 2.7 Hz), 7.07(1H, d, J=2.7 Hz)

Example 456

Synthesis of N-(2-ethylamino-5-(N'-ethylguanidino) phenylmethyl)amine trihydrochloride Using the compound obtained in Example 455 as a starting material, the same procedure of Example 5 gave the titled compound (yield, 89%).

$^1$H-NMR($D_2O$) δ: 1.24(3H, t, J=7.3 Hz), 1.36(3H, t, J=7.3 Hz), 3.34(2H, q, J=7.3 Hz), 3.48(2H, q, J=7.3 Hz), 4.44(2H, s), 7.50–7.52(3H, m)

MS(m/z)235($M^+$)

Example 457

Synthesis of N-(2-ethylamino-5-thioureidophenylmethyl)iminodicarboxylic acid di-t-butyl ester Using the compound obtained in Example 454 as a starting material, the same procedure of Example 120 gave the titled compound (yield, 55%).

$^1$H-NMR($CDCl_3$) δ: 1.29(3H, t, J=7.3 Hz), 1.47(18H, s), 3.14(2H, q, J=7.3 Hz), 4.64(2H, s), 5.90(2H, brs), 6.56(1H, d, J=8.6 Hz), 6.98–7.12(2H, m), 7.55(1H, brs), MS(m/z)424($M^+$)

Example 458

Synthesis of N-(2-ethylamino-5-(S-ethylisothioureido)phenylmethyl)iminodicarboxylic acid di-t-butyl ester Using the compound obtained in Example 457 as a starting material, the same procedure of Example 95 gave the titled compound (yield, 60%).

$^1$H-NMR($CDCl_3$) δ: 1.28(3H, t, J=7.3 Hz), 1.34(3H, t, J=7.3 Hz), 1.47(18H, s), 3.01(2H, q, J=7.3 Hz), 3.12(2H, q, J=7.3 Hz), 4.66(1H, d, J=8.3 Hz), 6.55(1H, d, J=8.3 Hz), 6.79(1H, dd, J=8.3, 2.4 Hz), 6.86(1H, d, J=2.4 Hz)

MS(m/z)453($M^+$+1)

Example 459

Synthesis of N-(2-ethylamino-5-(S-ethylisothioureido)phenylmethyl)amine trihydrochloride Using the compound obtained in Example 458 as a starting material, the same procedure of Example 5 gave the titled compound (yield, 63%).

$^1$H-NMR($D_2O$) δ: 1.31(3H, t, J=7.3 Hz), 1.41(3H, t, J=7.3 Hz), 3.23(2H, q, J=7.3 Hz), 3.32–3.42(2H, m), 4.28(2H, s), 7.30–7.49(3H, m)

MS(m/z)252($M^+$)

Example 460

Synthesis of N-(2-ethyl-5-nitrophenylmethyl) iminodicarboxylic acid di-t-butyl ester Using 3-chloromethyl-4-ethylnitrobenzene as a starting material, the same procedure of Example 127 gave the titled compound (yield, 72%).

$^1$H-NMR($CDCl_3$) δ: 1.28(3H, t, J=7.4 Hz), 1.49(18H, s), 2.76(2H, q, J=7.4 Hz), 4.88(2H, s), 7.33(1H, d, J=8.3 Hz), 7.99–8.10(2H, m)

Example 461

Synthesis of N-(5-amino-2-ethylphenylmethyl) iminodicarboxylic acid di-t-butyl ester Using the compound obtained in Example 460 as a starting material, the same procedure of Example 2 gave the titled compound (yield, 99%).

$^1$H-NMR($CDCl_3$) δ: 1.16(3H, t, J=7.3 Hz), 1.44(18H, s), 2.54(2H, q, J=7.3 Hz), 4.77(2H, brs), 6.45–6.60(2H, m), 6.95(1H, d, J=8.3 Hz)

MS(m/z)350($M^+$)

Example 462

Synthesis of N-(2-ethyl-5-thioureidophenylmethyl) iminodicarboxylic acid di-t-butyl ester Using the compound obtained in Example 461 as a starting material, the same procedure of Example 120 gave the titled compound (yield, 87%).

$^1$H-NMR($CDCl_3$) δ: 1.23(3H, t, J=7.5 Hz), 1.47(18H, s), 2.65(2H, q, J=7.5 Hz), 4.81(2H, s), 6.11(2H, brs), 7.00(1H, d, J=1.8 Hz), 7.04(1H, dd, J=8.0, 1.8 Hz), 7.23(1H, d, J=8.0 Hz) 7.99(1H, brs)

Example 463

Synthesis of N-(5-(S-ethylisothioureido)-2-ethylphenylmethyl)iminodicarboxylic acid di-t-butyl ester Using the compound obtained in Example 462 as a starting material, the same procedure of Example 95 gave the titled compound (yield, 76%).

$^1H$-NMR($CDCl_3$) δ: 1.19(3H, t, J=7.3 Hz), 1.28–1.34(3H, m), 1.43(18H, s), 2.61(2H, q, J=7.3 Hz), 3.00–3.10(2H, m), 4.80(2H, s), 6.67–7.10(3H, m)

MS(m/z)437($M^+$)

Example 464

Synthesis of N-(5-(S-ethylisothioureido)-2-ethylphenylmethyl)amine dihydrochloride Using the compound obtained in Example 463 as a starting material, the same procedure of Example 5 gave the titled compound (yield, 77%).

$^1H$-NMR($D_2O$) δ: 1.23(3H, t, J=7.4 Hz), 1.42(3H, t, J=7.4 Hz), 2.74(2H, q, J=7.4 Hz), 3.25(2H, q, J=7.4 Hz), 4.29(2H, s), 7.34–7.41(2H, m), 7.52(1H, d, J=8.2 Hz),

MS(m/z)237($M^+$)

Example 465

Synthesis of N-(5-(N'-t-butoxycarbonyl-N"-ethylguanidino)-2-ethylphenylmethyl) iminodicarboxylic acid di-t-butyl ester Using the compound obtained in Example 461 as a starting material, the same procedure of Example 233 gave the titled compound (yield, 80%).

$^1H$-NMR($CDCl_3$) δ: 1.08(3H, t, J=7.3 Hz), 1.26(3H, t, J=7.5 Hz), 1.43–1.69(27H, m), 2.66(2H, q, J=7.3 Hz), 3.39(2H, q, J=7.5 Hz), 4.81(2H, s), 6.96–7.27(3H, m), 10.61(1H, brs), Example 466

Synthesis of N-(2-ethyl-5-(N'-ethylguanidino) phenylmethyl)amine dihydrochloride Using the compound obtained in Example 465 as a starting material, the same procedure of Example 5 gave the titled compound (yield, 89%).

$^1H$-NMR($D_2O$) δ: 1.19–1.25(6H, m), 2.74(2H, q, J=7.5 Hz), 3.10(2H, q, J=7.3 Hz), 4.27(2H, s), 7.29–7.34(2H, m), 7.45(1H, d, J=7.9 Hz),

MS(m/z)221(M++1)

Example 467

Synthesis of N-(2-methyl-5-nitrophenylmethyl) iminodicarboxylic acid di-t-butyl ester Using 3-chloromethyl-4-methylnitrobenzene as a starting material, the same procedure of Example 127 gave the titled compound (yield, 37%).

$^1H$-NMR($CDCl_3$) δ: 1.49(18H, s), 2.42(3H, s), 4.83(2H, s), 7.27–7.32(1H, m), 7.99–8.03(2H, m)

Example 468

Synthesis of N-(5-amino-2-methylphenylmethyl) iminodicarboxylic acid di-t-butyl ester Using the compound obtained in Example 467 as a starting material, the same procedure of Example 2 gave the titled compound (yield, 82%).

$^1H$-NMR($CDCl_3$) δ: 1.44(18H, s), 2.18(3H, s), 3.51(2H, brs), 4.71(2H, s), 6.47–6.52(2H, m), 6.85(1H, d, J=8.1 Hz)

Example 469

Synthesis of N-(2-methyl-5-thioureidophenylmethyl)iminodicarboxylic acid di-t-butyl ester Using the compound obtained in Example 468 as a starting material, the same procedure of Example 120 gave the titled compound (yield, 99%).

$^1H$-NMR($CDCl_3$) δ: 1.48(18H, s), 2.30(3H, s), 4.75(2H, s), 6.04(2H, brs), 6.95–7.01(2H, m), 7.24(1H, d, J=7.3 Hz), 7.83(1H, brs)

MS(m/z)396($M^+$+1)

Example 470

Synthesis of N-(5-(S-ethylisothioureido)-2-methylphenylmethyl)iminodicarboxylic acid di-t-butyl ester Using the compound obtained in Example 469 as a starting material, the same procedure of Example 95 gave the titled compound (yield, 87%).

$^1H$-NMR($CDCl_3$) δ: 1.36(3H, t, J=7.3 Hz), 1.44(18H, s), 2.25(3H, s), 2.95–3.05(2H, m), 4.74(2H, s), 6.63–6.75(2H, m), 7.05(1H, d, J=7.9 Hz)

MS(m/z)424($M^+$+1)

Example 471

Synthesis of N-(5-(S-ethylisothioureido)-2-methylphenylmethyl)amine dihydrochloride Using the compound obtained in Example 470 as a starting material, the same procedure of Example 5 gave the titled compound (yield, 83%).

$^1H$-NMR($D_2O$) δ: 1.42(3H, t, J=7.3 Hz), 2.43(3H, 5), 3.25(2H, q, J=7.3 Hz), 4.28(2H, s), 7.31–7.50(3H, m)

MS(m/z)223($M^+$)

Example 472

Synthesis of N-(5-(N'-t-butoxycarbonyl-N"-ethylguanidino)-2-methylphenylmethyl) iminodicarboxylic acid di-t-butyl ester Using the compound obtained in Example 471 as a starting material, the same procedure of Example 233 gave the titled compound (yield, 55%).

$^1H$-NMR($CDCl_3$) δ: 1.07(3H, t, J=7.0 Hz), 1.44–1.53 (27H, m), 2.30(3H, s), 3.31–3.45(2H, m), 4.65(1H, brs), 4.75(2H, s), 6.95–7.20(3H, m)

MS(m/z)507($M^+$+1)

Example 473

Synthesis of N-(5-(N'-ethylguanidino)-2-methylphenylmethyl)amine dihydrochloride Using the compound obtained in Example 472 as a starting material, the same procedure of Example 5 gave the titled compound (yield, 85%).

$^1H$-NMR($D_2O$) δ: 1.23(3H, t, J=7.4 Hz), 2.71(3H, s), 3.31(2H, q, J=7.4 Hz), 4.24(2H, s), 7.24–7.29(2H, m), 7.39–7.44(1H, m)

MS(m/z)206($M^+$)

Example 474

Synthesis of N-(3-methoxy-4-methylphenyl) phthalimide

Using 3-methoxy-4-methylaniline as a starting material, the same procedure of Example 248 gave 1.55 g of the titled compound (yield, 14%)

$^1H$-NMR($CDCl_3$) δ: 2.26(3H, s), 3.85(3H, s), 6.82–6.95 (2H, m), 7.21–7.30(1H, m), 7.77–7.81(2H, m), 7.94–7.97 (2H, m)

Example 475

Synthesis of N-(4-bromomethyl-3-methoxyphenyl) phthalimide

Using the compound obtained in Example 474 as a starting material, the same procedure of Example 249 gave 80 mg of the titled compound (yield, 74%).

$^1$H-NMR($CDCl_3$) δ: 3.93(3H, s), 4.58(2H, s), 6.96–7.10 (2H, m), 7.42–7.50(1H, m), 7.79–7.82(2H, m), 7.95–7.98 (2H, m)

Example 476

Synthesis of N-(4-cyanomethyl-3-methoxyphenyl) phthalimide

Using the compound obtained in Example 475 as a starting material, the same procedure of Example 250 gave 26 mg of the titled compound (yield, 42%).

$^1$H-NMR($CDCl_3$) δ: 3.73(2H, s), 3.90(3H, s), 7.01–7.14 (2H, m), 7.48–7.53(1H, m), 7.80–7.83(2H, m), 7.96–7.99 (2H, m)

Example 477

Synthesis of 4-cyanomethyl-3-methoxyaniline

Using the compound obtained in Example 476 as a starting material, the same procedure of Example 251 gave 640 mg of the titled compound (yield, 94%).

$^1$H-NMR($CDCl_3$) δ: 3.55(2H, s), 3.75(2H, brs), 3.80(3H, s), 6.18–6.35(2H, m), 7.00–7.14(1H, m)

Example 478

Synthesis of 4-(2-aminoethyl)-3-methoxyaniline

Using the compound obtained in Example 477 as a starting material, the same procedure of Example 252 gave 608 mg of the titled compound (yield, 93%).

$^1$H-NMR($CDCl_3$) δ: 1.68(2H, brs), 2.64(2H, t, J=6.9 Hz), 2.84(2H, t, J=6.9 Hz), 3.61(2H, brs), 3.76(3H, s), 6.18–6.26 (2H, m), 6.84–6.95(1H, m)

Example 479

Synthesis of N-(2-(4-amino-2-methoxyphenyl)ethyl) carbamic acid t-butyl ester

Using the compound obtained in Example 478 as a starting material, the same procedure of Example 253 gave 253 mg of the titled compound (yield, 31%).

$^1$H-NMR($CDCl_3$) δ: 1.43(9H, s), 2.68(2H, t, J=6.9 Hz), 3.20–3.35(2H, m), 3.62(2H, brs), 3.77(3H, s), 4.63(1H, brs), 6.20–6.25(2H, m), 6.82–6.92(1H, m)

Example 480

Synthesis of N-(2-(2-methoxy-4-thioureidophenyl) ethyl)carbamic acid t-butyl ester Using the compound obtained in Example 479 as a starting material, the same procedure of Example 120 gave 70 mg of the titled compound (yield, 91%).

$^1$H-NMR($CDCl_3$) δ: 1.42(9H, s), 2.79(2H, t, J=6.9 Hz), 3.25–3.40(2H, m), 3.82(3H, s), 4.60(1H, brs), 6.12(2H, brs), 6.71–6.79(2H, m), 7.16–7.18(1H, m), 7.93(1H, s)

Example 481

Synthesis of N-(2-(4-(S-ethylisothioureido)-2-methoxyphenyl)ethyl)carbamic acid t-butyl ester Using the compound obtained in Example 480 as a starting material, the same procedure of Example 95 gave 50 mg of the titled compound (yield, 66%).

$^1$H-NMR($CDCl_3$) δ: 1.37(3H, t, J=7.3 Hz), 1.43(9H, s), 2.75(2H, t, J=6.6 Hz), 2.95–3.20(2H, m), 3.20–3.38(2H, m), 3.79(3H, s), 4.54(1H, brs), 4.61(1H, brs), 6.38–6.60(2H, m), 7.00–7.05(1H, m)

Example 482

Synthesis of N-(2-(4-(S-ethylisothioureido)-2-methoxyphenyl)ethyl)amine dihydrochloride Using the compound obtained in Example 481 as a starting material, the same procedure of Example 5 gave 45 mg of the titled compound (yield, 81%).

$^1$H-NMR($D_2O$) δ: 1.42(3H, t, J=7.3 Hz), 3.03(2H, t, J=6.9 Hz), 3.19–3.28(4H, m), 3.88(3H, s), 6.95–7.00(2H, m), 7.36–7.39(1H, m)

Example 483

Synthesis of N-(2-(4-(N'-t-butoxycarbonyl-N"-ethylguanidino)-2-methoxyphenyl)ethyl)carbamic acid t-butyl ester Using the compound obtained in Example 479 as a starting material, the same procedure of Example 233 gave 118 mg of the titled compound (yield, 95%).

$^1$H-NMR($CDCl_3$) δ: 1.19(3H, t, J=7.3 Hz), 1.43(9H, s), 1.52(9H, s), 2.78(2H, t, J=6.6 Hz), 3.32–3.44(4H, m), 3.80 (3H, s), 4.62(1H, brs), 6.56–6.90(2H, m), 7.30–7.80(1H, m), 8.02(1H, brs)

Example 484

Synthesis of N-(2-(4-(N'-ethylguanidino)-2-methoxyphenyl)ethyl)amine dihydrochloride Using the compound obtained in Example 483 as a starting material, the same procedure of Example 5 gave 72 mg of the titled compound quantitatively.

$^1$H-NMR($D_2O$) δ: 1.23(3H, t, J=7.3 Hz), 3.01(2H, t, J=6.9 Hz), 3.22–3.61(4H, m), 3.87(3H, s), 6.89–6.96(2H, m), 7.30–7.33(1H, m)

Example 485

Synthesis of N-(2-methoxy-4-methylphenyl) phthalimide

Using 2-methoxy-4-methylaniline as a starting material, the same procedure of Example 248 gave 4.46 g of the titled compound (yield, 11%).

$^1$H-NMR($CDCl_3$) δ: 2.41(3H, s), 3.77(3H, s), 6.86–6.90 (2H, m), 7.11–7.14(1H, m), 7.75–7.78(2H, m), 7.89–7.95 (2H, m)

Example 486

Synthesis of N-(4-bromomethyl-2-methoxyphenyl) phthalimide

Using the compound obtained in Example 485 as a starting material, the same procedure of Example 249 gave 4.46 g of the titled compound (yield, 76%).

$^1$H-NMR($CDCl_3$) δ: 3.82(3H, s), 4.52(2H, s), 7.08–7.24 (3H, m), 7.76–7.80(2H, m), 7.93–7.96(2H, m)

Example 487

Synthesis of N-(4-cyanomethyl-2-methoxyphenyl) phthalimide

Using the compound obtained in Example 486 as a starting material, the same procedure of Example 250 gave 2.0 g of the titled compound (yield, 50%).

$^1$H-NMR($CDCl_3$) δ: 3.83(5H, s), 7.02–7.29(3H, m), 7.77–7.81(2H, m), 7.93–7.96(2H, m)

Example 488

Synthesis of 4-cyanomethyl-2-methoxyaniline

Using the compound obtained in Example 487 as a starting material, the same procedure of Example 251 gave 844 mg of the titled compound (yield, 77%). $^1$H-NMR ($CDCl_3$) δ: 3.65(2H, s), 3.70–3.95(5H, m), 6.65–6.72(3H, m)

Example 489

Synthesis of 4-(2-aminoethyl)-2-methoxyaniline

Using the compound obtained in Example 488 as a starting material, the same procedure of Example 252 gave 230 mg of the titled compound (yield, 62%).

$^1$H-NMR($CDCl_3$) δ: 1.43(2H, brs), 2.65(2H, t, J=6.9 Hz), 2.92(2H, t, J=6.9 Hz), 3.69(2H, brs), 3.84(3H, s), 6.61–6.72 (3H, m)

Example 490

Synthesis of N-(2-(4-amino-3-methoxyphenyl)ethyl) carbamic acid t-butyl ester

Using the compound obtained in Example 489 as a starting material, the same procedure of Example 253 gave 95 mg of the titled compound (yield, 26%).

$^1$H-NMR($CDCl_3$) δ: 1.44(9H, s), 2.69(2H, t, J=6.9 Hz), 3.28–3.44(2H, m), 3.84(3H, s), 4.54(1H, brs), 6.59–6.72 (3H, m)

Example 491

Synthesis of N-(2-(3-methoxy-4-thioureidophenyl) ethyl)carbamic acid t-butyl ester Using the compound obtained in Example 490 as a starting material, the same procedure of Example 120 gave 38 mg of the titled compound (yield, 73%).

$^1$H-NMR($CDCl_3$) δ: 1.43(9H, s), 2.80(2H, t, J=7.3 Hz), 3.30–3.44(2H, m), 3.85(3H, s), 4.57(1H, brs), 6.07(2H, brs), 6.80–6.83(2H, m), 7.21–7.24(1H, m), 7.62(1H, brs)

Example 492

Synthesis of N-(2-(4-(S-ethylisothioureido)-3-methoxyphenyl)ethyl)carbamic acid t-butyl ester Using the compound obtained in Example 491 as a starting material, the same procedure of Example 95 gave 25 mg of the titled compound (yield, 61%).

$^1$H-NMR($CDCl_3$) δ: 1.38(3H, t, J=7.3 Hz), 1.44(9H, s), 2.75(2H, t, J=6.9 Hz), 2.88–3.14(2H, m), 3.30–3.42(2H, m), 3.82(3H, s), 4.52(1H, brs), 6.72–6.76(2H, m), 7.26(1H, s)

Example 493

Synthesis of N-(2-(4-(S-ethylisothioureido)-3-methoxyphenyl)ethyl)amine dihydrochloride Using the compound obtained in Example 492 as a starting material, the same procedure of Example 5 gave 19 mg of the titled compound (yield, 92%).

$^1$H-NMR($D_2O$) δ: 1.42(3H, t, J=7.3 Hz), 3.05(2H, t, J=7.3 Hz), 3.18–3.34(4H, m), 3.90(3H, s), 7.02(1H, d, J=7.9 Hz), 7.15(1H, s), 7.30(1H, d, J=7.9 Hz)

Example 494

Synthesis of 4-(2-aminoethyl)-2-chloroaniline

Using 2-chloro-4-cyanomethylaniline as a starting material, the same procedure of Example 252 gave 614 mg of the titled compound quantitatively.

$^1$H-NMR($CDCl_3$) δ: 1.21(2H, brs), 2.61(2H, t, J=6.9 Hz), 2.90(2H, t, J=6.9 Hz), 3.96(2H, brs), 6.69–7.09(3H, m)

Example 495

Synthesis of N-(2-(4-amino-3-chlorophenyl)ethyl) carbamic acid t-butyl ester

Using the compound obtained in Example 494 as a starting material, the same procedure of Example 253 gave 912 mg of the titled compound (yield, 94%).

$^1$H-NMR($CDCl_3$) δ: 1.44(9H, s), 2.66(2H, t, J=6.9 Hz), 3.20–3.40(2H, m), 3.97(2H, brs), 4.54(1H, brs), 6.69–7.07 (3H, m)

Example 496

Synthesis of N-(2-(3-chloro-4-thioureidophenyl) ethyl)carbamic acid t-butyl ester Using the compound obtained in Example 495 as a starting material, the same procedure of Example 120 gave 114 mg of the titled compound (yield, 94%).

$^1$H-NMR($CDCl_3$) δ: 1.43(9H, s), 2.79(2H, t, J=6.9 Hz), 3.33–3.40(2H, m), 4.68(1H, brs), 6.24(2H, brs), 7.15–7.18 (1H, m), 7.34–7.39(2H, m), 7.93(1H, brs)

Example 497

Synthesis of N-(2-(3-chloro-4-(S-ethylisothioureido) phenyl)ethyl)carbamic acid t-butyl ester Using the compound obtained in Example 496 as a starting material, the same procedure of Example 95 gave 118 mg of the titled compound (yield, 95%).

$^1$H-NMR($CDCl_3$) δ: 1.40(3H, t, J=7.3 Hz), 1.44(9H, s), 2.73(2H, t, J=6.9 Hz), 2.96–3.20(2H, m), 3.31–3.35(2H, m), 4.52(1H, brs), 6.92–7.04(2H, m), 7.22(1H, s)

Example 498

Synthesis of N-(2-(3-chloro-4-(S-ethylisothioureido) phenyl)ethyl)amine dihydrochloride Using the compound obtained in Example 497 as a starting material, the same procedure of Example 5 gave 95 mg of the titled compound quantitatively.

$^1$H-NMR($D_2O$) δ: 1.44(3H, t, J=7.3 Hz), 3.07(2H, t, J=7.3 Hz), 3.22–3.35(4H, m), 7.40–7.49(2H, m), 7.62(1H, s)

Example 499

Synthesis of N-(2-fluoro-4-methylphenyl) phthalimide

Using 2-fluoro-4-methylaniline as a starting material, the same procedure of Example 248 gave 8.8 g of the titled compound (yield, 22%).

$^1$H-NMR($CDCl_3$) δ: 2.42(3H, s), 7.06–7.26(3H, m), 7.78–7.81(2H, m), 7.94–7.97(2H, m)

Example 500

Synthesis of N-(4-bromomethyl-2-fluorophenyl) phthalimide

Using the compound obtained in Example 499 as a starting material, the same procedure of Example 249 gave 6.0 g of the titled compound (yield, 92%).

$^1H$-NMR($CDCl_3$) δ: 4.49(2H, s), 7.30–7.38(3H, m), 7.80–7.83(2H, m), 7.96–7.99(2H, m)

Example 501

Synthesis of N-(4-cyanomethyl-2-fluorophenyl) phthalimide

Using the compound obtained in Example 500 as a starting material, the same procedure of Example 250 gave 2.0 g of the titled compound (yield, 40%).

$^1H$-NMR($CDCl_3$) δ: 3.84(2H, s), 7.27–7.47(3H, m), 7.79–7.84(2H, m), 7.96–8.00(2H, m)

Example 502

Synthesis of 4-cyanomethyl-2-fluoroaniline

Using the compound obtained in Example 501 as a starting material, the same procedure of Example 251 gave 290 mg of the titled compound (yield, 93%).

$^1H$-NMR($CDCl_3$) δ: 3.62(2H, s), 3.78(2H, brs), 6.72–6.97 (3H, m)

Example 503

Synthesis of 4-(2-aminoethyl)-2-fluoroaniline

Using the compound obtained in Example 502 as a starting material, the same procedure of Example 252 gave 290 mg of the titled compound (yield, 97%).

$^1H$-NMR($CDCl_3$) δ: 1.21(2H, brs), 2.62(2H, t, J=6.9 Hz), 2.90(2H, t, J=6.9 Hz), 3.64(2H, brs), 6.67–6.85(3H, m)

Example 504

Synthesis of N-(2-(4-amino-3-fluorophenyl)ethyl) carbamic acid t-butyl ester

Using the compound obtained in Example 503 as a starting material, the same procedure of Example 253 gave 290 mg of the titled compound (yield, 65%).

$^1H$-NMR($CDCl_3$) δ: 1.44(9H, s), 2.67(2H, t, J=6.9 Hz), 2.65–2.75(2H, m), 3.64(2H, brs), 4.53(1H, brs), 6.68–6.84 (3H, m)

Example 505

Synthesis of N-(2-(3-fluoro-4-thioureidophenyl) ethyl)carbamic acid t-butyl ester Using the compound obtained in Example 504 as a starting material, the same procedure of Example 120 gave 88 mg of the titled compound (yield, 98%).

$^1H$-NMR($CDCl_3$) δ: 1.43(9H, s), 2.80(2H, t, J=6.9 Hz), 3.33–3.40(2H, m), 4.62(1H, brs), 6.15(2H, brs), 7.03–7.06 (2H, m), 7.29–7.35(1H, m), 7.74(1H, brs)

Example 506

Synthesis of N-(2-(4-(S-ethylisothioureido)-3-fluorophenyl)ethyl)carbamic acid t-butyl ester Using the compound obtained in Example 505 as a starting material, the same procedure of Example 95 gave 79 mg of the titled compound (yield, 83%).

$^1H$-NMR($CDCl_3$) δ: 1.37(3H, t, J=7.3 Hz), 1.44(9H, s), 2.74(2H, t, J=6.9 Hz), 2.95–3.20(2H, m), 3.28–3.44(2H, m), 4.53(1H, brs), 6.85–7.00(3H, m)

Example 507

Synthesis of N-(2-(4-(S-ethylisothioureido)-3-fluorophenyl)ethyl)amine dihydrochloride Using the compound obtained in Example 506 as a starting material, the same procedure of Example 5 gave 44 mg of the titled compound (yield, 64%).

$^1H$-NMR($D_2O$) δ: 1.42(3H, t, J=7.3 Hz), 3.07(2H, t, J=7.3 Hz), 3.20–3.34(4H, m), 7.25–7.45(3H, m)

Example 508

Synthesis of 2-(5-methoxy-2-nitrophenyl) ethylamine

To a solution of 2-(3-methoxyphenyl)ethylamine (1.51 g) in chloroform (30 ml), fuming nitric acid (specific gravity=1.52; 0.84 ml) and sulfuric acid (1.07 ml) were successively added dropwise under ice cooling and stirred under ice cooling for 3 h. Water and 2 N aqueous sodium hydroxide solution were added to the reaction mixture, which was extracted with ethyl acetate. The organic layer was washed with a saturated aqueous sodium chloride solution, dried with anhydrous sodium sulfate and concentrated under reduced pressure. The resulting residue was purified by silica gel column chromatography (eluent, chloroform:methanol=9:1) to give 400 mg of the titled compound (yield, 21%)

$^1H$-NMR($CDCl_3$) δ: 1.51(2H, brs), 3.00–3.20(4H, m), 3.89(3H, s), 6.81–6.84(2H, m), 8.04–8.08(1H, m)

Example 509

Synthesis of N-(2-(5-methoxy-2-nitrophenyl)ethyl) carbamic acid t-butyl ester

Using the compound obtained in Example 508 as a starting material, the same procedure of Example 22 gave 448 mg of the titled compound (yield, 74%).

$^1H$-NMR($CDCl_3$) δ: 1.43(9H, s), 3.14(2H, t, J=6.9 Hz), 3.42–3.50(2H, m), 3.88(3H, s), 4.73(1H, brs), 6.82–6.86 (2H, m), 8.05–8.08(1H, m)

Example 510

Synthesis of N-(2-(2-amino-5-methoxyphenyl)ethyl) carbamic acid t-butyl ester

Using the compound obtained in Example 509 as a starting material, the same procedure of Example 2 gave 300 mg of the titled compound (yield, 75%).

$^1H$-NMR($CDCl_3$) δ: 1.45(9H, s), 2.70(2H, t, J=6.9 Hz), 3.27–3.35(2H, m), 3.74(3H, s), 4.82(1H, brs), 6.62–6.64 (3H, m)

Example 511

Synthesis of N-(2-(5-methoxy-2-thioureidophenyl) ethyl)carbamic acid t-butyl ester Using the compound obtained in Example 510 as a starting material, the same procedure of Example 120 gave 170 mg of the titled compound quantitatively.

1H-NMR($CDCl_3$) δ: 1.34(9H, s), 2.76(2H, t, J=6.9 Hz), 3.28–3.40(2H, m), 3.79(3H, s), 4.82(1H, brs), 6.32(2H, brs), 6.78–6.81(2H, m), 7.15–7.27(1H, m), 8.03(1H, brs)

Example 512

Synthesis of N-(2-(2-(S-ethylisothioureido)-5-methoxyphenyl)ethyl)carbamic acid t-butyl ester Using the compound obtained in Example 511 as a starting material, the same procedure of Example 95 gave 54 mg of the titled compound (yield, 82%).

$^1H$-NMR($CDCl_3$) δ: 1.37(3H, t, J=7.3 Hz), 1.40(9H, s), 2.67(2H, t, J=6.6 Hz), 3.00–3.20(2H, m), 3.28–3.40(2H, m), 3.77(3H, s), 5.30(1H, brs), 6.70–6.81(3H, m)

Example 513

Synthesis of N-(2-(2-(S-ethylisothioureido)-5-methoxyphenyl)ethyl)amine dihydrochloride Using the compound obtained in Example 512 as a starting material, the same procedure of Example 5 gave 52 mg of the titled compound quantitatively.

$^1$H -NMR($D_2O$) δ: 1.40–1.50(3H, m), 2.94(2H, t, J=7.6 Hz), 3.19–3.25(4H, m), 3.87(3H, s), 7.00–7.10(2H, m), 7.30–7.34(1H, m)

Example 514

Synthesis of N-(2-(5-methoxy-2-(N'-nitroguanidino)phenyl)ethyl)carbamic acid t-butyl ester Using the compound obtained in Example 510 as a starting material, the same procedure of Example 6 gave 59 mg of the titled compound (yield, 57%).

$^1$H-NMR($CDCl_3$) δ: 1.29(9H, s), 2.77(2H, t, J=6.3 Hz), 3.30–3.37(2H, m), 3.81(3H, s), 4.78(1H, brs), 6.79–6.85 (2H, m), 7.19–7.22(1H, m)

Example 515

Synthesis of N-(2-(5-methoxy-2-(N'-nitroguanidino)phenyl)ethyl)amine hydrochloride Using the compound obtained in Example 514 as a starting material, the same procedure of Example 5 gave 45 mg of the titled compound quantitatively.

$^1$H-NMR($D_2O$) δ: 2.97(2H, t, J=7.9 Hz), 3.22(2H, t, J=7.9 Hz), 3.87(3H, s), 7.00–7.06(2H, m), 7.31–7.34(1H, m)

Example 516

Synthesis of N-(2-(2-(N'-t-butoxycarbonyl-N"-ethylguanidino)-5-methoxyphenyl)ethyl)carbamic acid t-butyl ester Using the compound obtained in Example 510 as a starting material, the same procedure of Example 233 gave 112 mg of the titled compound (yield, 90%).

$^1$H-NMR($CDCl_3$) δ: 0.96–1.18(3H, m), 1.35(9H, s), 1.54 (9H, s), 2.70–2.72(2H, m), 3.28–3.41(4H, m), 3.79(3H, s), 4.67(1H, brs), 6.70–6.82(2H, m), 7.02–7.20(1H, m), 8.02 (1H, brs)

Example 517

Synthesis of N-(2-(2-(N'-ethylguanidino)-5-methoxyphenyl)ethyl)amine dihydrochloride Using the compound obtained in Example 516 as a starting material, the same procedure of Example 5 gave 70 mg of the titled compound (yield, 94%).

$^1$H-NMR($D_2O$) δ: 1.21(3H, t, J=7.3 Hz), 2.96(2H, t, J=7.6 Hz), 3.20–3.34(4H, m), 3.87(3H, s), 7.00–7.10(2H, m), 7.28–7.32(1H, m)

Example 518

Synthesis of N-(4-hydroxymethyl-2-methylphenyl)carbamic acid t-butyl ester

Lithium aluminum hydride (5.02 g) was suspended in tetrahydrofuran (300 ml). To the suspension, 4-amino-3-methylbenzoic acid (10.53 g) was added slowly at room temperature and the reaction mixture was heated under reflux for 3 h. After addition of ethyl acetate and water, the reaction mixture was stirred for 30 min and then Celite and anhydrous sodium sulfate were added. The resulting reaction mixture was filtered and the filterate was concentrated under reduced pressure to give a crude procudt. Then, water, sodium hydroxide (3.07 g) and di-t-butyl dicarbonate (15.2 g) were successively added to the crude product, which was stirred overnight at room temperature. Ethyl acetate was added to the reaction mixture and, after washing with water once, the organic layer was dried with anhydrous sodium sulfate and the solvent was distilled off under reduced pressure. The resulting residue was purified by silica gel column chromatography (eluent, n-hexne:ethyl acetate=5:1) to give 7.658 g of the titled compound (yield, 46%).

$^1$H-NMR($CDCl_3$) δ: 7.77(1H, d, J=9.0 Hz), 7.22–7.13 (2H, m), 6.27(1H, brs), 4.59(2H, s), 2.25(3H, s), 1.79(1H, brs), 1.52(9H, s)

Example 519

Synthesis of N-(4-bromomethyl-2-methylphenyl)carbamic acid t-butyl ester

The compound (1.035 g) obtained in Example 518 was dissolved in methylene chloride (20 ml) and to the solution, triphenylphosphine (1.38 g) and carbon tetrabromide (1.74 g) were successively added under ice cooling. The reaction mixture was stirred for 30 min under ice cooling, then stirred at room temperature for 30 min and the solvent was distilled off under reduced pressure. The resulting residue was purified by silica gel column chromatography (eluent, n-hexane:ethyl acetate=5:1) to give 476.6 mg of the titled compound (yield, 36%).

$^1$H-NMR($CDCl_3$) δ: 7.84(1H, d, J=8.1 Hz), 7.29–7.15 (2H, m), 6.28(1H, brs), 4.46(2H, s), 2.24(3H, s), 1.52(9H, s)

Example 520

Synthesis of N-(4-cyanomethyl-2-methylphenyl)carbamic acid t-butyl ester

The compound (155.1 mg) obtained in Example 519 was dissolved in dimethyl sulfoxide (5 ml). To the solution, sodium cyanide (127 mg) was added and the mixture was heated at 50° C. under stirring for 10 min. To the resulting reaction mixture, ethyl acetate was added and the organic layer was washed with water twice, dried with anhydrous sodium sulfate and the solvent was distilled off under reduced pressure. The resulting residue was purified by silica gel column chromatography (eluent, n-hexane:ethyl acetate=3:1) to give 77.7 mg of the titled compound (yield, 61%).

$^1$H-NMR($CDCl_3$) δ: 7.84(1H, d, J=8.8 Hz), 7.17–7.08 (2H, m), 6.28(1H, brs), 3.67(2H, s), 2.25(3H, s), 1.52(9H, s)

Example 521

Synthesis of 4-cyanomethyl-2-methylaniline

The compound (1.16 g) obtained in Example 520 was dissolved in methylene chloride (15 ml); to the solution, trifluoroacetic acid (4 ml) was added and the mixture was stirred at room temperature for 1 h. A saturated aqueous sodium bicarbonate solution was added to the reaction mixture, which was extracted with methylene chloride. The organic layer was dried with anhydrous sodium sulfate and the solvent was distilled off under reduced pressure. The resulting residue was purified by silica gel column chromatography (eluent, n-hexane:ethyl acetate=3:1) to give 480.5 mg of the titled compound (yield, 70%).

$^1$H-NMR($CDCl_3$) δ: 7.06–6.93(2H, m), 6.65(1H, d, J=8.1 Hz), 3.67(2H, brs), 3.61(2H, s), 2.16(3H, s)

Example 522

Synthesis of 4-(2-aminoethyl)-2-methylaniline

Using the compound obtained in Example 521 as a starting material, the same procedure of Example 252 gave 486.5 mg of the titled compound (yield, 100%).

$^1$H-NMR($CDCl_3$) δ: 6.93–6.83(2H, m), 6.62(1H, d, J=8.3 Hz), 3.52(2H, brs), 2.90(2H, t, J=6.8 Hz), 2.62(2H, t, J=6.8 Hz), 2.15(3H, s), 1.69(2H, brs)

Example 523

Synthesis of N-(2-(4-amino-3-methylphenyl)ethyl) carbamic acid t-butyl ester

Using the compound obtained in Example 522 as a starting material, the same procedure of Example 253 gave 477.4 mg of the titled compound (yield, 59%).

$^1$H-NMR($CDCl_3$) δ: 6.91–6.83(2H, m), 6.62(1H, d, J=7.8 Hz), 4.52(1H, brs), 3.53(2H, brs), 3.31(2H, dt, J=5.4, 7.3 Hz), 2.66(2H, t, J=7.3 Hz), 2.15(3H, s), 1.44(9H, s)

Example 524

Synthesis of N-(2-(3-methyl-4-thioureidophenyl) ethyl)carbamic acid t-butyl ester Using the compound obtained in Example 523 as a starting material, the same procedure of Example 120 gave 82.7 mg of the titled compound (yield, 96%).

$^1$H-NMR($CDCl_3$) δ: 7.84(1H, brs), 7.20–7.04(3H, m), 6.00(2H, brs), 4.62(1H, brs), 3.36(2H, dt, J=6.3, 6.6 Hz), 2.77(2H, t, J=6.6 Hz), 2.29(3H, s), 1.43(9H, s)

Example 525

Synthesis of N-(2-(4-(S-ethylisothioureido)-3-methylphenyl)ethyl)carbamic acid t-butyl ester Using the compound obtained in Example 524 as a starting material, the same procedure of Example 27 gave 82.4 mg of the titled compound (yield, 94%).

$^1$H-NMR($CDCl_3$) δ: 7.00(1H, s), 6.96(1H, d, J=8.0 Hz), 6.75(1H, d, J=8.0 Hz), 4.52(1H, brs), 4.37(1H, brs), 3.34 (2H, dt, J=6.3, 6.6 Hz), 3.20–2.95(2H, m), 2.71(2H, t, J=6.6 Hz), 2.13(3H, s), 1.44(9H, s), 1.38(3H, t, J=7.3 Hz)

Example 526

Synthesis of N-(2-(4-(S-ethylisothioureido)-3-methylphenyl)ethyl)amine dihydrochloride Using the compound obtained in Example 525 as a starting material, the same procedure of Example 5 gave 75.5 mg of the titled compound (yield, 100%).

$^1$H-NMR(DMSO-$d_6$) δ: 11.55(1H, brs), 9.50(2H, brs), 8,23(3H, brs), 7.28(1H, s), 7.20(2H, s), 3.45–3.23(2H, m), 3.15–2.87(4H, m), 2.19(3H, s), 1.30(3H, t, J=7.1 Hz)

Example 527

Synthesis of N-(2-(4-(N'-t-butoxycarbonyl-N"-ethylguanidino)phenyl)ethyl)carbamic acid t-butyl ester Using the compound obtained in Example 49 as a starting material, the same procedure of Example 233 gave 74.4 mg of the titled compound (yield, 10%).

$^1$H-NMR($CDCl_3$) δ: 1.03–1.16(3H, m), 1.43(9H, s), 1.51 (9H, s), 2.76–2.82(2H, m), 3.27–3.46(4H, m), 4.62(1H, brs), 6.98–7.28(5H, m)

MS(m/z)406($M^+$)

Example 528

Synthesis of N-(2-(4-(N'-ethylguanidino)phenyl) ethyl)amine dihydrochloride

Using the compound obtained in Example 527 as a starting material, the same procedure of Example 5 gave 44.6 mg of the titled compound (yield, 89%).

$^1$H-NMR($D_2O$) δ: 1.21(3H, t, J=7.3 Hz), 3.03(2H, t, J=7.3 Hz), 3.25–3.35(4H, m), 7.29(2H, d, J=8.6 Hz), 7.40(2H, d, J=8.6 Hz)

MS(m/z)206($M^+$)

Example 529

Synthesis of N-(3-amino-2-methylphenylmethyl) iminodicarboxylic acid di-t-butyl ester Using the compound obtained in Example 127 as a starting material, the same procedure of Example 2 gave 4.4 g of the titled compound (yield, 80%).

$^1$H-NMR($CDCl_3$) δ: 1.43(18H, s), 2.03(3H, s), 3.45(2H, brs), 4.74(2H, s), 6.43–6.98(3H, m)

MS(m/z)336($M^+$)

Example 530

Synthesis of N-(2-methyl-3-thioureidophenylmethyl)iminodicarboxylic acid di-t-butyl ester Using the compound obtained in Example 529 as a starting material, the same procedure of Example 120 gave 1.896 g of the titled compound (yield, 86%).

1H-NMR($CDCl_3$) δ: 1.46(18H, s), 2.25(3H, s), 4.80(2H, s), 5.83(2H, brs), 7.15(2H, d, J=7.6 Hz), 7.23–7.29(1H, m), 7.80(1H, s)

Example 531

Synthesis of N-(3-(di-(t-butoxycarbonyl) aminomethyl)-2-methylphenyl)amidinosulfonic acid Using the compound obtained in Example 530 as a starting material, the same procedure of Example 277 gave 1.96 g of the titled compound (yield, 92%).

$^1$H-NMR($CDCl_3$) δ: 1.48(18H, s), 2.22(3H, s), 4.80(2H, s), 7.13–7.24(2H, m), 7.28–7.36(1H, m),

Example 532

Synthesis of N-(3-(N'-ethylguanidino)-2-methylphenylmethyl)iminodicarboxylic acid di-t-butyl ester Using the compound obtained in Example 531 as a starting material and also using ethylamine hydrochloride as a reagent, the same procedure of Example 278 gave the titled compound quantitatively.

$^1$H-NMR($CDCl_3$) δ: 1.17(3H, t, J=7.2 Hz), 1.43(18H, s), 2.09(3H, s), 3.24(2H, q, J=7.2 Hz), 3.89(2H, brs), 4.76(2H, s), 6.72–6.79(2H, m), 7.02–7.10(1H, m), 7.28(1H, s)

MS(m/z)406($M^+$)

Example 533

Synthesis of N-(3-(N'-ethylguanidino)-2-methylphenylmethyl)amine dihydrochloride Using the compound obtained in Example 532 as a starting material, the same procedure of Example 5 gave the titled compound quantitatively.

$^1$H-NMR($D_2O$) δ: 1.21(3H, t, J=7.3 Hz), 2.28(3H, s), 3.31(2H, q, J=7.3 Hz), 4.29(2H, s), 7.32–7.46(3H, m)

MS(m/z)206($M^+$)

Example 534

Synthesis of N-(3-(N'-ethyl-N'-methylguanidino)-2-methylphenylmethyl)iminodicarboxylic acid di-t-butyl ester Using the compound obtained in Example 531 as a starting material, the same procedure of Example 304 gave 77.6 mg of the titled compound (yield, 27%).

$^1$H-NMR($CDCl_3$) δ: 1.19(3H, t, J=6.9 Hz), 1.43(18H, s), 2.08(3H, s), 2.96(3H, s), 3.41(2H, q, J=6.9 Hz), 4.77(2H, s), 6.73(2H, t, J=7.6 Hz), 7.05(1H, t, J=7.6 Hz)

MS(m/z)420($M^+$)

Example 535

Synthesis of N-(3-(N'-ethyl-N'-methylguanidino)-2-ethylphenylmethyl)amine dihydrochloide Using the compound obtained in Example 534 as a starting material, the same procedure of Example 5 gave 42.7 mg of the titled compound (yield, 81%).

$^1$H-NMR($D_2O$) δ: 1.28(3H, t, J=7.3 Hz), 2.27(3H, s), 3.15(3H, s), 3.52(2H, q, J=7.3 Hz), 4.30(2H, s), 7.34(1H, dd, J=7.6, 2.0 Hz), 7.41–7.48(2H, m)

MS(m/z)220($M^+$)

Example 536

Synthesis of N-(2-chloro-3-(di-(t-butoxycarbonyl)aminomethyl)phenyl)amidinosulfonic acid Using the compound obtained in Example 135 as a starting material, the same procedure of Example 277 gave 0.68 g of the titled compound (yield, 97%).

$^1$H-NMR($CDCl_3$) δ: 1.45(18H, s), 4.90(2H, s), 7.22–7.29 (1H, m), 7.38–7.46(2H, m)

Example 537

Synthesis of N-(2-chloro-3-(N'-ethylguanidino)phenylmethyl)iminodicarboxylic acid di-t-butyl ester Using the compound obtained in Example 536 as a starting material, the same procedure of Example 442 gave the titled compound quantitatively.

1H-NMR($CDCl_3$) δ: 1.20(3H, t, J=7.3 Hz), 1.45(18H, s), 3.28(2H, q, J=7.3 Hz), 4.89(2H, s), 6.77(1H, d, J=7.7 Hz), 6.87(1H, d, J=7.7 Hz), 7.13(1H, t, J=7.7 Hz)

MS(m/z)426($M^+$)

Example 538

Synthesis of N-(2-chloro-3-(N'-ethylguanidino)phenylmethyl)amine dihydrochloride Using the compound obtained in Example 537 as a starting material, the same procedure of Example 5 gave the titled compound quantitatively.

$^1$H-NMR($D_2O$) δ: 1.22(3H, t, J=7.3 Hz), 3.33(2H, q, J=7.3 Hz), 4.39(2H, s), 7.51–7.62(3H, m)

MS(m/z)226($M^+$)

Example 539

Synthesis of N-(2-chloro-3-(N'-ethyl-N'-methylguanidino)phenylmethyl)iminodicarboxylic acid di-t-butyl ester Using the compound obtained in Example 536 as a starting material, the same procedure of Example 304 gave 0.12 g of the titled compound (yield, 38%).

$^1$H-NMR($CDCl_3$) δ: 1.21(3H, t, J=6.9 Hz), 1.44(18H, s), 2.98(3H, s), 3.43(2H, q, J=6.9 Hz), 3.85(1H, brs), 4.88(2H, s), 6.75(1H, d, J=7.6 Hz), 6.84(1H, d, J=7.6 Hz), 7.11(1H, t, J=7.6 Hz)

MS(m/z)440($M^+$)

Example 540

Synthesis of N-(2-chloro-3-(N'-ethyl-N'-methylguanidino)phenylmethyl)amine dihydrochloride Using the compound obtained in Example 539 as a starting material, the same procedure of Example 5 gave 76.2 mg of the titled compound (yield, 90%).

$^1$H-NMR($D_2O$) δ: 1.28(3H, t, J=7.3 Hz), 3.16(3H, s), 3.53(2H, q, J=7.3 Hz), 4.40(2H, s), 7.51–7.60(3H, m)

MS(m/z)240($M^+$)

Example 541

Synthesis of N-(3-(t-butoxycarbonylaminoethyl)phenyl)amidinosulfonic acid

Using the compound obtained in Example 58 as a starting material, the same procedure of Example 277 gave 1.99 g of the titled compound (yield, 80%).

$^1$H-NMR(DMSO-$d_6$) δ: 1.35(9H, s), 2.74(2H, t, J=6.9 Hz), 3.12–3.33(2H, m), 6.74(1H, brs), 7.10–7.20(3H, m),7.39(1H, t, J=7.6 Hz), 9.08(1H, brs), 9.63(1H, s), 11.45 (1H, s)

Example 542

Synthesis of N-(3-(N'-ethylguanidino)phenylethyl)carbamic acid t-butyl ester

Using the compound obtained in Example 541 as a starting material, the same procedure of Example 442 gave 0.415 g of the titled compound (yield, 93%).

$^1$H-NMR($CDCl_3$) δ: 1.16–1.21(3H, m), 1.46(9H, s), 2.68–2.81(2H, m), 3.22–3.47(4H, m), 4.95(2H, brs), 5.35 (1H, brs), 6.81–6.85(3H, m), 7.15–7.22(1H, m)

MS(m/z)306($M^+$)

Example 543

Synthesis of N-(3-(N'-ethylguanidino)phenylethyl)amine dihydrochloride

Using the compound obtained in Example 542 as a starting material, the same procedure of Example 5 gave 0.356 g of the titled compound (yield, 94%).

$^1$H-NMR($D_2O$) δ: 1.22(3H, t, J=7.3 Hz), 3.03(2H, t, J=7.3 Hz), 3.26–3.36(4H, m), 7.22–7.25(2H, m), 7.31(1H, d, J=8.3 Hz), 7.47(1H, d, J=8.6 Hz)

MS(m/z)206($M^+$)

Example 544

Synthesis of N-(3-(N'-ethyl-N'-methylguanidino)phenylethyl)carbamic acid t-butyl ester Using the compound obtained in Example 541 as a starting material, the same procedure of Example 304 gave 126.5 mg of the titled compound (yield, 27%).

$^1$H-NMR($CDCl_3$) δ: 1.17(3H, t, J=6.9 Hz), 1.40(9H, s), 2.70(2H, t, J=6.9 Hz), 2.93(3H, s), 3.33–3.41(4H, m), 3.86

(2H, br), 4.74(1H, brs), 6.65–6.78(3H, m), 7.16(1H, t, J=7.6 Hz)

FAB-MS(m/z)321($M^+$+1)

Example 545

Synthesis of N-(3-(N'-ethyl-N'-methylguanidino)phenylethyl)amine dihydrochloride Using the compound obtained in Example 544 as a starting material, the same procedure of Example 5 gave 106 mg of the titled compound (yield, 93%).

$^1$H-NMR($D_2O$) δ: 1.26(3H, t, J=7.3 Hz), 3.03(2H, t, J=7.3 Hz), 3.13(3H, s), 3.30(2H, t, J=7.3 Hz), 3.50(2H, q, J=7.3 Hz), 7.21–7.23(2H, m), 7.31(1H, d, J=7.9 Hz), 7.48(1H, t, J=8.2 Hz)

MS(m/z)220($M^+$)

Example 546

Synthesis of N-(5-nitro-2-piperidinophenylmethyl)iminodicarboxylic acid di-t-butyl ester Using the compound obtained in Example 263 as a starting material and also using piperidine as a reagent in the absence of a solvent, the same procedure of Example 264 gave 1.524 g of the titled compound (yield, 98%).

$^1$H-NMR($CDCl_3$) δ: 1.45(18H, s), 1.60–1.79(6H, m), 2.91–2.95(4H, m), 4.82(2H, s), 7.04(1H, d, J=8.6 Hz), 8.00(1H, d, J=2.3 Hz), 8.09(1H, dd, J=8.6, 2.3 Hz)

FAB-MS(m/z)436($M^+$+1)

Example 547

Synthesis of N-(5-amino-2-piperidinophenylmethyl)iminodicarboxylic acid di-t-butyl ester Using the compound obtained in Example 546 as a starting material, the same procedure of Example 2 gave 1.01 g of the titled compound (yield, 72%).

$^1$H-NMR($CDCl_3$) δ: 1.41(18H, s), 1.43–1.72(6H, m), 2.65–2.73(4H, m), 3.45(2H, br), 4.84(2H, s), 6.44(1H, d, J=2.6 Hz), 6.52(1H, dd, J=8.3, 2.6 Hz), 6.89(1H, d, J=8.3 Hz)

FAB-MS(m/z)406($M^+$+1)

Example 548

Synthesis of N-(2-piperidino-5-thioureidophenylmethyl)iminodicarboxylic acid di-t-butyl ester Using the compound obtained in Example 547 as a starting material, the same procedure of Example 120 gave 0.59 g of the titled compound (yield, 81%).

$^1$H-NMR($CDCl_3$) δ: 1.44(18H, s), 1.56–1.79(6H, m), 2.78–2.83(4H, m), 4.83(2H, s), 5.99(2H, brs), 6.93–6.94 (1H, m), 7.05–7.06(2H, m), 7.72(1H, brs)

MS(m/z)464($M^+$)

Example 549

Synthesis of N-(5-(S-ethylisothioureido)-2-piperidinophenylmethyl)iminodicarboxylic acid di-t-butyl ester Using the compound obtained in Example 548 as a starting material, the same procedure of Example 95 gave 0.271 g of the titled compound (yield, 85%).

$^1$H-NMR($CDCl_3$) δ: 1.26(3H, t, J=7.3 Hz), 1.41(18H, s), 1.48–1.73(6H, m), 2.67–2.85(4H, m), 2.92–3.13(2H, m), 4.82(1H, br), 4.86(2H, s), 6.62–6.78(2H, m), 7.00(1H, d, J=8.3 Hz)

MS(m/z)492($M^+$)

Example 550

Synthesis of N-(5-(S-ethylisothioureido)-2-piperidinophenylmethyl)amine trihydrochloride Using the compound obtained in Example 549 as a starting material, the same procedure of Example 5 gave 128.4 mg of the titled compound (yield, 58%).

$^1$H-NMR($D_2O$) δ: 1.41(3H, t, J=7.3 Hz), 1.67–1.85(2H, m), 1.94–2.11(4H, m), 3.24(2H, q, J=7.3 Hz), 3.40–3.69(4H, m), 4.42(2H, s), 7.56–7.68(2H, m), 7.78–7.92(1H, m)

MS(m/z)292($M^+$)

Example 551

Synthesis of N-(3-(di-(t-butoxycarbonyl)aminomethyl)-4-piperidinophenyl)amidinosulfonic acid Using the compound obtained in Example 548 as a starting material, the same procedure of Example 277 gave 152 mg of the titled compound (yield, 74%).

$^1$H-NMR($CDCl_3$) δ: 1.42(18H, s), 1.50–1.73(6H, m), 2.67–2.85(4H, m), 4.83(2H, s), 7.06(1H, s), 7.15(1H, d, J=8.6 Hz), 7.22–7.32(1H, m)

Example 552

Synthesis of N-(5-(N'-ethylguanidino)-2-piperidinophenylmethyl)iminodicarboxylic acid di-t-butyl ester Using the compound obtained in Example 551 as a starting material, the same procedure of Example 442 gave 0.11 g of the titled compound (yield, 53%).

$^1$H-NMR($CDCl_3$) δ: 1.17(3H, t, J=7.3 Hz), 1.40(18H, s), 1.47–1.75(6H, m), 2.68–2.83(4H, m), 3.21(2H, q, J=7.3 Hz), 4.84(2H, s), 6.69(1H, s), 6.75(1H, d, J=8.3 Hz), 6.97(1H, d, J=8.3 Hz)

MS(m/z)475($M^+$)

Example 553

Synthesis of N-(5-(N'-ethylguanidino)-2-piperidinophenylmethyl)amine trihydrochloride Using the compound obtained in Example 552 as a starting material, the same procedure of Example 5 gave 76.7 mg of the titled compound (yield, 87%).

$^1$H-NMR($D_2O$) δ: 1.23(3H, t, J=7.3 Hz), 1.69–1.81(2H, m), 1.97–2.09(4H, m), 3.34(2H, q, J=7.3 Hz), 3.51(4H, t, J=5.6 Hz), 4.39(2H, s), 7.48(1H, d, J=2.3 Hz), 7.53(1H, dd, J=8.9, 2.3 Hz), 7.77(1H, d, J=8.9 Hz)

FAB-MS(m/z)276($M^+$+1)

Example 554

Synthesis of N-(2-chloro-5-nitrophenylmethyl)iminodicarboxylic acid di-t-butyl ester Using 2-chloro-5-nitrobenzyl bromide as a starting material, the same procedure of Example 127 gave 3.5 g of the titled compound (yield, 92%).

$^1$H-NMR($CDCl_3$) δ: 1.49(9H, s), 1.50(9H, s), 4.95(2H, s), 7.53(1H, dd, J=5.6, 3.2 Hz), 8.02–8.13(2H, m)

FAB-MS(m/z)387($M^+$+1)

Example 555

Synthesis of N-(5-amino-2-chlorophenylmethyl) iminodicarboxylic acid di-t-butyl ester Using the compound obtained in Example 554 as a starting material and also using Raney nickel as a catalyst, the same procedure of Example 2 gave 3.17 g of the titled compound (yield, 98%).

$^1$H-NMR($CDCl_3$) δ: 1.48(18H, s), 3.69(2H, brs), 4.82 (2H, s), 6.47(1H, s), 6.49–6.52(1H, m), 7.08(1H, d, J=7.6 Hz)

MS(m/z)356($M^+$)

Example 556

Synthesis of N-(2-chloro-5-thioureidophenylmethyl) iminodicarboxylic acid di-t-butyl ester Using the compound obtained in Example 555 as a starting material, the same procedure of Example 120 gave 0.45 g of the titled compound (yield, 74%).

$^1$H-NMR($CDCl_3$) δ: 1.48(18H, s), 4.87(2H, s), 6.12(2H, brs), 7.04(1H, s), 7.09(1H, d, J=8.6 Hz),7.41(1H, d, J=8.6 Hz), 8.03(1H, brs)

MS(m/z)415($M^+$)

Example 557

Synthesis of N-(2-chloro-5-(S-ethylisothioureido) phenylmethyl)carbamic acid t-butyl ester Using the compound obtained in Example 556 as a starting material, the same procedure of Example 95 gave 0.37 g of the titled compound (yield, 99%).

$^1$H-NMR($CDCl_3$) δ: 1.26(3H, t, J=7.3 Hz), 1.44(9H, s), 4.12(2H, q, J=7.3 Hz), 4.35(2H. d, J=5.9 Hz), 5.00(1H, brs), 6.68–6.83(1H, m), 6.93(1H, s), 7.21–7.33(1H, m)

FAB-MS(m/z)343($M^+$+1)

Example 558

Synthesis of N-(2-chloro-5-(S-ethylisothioureido) phenylmethyl)amine dihydrochloride Using the compound obtained in Example 557 as a starting material, the same procedure of Example 5 gave 198.3 mg of the titled compound (yield, 59%).

$^1$H-NMR($D_2O$) δ: 1.42(3H, t, J=7.3 Hz), 3.25(2H, q, J=7.3 Hz), 4.38(2H, s), 7.47(1H, dd, J=8.6, 2.6 Hz), 7.55 (1H, d, J=2.6 Hz), 7.71(1H, d, J=8.6 Hz)

FBA-MS(m/z)244($M^+$+1)

Example 559

Synthesis of N-(5-(N'-t-butoxycarbonyl-N"-ethylguanidino)-2-chlorophenylmethyl) iminodicarboxylic acid di-t-butyl ester Using the compound obtained in Example 555 as a starting material, the same procedure of Example 233 gave 0.159 g of the titled compound (yield, 52%).

$^1$H-NMR($CDCl_3$) δ: 1.07–1.40(3H, m), 1.46(18H, s), 1.48(9H, s), 3.38–3.43(2H, m), 4.87(2H, s), 6.75–6.98(1H, m), 7.28–7.42(2H, m)

FAB-MS(m/z)527($M^+$+1)

Example 560

Synthesis of N-(2-chloro-5-(N'-ethylguanidino) phenylmethyl)amine dihydrochloride Using the compound obtained in Example 559 as a starting material, the same procedure of Example 5 gave 62.2 mg of the titled compound (yield, 69%).

$^1$H-NMR($D_2O$) δ: 1.23(3H, t, J=7.3 Hz), 3.33(2H, q, J=7.3 Hz), 4.35(2H, s), 7.38(1H, dd, J=8.6, 2.6 Hz), 7.45 (1H, d, J=2.6 Hz), 7.64(1H, d, J=8.6 Hz)

FAB-MS(m/z)277($M^+$+1)

Example 561

Synthesis of 2-(2-benzyloxyphenyl)-2-methylpropionic acid methyl ester

Using 2-benzyloxyphenylacetic acid methyl ester as a starting material and also using potassium t-butoxide as a base, the same procedure of Example la gave 2-(2-benzyloxyphenyl)propioic acid methyl ester. Using lithium diisopropylamide as a base, the resulting 2-(2-benzyloxyphenyl)propionic acid methyl ester was further treated as in Example la to give 4.72 g of the titled compound (yield, 70%).

$^1$H-NMR($CDCl_3$) δ: 1.58(6H, s), 3.42(3H, s), 5.07(2H, s), 6.91(1H, dd, J=7.3, 1.2 Hz), 6.99(1H, dd, J=7.3, 1.2 Hz), 7.21(1H, dd, J=7.9, 1.8 Hz), 7.33(1H, dd, J=7.9, 1.8 Hz), 7.35–7.40(5H, m)

Example 562

Synthesis of 2-(2-benzyloxy-5-nitrophenyl)-2-methylpropionic acid methyl ester

To a mixture of sulfuric acid (0.27 ml) and nitric acid (0.34 ml), a solution of the compound (1.0 g) obtained in Example 561 in acetic acid (30 ml) was added dropwise at 5° C. The reaction mixture was stirred at 45° C. for 4 h, poured into ice cold water and ethyl acetate was added to the mixture. The organic layer was washed with a saturated aqueous sodium bicarbonate solution and a saturated aqueous sodium chloride solution, dried with anhydrous sodium sulfate and the solvent was distilled off under reduced pressure. The resulting residue was purified by silica gel column chromatography (eluent, n-hexane:ethyl acetate=9:1) to give 530 mg of the titled compound (yield, 46%).

$^1$H-NMR($CDCl_3$) δ: 1.60(6H, s), 3.42(3H, s), 5.29(2H, s), 6.99(1H, d, J=9.2 Hz), 7.33–7.45(5H, m), 8.16(1H, dd, J=9.2, 3.1 Hz), 8.25(1H, d, J=3.1 Hz)

Example 563

Synthesis of 2-(2-benzyloxy-5-nitrophenyl)-2-methylpropionic acid

To the compound (1.54 g) obtained in Example 562 in 1, 4-dioxane (20 ml) was added an aqueous lithium hydroxide solution (1.0M, 47 ml). The reaction mixture was heated under reflux at 100° C. for 12 h and then 2 N HCl and ethyl acetate were added. The organic layer was washed with a saturated aqueous sodium chloride solution, dried with anhydrous sodium sulfate and the solvent was distilled off under reduced pressure. The resulting residue was recrystallized from ethyl acetate to give 1.355 g of the titled compound (yield, 92%).

$^1H$-NMR($CDCl_3$) δ: 1.60(6H, s), 5.02(2H, s), 6.91(1H, d, J=9.2 Hz), 7.30–7.37(5H, m), 8.16(1H, dd, J=9.2, 3.1 Hz), 8.25(1H, d, J=3.1 Hz)

Example 564

Synthesis of N-(1-(2-benzyloxy-5-nitrophenyl)-1-methylethyl)amine

To a mixture of the compound (1.6 g) obtained in Example 563, methylene chloride (20 ml) and triethylamine (0.92 ml), diphenylphosphorylazide (1.37 ml) was added. The reaction mixture was stirred at room temperature for 10 h and 2 N HCl and chloroform were added. The organic layer was washed with a saturated aqueous sodium chloride solution, dried with anhydrous sodium sulfate and the solvent was distilled off under reduced pressure. To the resulting residue, water (16 ml) and 1,4-dioxane (32 ml) were added. The reaction mixture was heated under reflux for 2 h and 2 N HCl and chloroform were added. After adding 2 N aqueous sodium hydroxide solution and chloroform to the aqueous layer, the organic layer was washed with a saturated aqueous sodium chloride solution, dried with anhydrous sodium sulfate and the solvent was distilled off under reduced pressure. The resulting residue was recrystallized from a mixture of ethyl acetate and n-hexane to give 1.09 g of the titled compound (yield, 75%).

$^1H$-NMR($CDCl_3$) δ: 1.58(6H, s), 2.01(2H, brs), 5.25(2H, s), 7.03(1H, d, J=9.2 Hz), 7.37–7.45(5H, m), 8.13(1H, dd, J=9.2, 3.1 Hz), 8.35(1H, d, J=3.1 Hz)

Example 565

Synthesis of N-(1-(2-benzyloxy-5-nitrophenyl)-1-methylethyl)carbamic acid t-butyl ester Using the compound obtained in Example 564 as a starting material and also using potassium carbonate as a base, the same procedure of Example 63 gave 828 mg of the titled compound (yield, 94%).

$^1H$-NMR($CDCl_3$) δ: 1.34(9H, s), 1.71(6H, s), 5.07(1H, brs), 5.18(2H, s), 7.00(1H, d, J=9.2 Hz), 7.35–7.48(5H, m), 8.13(1H, dd, J=9.2, 3.1 Hz), 8.29(1H, d, J=3.1 Hz)

Example 566

Synthesis of N-(1-(5-amino-2-benzyloxyphenyl)-1-methylethyl)carbamic acid t-butyl ester To a mixture of the compound (100 mg) obtained in Example 565, nickel (II) chloride hexahydrate (123 mg) and methanol (6 ml), sodium borohydride (39 mg) was added. The reaction mixture was stirred at room temperature for 10 min; then, 2 N HCl was added and a saturated aqueous sodium bicarbonate solution and chloroform were also added. The organic layer was washed with a saturated aqueous sodium chloride solution, dried with anhydrous sodium sulfate and the solvent was distilled off under reduced pressure. The resulting residue was purified by silica gel column chromatography (eluent, n-hexane:ethyl acetate=3:2) to give 87 mg of the titled compound (yield, 94%).

$^1H$-NMR($CDCl_3$) δ: 1.34(9H, s), 1.66(6H, s), 2.80(2H, br), 4.99(2H, s), 5.27(1H, brs), 6.54(1H, dd, J=8.6, 2.4 Hz), 6.74(1H, d, J=2.4 Hz), 6.78(1H, d, J=8.6 Hz), 7.29–7.49(5H, m)

Example 567

Synthesis of N-(1-(2-benzyloxy-5-(N'-nitroguanidino)phenyl)-1-methylethyl)carbamic acid t-butyl ester Using the compound obtained in Example 566 as a starting material, the same procedure of Example 6 gave 110 mg of the titled compound (yield, 89%).

$^1H$-NMR($CDCl_3$) δ: 1.36(9H, s), 1.69(6H, s), 5.11(2H, s), 7.01(1H, d, J=8.5 Hz), 7.18(1H, dd, J=8.5, 2.4 Hz), 7.31(1H, d, J=2.4 Hz), 7.34–7.46(5H, m), 9.35(1H, brs)

Example 568

Synthesis of N-(1-(2-benzyloxy-5-(N'-nitroguanidino)phenyl)-1-methylmethyl)amine Using the compound obtained in Example 567 as a starting material, the same procedure of Example 34 gave 47.4 mg of the titled compound (yield, 58%).

$^1H$-NMR($CDCl_3$) δ: 1.58(6H, s), 5.16(2H, s), 7.01(1H, d, J=8.5 Hz), 7.16(1H, dd, J=8.5 Hz, 2.4 Hz), 7.34(1H, d, J=2.4 Hz), 7.35–7.46(5H, m)

Example 569

Synthesis of N-(1-(2-benzyloxy-5-(N'-t-butoxycarbonyl-N"-ethylguanidino)phenyl)-1-methylethyl)carbamic acid t-butyl ester Using the compound obtained in Example 566 as a starting material, the same procedure of Example 233 gave 106 mg of the titled compound (yield, 72%).

$^1H$-NMR($CDCl_3$) δ: 1.09(3H, t, J=7.3 Hz), 1.34(9H, s), 1.53(9H, s), 1.67(6H, s), 3.34–3.46(2H, m), 4.80(1H, brs), 5.07(2H, s), 5.14(1H, brs), 6.94(1H, d, J=8.6 Hz), 7.02–7.07 (1H, m), 7.22(1H,s), 7.32–7.50(5H, m), 10.53(1H, br)

Example 570

Synthesis of N-(1-(2-benzyloxy-5-(N'-ethylguanidino)phenyl)-1-methylethyl)amine

Using the compound obtained in Example 569 as a starting material, the same procedure of Example 34 gave 58 mg of the titled compound (yield, 88%).

$^1H$-NMR($CDCl_3$) δ: 1.16(3H, t, J=7.3 Hz), 1.51(6H, s), 3.23(2H, q, J=7.3 Hz), 3.69(2H, br), 5.09(2H, s), 6.75(1H, dd, J=8.5, 2.4 Hz), 6.89(1H, d, J=8.5 Hz), 6.95(1H, d, J=2.4 Hz), 7.29–7.47(5H, m)

Example 571

Synthesis of N-(1-(2-benzyloxy-5-thioureidophenyl)-1-methylethyl)carbamic acid t-butyl ester Using the compound obtained in Example 566 as a starting material, the same procedure of Example 120 gave 114 mg of the titled compound (yield, 98%).

$^1H$-NMR($CDCl_3$) δ: 1.35(9H, s), 1.67(6H, s), 5.09(2H, s), 6.16(2H, brs), 6.95(1H, d, J=8.6 Hz), 7.05(1H, dd, J=8.6, 2.4 Hz), 7.27(1H, d, J=2.4 Hz), 7.36–7.46(5H, m), 7.80(1H, brs)

Example 572

Synthesis of N-(1-(2-benzyloxy-5-(S-ethylisothioureido)phenyl)-1-methylethyl)carbamic acid t-butyl ester Using the compound obtained in Example 571 as a starting material, the same procedure of Example 95 gave 105.5 mg of the titled compound (yield, 92%).

$^1H$-NMR($CDCl_3$) δ: 1.32–1.37(3H, m), 1.34(9H, s), 1.67 (6H, s), 3.03(2H, q, J=7.3 Hz), 5.04(2H, s), 5.22(1H, brs), 6.78(1H, dd, J=8.6, 2.4 Hz), 6.90(1H, d, J=8.6 Hz), 6.95(1H, d, J=2.4 Hz), 7.31–7.50(5H, m)

Example 573

Synthesis of N-(1-(2-benzyloxy-5-(S-ethylisothioureido)phenyl)-1-methylethyl)amine Using the compound obtained in Example 572 as a starting material, the same procedure of Example 34 gave 51 mg of the titled compound (yield, 63%).

$^1$H-NMR($CDCl_3$) δ: 1.32(3H, t, J=7.3 Hz), 1.68(6H, s), 2.97(2H, q, J=7.3 Hz), 5.15(2H, s), 5.63(4H, br), 6.67(1H, d, J=8.5 Hz), 6.77–6.82(2H, m), 7.32–7.42(5H, m)

Example 574

Synthesis of 2-(2-benzyloxy-3-nitrophenyl)-2-methylpropionic acid methyl ester

The same procedure of

Example 562 gave 140 mg of the titled compound (yield, 12%).

$^1$H-NMR($CDCl_3$) δ: 1.57(6H, s), 3.38(3H, s), 4.84(2H, s), 7.20(1H, t, J=7.9 Hz), 7.31–7.45(5H, m), 7.58(1H, dd, J=7.9, 1.8 Hz), 7.75(1H, dd, J=7.9, 1.8 Hz)

Example 575

Synthesis of 2-(2-benzyloxy-3-nitrophenyl)-2-methylpropionic acid

Using the compound obtained in Example 574 as a starting material, the same procedure of Example 563 gave 370 mg of the titled compound (yield, 86%).

$^1$H-NMR($CDCl_3$) δ: 1.54(6H, s), 4.83(2H, s), 7.19(1H, t, J=7.9 Hz), 7.29–7.41(5H, m), 7.57(1H, dd, J=7.9, 1.2 Hz), 7.76(1H, dd, J=7.9, 1.2 Hz)

Example 576

Synthesis of N-(1-(2-benzyloxy-3-nitrophenyl)-1-methylethyl)amine

Using the compound obtained in Example 575 as a starting material, the same procedure of Example 564 gave 268 mg of the titled compound (yield, 81%).

$^1$H-NMR($CDCl_3$) δ: 1.52(6H, s), 2.03(2H, s), 5.24(2H, s), 7.14(1H, t, J=7.9 Hz), 7.34–7.49(5H, m), 7.68(1H, dd, J=3.7, 1.8 Hz), 7.71(1H, dd, J=3.7, 1.8 Hz)

Example 577

Synthesis of N-(1-(2-benzyloxy-3-nitrophenyl)-1-methylethyl)carbamic acid t-butyl ester Using the compound obtained in Example 576 as a starting material, the same procedure of Example 565 gave 329 mg of the titled compound (yield, 91%).

$^1$H-NMR($CDCl_3$) δ: 1.37(9H, s), 1.69(6H, s), 4.86(2H, s), 5.03(1H, brs), 7.18(1H, t, J=7.9 Hz), 7.33–7.46(3H, m), 7.50–7.66(2H, m), 7.67(1H, dd, J=7.9, 1.8 Hz), 7.73(1H, dd, J=7.9, 1.8 Hz)

Example 578

Synthesis of N-(1-(3-amino-2-benzyloxyphenyl)-1-methylethyl)carbamic acid t-butyl ester Using the compound obtained in Example 577 as a starting material, the same procedure of Example 566 gave 244 mg of the titled compound (yield, 81%).

$^1$H-NMR($CDCl_3$) δ: 1.35(9H, s), 1.72(6H, s), 3.67(2H, s), 4.96(2H, s), 5.34(1H, br), 6.69(1H, dd, J=7.9, 1.8 Hz), 6.82(1H, dd, J=7.9, 1.8 Hz), 6.90(1H, t, J=7.9 Hz), 7.30–7.46(3H, m), 7.51–7.55(2H, m)

Example 579

Synthesis of N-(1-(2-benzyloxy-3-(N'-t-butoxycarbonyl-N"-ethylguanidino)phenyl)-1-methylethyl)carbamic acid t-butyl ester Using the compound obtained in Example 578 as a starting material, the same procedure of Example 233 gave 82.4 mg of the titled compound (yield, 70%).

$^1$H-NMR($CDCl_3$) δ: 1.03–1.14(3H, m), 1.37(9H, s), 1.20–1.60(9H, m), 1.69(6H, s), 3.15–3.43(2H, m), 4.81–5.16(3H, m), 6.97–7.23(3H, m), 7.30–7.42(3H, m), 7.45–7.53(2H, m)

Example 580

Synthesis of N-(1-(2-benzyloxy-3-(N'-ethylguanidino)phenyl)-1-methylethyl)amine

Using the compound obtained in Example 579 as a starting material, the same procedure of Example 34 gave 46.5 mg of the titled compound (yield, 92%).

$^1$H-NMR($CDCl_3$) δ: 1.12(3H, t, J=7.3 Hz), 1.53(6H, s), 3.19(2H, q, J=7.3 Hz), 5.17(2H, s), 6.86(1H, dd, J=7.9, 1.8 Hz), 6.97(1H, t, J=7.9 Hz), 7.04(1H, dd, J=7.9, 1.8 Hz), 7.25–7.46(3H, m), 7.47–7.49(2H, m)

Example 581

Synthesis of N-(1-(2-benzyloxy-3-thioureidophenyl)-1-methylethyl)carbamic acid t-butyl ester Using the compound obtained in Example 578 as a starting material, the same procedure of Example 120 gave 94 mg of the titled compound (yield, 99.6%).

$^1$H-NMR($CDCl_3$) δ: 1.34(9H, s), 1.65(6H, s), 4.92(2H, s), 5.13(1H, s), 6.38(2H, brs), 7.11(1H, t, J=7.9 Hz), 7.17–7.21 (1H, m), 7.30–7.44(4H, m), 7.56–7.61(2H, m), 8.37(1H, s)

Example 582

Synthesis of N-(1-(2-benzyloxy-3-(S-ethylisothioureido)phenyl)-1-methylethyl)carbamic acid t-butyl ester Using the compound obtained in Example 581 as a starting material, the same procedure of Example 95 gave 98 mg of the titled compound (yield, 98%).

$^1$H-NMR($CDCl_3$) δ: 1.28(3H, t, J=7.3 Hz), 1.35(9H, s), 1.68(6H, s), 3.00–3.07(2H, m), 4.52(2H, brs), 4.99(2H, s), 5.17(1H, brs), 6.80–6.85(1H, m), 7.01(1H, t, J=7.9 Hz), 7.11(1H, dd, J=7.9, 1.8 Hz), 7.27–7.42(3H, m), 7.49–7.54 (2H, m)

Example 583

Synthesis of N-(1-(2-benzyloxy-3-(S-ethylisothioureido)phenyl)-1-methylethyl)amine Using the compound obtained in Example 582 as a starting material, the same procedure of Example 34 gave 72 mg of the titled compound (yield, 95%).

$^1$H-NMR($CDCl_3$) δ: 1.30(3H, t, J=7.3 Hz), 1.53(6H, s), 2.12(2H, brs), 2.96–3.08(2H, m), 4.60(1H, brs), 5.10(2H, s), 6.79–6.87(1H, m), 7.00(1H, t, J=7.9 Hz), 7.10(1H, dd, J=7.9, 1.8 Hz), 7.28–7.41(5H, m), 7.47(1H, dd, J=7.9, 1.8 Hz)

Example 584

Synthesis of N-(5-nitro-2-(pyrrolidin-1-yl) phenylmethyl)iminodicarboxylic acid di-t-butyl ester Using the compound obtained in Example 263 as a starting material and also using pyrrolidine as a reagent, the same procedure of Example 264 gave the titled compound (yield, 80%).

$^1$H-NMR($CDCl_3$) δ: 1.47(18H, s), 1.95–2.05(4H, m), 3.38–3.42(4H, m), 4.87(2H, s), 6.70–6.80(1H, m), 7.95–8.03(2H, m)

Example 585

Synthesis of N-(5-amino-2-(pyrrolidin-1-yl) phenylmethyl)iminodicarboxylic acid di-t-butyl ester Using the compound obtained in Example 584 as a starting material, the same procedure of Example 2 gave the titled compound (yield, 98%).

$^1$H-NMR($CDCl_3$) δ: 1.40(18H, s), 1.84–1.88(4H, m), 2.89–2.93(4H, m), 4.50(2H, brs), 4.81(2H, s), 6.45–6.53 (2H, m), 6.88(1H, d, J=8.3 Hz)

MS(m/z) 392 ($M^+$+1)

Example 586

Synthesis of N-(2-(pyrrolidin-1-yl)-5-thioureidophenylmethyl)iminodicarboxylic acid di-t-butyl ester Using the compound obtained in Example 585 as a starting material, the same procedure of Example 120 gave the titled compound (yield, 94%).

$^1$H-NMR($CDCl_3$) δ: 1.44(18H, s), 1.94–1.97(4H, m), 3.12–3.16(4H, m), 4.78(2H, s), 5.94(2H, brs), 6.91–7.00 (3H, m), 7.66(1H, brs)

MS(m/z)450($M^+$)

Example 587

Synthesis of N-(5-(S-ethylisothioureido)-2-(pyrrolidin-1-yl)phenylmethyl)iminodicarboxylic acid di-t-butyl ester Using the compound obtained in Example 586 as a starting material, the same procedure of Example 95 gave the titled compound (yield, 85%).

$^1$H-NMR($CDCl_3$) δ: 1.33(3H, t, J=7.3 Hz), 1.41(18H, s), 1.87–1.90(4H, m), 2.90–3.10(4H, m), 4.39–4.69(2H, m), 4.81(2H, s), 6.62–6.82(2H, m), 6.95(1H, d, J=8.1 Hz)

Example 588

Synthesis of N-(5-(S-ethylisothioureido)-2-(pyrrolidin-1-yl)phenylmethyl)amine trihydrochloride Using the compound obtained in Example 587 as a starting material, the same procedure of Example 5 gave the titled compound (yield, 63%).

$^1$H-NMR($D_2O$) δ: 6 1.41(3H, t, J=7.5 Hz), 2.07–2.29(4H, m), 3.25(2H, q, J=7.5 Hz), 3.60–3.83(4H, m), 4.46(2H, s), 7.60–7.82(3H, m)

MS(m/z)278($M^+$)

Example 589

Synthesis of N-(5-(N'-t-butoxycarbonyl-N"-ethylguanidino)-2-(pyrrolidin-1-yl)phenylmethyl) iminodicarboxylic acid di-t-butyl ester Using the compound obtained in Example 585 as a starting material, the same procedure of Example 233 gave the titled compound (yield, 71%).

$^1$H-NMR($CDCl_3$) δ: 1.06(3H, t, J=7.3 Hz), 1.48(18H, s), 1.59(9H, s), 1.93–2.03(4H, m), 3.00–3.10(4H, m), 3.33–3.43(2H, m), 4.58(1H, brs), 4.79(2H, s), 6.90–6.95 (3H, m), 10.49(1H, brs)

Example 590

Synthesis of N-(5-(N'-ethylguanidino)-2-(pyrrolidin-1-yl)phenylmethyl)amine trihydrochloride Using the compound obtained in Example 589 as a starting material, the same procedure of Example 5 gave the titled compound (yield, 91%).

$^1$H-NMR($D_2O$) δ: 1.24(3H, t, J=7.3 Hz), 2.29–2.31(4H, m), 3.35(2H, q, J=7.3 Hz), 3.84–4.00(4H, m), 4.45(2H, s), 7.51–7.78(3H, m)

Example 591

Synthesis of N-(2-(4-(N'-t-butoxcyarbonyl-N"-ethylguanidino)-3-methoxyphenyl)ethyl)carbamic acid t-butyl ester Using the compound obtained in Example 490 as a starting material, the same procedure of Example 233 gave 12 mg of the titled compound (yield, 16%).

$^1$H-NMR($CDCl_3$) δ: 1.05–1.20(3H, m), 1.44(9H, s), 1.52 (9H, s), 2.78(2H, t, J=6.9 Hz), 3.32–3.47(4H, m), 3.84(3H, s), 4.57(1H, brs), 6.74–6.92(3H, m)

Example 592

Synthesis of N-(2-(4-(N'-ethylguanidino)-3-methoxyphenyl)ethyl)amine dihydrochloride Using the compound obtained in Example 591 as a starting material, the same procedure of Example 5 gave 8 mg of the titled compound (yield, 94%).

$^1$H-NMR($D_2O$) δ: 1.20(3H, t, J=7.3 Hz), 3.03(2H, t, J=7.3 Hz), 3.24–3.33(4H, m), 3.89(3H, s), 6.99(1H, d, J=7.9 Hz), 7.10(1H, s), 7.27(1H, d, J=7.9 Hz)

Example 593

Synthesis of N-(2-(4-(N'-t-butoxycarbonyl-N"-ethylguanidino)-3-chlorophenyl)ethyl)carbamic acid t-butyl ester Using the compound obtained in Example 495 as a starting material, the same procedure of Example 233 gave 27 mg of the titled compound (yield, 17%).

$^1$H-NMR($CDCl_3$) δ: 1.27(3H, t, J=7.3 Hz), 1.44(9H, s), 1.47(9H, s), 2.75(2H, t, J=6.9 Hz), 3.30–3.50(4H, m), 4.53 (1H, brs), 7.00–7.30(3H, m)

Example 594

Synthesis of N-(2-(3-chloro-4-(N'-ethylguanidino) phenyl)ethyl)amine dihydrochloride Using the compound obtained in Example 593 as a starting material, the same procedure of Example 5 gave 17 mg of the titled compound (yield, 88%).

$^1$H-NMR($D_2O$) δ: 1.22(3H, t, J=7.3 Hz), 3.04(2H, t, J=7.3 Hz), 3.27–3.36(4H, m), 7.33–7.44(2H, m), 7.56(1H, s)

Example 595

Synthesis of N-(2-(4-(N'-t-butoxycarbonyl-N"-ethylguanidino)-3-fluorophenyl)ethyl)carbamic acid t-butyl ester Using the compound obtained in Example 504 as a starting material, the same procedure of Example 233 gave 90 mg of the titled compound (yield, 54%)

$^1$H-NMR($CDCl_3$) δ: 1.10–1.32(3H,m), 1.44(9H,s), 1.48 (9H,s), 2.77(2H, t, J=6.9 Hz), 3.35–3.46(4H,m), 4.55(1H, brs), 6.90–7.00(3H,m)

Example 596

Synthesis of N-(2-(4-(N'-t-butoxycarbonyl-N"-ethylguanidino)-3-fluorophenyl)ethyl)amine dihydrochloride Using the compound obtained in Example 595 as a starting material, the same procedure of Example 5 gave 53 mg of the titled compound (yield, 93%)

$^1$H-NMR($D_2O$) δ: 1.22(3H, t, J=7.3 Hz), 3.04(2H, t, J=7.3 Hz), 3.27–3.36(4H,m), 7.19–7.41(3H,m)

Example 597

Synthesis of N-(1-(3-(N'-t-butoxycarbonyl)-N"-ethylguanidino)phenyl)ethyl)carbamic acid t-butyl ester Using the compound obtained in Example 9 as a starting material, the same procedure of Example 233 gave 280 mg of the titled compound (yield, 81%)

$^1$H-NMR($CDCl_3$) δ: 1.02–1.20(3H,m), 1.42(12H,brs), 1.51(9H,s), 3.38–3.43(2H,m), 4.64–4.90(2H,m), 6.90–7.20 (4H,m)

Example 598

Synthesis of N-(1-(3-(N'-ethylguanidino)phenyl) ethyl)amine dihydrochloride

Using the compound obtained in Example 597 as a starting material, the same procedure of Example 5 gave 54 mg of the titled compound (yield, 88%)

$^1$H-NMR($D_2O$) δ: 1.22(3H, t, J=7.3 Hz), 1.65(3H, d, J=6.9 Hz), 3.32(2H, q, J=7.3 Hz), 4.57(1H, q, J=6.9 Hz), 7.34–7.60(4H,m)

Example 599

Synthesis of N-(2-(4-(N'-t-butoxycarbonyl-N"-ethylguanidino)-3-methylphenyl)ethyl)carbamic acid t-butyl ester Using the compound obtained in Example 523 as a starting material, the same procedure of Example 233 gave 43.5 mg of the titled compound (yield, 39%)

$^1$H-NMR($CDCl_3$) δ: 10.5(1H,brs), 7.18–7.00(3H,m), 4.57 (1H,brs), 4.40(1H,brs), 3.36(2H, dt, J=5.4, 6.4 Hz), 2.76(2H, t, J=6.4 Hz), 2.23(3H,s), 1.52(9H,s), 1.44(9H,s), 1.03–1.19 (3H,m)

Example 600

Synthesis of N-(2-(4-(N'-ethylguanidino)-3-methylphenyl)ethyl)amine dihydrochloride Using the compound obtained in Example 599 as a starting material, the same procedure of Example 5 gave 28.3 mg of the titled compound (yield, 93%)

$^1$H-NMR(DMSO-$d_6$) δ: 9.54(1H,s), 8.00–8.25(4H,m), 7.80(1H,brs), 7.50(2H,brs), 7.23(1H,s), 7.20–7.12(2H,m), 3.34–3.17(2H,m), 3.18–2.82(4H,m), 2.19(3H,s), 1.11(3H, t, J=7.1 Hz)

Example 601

Synthesis of N-(3-chloro-4-hydroxymethylphenyl) carbamic acid t-butyl ester

Water was added to 4-amino-2-chlorobenzyl alcohol (1.0125 g) and, after addition of sodium hydroxide (283 mg) and di-t-butyl dicarbonate (1.543 g) at room temperature, the mixture was stirred overnight at room temperature. Ethyl acetate was added to the reaction mixture and the organic layer was washed with water once, dried with anhydrous sodium sulfate and the solvent was distilled off under reduced pressure. The resulting residue was purified by silica gel column chromatography (eluent, n-hexane:ethyl acetate=3:1) to give 1.0576 g of the titled compound (yield, 64%).

$^1$H-NMR($CDCl_3$) δ: 7.56(1H, d, J=2.1 Hz), 7.35(1H, d, J=8.3 Hz), 7.15(1H, dd, J=2.1, 8.3 Hz), 6.55(1H,s), 4.71 (2H,s), 2.01(1H,brs), 1.52(9H,s)

Example 602

Synthesis of N-(3-chloro-4-cyanomethylphenyl) carbamic acid t-butyl ester

The compound (555.3 mg) obtained in Example 601 was dissolved in methylene chloride (10 ml); to the solution, triphenylphosphine (735 mg) and carbon tetrabromide (930 mg) were successively added under ice cooling and the mixture was stirred for 30 minutes, then stirred at room temperature for 30 minutes. Subsequently, the solvent was distilled off under reduced pressure and the resulting residue was dissolved in dimethyl sulfoxide (5 ml); to the solution, potassium cyanide (117.8 mg) was added, heated at 50° C. and stirred for 10 minutes. To the resulting reaction mixture, ethyl acetate was added and the organic layer was washed with water twice, dried with anhydrous sodium sulfate and the solvent was distilled off under reduced pressure. The resulting residue was purified by silica gel column chromatography (eluent, n-hexane:ethyl acetate=3:1) to give 89.6 mg of the titled compound (yield, 16%).

$^1$H-NMR($CDCl_3$) δ: 7.66(1H, d, J=2.2 Hz), 7.39(1H, d, J=8.6 Hz), 7.18(1H, dd, J=2.2, 8.6 Hz), 6.53(1H,brs), 3.78 (2H,s), 1.52(9H,s)

Example 603

Synthesis of 3-chloro-4-cyanomethylaniline

Using the compound obtained in Example 602 as a starting material, the same procedure of Example 521 gave 184.7 mg of the titled compound (yield, 88%).

$^1$H-NMR($CDCl_3$) δ: 7.21(1H, d, J=8.1 Hz), 6.73(1H, d, J=2.5 Hz), 6.57(1H, dd, J=2.5, 8.3 Hz), 3.80(2H,brs), 3.71 (2H,s)

Example 604

Synthesis of 4-(2-aminoethyl)-3-chloroaniline

Using the compound obtained in Example 603 as a starting material, the same procedure of Example 252 gave 189 mg of the titled compound (yield, 100%).

$^1$H-NMR($CDCl_3$) δ: 7.00(1H, d, J=8.3 Hz), 6.71(1H, d, J=2.4 Hz), 6.52(1H, dd, J=2.4, 8.3 Hz), 3.64(2H,brs), 2.98–2.87(2H,m), 2.83–2.71(2H,m), 1.24(2H,brs)

Example 605

Synthesis of N-(2-(4-amino-2-chlorophenyl)ethyl) carbamic acid t-butyl ester

Using the compound obtained in Example 604 as a starting material, the same procedure of Example 253 gave 208.3 mg of the titled compound (yield, 64%).

$^1$H-NMR($CDCl_3$) δ: 6.98(1H, d, J=8.1 Hz), 6.70(1H, d, J=2.4 Hz), 6.52(1H, dd, J=2.4, 8.1 Hz), 4.55(1H,brs), 3.64 (2H,brs), 3.32(2H, dt, J=6.6, 6.6 Hz), 2.81(2H, t, J=6.6 Hz), 1.43(9H,s)

Example 606

Synthesis of N-(2-(2-chloro-4-thioureidophenyl) ethyl)carbamic acid t-butyl ester Using the compound obtained in Example 605 as a starting material, the same procedure of Example 120 gave 78.9 mg of the titled compound (yield, 100%).

$^1$H-NMR($CDCl_3$) δ: 8.42(1H,brs), 7.38–7.20(2H,m), 7.17–7.04(1H,m), 6.30(2H,brs), 4.69(1H,brs), 3.38(2H, dt, J=6.6, 6.6 Hz), 2.94(2H, t, J=6.6 Hz), 1.42(9H,s)

Example 607

Synthesis of N-(2-(2-chloro-4-(S-ethylisothioureido) phenyl)ethyl)carbamic acid t-butyl ester Using the compound obtained in Example 606 as a starting material, the same procedure of Example 27 gave 66.7 mg of the titled compound (yield, 78%).

$^1$H-NMR($CDCl_3$) δ: 7.15(1H, d, J=8.3 Hz), 6.96(1H, d, J=2.2 Hz), 6.77(1H, dd, J=2.2, 8.3 Hz), 4.58(1H,brs), 4.28 (2H,brs), 3.36(2H, dt, J=6.6, 6.6 Hz), 3.01(2H, q, J=7.3 Hz), 2.88(2H, t, J=6.6 Hz), 1.44(9H,s), 1.36(3H, t, J=7.3 Hz)

Example 608

Synthesis of N-(2-(2-chloro-4-(S-ethylisothioureido) phenyl)ethyl)amine dihydrochloride Using the compound obtained in Example 607 as a starting material, the same procedure of Example 5 gave 65.3 mg of the titled compound (yield, 100%).

$^1$H-NMR(DMSO-$d_6$) δ: 11.88(1H,brs), 9.58(2H,brs), 8.32 (3H,brs), 7.53(1H, d, J=8.1 Hz), 7.52(1H, d, J=2.2 Hz), 4.10–3.60(2H,m), 3.35(2H, q, J=7.3 Hz), 3.14–2.93(2H,m), 1.30(3H, t, J=7.3 Hz)

Example 609

Synthesis of N-(2-(4-(N'-t-butoxycarbonyl-N"-ethylguanidino)-2-chlorophenyl)ethyl)carbamic acid t-butyl ester Using the compound obtained in Example 605 as a starting material, the same procedure of Example 233 gave 71.5 mg of the titled compound (yield, 52%).

$^1$H-NMR($CDCl_3$) δ: 10.70(1H,brs), 7.25–6.72(4H,m), 4.58(1H,brs), 3.47–3.27(4H,m), 2.91(2H, t, J=6.4 Hz), 1.49 (9H,s), 1.44(9H,s), 1.19(3H, t, J=7.3 Hz)

Example 610

Synthesis of N-(2-(2-chloro-4-(N'-ethylguanidino) phenyl)ethyl)amine dihydrochloride Using the compound obtained in Example 609 as a starting material, the same procedure of Example 5 gave 51.7 mg of the titled compound (yield, 100%).

$^1$H-NMR(DMSO-$d_6$) δ: 9.98(1H,s), 8.35(3H,brs), 8.11 (1H,brs), 7.83(2H,brs), 7.44(1H, d, J=8.3 Hz), 7.35(1H, d, J=2.2 Hz), 7.18(1H, dd, J=2.2, 8.3 Hz), 5.00–3.50(2H,m), 3.36–3.15(2H,m), 3.10–2.90(2H,m), 1.13(3H, t, J=7.1 Hz)

Example 611

Synthesis of N-(2-(N-benzyl-N-methylamino)-5-nitrophenylmethyl)iminodicarboxylic acid di-t-butyl ester Using the compound obtained in Example 263 as a starting material and also using N-methylbenzylamine as a reagent, the same procedure of Example 264 gave the titled compound (yield, 56%).

$^1$H-NMR($CDCl_3$) δ: 1.47(18H,s), 2.73(3H,s), 4.19(2H,s), 4.93(2H,s), 7.07(1H, d, J=8.9 Hz), 7.26–7.33(5H,m), 8.03–8.09(2H,m)

Example 612

Synthesis of N-(5-amino-2-(N-benzyl-N-methylamino)phenylmethyl)iminodicarboxylic acid di-t-butyl ester Using the compound obtained in Example 611 as a starting material, the same procedure of Example 566 gave the titled compound (yield, 91%).

$^1$H-NMR($CDCl_3$) δ: 1.43(18H,s), 2.48(3H,s), 3.50(2H,s), 3.91(2H,s), 4.98(2H,s), 6.45–6.47(1H,m), 6.52–6.56(1H,m), 6.98(1H, d, J=8.3 Hz), 7.25–7.40(5H,m)

Example 613

Synthesis of N-(2-(N-benzyl-N-methylamino)-5-thioureidophenylmethyl)iminodicarboxylic acid t-butyl ester Using the compound obtained in Example 612 as a starting material, the same procedure of Example 120 gave the titled compound (yield, 94%).

$^1$H-NMR($CDCl_3$) δ: 1.46(18H,s), 2.59(3H,s), 4.02(2H,s), 4.96(2H,s), 6.03(2H,brs), 6.98–7.00(1H,m), 7.03–7.08(1H, m), 7.16(1H, d, J=8.3 Hz), 7.26–7.37(5H,m), 7.80(1H,brs)

Example 614

Synthesis of N-(2-(N-benzyl-N-methylamino)-5-(S-ethylisothioureido)phenylmethyl)amine trihydrochloride Using the compound obtained in Example 613 as a starting material, treatment was performed as in Example 95 and the resulting compound was processed as in Example 5 to give the titled compound (yield, 95%)

$^1$H-NMR($D_2O$) δ: 1.41(3H, t, J=7.3 Hz), 3.12(3H,s), 3.23(2H, q, J=7.3 Hz), 3.94(2H,s), 4.46(2H,s), 7.20–7.23 (2H,m), 7.34–7.46(4H,m), 7.58(1H, dd, J=8.9, 2.6 Hz), 7.76(1H, d, J=8.9 Hz)

Example 615

Synthesis of N-(2-(N-benzyl-N-methylamino)-5-(N'-t-butoxycarbonyl-N"-ethylguanidino)phenylmethyl) iminodicarboxylic acid di-t-butyl ester Using the compound obtained in Example 612 as a starting material, the same procedure of Example 233 gave the titled compound (yield, 58%).

$^1$H-NMR($CDCl_3$) δ: 1.05–1.11(3H,m), 1.45(18H,s), 1.53 (9H,s), 2.58(3H,s), 3.32–3.45(2H,m), 4.01(2H,s), 4.97(2H, s), 6.92–7.17(3H,m), 7.26–7.39(5H,m)

Example 616

Synthesis of N-(2-(N-benzyl-N-methylamino)-5-(N'-ethylguanidino)phenylmethyl)amine trihydrochloride Using the compound obtained in Example 615 as a starting material, the same procedure of Example 5 gave the titled compound (yield, 89%).

$^1$H NMR($D_2O$) δ: 1.23(3H, t, J=7.6 Hz), 3.23(3H,s), 3.33(2H, q, J=7.6 Hz), 3.82(2H,s), 4.54(2H,s), 7.18–7.25 (3H,m), 7.34–7.48(3H,m), 7.53(1H, dd, J=8.9, 2.3 Hz), 7.77(1H, d, J=8.9 Hz)

Example 617

Synthesis of N-(1-(2-methyl-3-nitrophenyl)ethyl) phthalimide

Using 1-(2-methyl-3-nitrophenyl)ethanol as a starting material, the same procedure of Example 179 gave the titled compound (yield, 52%).

$^1$H-NMR(DMSO-$d_6$) δ: 1.81(3H, d, J=7.3 Hz), 2.31(3H, s), 5.69(1H, q, J=7.3 Hz), 7.48(1H, dd, J=7.9, 7.9 Hz), 7.75(1H, d, J=7.9 Hz), 7.84(4H,s), 7.97(1H, d, J=7.9 Hz)

Example 618

Synthesis of N-(1-(2-methyl-3-nitrophenyl)ethyl) carbamic acid t-butyl ester

Using the compound obtained in Example 617 as a starting material, the same procedure of Example 309 gave the titled compound (yield, 85%).

$^1$H-NMR($CDCl_3$) δ: 1.40(9H,s), 1.41(3H, d, J=6.3 Hz), 2.46(3H,s), 4.83(1H,brs), 4.98–5.14(1H,m), 7.31(1H, dd, J=7.9, 7.9 Hz), 7.53(1H, d, J=7.9 Hz), 7.61(1H, d, J=7.9 Hz)

Example 619

Synthesis of N-(1-(3-amino-2-methylphenyl)ethyl) carbamic acid t-butyl ester

Using the compound obtained in Example 618 as a starting material, the same procedure of Example 566 gave the titled compound (yield, 70%).

$^1$H-NMR($CDCl_3$) δ: 1.41(3H, d, J=6.3 Hz), 1.42(9H,s), 2.14(3H,s), 3.61(2H,brs), 4.74(1H,brs), 4.98–5.15(1H,m), 6.62(1H, d, J=7.9 Hz), 6.74(1H, d, J=7.9 Hz), 7.02(1H, dd, J=7.9, 7.9 Hz)

Example 620

Synthesis of N-(1-(2-methyl-3-thioureidophenyl) ethyl)carbamic acid t-butyl ester Using the compound obtained in Example 619 as a starting material, the same procedure of Example 120 gave the titled compound quantitatively.

$^1$H-NMR($CDCl_3$) δ: 1.39(3H, d, J=6.3 Hz), 1.41(9H,s), 2.33(3H,s), 4.89(1H,brs), 4.90–5.03(1H,m), 7.15(1H, d, J=7.6 Hz), 7.24–7.34(2H,m), 7.71(1H,brs)

Example 621

Synthesis of N-(1-(3-(S-ethylisothioureido)-2-methylphenyl)ethyl)carbamic acid t-butyl ester Using the compound obtained in Example 620 as a starting material, the same procedure of Example 95 gave the titled compound (yield, 80%).

$^1$H-NMR($CDCl_3$) δ: 1.36–1.45(3H,m), 1.40(3H, d, J=7.3 Hz), 1.42(9H,s), 2.16(3H,s), 3.02–3.18(2H,m), 4.36(1H, brs), 4.75(1H,brs), 4.93–5.08(1H,m), 6.73(1H, d, J=7.6 Hz), 6.98(1H, d, J=7.6 Hz), 7.13(1H, dd, J=7.6, 7.6 Hz)

Example 622

Synthesis of N-(1-(3-(S-ethylisothioureido)-2-methylphenyl)ethyl)amine dihydrochloride Using the compound obtained in Example 621 as a starting material, the same procedure of Example 5 gave the titled compound (yield, 92%).

$^1$H-NMR($D_2O$) δ: 1.43(3H, t, J=7.3 Hz), 1.62(3H, d, J=6.9 Hz), 2.29(3H,s), 3.24–3.28(2H,m), 4.88(1H, q, J=6.9 Hz), 7.37(1H, dd, J=7.9, 1.3 Hz), 7.50(1H, dd, J=7.9, 7.9 Hz), 7.60(1H, dd, J=7.9, 1.3 Hz)

Example 623

Synthesis of N-(1-(3-(N'-t-butoxycarbonyl)-N"-ethylguanidino)-2-methylphenyl)ethyl)carbamic acid t-butyl ester Using the compound obtained in Example 619 as a starting material, the same procedure of Example 233 gave the titled compound (yield, 38%).

$^1$H-NMR($CDCl_3$) δ: 1.00–1.20(3H,m), 1.40(3H, d, J=7.3 Hz), 1.41(9H,s), 1.54(9H,s), 2.29(3H,s), 3.36–3.45(2H,m), 4.80(1H,brs), 4.90–5.10(1H,m), 7.10–7.30(2H,m)

Example 624

Synthesis of N-(1-(3-(N'-ethylguanidino)-2-methylphenyl)ethyl)amine dihydrochloride Using the compound obtained in Example 623 as a starting material, the same procedure of Example 5 gave the titled compound (yield, 92%).

$^1$H-NMR($D_2O$) δ: 1.22(3H, t, J=7.3 Hz), 1.62(3H, d, J=6.6 Hz), 2.28(3H,s), 3.31(2H, q, J=7.3 Hz), 4.87(1H, q, J=6.6 Hz), 7.34(1H, dd, J=7.6, 1.3 Hz), 7.45(1H, dd, J=7.6, 7.6 Hz), 7.53(1H, dd, J=7.6, 1.3 Hz)

Example 625

Synthesis of N-benzoyl-4-thioureidobenzylamine

Using 4-amino-N-benzoylbenzylamine as a starting material, the same procedure of Example 120 gave 143.5 mg of the titled compound (yield, 76%).

$^1$H-NMR(DMSO-$d_6$) δ: 4.44(2H, d, J=5.9 Hz), 7.20–7.38 (5H,m), 7.40–7.58(4H,m), 7.89(1H, d, J=6.6 Hz), 9.03(1H, t, J=5.9 Hz), 9.64(1H,s)

Example 626

Synthesis of N-benzoyl-4-(S-ethylisothioureido) benzylamine

To a mixture of N-benzoyl-4-thioureidobenzylamine (139.1 mg) and acetonitrile (10 ml), ethyl iodide (0.5 ml) was added and heated under reflux for 3 h. A saturated aqueous sodium bicarbonate solution was added to the reaction mixture, which was extracted with ethyl acetate. The organic layer was washed successively with water and a saturated aqueous sodium chloride solution, dried with anhydrous sodium sulfate and the solvent was distilled off under reduced pressure. The resulting residue was purified by silica gel column chromatography (eluent, chloroform:methanol=20:1) to give 134.8 mg of the titled compound (yield, 88%).

$^1$H-NMR($CDCl_3$) δ: 1.36(3H, t, J=6.9 Hz), 2.67(1H,brs), 2.90–3.11(2H,m), 4.46(1H,brs), 4.60(2H, d, J=5.6 Hz), 6.25–6.41(1H,m), 6.91(2H, brd, J=8.3 Hz), 7.29(2H, d, J=8.3 Hz), 7.38–7.53(3H,m), 7.75–7.83(3H,m), 7.79(2H, d, J=6.6 Hz)

Example 627

Synthesis of N-benzoyl-4-(N'-t-butoxycarbonyl-N"-ethylguanidino)benzylamine

Using the compound obtained in Example 625 as a starting material, the same procedure of Example 233 gave 180.8 mg of the titled compound (yield, 66%).

$^1$H-NMR($CDCl_3$) δ: 1.10–1.21(3H,m), 1.47(9H,s), 3.32–3.48(2H,m), 4.62(2H, d, J=5.9 Hz), 6.62(1H,brs), 7.11 (2H,brs), 7.25–7.60(6H,m), 7.78–7.88(2H,m), 10.70(1H, brs)

Example 628

Synthesis of N-benzoyl-3-(N'-ethylguanidno) benzylamine

A mixture of the compound (180.8 mg) obtained in Example 627 and trifluoroacetic acid (5 ml) was stirred at room temperature for 30 min. The reaction mixture was concentrated under reduced pressure and, after addition of a saturated aqueous sodium bicarbonate solution, extracted with ethyl acetate. The organic layer was dried with anhydrous sodium sulfate and the solvent was distilled off under reduced pressure to give 46.1 mg of the titled compound (yield, 34%).

$^1$H-NMR(DMSO-$d_6$) δ: 1.06(3H, t, 7.3 Hz), 3.11(2H, q, J=7.3 Hz), 4.40(2H, d, J=6.5 Hz), 5.30(2H,brs), 6.73(2H, d, J=8.3 Hz), 7.14(2H, d, J=8.3 Hz), 7.43–7.58(3H,m), 7.86–7.96(2H,m), 8.96(1H, t, J=6.5 Hz)

Example 629

Synthesis of 3-amino-N-benzoylbenzylamine

Using N-benzoyl-3-nitrobenzylamine as a starting material, the same procedure of Example 566 gave 985 mg of the titled compound (yield, 86%).

$^1$H-NMR($CDCl_3$) δ: 3.69(2H,s), 4.55(2H, d, J=5.3 Hz), 6.39(1H,brs), 6.57–6.60(1H,m), 6.67(1H,s), 6.72(1H, d, J=7.7 Hz), 7.13(1H, t, J=7.9 Hz), 7.37–7.54(3H,m), 7.77 (1H,s), 7.78(1H, d, J=8.3 Hz)

Example 630

Synthesis of N-benzoyl-3-thioureidobenzylamine

Using the compound obtained in Example 629 as a starting material, the same procedure of Example 3 gave 147 mg of the titled compound (yield, 58%).

$^1$H-NMR(DMSO-$d_6$) δ: 4.48(2H, d, J=5.9 Hz), 7.08(1H, d, J=7.6 Hz), 7.22–7.57(8H,m), 7.90(2H, d, J=6.6 Hz), 8.98(1H,brs), 9.68(1H,s)

Example 631

Synthesis of N-benzoyl-3-(S-ethylisothioureido) benzylamine

Using the compound obtained in Example 630 as a starting material, the same procedure of Example 626 gave 39.0 mg of the titled compound (yield, 93%).

$^1$H-NMR($CDCl_3$) δ: 1.35(3H, t, J=7.3 Hz), 3.00(2H, q, J=7.3 Hz), 4.52(1H,brs), 4.59(2H, d, J=5.6 Hz), 6.50(1H, brs), 6.85(1H, d, J=8.1 Hz), 6.90(1H,s), 7.01(1H, d, J=7.6 Hz), 7.27(1H, dd, J=8.1, 7.6 Hz), 7.38–7.50(3H,m), 7.76–7.79(2H,m)

Example 632

Synthesis of N-benzoyl-3-(N'-t-butoxycarbonyl-N"-ethylguanidino)benzylamine

Using the compound obtained in Example 629 as a starting material, the same procedure of Example 233 gave 57 mg of the titled compound (yield, 59%).

$^1$H-NMR($CDCl_3$) δ: 1.03–1.20(3H,m), 1.47(9H,s), 3.30–3.42(2H,m), 4.61(2H, d, J=5.6 Hz), 4.88(1H,brs), 6.91 (1H,brs), 6.92–7.20 (4H,m), 7.26–7.55(5H,m), 7.82(2H, d, J=6.9 Hz)

Example 633

Synthesis of N-benzoyl-3-(N'-ethylguanidino) benzylamine monohydrochloride

Using the compound obtained in Example 632 as a starting material, the same procedure of Example 5 gave 31.7 mg of the titled compound quantitatively.

$^1$H-NMR(DMSO-$d_6$) δ: 1.14(3H, t, J=6.9 Hz), 3.21–3.38 (2H,m), 4.50(2H, d, J=5.6 Hz), 7.10(1H, d, J=6.9 Hz), 7.19(1H,s), 7.24(1H, d, J=7.9 Hz), 7.34–7.71(5H,m), 7.75–7.79(3H,m), 9.04 (1H,brs), 9.46–9.59(1H,m)

Example 634

Synthesis of 1-(2-methoxy-5-nitrophenyl)ethanol

To a solution of 2-methoxy-5-nitrobenzaldehyde (450 mg) in toluene (30 ml), a solution of trimethylaluminum in hexane (3.0 ml) was added dropwise under ice cooling. After stirring at room temperature for 1 h, water was added to the reaction mixture, which was extracted with ethyl acetate. The organic layer was washed successively with water and a saturated aqueous sodium chloride solution, dried with anhydrous sodium sulfate and the solvent was distilled off under reduced pressure. The resulting residue was purified by silica gel column chromatography (eluent, n-hexane:ethyl acetate=2:1) to give 385 mg of the titled compound (yield, 79%).

$^1$H-NMR($CDCl_3$) δ: 1.51(3H, d, J=6.3 Hz), 2.25(1H, d, J=3.3 Hz), 3.96(3H,s), 5.12–5.23(1H,m), 6.93(1H, d, J=9.2 Hz), 8.18(1H, dd, J=9.2, 2.6 Hz), 8.35(1H, d, J=2.6 Hz)

Example 635

Synthesis of N-((1-(2-methoxy-5-nitrophenyl))ethyl) phthalimide

Using the compound obtained in Example 634 as a starting material, the same procedure of Example 179 gave 358 mg of the titled compound (yield, 57%).

$^1$H-NMR($CDCl_3$) δ: 1.87(3H, d, J=7.3 Hz), 3.87(3H,s), 5.82(1H, q, J=7.3 Hz), 6.89(1H, d, J=9.2 Hz), 7.70(2H, dd, J=5.3, 3.0 Hz), 7.81(2H, dd, J=5.3, 3.0 Hz), 8.21(1H, dd, J=9.2, 2.7 Hz), 8.54(1H, d, J=2.7 Hz)

Example 636

Synthesis of N-(1-(5-amino-2-methoxyphenyl)ethyl) carbamic acid t-butyl ester

Using the compound obtained in Example 635 as a starting material, the same procedure of Example 309 gave N-((1-(2-methoxy-5-nitrophenyl))ethyl)carbamic acid t-butyl ester. The resulting nitro compound was subjected to the same reaction as in Example 2 to give 165 mg of the titled compound (yield, 58%).

$^1$H-NMR($CDCl_3$) δ: 1.39(3H, d, J=7.3 Hz), 1.42(9H,s), 3.40(2H,brs), 3.79(3H,s), 4.78–4.90(1H,m), 5.28–5.41(1H, m), 6.52–6.60(2H,m), 6.71(1H, d, J=8.4 Hz)

Example 637

Synthesis of N-(1-(2-methoxy-5-thioureidophenyl) ethyl)carbamic acid t-butyl ester Using the compound obtained in Example 636 as a starting material, the same procedure of Example 120 gave 110 mg of the titled compound (yield, 90%).

$^1$H-NMR($CDCl_3$) δ: 1.38(3H, d, J=6.9 Hz), 1.41(9H,s), 3.87(3H,s), 4.90–5.01(1H,m), 5.02–5.09(1H,m), 5.91(2H, brs), 6.88(1H, d, J=8.3 Hz), 7.05–7.17(2H,m), 7.58(1H,s)

Example 638

Synthesis of N-(1-(5-(S-ethylisothioureido)-2-methoxyphenyl)ethyl)carbamic acid t-butyl ester hydroiodide Using the compound obtained in Example 637 as a starting material, the same procedure of Example 95 gave 129 mg of the titled compound (yield, 81%).

$^1$H-NMR($CDCl_3$) δ: 1.36(3H, t, J=7.3 Hz), 1.39(3H, d, J=6.9 Hz), 1.42(9H,s), 3.02(2H, q, J=7.3 Hz), 3.83(3H,s), 4.82–4.95(1H,m), 5.10–5.28(1H,m), 6.73–7.01(3H,m)

Example 639

Synthesis of N-(1-(5-(S-ethylisothioureido)-2-methoxyphenyl)ethyl)amine dihydrochloride Using the compound obtained in Example 638 as a starting material, the same procedure of Example 5 gave 112.6 mg of the titled compound quantitatively.

$^1$H-NMR(DMSO-$d_6$) δ: 1.33(3H, t, J=7.3 Hz), 1.52(3H, d, J=6.6 Hz), 3.22–3.40(2H,m), 3.89(3H,s), 4.50–4.71(1H,m), 7.18(1H, d, J=8.6 Hz), 7.31(1H, d, J=8.6 Hz), 7.49(1H,s), 8.55(2H,brs), 9.18(1H,brs), 9.74(1H,brs), 11.56(1H,brs)

Example 640

Synthesis of N-(1-(5-(N'-t-butoxycarbonyl-N"-ethylguanidino)-2-methoxyphenyl)ethyl)carbamic acid t-butyl ester Using the compound obtained in Example 636 as a starting material, the same procedure of Example 233 gave 66 mg of the titled compound (yield, 62%).

$^1$H-NMR($CDCl_3$) δ: 1.06(3H, t, J=6.9 Hz), 1.38(3H, d, J=7.0 Hz), 1.42(9H,s), 1.53(9H,s), 3.31–3.46(2H,m), 3.86 (3H,s), 4.53(1H,brs), 4.90–5.03(1H,m), 5.07(1H,brs), 6.86 (1H, d, J=8.9 Hz), 7.02–7.12(2H,m), 10.50(1H,brs)

Example 641

Synthesis of N-(1-(5-(N'-ethylguanidino)-2-methoxyphenyl)ethyl)amine dihydrochloride Using the compound obtained in Example 640 as a starting material, the same procedure of Example 5 gave 58.8 mg of the titled compound quantitatively. $^1$H-NMR (DMSO-$d_6$) δ: 1.15(3H, t, J=6.9 Hz), 1.49(3H, d, J=6.8 Hz), 3.28(2H, dq, J=6.0, 6.9 Hz), 3.88(3H,s), 4.52–4.65(1H,m), 7.14(1H, d, J=8.6 Hz), 7.18–7.26(1H,m), 7.30–7.34(1H,m), 7.43–7.58(2H,m), 7.66–7.78(1H,m), 8.36(2H,brs), 9.59(1H, brs)

Example 642

Synthesis of N-(2-(N-acetyl-N-methylamino)-5-nitrophenylmethyl)iminodicarboxylic acid di-t-butyl ester To a mixture of the compound (540 mg) obtained in Example 446, potassium carbonate (1.96 g) and acetonitrile (30 ml), acetyl chloride(890 mg) was added and heated under reflux for 24 h. Ethyl acetate was added to the reaction mixture, which was washed with water, dried with magnesium sulfate and concentrated under reduced pressure. The resulting residue was purified by silica gel column chromatography (eluent, methylene chloride:ethyl acetate=5:1) to give 330 mg of the titled compound (yield, 55%).

$^1$H-NMR($CDCl_3$) δ: 1.50(18H,s), 1.84(3H,s), 3.23(3H,s), 4.79(2H,s), 7.33(1H, d, J=8.4 Hz), 8.12(1H, d, J=2.3 Hz), 8.19(1H, dd, J=8.4, 2.3 Hz)

Example 643

Synthesis of N-(2-(N-acetyl-N-methylamino)-5-aminophenylmethyl)iminodicarboxylic acid di-t-butyl ester Using the compound obtained in Example 642 as a starting material, the same procedure of Example 2 gave the titled compound (yield, 96%).

$^1$H-NMR($CDCl_3$) δ: 1.48(18H,s), 1.80(3H,s), 3.15(3H,s), 3.77(2H,brs), 4.64(1H, d, J=17.2 Hz), 4.65(1H, d, J=17.2 Hz), 6.45(1H, d, J=2.3 Hz), 6.55(1H, dd, J=8.3, 2.3 Hz), 6.86(1H, d, J=8.3 Hz)

Example 644

Synthesis of N-(2-(N-acetyl-N-methylamino)-5-thioureidophenylmethyl)iminodicarboxylic acid di-t-butyl ester Using the compound obtained in Example 643 as a starting material, the same procedure of Example 120 gave the titled compound (yield, 80%).

$^1$H-NMR($CDCl_3$) δ: 1.48(18H,s), 1.83(3H,s), 3.19(3H,s), 4.70(1H, d, J=17.2 Hz), 4.71(1H, d, J=17.2 Hz), 6.26(2H, brs), 7.14–7.26(3H,m), 8.32(1H,brs)

Example 645

Synthesis of N-(2-(N-acetyl-N-methylamino)-5-(S-ethylisothioureido)phenylmethyl)iminodicarboxylic acid di-t-butyl ester Using the compound obtained in Example 644 as a starting material, the same procedure of Example 95 gave the titled compound (yield, 83%).

$^1$H-NMR($CDCl_3$) δ: 1.35(3H, t, J=6.9 Hz), 1.45(18H,s), 1.82(3H,s), 2.90–3.15(2H,m), 3.18(3H,s), 4.53(2H,brs), 4.69(1H, d, J=17.2 Hz), 4.70(1H, d, J=17.2 Hz), 6.76(1H, brs), 6.79–6.92(1H,m), 7.04(1H, d, J=7.9 Hz)

Example 646

Synthesis of N-(2-(N-acetyl-N-methylamino)-5-(S-ethylisothioureido)phenylmethyl)amine dihydrochloride Using the compound obtained in Example 645 as a starting material, the same procedure of Example 5 gave the titled compound (yield, 53%).

$^1$H-NMR($D_2O$) δ: 1.43(3H, t, J=7.6 Hz), 2.37(3H,s), 3.26(2H, q, J=7.6 Hz), 3.44(3H,s), 4.12(1H, d, J=14.2 Hz), 4.14(1H, d, J=14.2 Hz), 7.50–7.60(3H,m)

Example 647

Synthesis of N-(2-(N-acetyl-N-methylamino)-(5-(N'-t-butoxycarbonyl-N"-ethylguanidino) phenylmethyl)iminodicarboxylic acid di-t-butyl ester Using the compound obtained in Example 643 as a starting material, the same procedure of Example 233 gave the titled compound (yield, 69%).

$^1$H-NMR($CDCl_3$) δ: 1.19(3H, t, J=7.4 Hz), 1.47(27H,s), 1.82(3H,s), 3.20(3H,s), 3.30–3.44(2H,m), 4.70(1H, d, J=16.8 Hz), 4.71(1H, d, J=16.8 Hz), 6.85–7.05(2H,m), (7.08, 1H, d, J=7.6 Hz)

Example 648

Synthesis of N-(2-(N-acetyl-N-methylamino)-5-(N'-ethylguanidino)phenylmethyl)amine dihydrochloride Using the compound obtained in Example 647 as a starting material, the same procedure of Example 5 gave the titled compound (yield, 27%).

$^1$H-NMR($D_2O$) δ: 1.24(3H, t, J=7.6 Hz), 2.36(3H,s), 3.34(2H, q, J=7.6 Hz), 3.42(3H,s), 4.09(1H, d, J=14.2 Hz), 4.12(1H, d, J=14.2 Hz), 7.43–7.53(3H,m)

Example 649

Synthesis of 2-dimethylamino-3-nitrobenzoic acid

Using 2-bromo-3-nitrobenzoic acid as a starting material, the same procedure of Example 264 gave 4.8 g of the titled compound (yield, 96%).

$^1$H-NMR($CDCl_3$) δ: 2.99(6H,s), 7.56(1H, dd, J=7.9, 7.9 Hz), 7.91(1H, dd, J=7.9, 1.7 Hz), 8.60(1H, dd, J=7.9, 1.7 Hz)

FAB-MS(m/s) 211($M^+$+1)

Example 650

Synthesis of (2-dimethylamino-3-nitrophenyl) methanol

Using the compound obtained in Example 650 as a starting material, the same procedure of Example 132 gave 4.23 g of the titled compound (yield, 94%).

$^1$H-NMR($CDCl_3$) δ: 2.80(6H,s), 3.16–3.28(1H,m), 4.80 (2H, d, J=4.4 Hz), 7.19(1H, dd, J=7.8, 7.8 Hz), 7.53–7.61 (2H,m)

FAB-MS(m/s) 197($M^+$+1)

Example 651

Synthesis of N-(2-dimethylamino-3-nitrophenylmethyl)phthalimide

Using the compound obtained in Example 650 as a starting material, the same procedure of Example 179 gave 4.4 g of the titled compound (yield, 63%).

$^1$H-NMR($CDCl_3$) δ: 2.84(6H,s), 4.99(2H,s), 7.09(1H, dd, J=7.9, 7.9 Hz), 7.31(1H, d, J=7.9 Hz), 7.53(1H, d, J=7.9 Hz), 7.74–7.79(2H,m) 7.87–7.91(2H,m)

FAB-MS(m/s) 325($M^+$)

Example 652

Synthesis of N-(2-dimethylamino-3-nitrophenylmethyl)carbamic acid t-butyl ester

Using the compound obtained in Example 651 as a starting material, the same procedure of Example 309 gave 3.74 g of the titled compound (yield, 94%).

$^1$H-NMR($CDCl_3$) δ: 1.46(9H,s), 2.77(6H,s), 4.42(2H, d, J=5.6 Hz), 5.02(1H,brs), 7.15(1H, dd, J=7.9, 7.9 Hz), 7.52 (2H, d, J=7.9 Hz)

FAB-MS(m/s) 295($M^+$)

Example 653

Synthesis of N-(3-(N'-t-butoxycarbonyl-N"-ethylguanidino)-2-dimethylaminophenylmethyl) carbamic acid t-butyl ester Using the compound obtained in Example 652 as a starting material, the same procedure of Example 233 gave the titled compound (yield, 71%).

$^1$H-NMR($CDCl_3$) δ: 1.06–1.25(3H,m), 1.46(9H,s), 1.51 (9H,s), 2.78(6H,s), 3.32–3.48(2H,m), 4.28–4.43(2H,m), 4.67–5.33(2H,m), 6.55–6.68(1H,m), 6.94(1H, dd, J=7.6, 7.6 Hz), 7.05–7.23(2H,m)

FAB-MS(m/s) 436($M^+$+1)

Example 654

Synthesis of N-(3-(N'-ethylguanidino)-2-dimethylaminophenylmethyl)amine trihydrochloride Using the compound obtained in Example 653 as a starting material, the same procedure of Example 5 gave the titled compound quantitatively.

$^1$H-NMR($D_2O$) δ: 1.22(3H, t, J=7.3 Hz), 2.90(3H,s), 2.91(3H,s), 3.33(2H, q, J=7.3 Hz), 4.32(2H,s), 7.37–7.58 (3H,m)

Example 655

Synthesis of N-(5-(N'-t-butoxycarbonyl-N"-ethylguanidino)-2-hydroxyphenylmethyl)carbamic acid t-butyl ester Using the compound obtained in Example 338 as a starting material, the same procedure of Example 2 gave the titled compound (yield, 74%).

$^1$H-NMR($CDCl_3$) δ: 1.06(3H, t, J=7.3 Hz), 1.46(9H,s), 1.52(9H,s), 3.32–3.40(2H,m), 4.19(2H, d, J=6.9 Hz), 5.22–5.30(1H,m), 6.88–7.08(3H,m)

Example 656

Synthesis of N-(5-(N'-ethylguanidino)-2-hydroxyphenylmethyl)amine dihydrochloride Using the compound obtained in Example 655 as a starting material, the same procedure of Example 5 gave the titled compound (yield, 77%).

$^1$H-NMR($D_2O$) δ: 1.21(3H, t, J=7.3 Hz), 3.29(2H, q, J=7.3 Hz), 4.17(2H,s), 7.02–7.04(1H,m), 7.22–7.26(2H,m)

TEST EXAMPLES

Test Example 1

Compounds of the invention were evaluated for their inhibitory effect on the presently known three NOS isoforms as compared with existing NOS inhibitors.

The following NOS inhibitors were used as control compounds:

L-NNA,

L-CPA,

L-MIN,

L-EIN,

L-NAME, $N^G$-amino-L-arginine (L-AA),

L-NIO, $N^G$-monomethyl-L-arginine (L-NMMA)

Crude enzyme samples of the NOS isoforms were prepared by the following procedures (Nagafuji et al., Neuroreport 6, 1541–1545, 1995).

The crude enzyme sample of N-cNOS was prepared by the following procedure. Normal untreated male Sprague Dawley (SD) rats (body weight, 300–400 g) were decapitated; the whole brain was immediately taken out from each animal and the cerebral cortex was separated on ice. Then, 5 volumes of 50 mM Tris-HCl containing 1 mM DTT (pH 7.4) was added and the mixture was homogenized for 3 min and centrifuged at 1,000×g for 10 min. The resulting supernatant was further centrifuged at 100,000×g for 60 min and a soluble cytosolic fraction of the finally obtained supernatant was used as the crude enzyme sample of N-cNOS.

The crude enzyme sample of E-cNOS was prepared by the following procedure. A cow pulmonary arterial endothielium cell (CPAE) was cultured in a MEM medium containing 20% FBS. Several days later, the cells were detached from the flask using a 0.25% tripsin solution containing 1 mM EDTA and, after addition of a suitable amount of FBS, centrifuged at 1,000 rpm for 10 min. A suitable amount of Ca- and Mg-free phosphate buffer (pH 7.4) was added to the precipitating cells and they were centrifuged at 1,000 rpm for 10 min. The same step was repeated to wash the cells which, upon addition of 50 mM Tris-HCl (pH 7.4) containing 1% Triton X-100 and 1 mM DTT, were left to stand in ice for 1 h. Subsequently, the mixture was homogenized for 3 min and kept in ice for 30 min with occasional stirring. Finally, the mixture was centrifuged at 100,000×g for 60 min and the resulting supernatant was used as the crude enzyme sample of E-cNOS.

The crude enzyme sample of iNOS was prepared by the following procedure. Rats were administered intraperitoneally with LPS (10 mg/kg) and, 6 h later, perfused in a transcardiac manner with physiological saline containing 10 U/ml of heparin; thereafter, lungs were taken out. Subsequently, 5 volumes of 50 mM Tris-HCl containing 1 mM DTT (pH 7.4) was added and the mixture was homogenized for 3 min, followed by centrifugation of the homogenate at 1,000×g for 10 min. The resulting supernatant was centrifuged at 100,000×g for 60 min and a soluble cytosolic fraction of the finally obtained supernatant was used as the crude enzyme sample of iNOS.

The method of measuring NOS activity was basically the same as already reported by the present inventors and consisted of determining quantitatively the conversion of a substrate L-[$^3$H]arginine to a reaction product L-[$^3$H]citrulline (Nagafuji et al., in Brain Edema IX (Ito et al., eds.) 60, pp. 285–288, 1994; Nagafuji et al., Neuroreport 6, 1541–1545, 1995).

The reaction solution consisted of 100 nM L-[$^3$H]arginine, a prepared curde NOS enzyme sample (10–30 $\mu$g/ml protein), 1.25 mM $CaCl_2$, 1 mM EDTA, 10 $\mu$g/ml calmodulin, 1 mM NADPH, 100 $\mu$m tetrahydrobiopterine, 10 $\mu$m FAD, 10 $\mu$m FMN and 50 mM Tris-HCl (pH 7.4), to which one of the compounds of the invention or one of the control compounds was added.

The reaction was started by addition of L-[$^3$H]arginine and following incubation at 37° C. for 10 min, the reaction was terminated by addition of 2 ml of 50 mM Tris-HCl (pH 5.5) containing 1 mM EDTA and placing the mixture on ice. The reaction solution was passed through a cation-exchange resin column (Dowex AG50WX-8, $Na^+$ form, 3.2 ml) to separate the reaction product L-[$^3$H]citrulline from the unreacted residual substrate L-[$^3$H]arginine. The eluate was combined with another eluate resulting from the passage of a given amount of distilled water through the column and put into a minivial for recovery of L-[$^3$H]citrulline. Thereafter, a scintillation fluid was added and the contained radioactivity was measured with a liquid scintillation counter to determine the amount of L-[$^3$H]citrulline.

The activity of N-cNOS or E-cNOS was determined by subtracting the activity as detected in the absence of $CaCl_2$ and calmodulin from the activity as detected in the presence of $CaCl_2$ and calmodulin. The activity of iNOS was detected in the absence of $CaCl_2$ and calmodulin. The protein concentration of each crude enzyme sample was determined with a micro-assay kit of Biorad Co. Each experiment was conducted in a duplicate.

Tables 49, 50 and 51 list the mean values of $IC_{50}$ (the concentration necessary to inhibit 50% activity) of all test compounds against each NOS isoform, as obtained in one to four independent experiments. The tables also list the ratios of $IC_{50}$ values to each other as an index of selectivity.

TABLE 49

Inhibitory Potency and Selectivity of Test Compounds against Three NOS Isoforms

| Example No. or Control Compound | $IC_{50}$ value, nM N-cNOS (Type 1) | E-cNOS (Type 3) | iNOS (Type 2) | Ratio of $IC_{50}$ values E-cNOS/ N-cNOS | iNOS/ N-cNOS | E-cNOS/ iNOS |
|---|---|---|---|---|---|---|
| 96 | 2.1 | 198.3 | 28.6 | 94.4 | 13.6 | 6.9 |
| 122 | 3.8 | 3,525.3 | 24,649.9 | 927.7 | 6486.8 | 0.1 |
| 175 | 4.0 | 199.8 | n.d. | 50.0 | n.d. | n.d. |
| 270 | 4.3 | 3,586.1 | 4528.7 | 834.0 | 1053.2 | 0.8 |
| 131 | 4.5 | 481.1 | 78.2 | 106.9 | 17.4 | 6.2 |
| 324 | 4.8 | 2,305.6 | 8728.2 | 480.3 | 1818.4 | 0.3 |
| 171 | 5.0 | 29.2 | n.d. | 5.8 | n.d. | n.d. |
| 104 | 5.2 | 117.8 | 86.5 | 22.7 | 16.6 | 1.4 |
| 28 | 5.5 | n.d. | 32.7 | n.d. | 5.9 | n.d. |
| L-MIN | 5.7 | 152.0 | 247.6 | 26.7 | 43.4 | 0.6 |
| 14 | 5.9 | n.d. | 3,681.3 | n.d. | 623.9 | n.d. |
| 21 | 5.9 | n.d. | 2,606.2 | n.d. | 441.7 | n.d. |
| 411 | 5.9 | 341.3 | n.d. | 57.8 | n.d. | n.d. |
| 452 | 6.4 | 3631.7 | 6,963.2 | 567.5 | 1088.0 | 0.5 |

TABLE 49-continued

| Example No. or Control Compound | IC$_{50}$ value, nM N-cNOS (Type 1) | E-cNOS (Type 3) | iNOS (Type 2) | Ratio of IC$_{50}$ values E-cNOS/ N-cNOS | iNOS/ N-cNOS | E-cNOS/ iNOS |
|---|---|---|---|---|---|---|
| 137 | 7.1 | 484.6 | n.d. | 68.3 | n.d. | n.d. |
| 7 | 7.6 | 42.4 | 2,123.2 | 5.6 | 279.4 | 0.02 |
| 162 | 7.9 | 575.7 | n.d. | 72.9 | n.d. | n.d. |
| 173 | 8.2 | 24.1 | n.d. | 2.9 | n.d. | n.d. |
| L-EIN | 8.4 | 732.2 | 6,760.8 | 87.2 | 804.9 | 0.1 |
| 458 | 8.4 | 4101.1 | n.d. | 488.2 | n.d. | n.d. |
| 47 | 8.8 | 72.9 | n.d. | 8.3 | n.d. | n.d. |
| 112 | 10.8 | 407.6 | n.d. | 37.7 | n.d. | n.d. |
| 177 | 11.6 | 510 | n.d. | 44.0 | n.d. | n.d. |
| 317 | 12.2 | 238.6 | n.d. | 19.6 | n.d. | n.d. |
| 167 | 13.3 | 365.8 | n.d. | 27.5 | n.d. | n.d. |
| 169 | 14.0 | 41.5 | n.d. | 3.0 | n.d. | n.d. |
| 12 | 14.2 | 538.5 | 239.3 | 37.9 | 16.9 | 2.3 |
| L-NNA | 16.9 | 68.2 | 3,464.3 | 4.0 | 205.0 | 0.02 |
| 288 | 19.9 | 1263.8 | n.d. | 63.5 | n.d. | n.d. |
| 26 | 20.9 | 430.5 | 1,345.9 | 20.6 | 64.4 | 0.3 |
| 376 | 21.3 | 338.6 | n.d. | 15.9 | n.d. | n.d. |
| 153 | 22.2 | 422.8 | n.d. | 19.0 | n.d. | n.d. |
| 528 | 22.8 | 436.2 | n.d. | 19.1 | n.d. | n.d. |
| 5 | 23.4 | 429.2 | 448.7 | 18.3 | 19.2 | 1.0 |
| 372 | 23.6 | 359.9 | n.d. | 15.3 | n.d. | n.d. |
| 538 | 24.4 | 2543.3 | 305.9 | 104.2 | 12.5 | 8.3 |

Inhibitory Potency and Selectivity of Test Compounds against Three NOS Isoforms

Note:
Symbol "n.d." means not determined.

TABLE 50

Inhibitory Potency and Selectivity of Test Compounds against Three NOS Isoforms

| Example No. or Control Compound | IC$_{50}$ value, nM N-cNOS (Type 1) | E-cNOS (Type 3) | iNOS (Type 2) | Ratio of IC$_{50}$ values E-cNOS/ N-cNOS | iNOS/ N-cNOS | E-cNOS/ iNOS |
|---|---|---|---|---|---|---|
| L-CPA | 27.3 | 986.6 | 7,153.9 | 36.1 | 262.0 | 0.1 |
| 52 | 35.2 | 483.5 | 2,760.6 | 13.7 | 78.4 | 0.2 |
| 298 | 36.4 | 4141.6 | n.d. | 113.8 | n.d. | n.d. |
| 160 | 36.6 | 477.2 | n.d. | 13.0 | n.d. | n.d. |
| 144 | 37.5 | 898.2 | n.d. | 24.0 | n.d. | n.d. |
| 151 | 37.6 | 262.3 | n.d. | 7.0 | n.d. | n.d. |
| 482 | 39.7 | 1992.1 | n.d. | 50.2 | n.d. | n.d. |
| 438 | 41.3 | 6946 | n.d. | 168.2 | n.d. | n.d. |
| 142 | 44.0 | 662.6 | n.d. | 15.1 | n.d. | n.d. |
| 337 | 44.8 | 5201.8 | 1,5473.6 | 116.1 | 345.4 | 0.3 |
| 355 | 46.0 | 662.5 | n.d. | 14.4 | n.d. | n.d. |
| 533 | 46.1 | 3771.3 | n.d. | 81.8 | n.d. | n.d. |
| 305 | 53.9 | 1706.9 | n.d. | 31.7 | n.d. | n.d. |
| 236 | 56.8 | 325.2 | n.d. | 5.7 | n.d. | n.d. |
| 226 | 57.9 | 1,436.8 | n.d. | 24.8 | n.d. | n.d. |
| 110 | 58.1 | n.d. | n.d | n.d. | n.d. | n.d. |
| 238 | 63.9 | 1164.3 | n.d. | 18.2 | n.d. | n.d. |
| 54 | 67.0 | n.d. | 5,023.4 | n.d. | 75.0 | n.d. |
| 300 | 69.8 | 492.0 | n.d. | 7.0 | n.d. | n.d. |
| 258 | 72.7 | 1085.8 | n.d. | 14.9 | n.d. | n.d. |
| 374 | 77.1 | 1288.8 | n.d. | 16.7 | n.d. | n.d. |
| L-NAME | 79.4 | 923.0 | 13,533.1 | 11.6 | 170.4 | 0.1 |
| 19 | 88.4 | n.d. | 2,404.4 | n.d. | 27.2 | n.d. |
| 234 | 88.8 | 1167.2 | n.d. | 13.1 | n.d. | n.d. |
| 543 | 95.0 | 3120.6 | n.d. | 32.8 | n.d. | n.d. |
| 267 | 99.6 | 50,081.6 | 4,788.8 | 502.8 | 48.1 | 10.5 |
| 350 | 105.7 | 15,842.9 | 58,397.6 | 149.9 | 552.5 | 0.3 |
| 281 | 107.9 | 1,620.2 | n.d. | 15.0 | n.d. | n.d. |
| 39 | 116.4 | n.d. | 22,856.0 | n.d. | 196.4 | n.d. |
| 41 | 121.0 | n.d. | n.d. | n.d. | n.d. | n.d. |
| 193 | 127.8 | 1,541.9 | n.d. | 12.1 | n.d. | n.d. |
| L-AA | 152.5 | 167.0 | 1,281.0 | 1.1 | 8.4 | 0.1 |
| 341 | 160.2 | 874.0 | n.d. | 5.5 | n.d. | n.d. |

TABLE 50-continued

| Example No. or Control Compound | IC$_{50}$ value, nM N-cNOS (Type 1) | E-cNOS (Type 3) | iNOS (Type 2) | Ratio of IC$_{50}$ values E-cNOS/ N-cNOS | iNOS/ N-cNOS | E-cNOS/ iNOS |
|---|---|---|---|---|---|---|
| 30 | 162.6 | n.d. | n.d. | n.d. | n.d. | n.d. |
| 60 | 170.6 | n.d. | 6,745.3 | n.d. | 39.5 | n.d. |
| 367 | 193.4 | 3,707.3 | n.d. | 19.2 | n.d. | n.d. |
| 285 | 198.9 | 7,305.4 | n.d. | 36.7 | n.d. | n.d. |

Inhibitory Potency and Selectivity of Test Compounds against Three NOS Isoforms

Note:
Symbol "n.d." means not determined.

TABLE 51

| Example No. or Control Compound | IC$_{50}$ value, nM N-cNOS (Type 1) | E-cNOS (Type 3) | iNOS (Type 2) | Ratio of IC$_{50}$ values E-cNOS/ N-cNOS | iNOS/ N-cNOS | E-cNOS/ iNOS |
|---|---|---|---|---|---|---|
| L-NIO | 277.0 | 1,226.3 | 457.8 | 4.4 | 1.7 | 2.7 |
| 339 | 280.5 | n.d. | n.d. | n.d. | n.d. | n.d. |
| 34 | 280.8 | n.d. | 6,760.8 | n.d. | 24.1 | n.d. |
| 185 | 298.6 | 3,165.1 | n.d. | 10.6 | n.d. | n.d. |
| L-NMMA | 337.8 | 489.9 | 3,480.9 | 1.5 | 10.3 | 0.1 |

Inhibitory Potency and Selectivity of Test Compounds against Three NOS Isoforms

Note:
Symbol "n.d." means not determined.

From Tables 49, 50 and 51, the following are clear:

1. The compounds of Examples 28, 96, 104, 122, 131, 171, 175, 270 and 324 are more potent in inhibiting N-cNOS than L-MIN which exhibited the strongest N-cNOS inhibitory activity in the existing NOS inhibitors;
2. From a viewpoint of the selectivity for N-cNOS compared to E-cNOS, the compounds of Examples 96, 122, 131, 175, 267, 270, 298, 324, 337, 350, 438, 452, 458, 466, 473, 538 and 560 have more selective inhibitory effect on N-cNOS than L-EIN which exhibited the highest selective inhibitory effect on N-cNOS in the existing NOS inhibitors;
3. The compounds of Examples 12, 28, 96, 104 and 131 are more potent in inhibiting iNOS than L-MIN which exhibited the strongest iNOS inhibitory activity in the existing NOS inhibitors;
4. From a viewpoint of the selectivity for iNOS compared to E-cNOS, the compounds of Examples 96, 131, 267 and 538 have more selective inhibitory effect on iNOS than L-NIO which exhibited the highest selective inhibitory effect on iNOS in the exisiting NOS inhibitors.

Test Example 2

An experiment was conducted to evaluate the effectiveness of a compound within the scope of the invention using a rat model of focal cerebral ischemia. Such models were prepared by occluding the left middle cerebral artery (MCA) in accordance with the method already reported by the present inventors (Nagafuji et al., Neurosci. Lett. 147, 159–162, 1992; Nagafuji et al., in Brain Edema IX (Ito et al., eds.) 60, pp. 285–288, 1994, Springer-Verlag; Nagafuji et al., Neuroreport 6, 1541–1545, 1995).

Eight- to nine-week old male SD rats were allowed to inhale 2% halothane (70% $N_2O$ and 30% $O_2$) for inducing anesthesia, then 1% halothane to maintain, and fitted with a polyethylene catheter into the right femoral vein for drug administration. Each of the thus anesthesized rats was placed in lateral position on an operating bench. A skin incision was made between the left external auditory pore and the lateral angle of eye and incision was effected along the anterior margin of the temporal muscle down to the zygomatic arch, with the temporal muscle being later extracted with a bipolar coagulator. Under a surgical microscope, the third branch of the trigeminal nerve was identified in the bottom part of the temporal bone as running inside the temporal muscle and a small hole with a diameter of about 3 mm was opened by means of a dental drill, the blade of which had been immersed in ice-cold physiological saline, in a position between the foramen oval from which the identified third branch extended and the orbital fissure. A thin layer of the bone was removed by means of a micro-hook and a micro-needle holder.

Subsequently, the dura mater and arachnoidea were slightly cut by means of a needle (27G) and a micro-hook and the MCA trunk was occluded with a mini-clip at a proximal portion to the lenticulostriate artery (LSA)

In permanent occlusion models, both the MCA trunk and the LSA were cut off by cauterizing with a bipolar coagulator. In temporary occlusion models, only occlusion with a mini-clip was performed and the clip was removed under a surgical microscope to allow for reperfusion.

Immediately after occlusion of the MCA, either a control solvent (0.9% physiological saline, 10 μl/h) or the compound of Example 96 (0.12–3.6 μg/kg) was injected through the right femoral vein. Thereafter, an osmotic pump (Alzet) connected to the catheter was buried under the skin of each rat and sustained infusion of the solvent or the test compound was started (0.01–0.3 μg/kg/min). Finally, a gel foam that had been immersed in antibiotic-containing physiological saline was packed into the incised cavity, the wound was sutured and all animals were returned to individual cages.

The water content in the brain which was an index of brain edema formation was measured by the dry-wet method (Nagafuji et al., Neurosci. Lett. 147, 159–162, 1992) in the following manner. Forty-eight hours after the MCA occlusion, the rats were decapitated and both the right and left cerebral hemispheres were extracted from each animal within 60 seconds; the wet weight of the brain tissue of each hemisphere was measured with a chemical balance within 90 seconds. Thereafter, the hemispheres were dried in an oven at 105° C. for 3 days and their dry weights were measured. The water content in the brain was determined by the following forumula: (wet weight–dry weight)/(wet weight)×100 (%). The percentage of the water content in the stroke side (left hemisphere) to the water content in contralateral side (right hemisphere) is shown in FIG. 1.

In the experiment for evaluating the action in reducing brain infarct volume, the rats were decapitated after 3-h MCA occlusion followed by 24-h reperfusion and the whole brain was extracted; thereafter, six serial coronal sections were sliced at 2-mm intervals from the frontal lobe (Nagafuji et al., Neuroreport 6, 1541–1545, 1995). The slices were immersed in a solution of 2% 2,3,5-triphenyltetrazolium hydrochloride (TTC) in physiological saline at 37° C. for 30 min and a photograph was taken of both sides of each slice. The photographic images were read with a scanner and the infarct area in each slice was determined on a computer in accordance with the following equation: the infarct area in the stroke hemisphere=(the normal area in the contralateral hemisphere)–(the normal area in the stroke hemisphere) using an image analyzing software (NIH Image) to avoid overestamination of the infarct area due to edema formation.

Figure 2:
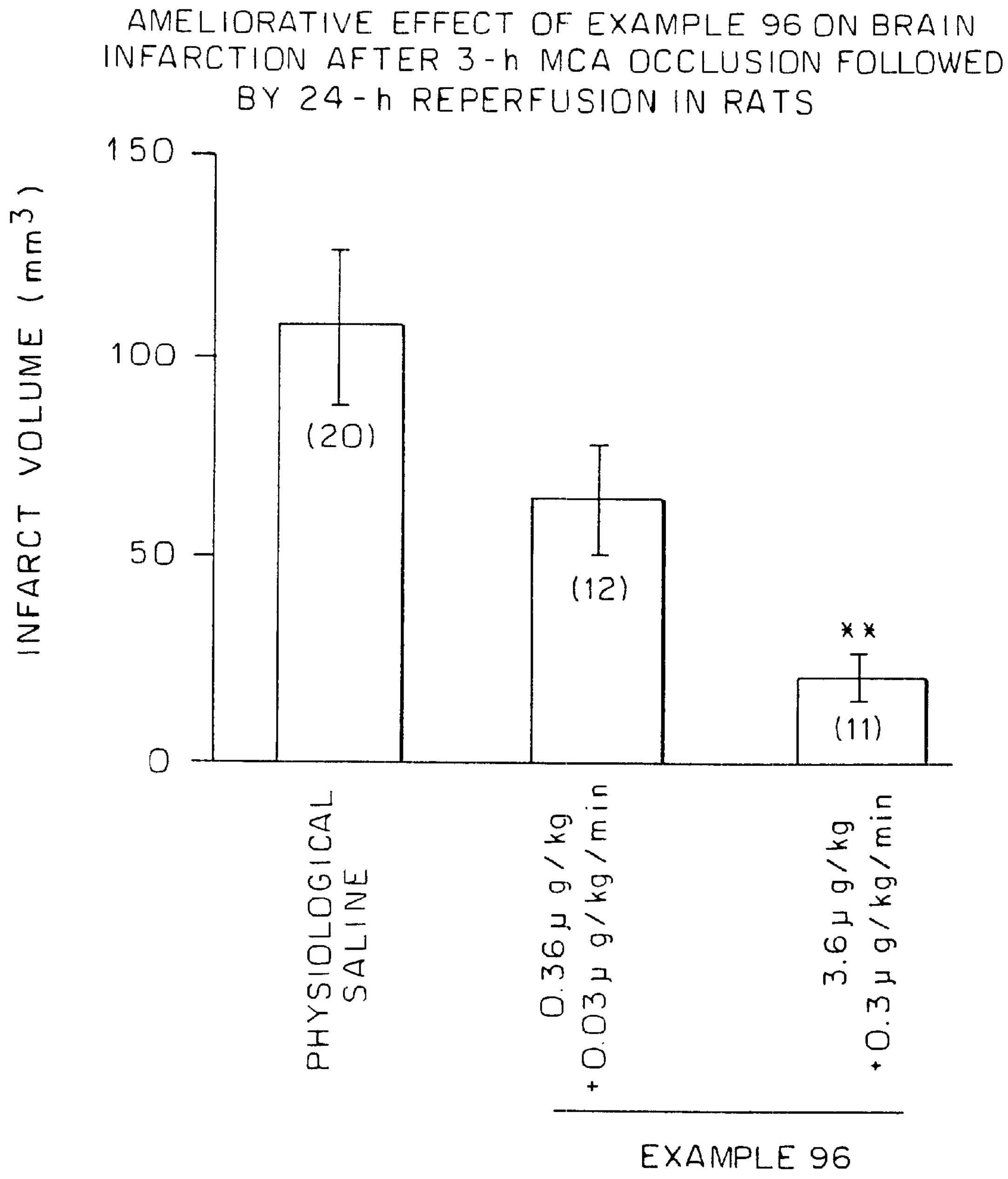
FIG. 2 is a graph showing the efficacy of the compound of Example 96 in ameliorating the brain infarction formed after 3-h occlusion of the left middle cerebral artery and subsequent 24-h reperfusion in rats.

The infarct volume was calculated as the total sum of the volumes of individual foci which were determined by the formula of (infarct area)×(1 mm) and the results are shown in FIG. 2.

All experimental data are expressed by mean ± standard error, with the number of animals in each group indicated within parentheses. For statistical analysis, a parametric Dunnett's multiple comparative test was conducted and the case having a risk factor (p value) of less than 0.05 was regarded as "statistically significant".

As shown in FIG. 1, the percentage of the water content in the stroke hemisphere to the contralateral hemisphere of the control group increased to about 103.8% after 48 hours of the MCA occlusion, obviously indicating the edema formation. This increase in the percentage of the water content was reduced in a dose-dependent manner by the administration of the compound of Example 96; in the group which was given by a sustained infusion of the compound at 0.3 μg/kg/min following an intravenous bolus administration of 3.6 μg/kg, the percentage of the water content decreased to about 102.1%, which was statistically significant ($p<0.01$). The absolute water content in the contralateral hemisphere of the control group was 79.29±0.06%.

As shown in FIG. 2, the extensive infarction over the dorsal striatum and the cerebral cortex in the left hemisphere which was estimated about 104.2 $mm^3$ was observed after 3-h MCA occlusion and 24-h reperfusion. This infarction could be ameliorated in a dose-dependent manner by the administration of the compound of Example 96; in the group which was given by a sustained infusion of 0.3 μg/kg/min following an intravenous bolus administration of 3.6 μg/kg, the infarct volume decreased by about 79.7%, which was statistically significant ($p<0.01$).

These experimental data suggest that the compounds of the invention including Exmaple 96 offer advantages that are effective and preferred for the purpose of treating cerebrovascular diseases.

INDUSTRIAL APPLICABILITY

The compounds of the invention exhibit a stronger N-cNOS or iNOS inhibiting activity than existing NOS inhibitors or they exhibit particularly high selectivity in inhibitory action against N-cNOS or iNOS among the three NOS isoforms; hence, the compounds are useful as therapeutics of the pathology in cerebrovascular diseases, in particular, occlusive cerebrovascular diseases, as well as traumatic brain injuries, seizure, headache and other pains, morphine tolerance and dependence, alzheimer's disease, Parkinson's disease, septic shocks, chronic rheumatoid arthritis, osteoarthritis, viral, or nonviral infections and diabetes.

What is claimed is:

1. A compound represented by the formula (1) or a possible stereoisomer or an optically active form of the compound or a pharmaceutically acceptable salt thereof:

(1)

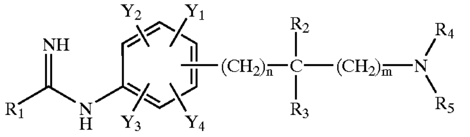

(where $R_1$ is $SR_6$ or $NR_7R_8$;

$R_6$ is an optionally substituted straight-chained or branched alkyl group having 1–6 carbon atoms or a straight-chained or branched alkenyl group having 2–6 carbon atoms;

$R_7$ is a hydrogen atom, a straight-chained or branched alkyl group having 1–6 carbon atoms, a cyclic alkyl group having 3–8 carbon atoms, a straight-chained or branched alkenyl group having 2–6 carbon atoms, a straight-chained or branched alkynyl group having 3–6 carbon atoms, a straight-chained or branched alkoxy group having 1–6 carbon atoms, or a nitro group;

$R_8$ is a hydrogen atom or a straight-chained or branched alkyl group having 1–6 carbon atoms;

$R_2$ is a hydrogen atom, a straight-chained or branched alkyl group having 1–6 carbon atoms, an alkoxycarbonyl group of which the alkyl portion is a straight-chained or branched alkyl group having 1–6 carbon atoms or a carboxyl group, or may combine with $R_3$ to form a 3- to 8-membered ring;

$R_3$ is a hydrogen atom or a straight-chained or branched alkyl group having 1–6 carbon atoms, or may combine with $R_2$ to form a 3- to 8-membered ring;

$R_4$ is a hydrogen atom, a straight-chained or branched alkyl group having 1–6 carbon atoms, an alkoxycarbonyl group of which the alkyl portion is a straight-chained or branched alkyl group having 1–6 carbon atoms, an optionally substituted acyl group having 1–8 carbon atoms or an amidino group that may be substituted on the nitrogen atom with a straight-chained or branched alkyl group having 1–6 carbon atoms or a cyclic alkyl group having 3–8 carbon atoms or a nitro group, or may combine with $R_5$ to form a 3- to 8-membered ring; carbon atoms, or an optionally substituted cyclic alkyl group having 3–6 carbon atoms, an acyl group having 1–8 carbon atoms, an alkoxycarbonyl group of which the alkyl portion is a straight-chained or branched alkyl group having 1–6 carbon atoms, or $Y_5$ and $Y_6$ may combine together to form a 3- to 8-membered ring;

$R_5$ is a hydrogen atom, a straight-chained or branched alkyl group having 1–6 carbon atoms, an alkoxycarbonyl group of which the alkyl portion is a straight-chained or branched alkyl group having 1–6 carbon atoms, an alkoxycabonylamino group of which the alkyl portion is a straight-chained or branched alkyl group having 1–6 carbon atoms or an amino group, or may combine with $R_4$ to form a 3- to 8-membered ring;

$Y_1$, $Y_2$, $Y_3$ and $Y_4$ which may be the same or different are each a hydrogen atom, a halogen atom, a nitro group, a cyano group, a hydroxyl group, a straight-chained or branched alkyl group having 1–6 carbon atoms that may be substituted by 1–3 halogen atoms, a cyclic alkyl group having 3–6 carbon atoms that may be substituted by 1–3 halogen atoms, a straight-chained or branched alkenyl group having 2–6 carbon atoms, a straight-chained or branched alkynyl group having 2–6 carbon atoms, an optionally substituted straight-chained or branched alkoxy group having 1–6 carbon atoms, a straight-chained or branched alkylthio group having 1–6 carbon atoms, $NY_5Y_6$ or $COY_7$;

where $Y_5$ and $Y_6$ which may be the same or different are each a hydrogen atom, an optionally substituted straight-chained or branched alkyl group having 1–6

$Y_7$ is a hydrogen atom, a hydroxyl group, a straight-chained or branched alkyl group having 1–6 carbon atoms or a cyclic alkyl group having 3–6 carbon atoms, an alkoxy group of which the alkyl portion is a straight-chained or branched alkyl group having 1–6 carbon atoms or $NY_5Y_6$;

where $Y_5$ and $Y_6$ which may be the same or different are each a hydrogen atom, a straight-chained or branched alkyl group having 1–6 carbon atoms or a cyclic alkyl group having 3–6 carbon atoms; and n and m are each an integer of 0 or 1, with the proviso that
2-benzyloxycarbonylamino-3-(4-(N'-nitro)guanidinophenyl)propionic acid,
2-t-butoxycarbonylamino-3-(4-(N'-nitro)guanidinophenyl)propionic acid,
2-amino-3-(4-(N'-nitro)guanidinophenyl)propionic acid,
2-amino-3-(4-guanidinophenyl)propionic acid, and
an optically active form thereof are excluded and with the further proviso that when $R_1$ is $NR_7R_8$, then $R_2$ is neither a carboxyl group nor an ester thereof, and with the further proviso that $R_7$, $R_8$, $R_2$, $R_3$, $R_4$, $R_5$, $Y_1$, $Y_2$, $Y_3$ and $Y_4$ are not all hydrogen when m and n are O.

2. A compound of the general formula (1) according to claim 1 or a possible stereoisomer or optically active form of the compound or a pharmaceutically acceptable salt thereof, in which:

$R_1$ is $SR_6$, where $R_6$ is an optionally substituted straight-chained or branched alkyl group having 1–6 carbon atoms or a straight-chained or branched alkenyl group having 2–6 carbon atoms;

$R_2$ is a hydrogen atom, a straight-chained or branched alkyl group having 1–6 carbon atoms, an alkoxycarbonyl group of which the alkyl portion is a straight-chained or branched alkyl group having 1–6 carbon atoms or a carboxyl group, or may combine with $R_3$ to form a 3- to 8-membered ring;

$R_3$ is a hydrogen atom or a straight-chained or branched alkyl group having 1–6 carbon atoms, or may combine with $R_2$ to form a 3- to 8-membered ring;

$R_4$ is a hydrogen atom, a straight-chained or branched alkyl group having 1–6 carbon atoms, an alkoxycarbonyl group of which the alkyl portion is a straight-chained or branched alkyl group having 1–6 carbon atoms, an optionally substituted acyl group having 1–8 carbon atoms or an amidino group that may be substituted on the nitrogen atom with a straight-chained or branched alkyl group having 1–6 carbon atoms or a cyclic alkyl group having 3–8 carbon atoms or a nitro group, or may combine with $R_5$ to form a 3- to 8-membered ring;

$R_5$ is a hydrogen atom, a straight-chained or branched alkyl group having 1–6 carbon atoms or an alkoxycarbonyl group of which the alkyl portion is a straight-chained or branched alkyl group having 1–6 carbon atoms, or may combine with $R_4$ to form a 3- to 8-membered ring;

$Y_1$, $Y_2$, $Y_3$ and $Y_4$ which may be the same or different are each a hydrogen atom, a halogen atom, a nitro group, a cyano group, a hydroxyl group, a straight-chained or branched alkyl group having 1–6 carbon atoms that may be substituted by 1–3 halogen atoms, a cyclic alkyl group having 3–6 carbon atoms that may be substituted by 1–3 halogen atoms, a straight-chained or branched alkenyl group having 2–6 carbon atoms, a straight-chained or branched alkynyl group having 2–6 carbon atoms, an optionally substituted straight-chained or branched alkoxy group having 1–6 carbon atoms, a straight-chained or branched alkylthio group having 1–6 carbon atoms, $NY_5Y_6$ or $COY_7$;

where $Y_5$ and $Y_6$ which may be the same or different are each a hydrogen atom, an optionally substituted straight-chained or branched alkyl group having 1–6 carbon atoms, or an optionally substituted cyclic alkyl group having 3–6 carbon atoms, an acyl group having 1–8 carbon atoms, an alkoxycarbonyl group of which the alkyl portion is a straight-chained or branched alkyl group having 1–6 carbon atoms, or $Y_5$ and $Y_6$ may combine together to form a 3- to 8-membered ring;

$Y_7$ is a hydrogen atom, a hydroxyl group, a straight-chained or branched alkyl group having 1–6 carbon atoms or a cyclic alkyl group having 3–6 carbon atoms, an alkoxy group of which the alkyl portion is a straight-chained or branched alkyl group having 1–6 carbon atoms or $NY_5Y_6$;

where $Y_5$ and $Y_6$ which may be the same or different are each a hydrogen atom, a straight-chained or branched alkyl group having 1–6 carbon atoms or a cyclic alkyl group having 3–6 carbon atoms; and n and m are each an integer of 0 or 1.

3. A compound of the general formula (1) according to claim 1 or a possible stereoisomer or optically active form of the compound or a pharmaceutically acceptable salt thereof, in which:

$R_1$ is $SR_6$, where $R_6$ is an optionally substituted straight-chained or branched alkyl group having 1–6 carbon atoms;

$R_2$ and $R_3$ which may be the same or different are each a hydrogen atom or a straight-chained or branched alkyl group having 1–6 carbon atoms, or $R_2$ and $R_3$ may combine together to form a 3- to 8-membered ring;

$R_4$ and $R_5$ are each a hydrogen atom;

$Y_1$, $Y_2$, $Y_3$ and $Y_4$ which may be the same or different are each a hydrogen atom, a halogen atom, a nitro group, a cyano group, a hydroxyl group, a straight-chained or branched alkyl group having 1–6 carbon atoms that may be substituted by 1–3 halogen atoms, a cyclic alkyl group having 3–6 carbon atoms that may be substituted by 1–3 halogen atoms, a straight-chained or branched alkenyl group having 2–6 carbon atoms, a straight-chained or branched alkynyl group having 2–6 carbon atoms, an optionally substituted straight-chained or branched alkoxy group having 1–6 carbon atoms, a straight-chained or branched alkylthio group having 1–6 carbon atoms, $NY_5Y_6$ or $COY_7$;

where $Y_5$ and $Y_6$ which may be the same or different are each a hydrogen atom, an optionally substituted straight-chained or branched alkyl group having 1–6 carbon atoms, or an optionally substituted cyclic alkyl group having 3–6 carbon atoms, an acyl group having 1–8 carbon atoms, an alkoxycarbonyl group of which the alkyl portion is a straight-chained or branched alkyl group having 1–6 carbon atoms, or $Y_5$ and $Y_6$ may combine together to form a 3- to 8-membered ring;

$Y_7$ is a hydrogen atom, a hydroxyl group, a straight-chained or branched alkyl group having 1–6 carbon atoms or a cyclic alkyl group having 3–6 carbon atoms, an alkoxy group of which the alkyl portion is a straight-chained or branched alkyl group having 1–6 carbon atoms or $NY_5Y_6$;

where $Y_5$ and $Y_6$ which may be the same or different are each a hydrogen atom, a straight-chained or branched alkyl group having 1–6 carbon atoms or a cyclic alkyl group having 3–6 carbon atoms; and n and m are each an integer of 0 or 1.

4. A compound of the general formula (1) according to claim 1 or a possible stereoisomer or optically active form of the compound or a pharmaceutically acceptable salt thereof, in which:

the substituents other than $Y_1$, $Y_2$, $Y_3$ and $Y_4$ are m-substituted on the benzene nucleus;

$R_1$ is a methylthio or ethylthio group;

$R_2$ is a hydrogen atom or a straight-chained or branched alkyl group having 1–6 carbon atoms or may combine with $R_3$ to form a 3- to 8-membered ring;

$R_3$ is a hydrogen atom or a straight-chained or branched alkyl group having 1–6 carbon atoms, or may combine with $R_2$ to form a 3- to 8-membered ring;

$R_4$ and $R_5$ are each a hydrogen atom;

$Y_1$, $Y_2$, $Y_3$ and $Y_4$ which may be the same or different are each a hydrogen atom, a halogen atom, a nitro group, a cyano group, a hydroxyl group, a straight-chained or branched alkyl group having 1–6 carbon atoms that may be substituted by 1–3 halogen atoms, a cyclic alkyl group having 3–6 carbon atoms that may be substituted by 1–3 halogen atoms, a straight-chained or branched alkenyl group having 2–6 carbon atoms, a straight-chained or branched alkynyl group having 2–6 carbon atoms, an optionally substituted straight-chained or branched alkoxy group having 1–6 carbon atoms, a straight-chained or branched alkylthio group having 1–6 carbon atoms, $NY_5Y_6$ or $COY_7$;

where $Y_5$ and $Y_6$ which may be the same or different are each a hydrogen atom, an optionally substituted straight-chained or branched alkyl group having 1–6 carbon atoms, or an optionally substituted cyclic alkyl group having 3–6 carbon atoms, an acyl group having 1–8 carbon atoms, an alkoxycarbonyl group of which the alkyl portion is a straight-chained or branched alkyl group having 1–6 carbon atoms, or $Y_5$ and $Y_6$ may combine together to form a 3- to 8-membered ring;

$Y_7$ is a hydrogen atom, a hydroxyl group, a straight-chained or branched alkyl group having 1–6 carbon atoms or a cyclic alkyl group having 3–6 carbon atoms, an alkoxy group of which the alkyl portion is a straight-chained or branched alkyl group having 1–6 carbon atoms or $NY_5Y_6$;

where $Y_5$ and $Y_6$ which may be the same or different are each a hydrogen atom, a straight-chained or branched alkyl group having 1–6 carbon atoms or a cyclic alkyl group having 3–6 carbon atoms; and n and m are each an integer of 0 or 1.

5. A compound of the general formula (1) according to claim 1 or a possible stereoisomer or optically active form of the compound or a pharmaceutically acceptable salt thereof, in which:

the substituents other than $Y_1$, $Y_2$, $Y_3$ and $Y_4$ are m-substituted on the benzene nucleus;

$R_1$ is a methylthio or ethylthio group;

$R_2$ and $R_3$ are each a hydrogen atom;

$R_4$ is a hydrogen atom, a straight-chained or branched alkyl group having 1–6 carbon atoms, or may combine with $R_5$ to form a 3- to 8-membered ring;

$R_5$ is a hydrogen atom or a straight-chained or branched alkyl group having 1–6 carbon atoms, or may combine with $R_4$ to form a 3- to 8-membered ring;

$Y_1$, $Y_2$, $Y_3$ and $Y_4$ which may be the same or different are each a hydrogen atom, a halogen atom, a nitro group, a cyano group, a hydroxyl group, a straight-chained or branched alkyl group having 1–6 carbon atoms that may be substituted by 1–3 halogen atoms, a cyclic alkyl group having 3–6 carbon atoms that may be substituted by 1–3 halogen atoms, a straight-chained or branched alkenyl group having 2–6 carbon atoms, a straight-chained or branched alkynyl group having 2–6 carbon atoms, an optionally substituted straight-chained or branched alkoxy group having 1–6 carbon atoms, a straight-chained or branched alkylthio group having 1–6 carbon atoms, $NY_5Y_6$ or $COY_7$;

where $Y_5$ and $Y_6$ which may be the same or different are each a hydrogen atom, an optionally substituted straight-chained or branched alkyl group having 1–6 carbon atoms, or an optionally substituted cyclic alkyl group having 3–6 carbon atoms, an acyl group having 1–8 carbon atoms, an alkoxycarbonyl group of which the alkyl portion is a straight-chained or branched alkyl group having 1–6 carbon atoms, or $Y_5$ and $Y_6$ may combine together to form a 3- to 8-membered ring;

$Y_7$ is a hydrogen atom, a hydroxyl group, a straight-chained or branched alkyl group having 1–6 carbon atoms or a cyclic alkyl group having 3–6 carbon atoms, an alkoxy group of which the alkyl portion is a straight-chained or branched alkyl group having 1–6 carbon atoms or $NY_5Y_6$;

where $Y_5$ and $Y_6$ which may be the same or different are each a hydrogen atom, a straight-chained or branched alkyl group having 1–6 carbon atoms or a cyclic alkyl group having 3–6 carbon atoms; and n and m are each an integer of 0 or 1.

6. A compound of the general formula (1) according to claim 1 or a possible stereoisomer or optically active form of the compound or a pharmaceutically acceptable salt thereof, in which;

the substituents other than $Y_1$, $Y_2$, $Y_3$ and $Y_4$ are m-substituted on the benzene nucleus;

$R_1$ is a methylthio or ethylthio group;

$R_2$ is a hydrogen atom or a methyl or ethyl group;

$R_3$ is a hydrogen atom or a methyl group;

$R_4$ and $R_5$ are each a hydrogen atom;

$Y_1$, $Y_2$, $Y_3$ and $Y_4$ which may be the same or different are each a hydrogen atom, a halogen atom, a nitro group, a cyano group, a hydroxyl group, a straight-chained or branched alkyl group having 1–6 carbon atoms that may be substituted by 1–3 halogen atoms, a cyclic alkyl group having 3–6 carbon atoms that may be substituted by 1–3 halogen atoms, a straight-chained or branched alkenyl group having 2–6 carbon atoms, a straight-chained or branched alkynyl group having 2–6 carbon atoms, an optionally substituted straight-chained or branched alkoxy group having 1–6 carbon atoms, a straight-chained or branched alkylthio group having 1–6 carbon atoms, $NY_5Y_6$ or $COY_7$;

where $Y_5$ and $Y_6$ which may be the same or different are each a hydrogen atom, an optionally substituted straight-chained or branched alkyl group having 1–6 carbon atoms, or an optionally substituted cyclic alkyl group having 3–6 carbon atoms, an acyl group having 1–8 carbon atoms, an alkoxycarbonyl group of which the alkyl portion is a straight-chained or branched alkyl group having 1–6 carbon atoms, or $Y_5$ and $Y_6$ may combine together to form a 3- to 8-membered ring;

$Y_7$ is a hydrogen atom, a hydroxyl group, a straight-chained or branched alkyl group having 1–6 carbon atoms or a cyclic alkyl group having 3–6 carbon atoms, an alkoxy group of which the alkyl portion is a straight-chained or branched alkyl group having 1–6 carbon atoms or $NY_5Y_6$;

where $Y_5$ and $Y_6$ which may be the same or different are each a hydrogen atom, a straight-chained or branched alkyl group having 1–6 carbon atoms or a cyclic alkyl group having 3–6 carbon atoms; and n and m are each an integer of 0 or 1.

7. A compound of the general formula (1) according to claim 1 or a possible stereoisomer or optically active form of the compound or a pharmaceutically acceptable salt thereof, in which;

the substituents other than $Y_1$, $Y_2$, $Y_3$ and $Y_4$ are p-substituted on the benzene nucleus;

$R_1$ is a methylthio or ethylthio group;

$R_2$ is a hydrogen atom or a methyl or ethyl group;

$R_3$ is a hydrogen atom or a methyl group;

$R_4$ and $R_5$ are each a hydrogen atom;

$Y_1$, $Y_2$, $Y_3$ and $Y_4$ which may be the same or different are each a hydrogen atom, a halogen atom, a nitro group, a cyano group, a hydroxyl group, a straight-chained or branched alkyl group having 1–6 carbon atoms that may be substituted by 1–3 halogen atoms, a cyclic alkyl group having 3–6 carbon atoms that may be substituted by 1–3 halogen atoms, a straight-chained or branched alkenyl group having 2–6 carbon atoms, a straight-chained or branched alkynyl group having 2–6 carbon atoms, an optionally substituted straight-chained or branched alkoxy group having 1–6 carbon atoms, a straight-chained or branched alkylthio group having 1–6 carbon atoms, $NY_5Y_6$ or $COY_7$;

where $Y_5$ and $Y_6$ which may be the same or different are each a hydrogen atom, an optionally substituted straight-chained or branched alkyl group having 1–6 carbon atoms, or an optionally substituted cyclic alkyl group having 3–6 carbon atoms, an acyl group having 1–8 carbon atoms, an alkoxycarbonyl group of which the alkyl portion is a straight-chained or branched alkyl group having 1–6 carbon atoms, or $Y_5$ and $Y_6$ may combine together to form a 3- to 8-membered ring;

$Y_7$ is a hydrogen atom, a hydroxyl group, a straight-chained or branched alkyl group having 1–6 carbon atoms or a cyclic alkyl group having 3–6 carbon atoms, an alkoxy group of which the alkyl portion is a straight-chained or branched alkyl group having 1–6 carbon atoms or $NY_5Y_6$;

where $Y_5$ and $Y_6$ which may be the same or different are each a hydrogen atom, a straight-chained or branched alkyl group having 1–6 carbon atoms or a cyclic alkyl group having 3–6 carbon atoms; and n and m are each an integer of 0 or 1.

8. A compound of the general formula (1) according to claim 1 or a possible stereoisomer or optically active form of the compound or a pharmaceutically acceptable salt thereof, in which $R_1$ is $NR_7R_8$, where $R_7$ is a hydrogen atom, a straight-chained or branched alkyl group having 1–6 carbon atoms, a cyclic alkyl group having 3–8 carbon atoms, or a nitro group and $R_8$ is a hydrogen atom, a hydrogen atom or a straight-chained or branched alkyl group having 1–6 carbon atoms;

$R_2$ is a hydrogen atom, a straight-chained or branched alkyl group having 1–6 carbon atoms, an alkoxycarbonyl group of which the alkyl portion is a straight-chained or branched alkyl group having 1–6 carbon atoms or a carboxyl group, or may combine with $R_3$ to form a 3- to 8-membered ring;

$R_3$ is a hydrogen atom or a straight-chained or branched alkyl group having 1–6 carbon atoms, or may combine with $R_2$ to form a 3- to 8-membered ring;

$R_4$ is a hydrogen atom, a straight-chained or branched alkyl group having 1–6 carbon atoms, an alkoxycarbonyl group of which the alkyl portion is a straight-chained or branched alkyl group having 1–6 carbon atoms or an amidino group that may be substituted on the nitrogen atom with a straight-chained or branched alkyl group having 1–6 carbon atoms or a cyclic alkyl group having 3–8 carbon atoms or a nitro group, or may combine with $R_5$ to form a 3- to 8-membered ring;

$R_5$ is a hydrogen atom or a straight-chained or branched alkyl group having 1–6 carbon atoms, or may combine with $R_4$ to form a 3- to 8-membered ring;

$Y_1$, $Y_2$, $Y_3$ and $Y_4$ which may be the same or different are each a hydrogen atom, a halogen atom, a nitro group, a cyano group, a hydroxyl group, a straight-chained or branched alkyl group having 1–6 carbon atoms that may be substituted by 1–3 halogen atoms, a cyclic alkyl group having 3–6 carbon atoms that may be substituted by 1–3 halogen atoms, a straight-chained or branched alkenyl group having 2–6 carbon atoms, a straight-chained or branched alkynyl group having 2–6 carbon atoms, an optionally substituted straight-chained or branched alkoxy group having 1–6 carbon atoms, a straight-chained or branched alkylthio group having 1–6 carbon atoms, $NY_5Y_6$ or $COY_7$;

where $Y_5$ and $Y_6$ which may be the same or different are each a hydrogen atom, an optionally substituted straight-chained or branched alkyl group having 1–6 carbon atoms, or an optionally substituted cyclic alkyl group having 3–6 carbon atoms, an acyl group having 1–8 carbon atoms, an alkoxycarbonyl group of which the alkyl portion is a straight-chained or branched alkyl group having 1–6 carbon atoms, or $Y_5$ and $Y_6$ may combine together to form a 3- to 8-membered ring;

$Y_7$ is a hydrogen atom, a hydroxyl group, a straight-chained or branched alkyl group having 1–6 carbon atoms or a cyclic alkyl group having 3–6 carbon atoms, an alkoxy group of which the alkyl portion is a straight-chained or branched alkyl group having 1–6 carbon atoms or $NY_5Y_6$;

where $Y_5$ and $Y_6$ which may be the same or different are each a hydrogen atom, a straight-chained or branched alkyl group having 1–6 carbon atoms or a cyclic alkyl group having 3–6 carbon atoms; and n and m are each an integer of 0 or 1.

9. A compound of the general formula (1) according to claim 1 or a possible stereoisomer or optically active form of the compound or a pharmaceutically acceptable salt thereof, in which:

the substituents other than $Y_1$, $Y_2$, $Y_3$ and $Y_4$ are m-substituted on the benzene nucleus;

$R_1$ is $NR_7R_8$, where $R_7$ is a hydrogen atom, a straight-chained or branched alkyl group having 1–6 carbon atoms, a cyclic alkyl group having 3–8 carbon atoms, or a nitro group and $R_8$ is a hydrogen atom or a straight-chained or branched alkyl group having 1–6 carbon atoms;

$R_2$ is a hydrogen atom, a straight-chained or branched alkyl group having 1–6 carbon atoms, an alkoxycarbonyl group of which the alkyl portion is a straight-chained or branched alkyl group having 1–6 carbon atoms or a carboxyl group, or may combine with $R_3$ to form a 3- to 8-membered ring;

$R_3$ is a hydrogen atom or a straight-chained or branched alkyl group having 1–6 carbon atoms, or may combine with $R_2$ to form a 3- to 8-membered ring;

$R_4$ is a hydrogen atom, a straight-chained or branched alkyl group having 1–6 carbon atoms, an alkoxycarbonyl group of which the alkyl portion is a straight-chained or branched alkyl group having 1–6 carbon atoms or an amidino group that may be substituted on the nitorogen atom with a straight-chained or branched alkyl group having 1–6 carbon atoms, a cyclic alkyl group having 3–8 carbon atoms or a nitro group, or may combine with $R_5$ to form a 3- to 8-membered ring;

$R_5$ is a hydrogen atom or a straight-chained or branched alkyl group having 1–6 carbon atoms, or may combine with $R_4$ to form a 3- to 8-membered ring;

$Y_1$, $Y_2$, $Y_3$ and $Y_4$ which may be the same or different are each a hydrogen atom, a halogen atom, a nitro group, a cyano group, a hydroxyl group, a straight-chained or branched alkyl group having 1–6 carbon atoms that may be substituted by 1–3 halogen atoms, a cyclic alkyl group having 3–6 carbon atoms that may be substituted by 1–3 halogen atoms, a straight-chained or branched alkenyl group having 2–6 carbon atoms, a straight-chained or branched alkynyl group having 2–6 carbon atoms, an optionally substituted straight-chained or branched alkoxy group having 1–6 carbon atoms, a straight-chained or branched alkylthio group having 1–6 carbon atoms, $NY_5Y_6$ or $COY_7$;

where $Y_5$ and $Y_6$ which may be the same or different are each a hydrogen atom, an optionally substituted straight-chained or branched alkyl group having 1–6 carbon atoms, or an optionally substituted cyclic alkyl group having 3–6 carbon atoms, an acyl group having 1–8 carbon atoms, an alkoxycarbonyl group of which the alkyl portion is a straight-chained or branched alkyl group having 1–6 carbon atoms, or $Y_5$ and $Y_6$ may combine together to form a 3- to 8-membered ring;

$Y_7$ is a hydrogen atom, a hydroxyl group, a straight-chained or branched alkyl group having 1–6 carbon atoms or a cyclic alkyl group having 3–6 carbon atoms, an alkoxy group of which the alkyl portion is a straight-chained or branched alkyl group having 1–6 carbon atoms or $NY_5Y_6$;

where $Y_5$ and $Y_6$ which may be the same or different are each a hydrogen atom, a straight-chained or branched alkyl group having 1–6 carbon atoms or a cyclic alkyl group having 3–6 carbon atoms; and n and m are each an integer of 0 or 1.

10. A compound of the general formula (1) according to claim 1 or a possible stereoisomer or optically active form of the compound or a pharmaceutically acceptable salt thereof, in which:

$R_1$ is a nitroamino or ethylamino group;

$R_2$ and $R_3$ which may be the same or different are each a hydrogen atom or a straight-chained or branched alkyl group having 1–6 carbon atoms, or $R_2$ and $R_3$ may combine together to form a 3- to 8-membered ring;

$R_4$ and $R_5$ are each a hydrogen atom;

$Y_1$, $Y_2$, $Y_3$ and $Y_4$ which may be the same or different are each a hydrogen atom, a halogen atom, a nitro group, a cyano group, a hydroxyl group, a straight-chained or branched alkyl group having 1–6 carbon atoms that may be substituted by 1–3 halogen atoms, a cyclic alkyl group having 3–6 carbon atoms that may be substituted by 1–3 halogen atoms, a straight-chained or branched alkenyl group having 2–6 carbon atoms, a straight-chained or branched alkynyl group having 2–6 carbon atoms, an optionally substituted straight-chained or branched alkoxy group having 1–6 carbon atoms, a straight-chained or branched alkylthio group having 1–6 carbon atoms, $NY_5Y_6$ or $COY_7$;

where $Y_5$ and $Y_6$ which may be the same or different are each a hydrogen atom, an optionally substituted straight-chained or branched alkyl group having 1–6 carbon atoms, or an optionally substituted cyclic alkyl group having 3–6 carbon atoms, an acyl group having 1–8 carbon atoms, an alkoxycarbonyl group of which the alkyl portion is a straight-chained or branched alkyl group having 1–6 carbon atoms, or $Y_5$ and $Y_6$ may combine together to form a 3- to 8-membered ring;

$Y_7$ is a hydrogen atom, a hydroxyl group, a straight-chained or branched alkyl group having 1–6 carbon atoms or a cyclic alkyl group having 3–6 carbon atoms, an alkoxy group of which the alkyl portion is a straight-chained or branched alkyl group having 1–6 carbon atoms or $NY_5Y_6$;

where $Y_5$ and $Y_6$ which may be the same or different are each a hydrogen atom, a straight-chained or branched alkyl group having 1–6 carbon atoms or a cyclic alkyl group having 3–6 carbon atoms; and n and m are each an integer of 0 or 1.

11. A compound of the general formula (1) according to claim 1 or a possible stereoisomer or optically active form of the compound or a pharmaceutically acceptable salt thereof, in which:

the substituents other than $Y_1$, $Y_2$, $Y_3$ and $Y_4$ are m-substituted on the benzene nucleus;

$R_1$ is a nitroamino or ethylamino group;

$R_2$ is a hydrogen atom or a straight-chained or branched alkyl group having 1–6 carbon atoms, or may combine with $R_3$ to form a 3- to 8-membered ring;

$R_3$ is a hydrogen atom or a straight-chained or branched alkyl group having 1–6 carbon atoms, or may combine with $R_2$ to form a 3- to 8-membered ring;

$R_4$ and $R_5$ are each a hydrogen atom;

$Y_1$, $Y_2$, $Y_3$ and $Y_4$ which may be the same or different are each a hydrogen atom, a halogen atom, a nitro group, a cyano group, a hydroxyl group, a straight-chained or branched alkyl group having 1–6 carbon atoms that may be substituted by 1–3 halogen atoms, a cyclic alkyl group having 3–6 carbon atoms that may be substituted by 1–3 halogen atoms, a straight-chained or branched alkenyl group having 2–6 carbon atoms, a straight-chained or branched alkynyl group having 2–6 carbon atoms, an optionally substituted straight-chained or branched alkoxy group having 1–6 carbon atoms, a straight-chained or branched alkylthio group having 1–6 carbon atoms, $NY_5Y_6$ or $COY_7$;

where $Y_5$ and $Y_6$ which may be the same or different are each a hydrogen atom, an optionally substituted straight-chained or branched alkyl group having 1–6 carbon atoms, or an optionally substituted cyclic alkyl group having 3–6 carbon atoms, an acyl group having 1–8 carbon atoms, an alkoxycarbonyl group of which the alkyl portion is a straight-chained or branched alkyl group having 1–6 carbon atoms, or $Y_5$ and $Y_6$ may combine together to form a 3- to 8-membered ring;

$Y_7$ is a hydrogen atom, a hydroxyl group, a straight-chained or branched alkyl group having 1–6 carbon atoms or a cyclic alkyl group having 3–6 carbon atoms, an alkoxy group of which the alkyl portion is a straight-chained or branched alkyl group having 1–6 carbon atoms or $NY_5Y_6$;

where $Y_5$ and $Y_6$ which may be the same or different are each a hydrogen atom, a straight-chained or branched alkyl group having 1–6 carbon atoms or a cyclic alkyl group having 3–6 carbon atoms; and n and m are each an integer of 0 or 1.

12. A compound of the general formula (1) according to claim 1 or a possible stereoisomer or optically active form of the compound or a pharmaceutically acceptable salt thereof, in which;

the substituents other than $Y_1$, $Y_2$, $Y_3$ and $Y_4$ are m-substituted on the benzene nucleus;

$R_1$ is a nitroamino or ethylamino group;

$R_2$ is a hydrogen atom or a methyl or ethyl group;

$R_3$ is a hydrogen atom or a methyl group;

$R_4$ and $R_5$ are each a hydrogen atom;

$Y_1$, $Y_2$, $Y_3$ and $Y_4$ which may be the same or different are each a hydrogen atom, a halogen atom, a nitro group, a cyano group, a hydroxyl group, a straight-chained or branched alkyl group having 1–6 carbon atoms that may be substituted by 1–3 halogen atoms, a cyclic alkyl group having 3–6 carbon atoms that may be substituted by 1–3 halogen atoms, a straight-chained or branched alkenyl group having 2–6 carbon atoms, a straight-chained or branched alkynyl group having 2–6 carbon atoms, an optionally substituted straight-chained or branched alkoxy group having 1–6 carbon atoms, a straight-chained or branched alkylthio group having 1–6 carbon atoms, $NY_5Y_6$ or $COY_7$;

where $Y_5$ and $Y_6$ which may be the same or different are each a hydrogen atom, an optionally substituted straight-chained or branched alkyl group having 1–6 carbon atoms, or an optionally substituted cyclic alkyl group having 3–6 carbon atoms, an acyl group having 1–8 carbon atoms, an alkoxycarbonyl group of which the alkyl portion is a straight-chained or branched alkyl group having 1–6 carbon atoms, or $Y_5$ and $Y_6$ may combine together to form a 3- to 8-membered ring;

$Y_7$ is a hydrogen atom, a hydroxyl group, a straight-chained or branched alkyl group having 1–6 carbon atoms or a cyclic alkyl group having 3–6 carbon atoms, an alkoxy group of which the alkyl portion is a straight-chained or branched alkyl group having 1–6 carbon atoms or $NY_5Y_6$;

where $Y_5$ and $Y_6$ which may be the same or different are each a hydrogen atom, a straight-chained or branched alkyl group having 1–6 carbon atoms or a cyclic alkyl group having 3–6 carbon atoms; and n and m are each an integer of 0 or 1.

13. A compound of the general formula (1) according to claim 1 or a possible stereoisomer or optically active form of the compound or a pharmaceutically acceptable salt thereof, in which;

the substituents other than $Y_1$, $Y_2$, $Y_3$ and $Y_4$ are p-substituted on the benzene nucleus;

$R_1$ is a nitroamino or ethylamino group;

$R_2$ is a hydrogen atom or a methyl or ethyl group;

$R_3$ is a hydrogen atom or a methyl group;

$R_4$ and $R_5$ are each a hydrogen atom;

$Y_1$, $Y_2$, $Y_3$ and $Y_4$ which may be the same or different are each a hydrogen atom, a halogen atom, a nitro group, a cyano group, a hydroxyl group, a straight-chained or branched alkyl group having 1–6 carbon atoms that may be substituted by 1–3 halogen atoms, a cyclic alkyl group having 3–6 carbon atoms that may be substituted by 1–3 halogen atoms, a straight-chained or branched alkenyl group having 2–6 carbon atoms, a straight-chained or branched alkynyl group having 2–6 carbon atoms, an optionally substituted straight-chained or branched alkoxy group having 1–6 carbon atoms, a straight-chained or branched alkylthio group having 1–6 carbon atoms, $NY_5Y_6$ or $COY_7$;

where $Y_5$ and $Y_6$ which may be the same or different are each a hydrogen atom, an optionally substituted straight-chained or branched alkyl group having 1–6 carbon atoms, or an optionally substituted cyclic alkyl group having 3–6 carbon atoms, an acyl group having 1–8 carbon atoms, an alkoxycarbonyl group of which the alkyl portion is a straight-chained or branched alkyl group having 1–6 carbon atoms, or $Y_5$ and $Y_6$ may combine together to form a 3- to 8-membered ring;

$Y_7$ is a hydrogen atom, a hydroxyl group, a straight-chained or branched alkyl group having 1–6 carbon atoms or a cyclic alkyl group having 3–6 carbon atoms, an alkoxy group of which the alkyl portion is a straight-chained or branched alkyl group having 1–6 carbon atoms or $NY_5Y_6$;

where $Y_5$ and $Y_6$ which may be the same or different are each a hydrogen atom, a straight-chained or branched alkyl group having 1–6 carbon atoms or a cyclic alkyl group having 3–6 carbon atoms; and n and m are each an integer of 0 or 1.

14. A compound of the general formula (1) according to claim 1 or a possible stereoisomer or optically active form of the compound or a pharmaceutically acceptable salt thereof, in which:

the substituents other than $Y_1$, $Y_2$, $Y_3$ and $Y_4$ are m-substituted on the benzene nucleus;

$R_1$ is a nitroamino or ethylamino group;

$R_2$ and $R_3$ are each a hydrogen atom;

$R_4$ is a hydrogen atom or a straight-chained or branched alkyl group having 1–6 carbon atoms, or may combine with $R_5$ to form a 3- to 8-membered ring;

$R_5$ is a hydrogen atom or a straight-chained or branched alkyl group having 1–6 carbon atoms, or may combine with $R_4$ to form a 3- to 8-membered ring;

$Y_1$, $Y_2$, $Y_3$ and $Y_4$ which may be the same or different are each a hydrogen atom, a halogen atom, a nitro group, a cyano group, a hydroxyl group, a straight-chained or branched alkyl group having 1–6 carbon atoms that may be substituted by 1–3 halogen atoms, a cyclic alkyl group having 3–6 carbon atoms that may be substituted by 1–3 halogen atoms, a straight-chained or branched alkenyl group having 2–6 carbon atoms, a straight-chained or branched alkynyl group having 2–6 carbon atoms, an optionally substituted straight-chained or branched alkoxy group having 1–6 carbon atoms, a straight-chained or branched alkylthio group having 1–6 carbon atoms, $NY_5Y_6$ or $COY_7$;

where $Y_5$ and $Y_6$ which may be the same or different are each a hydrogen atom, a straight-chained or branched alkyl group having 1–6 carbon atoms, a cyclic alkyl group having 3–6 carbon atoms, an acyl group having 1–8 carbon atoms, an alkoxycarbonyl group of which the alkyl portion is a straight-chained or branched alkyl group having 1–6 carbon atoms, or $Y_5$ and $Y_6$ may combine together to form a 3- to 8-membered ring;

$Y_7$ is a hydrogen atom, a hydroxyl group, a straight-chained or branched alkyl group having 1–6 carbon atoms or a cyclic alkyl group having 3–6 carbon atoms, an alkoxy group of which the alkyl portion is a straight-chained or branched alkyl group having 1–6 carbon atoms or $NY_5Y_6$;

where $Y_5$ and $Y_6$ which may be the same or different are each a hydrogen atom, a straight-chained or branched alkyl group having 1–6 carbon atoms or a cyclic alkyl group having 3–6 carbon atoms; and n and m are each an integer of 0 or 1.

15. A therapeutic composition for treatment of a cerebrovascular disease, Alzheimer's disease, pain, morphine tolerance or dependence, Parkinson's disease, or traumatic brain injuries, containing an N-cNOS inhibitor as an effective ingredient in an N-cNOS effective amount for the therapy of said disease, and a pharmaceutically acceptable adjuvant, wherein said N-cNOS inhibitor is a compound represented by the formula (1) of claim 1 or a possible stereoisomer or optically active form of the compound or a pharmaceutically acceptable salt thereof.

16. A therapeutic composition for treatment of septic shock, chronic rheumatoid arthritis, osteoarthritis, viral or nonviral infection, or diabetes, containing as an effective ingredient an iNOS inhibitor in an iNOS effective amount for said treatment, and a pharmaceutically acceptable diluent, wherein said iNOS inhibitor is a compound represented by the formula (1) of claim 1 or a possible stereoisomer or optically active form of the compound or a pharmaceutically acceptable salt thereof.

17. The therapeutic composition for cerebrovascular disease according to claim 15 wherein said N-cNOS inhibitor is N-(5-(S-ethylisothioureido)-2-methhoxyphenylmethyl) amine or a pharmaceutically acceptable salt thereof.

18. A compound according to claim 1 which is selected form the group consisting of:

N-(1-(3-(S-methylisothioureido)phenyl)-1-methyl)ethyl) amine;
N-(1-methyl-1-(3-(N'-nitroguanidino)phenyl)ethyl)amine;
N-(1-(3-(S-methylisothioureido)phenyl)ethyl)amine;
N-(1(3-(N'-nitoroguanidino)phenyl)ethyl)amine;
N-(1-(3-(N'-nitoroguanidino)phenyl)propyl)amine;
N-(3-(S-methylisothioureido)phenylmethyl)amine;
N-(3-(S-ethylisothioureido)phenylmethyl)amine;
N-(3-(S-ethylisothioureido)phenylmethyl)methylamine;
N-(4-(S-methylisothioureido)phenylethyl)amine;
N-(1-(3-(S-ethylisothioureido)phenyl)-1-methyl)ethyl) amine;
N-(4-(S-ethylisothioureido)phenylethyl)dimethylamine;
N-(4-(S-ethylisothioureido)phenylethyl)amine;
N-(3-(S-methylisothioureido)phenylethyl)methylamine;
N-(1-(3-(S-ethylisothioureido)phenyl)ethyl)methylamine;
N-(1-(3-(S-ethylisothioureido)phenyl)cyclopentyl)amine;
N-(1-(3-(N'-nitoroguanidino)phenyl)cyclopentyl)amine;
N-(1-(3-(S-methylisothioureido)phenyl)cyclohexyl)amine;
N-(1-(3-(S-ethylisothioureido)phenyl)cyclohexyl)amine;
N-(1-(3-(N'-nitoroguanidino)phenyl)cyclohexyl)amine;
N-(1-(3-(S-ethylisothioureido)phenyl)ethyl)amine;
N-(1-(3-(N'-nitoroguanidino)phenyl)cyclobutyl)amine;
N-(1-(3-(S-methylisothioureido)phenyl)cyclobutyl)amine;
N-(1-(3-(S-ethylisothioureido)phenyl)cyclobutyl)amine;
N-(1-(3-(S-ethylisothioureido)phenyl)cyclopropyl)amine;
N-(5-(S-ethylisothioureido)-2-methoxyphenylmethyl) amine;
N-(3-(S-ethylisothioureido)-2-methylyphenylmethyl) amine;
N-(2-chloro-3-(S-ethylisothioureido)phenylmethyl)amine;
N-(1-(3-(S-ethylisothioureido)phenyl)propyl)amine;
N-(2-dimethylamino-5-(N'-ethylguanidino)phenylmethyl) amine;
N-(2-dimethylamino-5-(S-ethylisothioureido) phenylmethyl)amine;
N-(5-(S-ethylisothioureido)-2-(N-ethyl-N-methylamino) phenylmethyl)amine;
N-(2,6-dimethoxy-3-(S-etylisothioureido)phenylmethyl) mine;
N-(2-ethoxy-5-(S-ethylisothioureido)phenylmethyl)amine;
N-(2-benzyloxy-5-(S-ethylisothioureido)phenylmethyl) amine;
N-(1-(5-(S-ethylisothioureido)-2-methoxyphenyl)-1-methylethyl)amine;
N-(3-(N'-ethylguanidino)phenylmethyl)amine;
N-(3-(S-ethylisothioureido)-2-methylphenylmethyl) methylamine:
N-(2-benzylamino-5-(S-ethylisothioureido)phenylmethyl) amine;
N-(5-(N'-ethylguanidino)-2-fluorophenylmethyl)amine;
N-(5-(S-ethylisothioureido)-2-methylaminophenylmethyl) amine;
N-(2-ethylamino-(S-ethylisothioureido)phenylmethyl) amine;
N-(2-ethyl-5-(N'-ethylguanidino)phenylmethyl)amine;

N-(5-(N'-ethylguanidino)-2-methylphenylmethyl)amine;
N-(2-(4-(S-ethylisothioureido)-2-methoxyphenyl)ethyl)amine;
N-(3-(N'-ethylguanidino)-2-methylphenylmethyl)amine;
N-(2-chloro-3-(N'-ethylguanidino)phenylmethyl)amine; and
N-(2-chloro-5-(N'-ethylguanidino)phenylmethyl)amine;
or a possible optically active form of the compound or a pharmaceutically acceptable salt thereof.

19. A compound represented by the formula (1), a possible stereoisomer thereof or an optically active form of the compound or a pharmaceutically acceptable salt thereof:

(1)

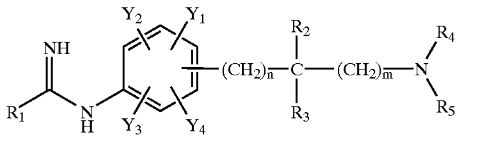

(where $R_1$ is $SR_6$ or $NHR_7$;

where $R_6$ is an optionally substituted straight-chained or branched alkyl group having 1–6 carbon atoms or a straight-chained or branched alkenyl group having 2–6 carbon atoms;

$R_7$ is a hydrogen atom, a straight-chained or branched alkyl group having 1–6 carbon atoms, a cyclic alkyl group having 3–8 carbon atoms, or a nitro group;

$R_2$ is a hydrogen atom, a straight-chained or branched alkyl group having 1–6 carbon atoms, an alkoxycarbonyl group of which the alkyl portion is a straight-chained or branched alkyl group having 1–6 carbon atoms or a carboxyl group, or may combine with $R_3$ to form a 3- to 8-membered ring;

$R_3$ is a hydrogen atom or a straight-chained or branched alkyl group having 1–6 carbon atoms, or may combine with $R_2$ to form a 3- to 8-membered ring;

$R_4$ is a hydrogen atom, a straight-chained or branched alkyl group having 1–6 carbon atoms, an alkoxycarbonyl group of which the alkyl portion is a straight-chained or branched alkyl group having 1–6 carbon atoms or an amidino group that may be substituted on the nitrogen atom with a straight-chained or branched alkyl group having 1–6 carbon atoms or a cyclic alkyl group having 3–8 carbon atoms or a nitro group, or may combine with $R_5$ to form a 3- to 8-membered ring;

$R_5$ is a hydrogen atom or a straight-chained or branched alkyl group having 1–6 carbon atoms, or may combine with $R_4$ to form a 3- to 8-membered ring;

$Y_1$, $Y_2$, $Y_3$ and $Y_4$ are each a hydrogen atom;

n is an integer of 0 or 1; and m is 0, with the proviso that 2-benzyloxycarbonylamino-3-(4-(N'-nitro)guanidinophenyl)-propionic acid, 2-t-butoxycarbonylamino-3-(4-(N'-nitro)guanidinophenyl)-propionic acid, 2-amino-3-(4-(N'-nitro)guanidinophenyl)propionic acid, 2-amino-3-(4-guanidinophenyl)propionic acid, and an optically active form thereof are excluded, and with the further proviso that when $R_1$ is $NR_7R_8$, then $R_2$ is neither a carboxyl group nor an ester thereof, and with the further proviso that when m and n are both O, $R_7$, $R_8$, $R_2$, $R_3$, $R_4$, $R_5$, $Y_1$, $Y_2$, $Y_3$ and $Y_4$ are not all hydrogen.

20. A compound of the general formula (1) according to claim 19 or a possible stereoisomer or optically active form of the compound or a pharmaceutically acceptable salt thereof, in which:

$R_1$ is $SR_6$, where $R_6$ is an optionally substituted straight-chained or branched alkyl group having 1–6 carbon atoms or a straight-chained or branched alkenyl group having 2–6 carbon atoms;

$R_2$ is a hydrogen atom, a straight-chained or branched alkyl group having 1–6 carbon atoms, an alkoxycarbonyl group of which the alkyl portion is a straight-chained or branched alkyl group having 1–6 carbon atoms or a carboxyl group, or may combine with $R_3$ to form a 3- to 8-membered ring;

$R_3$ is a hydrogen atom or a straight-chained or branched alkyl group having 1–6 carbon atoms, or may combine with $R_2$ to form a 3- to 8-membered ring;

$R_4$ is a hydrogen atom, a straight-chained or branched alkyl group having 1–6 carbon atoms, an alkoxycarbonyl group of which the alkyl portion is a straight-chained or branched alkyl group having 1–6 carbon atoms, or an amidino group that may be substituted on the nitrogen atom with a straight-chained or branched alkyl group having 1–6 carbon atoms or a cyclic alkyl group having 3–8 carbon atoms or a nitro group, or may combine with $R_5$ to form a 3- to 8-membered ring;

$R_5$ is a hydrogen atom or a straight-chained or branched alkyl group having 1–6 carbon atoms, or may combine with $R_4$ to form a 3- to 8-membered ring; $Y_1$, $Y_2$, $Y_3$ and $Y_4$ are each a hydrogen atom;

n is an integer of 0 or 1; and m is 0.

21. A compound of the general formula (1) according to claim 19 or a possible stereoisomer or optically active form of the compound or a pharmaceutically acceptable salt thereof, in which:

$R_1$ is $SR_6$, where $R_6$ is an optionally substituted straight-chained or branched alkyl group having 1–6 carbon atoms;

$R_2$ and $R_3$ which may be the same or different are each a hydrogen atom or a straight-chained or branched alkyl group having 1–6 carbon atoms;

$R_4$ and $R_5$ are each a hydrogen atom;

$Y_1$, $Y_2$, $Y_3$ and $Y_4$ are each a hydrogen atom;

n is an integer of 0 or 1; and m is 0.

22. A compound of the general formula (1) according to claim 19 or a possible stereoisomer or optically active form of the compound or a pharmaceutically acceptable salt thereof, in which:

the substituents other than $Y_1$, $Y_2$, $Y_3$ and $Y_4$ are m-substituted on the benzene nucleus;

$R_1$ is a methylthio or ethylthio group;

$R_2$ is a hydrogen atom or a straight-chained or branched alkyl group having 1–6 carbon atom, or may combine with $R_3$ to form a 3- to 8-membered ring;

$R_3$ is a straight-chained or branched alkyl group having 1–6 carbon atoms or may combine with $R_2$ to form a 3- to 8-membered ring;

$R_4$ and $R_5$ are each a hydrogen atom;

$Y_1$, $Y_2$, $Y_3$ and $Y_4$ are each a hydrogen atom;

n is an integer of 0 or 1; and m is 0.

23. A compound of the general formula (1) according to claim 19 or a possible stereoisomer or optically active form of the compound or a pharmaceutically acceptable salt thereof, in which:

the substituents other than $Y_1$, $Y_2$, $Y_3$ and $Y_4$ are m-substituted;

$R_1$ is a methylthio or ethylthio group;

$R_2$ and $R_3$ are each a hydrogen atom;

$R_4$ is a hydrogen atom or a straight-chained or branched alkyl group having 1–6 carbon atoms, or may combine with $R_5$ to form a 3- to 8-membered ring;

$R_5$ is a straight-chained or branched alkyl group having 1–6 carbon atoms or may combine with $R_4$ to form a 3- to 8-membered ring;

$Y_1$, $Y_2$, $Y_3$ and $Y_4$ are each a hydrogen atom;

n is an integer of 0 or 1; and m is 0.

24. A compound of the general formula (1) according to claim 19 or a possible stereoisomer or optically active form of the compound or a pharmaceutically acceptable salt thereof, in which:

the substituents other than $Y_1$, $Y_2$, $Y_3$ and $Y_4$ are m-substituted on the benzene nucleus;

$R_1$ is a methylthio or ethylthio group;

$R_2$ is a hydrogen atom or a methyl or ethyl group;

$R_3$ is a hydrogen atom or a methyl group;

$R_4$ and $R_5$ are each a hydrogen atom;

$Y_1$, $Y_2$, $Y_3$ and $Y_4$ are each a hydrogen atom; and n and m are each 0.

25. A compound of the general formula (1) according to claim 19 or a possible stereoisomer or optically active form of the compound or a pharmaceutically acceptable salt thereof, in which:

the substituents other than $Y_1$, $Y_2$, $Y_3$ and $Y_4$ are p-substituted on the benzene nucleus;

$R_1$ is a methylthio or ethylthio group;

$R_2$ is a hydrogen atom or a methyl or ethyl group;

$R_3$ is a hydrogen atom or a methyl group;

$R_4$ and $R_5$ are each a hydrogen atom;

$Y_1$, $Y_2$, $Y_3$ and $Y_4$ are each a hydrogen atom;

n is 1; and m is 0.

26. A compound of the general formula (1) according to claim 19 or a possible stereoisomer or optically active form of the compound or a pharmaceutically acceptable salt thereof, in which:

$R_1$ is $NHR_7$, where $R_7$ is a hydrogen atom, a straight-chained or branched alkyl group having 1–6 carbon atoms, a cyclic alkyl group having 3–8 carbon atoms, or a nitro group;

$R_2$ is a hydrogen atom, a straight-chained or branched alkyl group having 1–6 carbon atoms, an alkoxycarbonyl group of which the alkyl portion is a straight-chained or branched alkyl group having 1–6 carbon atoms or a carboxyl group, or may combine with $R_3$ to form a 3- to 8-membered ring;

$R_3$ is a hydrogen atom or a straight-chained or branched alkyl group having 1–6 carbon atoms, or may combine with $R_2$ to form a 3- to 8-membered ring;

$R_4$ is a hydrogen atom, a straight-chained or branched alkyl group having 1–6 carbon atoms, an alkoxycarbonyl group of which the alkyl portion is a straight-chained or branched alkyl group having 1–6 carbon atoms or an amidino group that may be substituted on the nitrogen atom with a straight-chained or branched alkyl group having 1–6 carbon atoms or a cyclic alkyl group having 3–8 carbon atoms or a nitro group, or may combine with $R_5$ to form a 3- to 8-membered ring;

$R_5$ is a hydrogen atom or a straight-chained or branched alkyl group having 1–6 carbon atoms, or may combine with $R_4$ to form a 3- to 8-membered ring;

$Y_1$, $Y_2$, $Y_3$ and $Y_4$ are each a hydrogen atom;

n is an integer of 0 or 1; and m is 0.

27. A compound of the general formula (1) according to claim 19 or a possible stereoisomer or optically active form of the compound or a pharmaceutically acceptable salt thereof, in which:

the substituents other than $Y_1$, $Y_2$, $Y_3$ and $Y_4$ are m-substituted on the benzene nucleus;

$R_1$ is $NHR_7$, where $R_7$ is a hydrogen atom, a straight-chained or branched alkyl group having 1–6 carbon atoms, a cyclic alkyl group having 3–8 carbon atoms or a nitro group;

$R_2$ is a hydrogen atom, a straight-chained or branched alkyl group having 1–6 carbon atoms, an alkoxycarbonyl group of which the alkyl portion is a straight-chained or branched alkyl group having 1–6 carbon atoms or a carboxyl group, or may combine with $R_3$ to form a 3- to 8-membered ring;

$R_3$ is a hydrogen atom or a straight-chained or branched alkyl group having 1–6 carbon atoms, or may combine with $R_2$ to form a 3- to 8-membered ring;

$R_4$ is a hydrogen atom, a straight-chained or branched alkyl group having 1–6 carbon atoms, an alkoxycarbonyl group of which the alkyl portion is a straight-chained or branched alkyl group having 1–6 carbon atoms or an amidino group that may be substituted on the nitrogen atom with a straight-chained or branched alkyl group having 1–6 carbon atoms or a cyclic alkyl group having 3–8 carbon atoms or a nitro group, or may combine with $R_5$ to form a 3- to 8-membered ring;

$R_5$ is a hydrogen atom or a straight-chained or branched alkyl group having 1–6 carbon atoms, or may combine with $R_4$ to form a 3- to 8-membered ring;

$Y_1$, $Y_2$, $Y_3$ and $Y_4$ are each a hydrogen atom;

n is an integer of 0 or 1; and m is 0.

28. A compound of the general formula (1) according to claim 19 or a possible stereoisomer or optically active form of the compound or a pharmaceutically acceptable salt thereof, in which:

$R_1$ is a nitroamino group;

$R_2$ and $R_3$ which may be the same or different are each a hydrogen atom or a straight-chained or branched alkyl group having 1–6 carbon atoms;

$R_4$ and $R_5$ are each a hydrogen atom;

$Y_1$, $Y_2$, $Y_3$ and $Y_4$ are each a hydrogen atom;

n is an integer of 0 or 1; and m is 0.

29. A compound of the general formula (1) according to claim 19 or a possible stereoisomer or optically active form of the compound or a pharmaceutically acceptable salt thereof, in which:

the substituents other than $Y_1$, $Y_2$, $Y_3$ and $Y_4$ are m-substituted on the benzene nucleus;

$R_1$ is a nitroamino group;

$R_2$ is a hydrogen atom or a straight-chained or branched alkyl group having 1–6 carbon atoms, or may combine with $R_3$ to form a 3- to 8-membered ring;

$R_3$ is a straight-chained or branched alkyl group having 1–6 carbon atoms or may combine with $R_2$ to form a 3- to 8-membered ring;

$R_4$ and $R_5$ are each a hydrogen atom;

$Y_1$, $Y_2$, $Y_3$ and $Y_4$ are each a hydrogen atom; and n is an integer of 0 or 1; and m is 0.

30. A compound of the general formula (1) according to claim 19 or a possible stereoisomer or optically active form of the compound or a pharmaceutically acceptable salt thereof, in which:

the substituents other than $Y_1$, $Y_2$, $Y_3$ and $Y_4$ are m-substituted on the benzene nucleus;

$R_1$ is a nitroamino group;

$R_2$ is a hydrogen atom or a methyl or ethyl group;

$R_3$ is a hydrogen atom or a methyl group $R_4$ and $R_5$ are each a hydrogen atom;

$Y_1$, $Y_2$, $Y_3$ and $Y_4$ are each a hydrogen atom; and n and m are each 0.

31. A compound of the general formula (1) according to claim 19 or a possible stereoisomer or optically active form of the compound or a pharmaceutically acceptable salt thereof, in which:

the substituents other than $Y_1$, $Y_2$, $Y_3$ and $Y_4$ are p-substituted on the benzene nucleus;

$R_1$ is a nitroamino group;

$R_2$ is a hydrogen atom or a methyl or ethyl group;

$R_3$ is a hydrogen atom or a methyl group;

$R_4$ and $R_5$ are each a hydrogen atom;

$Y_1$, $Y_2$, $Y_3$ and $Y_4$ are each a hydrogen atom;

n is 1; and m is 0.

32. A compound of the general formula (1) according to claim 19 or a possible stereoisomer or optically active form of the compound or a pharmaceutically acceptable salt thereof, in which:

the substituents other than $Y_1$, $Y_2$, $Y_3$ and $Y_4$ are m-substituted on the benzene nucleus;

$R_1$ is a nitroamino group;

$R_2$ and $R_3$ are each a hydrogen atom;

$R_4$ is a hydrogen atom or a straight-chained or branched alkyl group having 1–6 carbon atoms, or may combine with $R_5$ to form a 3- to 8-membered ring;

$R_5$ is a hydrogen atom or a straight-chained or branched alkyl group having 1–6 carbon atoms, or may combine with $R_4$ to form a 3- to 8-membered ring;

$Y_1$, $Y_2$, $Y_3$ and $Y_4$ are each a hydrogen atom;

n is an integer of 0 or 1; and m is 0.

33. A compound according to claim 19 which is N-(4-(S-methylisothioureido)phenylethyl)amine or a pharmaceutically acceptable salt thereof.

34. A compound according to claim 19 which is N-(4-(S-ethylisothioureido)phenylethyl)amine or a pharmaceutically acceptable salt thereof.

35. A therapeutic composition for treatment of cerebrovascular disease, containing an N-cNOS inhibitor as an effective ingredient in an N-cNOS inhibiting effective amount for the therapy of said disease, and a pharmaceutically acceptable adjuvant, wherein said N-cNOS inhibitor is a compound represented by the formula (1) according to claim 19 or a possible stereoisomer or optically active form of the compound or a pharmaceutically acceptable salt thereof.

36. The therapeutic composition for cerebrovascular disease of claim 35 wherein said N-cNOS inhibitor is N-(4-(S-methylisothioureido)phenylethyl)amine or a pharmaceutically acceptable salt thereof.

37. The therapeutic composition for cerebrovascular disease of claim 35 wherein the N-cNOS inhibitor is N-(4-(S-ethylisothioureido)phenylethyl)amine or a pharmaceutically acceptable salt thereof.

38. A therapeutic composition for treatment of septic shock containing as an effective ingredient an iNOS-effective amount sufficient for said treatment of an iNOS compound represented by the compound of claim 19 or a possible stereoisomer or optically active form or a pharmaceutically acceptable salt thereof, and a pharmaceutically acceptable adjuvant.

39. A compound of the general formula (1) according to claim 1 or a possible stereoisomer or optically active form of the compound or a pharmaceutically acceptable salt thereof, in which:

$R_1$ is $SR_6$, where $R_6$ is an optionally substituted straight-chained or branched alkyl group having 1–6 carbon atoms or a straight-chained or branched alkenyl group having 2–6 carbon atoms;

$R_2$ and $R_3$ which may be the same or different are each a hydrogen atom or a straight-chained or branched alkyl group having 1–6 carbon atoms, or $R_2$ and $R_3$ may combine together to form a 3- to 8-membered ring;

$R_4$ is a hydrogen atom, a straight-chained or branched alkyl group having 1–6 carbon atoms, an alkoxycarbonyl group of which the alkyl portion is a straight-chained or branched alkyl group having 1–6 carbon atoms, an optionally substituted acyl group having 1–8 carbon atoms or an amidino group that may be substituted on the nitrogen atom with a straight-chained or branched alkyl group having 1–6 carbon atoms or a cyclic alkyl group having 3–8 carbon atoms or a nitro group, or may combine with $R_5$ to form a 3- to 8-membered ring;

$R_5$ is a hydrogen atom, a straight-chained or branched alkyl group having 1–6 carbon atoms or an alkoxycarbonyl group of which the alkyl portion is a straight-chained or branched alkyl group having 1–6 carbon atoms, or may combine with $R_4$ to form a 3- to 8-membered ring;

$Y_1$, $Y_2$, $Y_3$ and $Y_4$ which may be the same or different are each a hydrogen atom, a halogen atom, a nitro group, a cyano group, a hydroxyl group, a straight-chained or branched alkyl group having 1–6 carbon atoms that may be substituted by 1–3 halogen atoms, a cyclic alkyl group having 3–6 carbon atoms that may be substituted by 1–3 halogen atoms, a straight-chained or branched alkenyl group having 2–6 carbon atoms, a straight-chained or branched alkynyl group having 2–6 carbon atoms, an optionally substituted straight-chained or branched alkoxy group having 1–6 carbon atoms, a straight-chained or branched alkylthio group having 1–6 carbon atoms, $NY_5Y_6$ or $COY_7$;

where $Y_5$ and $Y_6$ which may be the same or different are each a hydrogen atom, an optionally substituted straight-chained or branched alkyl group having 1–6 carbon atoms, or an optionally substituted cyclic alkyl group having 3–6 carbon atoms, an acyl group having 1–8 carbon atoms, an alkoxycarbonyl group of which the alkyl portion is a straight-chained or branched alkyl group having 1–6 carbon atoms, or $Y_5$ and $Y_6$ may combine together to form a 3- to 8-membered ring;

$Y_7$ is a hydrogen atom, a hydroxyl group, a straight-chained or branched alkyl group having 1–6 carbon atoms or a cyclic alkyl group having 3–6 carbon atoms, an alkoxy group of which the alkyl portion is a straight-chained or branched alkyl group having 1–6 carbon atoms or $NY_5Y_6$;

where $Y_5$ and $Y_6$ which may be the same or different are each a hydrogen atom, a straight-chained or branched alkyl group having 1–6 carbon atoms or a cyclic alkyl group having 3–6 carbon atoms; and n and m are each an integer of 0 or 1.

40. A compound of the general formula (1) according to claim 1 or a possible stereoisomer or optically active form of the compound or a pharmaceutically acceptable salt thereof, in which:

$R_1$ is $NR_7R_8$, where $R_7$ is a hydrogen atom, a straight-chained or branched alkyl group having 1–6 carbon atoms, a cyclic alkyl group having 3–8 carbon atoms or a nitro group, and $R_8$ is a hydrogen atom, a hydrogen atom or a straight-chained or branched alkyl group having 1–6 carbon atoms;

$R_2$ and $R_3$ which may be the same or different are each a hydrogen atom or a straight-chained or branched alkyl group having 1–6 carbon atoms, or $R_2$ and $R_3$ may combine together to form a 3- to 8-membered ring;

$R_4$ is a hydrogen atom, a straight-chained or branched alkyl group having 1–6 carbon atoms, an alkoxy-carbonyl group of which the alkyl portion is a straight-chained or branched alkyl group having 1–6 carbon atoms or an amidino group that may be substituted on the nitrogen atom with a straight-chained or branched alkyl group having 1–6 carbon atoms or a cyclic alkyl group having 3–8 carbon atoms or a nitro group, or may combine with $R_5$ to form a 3- to 8-membered ring;

$R_5$ is a hydrogen atom or a straight-chained or branched alkyl group having 1–6 carbon atoms, or may combine with $R_4$ to form a 3- to 8-membered ring;

$Y_1$, $Y_2$, $Y_3$ and $Y_4$ which may be the same or different are each a hydrogen atom, a halogen atom, a nitro group, a cyano group, a hydroxyl group, a straight-chained or branched alkyl group having 1–6 carbon atoms that may be substituted by 1–3 halogen atoms, a cyclic alkyl group having 3–6 carbon atoms that may be substituted by 1–3 halogen atoms, a straight-chained or branched alkenyl group having 2–6 carbon atoms, a straight-chained or branched alkynyl group having 2–6 carbon atoms, an optionally substituted straight-chained or branched alkoxy group having 1–6 carbon atoms, a straight-chained or branched alkylthio group having 1–6 carbon atoms, $NY_5Y_6$, or $COY_7$;

where $Y_5$ and $Y_6$ which may be the same or different are each a hydrogen atom, an optionally substituted straight-chained or branched alkyl group having 1–6 carbon atoms, or an optionally substituted cyclic alkyl group having 3–6 carbon atoms, an acyl group having 1–8 carbon atoms, an alkoxycarbonyl group of which the alkyl portion is a straight-chained or branched alkyl group having 1–6 carbon atoms, or $Y_5$ and $Y_6$ may combine together to form a 3- to 8-membered ring;

$Y_7$ is a hydrogen atom, a hydroxyl group, a straight-chained or branched alkyl group having 1–6 carbon atoms or a cyclic alkyl group having 3–6 carbon atoms, an alkoxy group of which the alkyl portion is a straight-chained or branched alkyl group having 1–6 carbon atoms or $NY_5Y_6$;

where $Y_5$ and $Y_6$ which may be the same or different are each a hydrogen atom, a straight-chained or branched alkyl group having 1–6 carbon atoms or a cyclic alkyl group having 3–6 carbon atoms; and n and m are each an integer of 0 or 1.

41. A therapeutic composition for cerebrovascular diseases containing a pharmaceutical carrier and as an effective ingredient an amount sufficient therefor of an N-cNOS inhibitor compound of the formula (1) according to claim 1 or a possible stereoisomer or optically active form of the compound or a pharmaceutically acceptable salt thereof, in which:

$R_1$ is $SR_6$, where $R_6$ is an optionally substituted straight-chained or branched alkyl group having 1–6 carbon atoms or a straight-chained or branched alkenyl group having 2–6 carbon atoms;

$R_2$ and $R_3$ which may be the same or different are each a hydrogen atom or a straight-chained or branched alkyl group having 1–6 carbon atoms, or $R_2$ and $R_3$ may combine together to form a 3- to 8-membered ring;

$R_4$ is a hydrogen atom, a straight-chained or branched alkyl group having 1–6 carbon atoms, an alkoxycarbonyl group of which the alkyl portion is a straight-chained or branched alkyl group having 1–6 carbon atoms, an optionally substituted acyl group having 1–8 carbon atoms or an amidino group that may be substituted on the nitrogen atom with a straight-chained or branched alkyl group having 1–6 carbon atoms or a cyclic alkyl group having 3–8 carbon atoms or a nitro group, or may combine with $R_5$ to form a 3- to 8-membered ring;

$R_5$ is a hydrogen atom, a straight-chained or branched alkyl group having 1–6 carbon atoms or an alkoxycarbonyl group of which the alkyl portion is a straight-chained or branched alkyl group having 1–6 carbon atoms, or may combine with $R_4$ to form a 3- to 8-membered ring;

$Y_1$, $Y_2$, $Y_3$ and $Y_4$ which may be the same or different are each a hydrogen atom, a halogen atom, a nitro group, a cyano group, a hydroxyl group, a straight-chained or branched alkyl group having 1–6 carbon atoms that may be substituted by 1–3 halogen atoms, a cyclic alkyl group having 3–6 carbon atoms that may be substituted by 1–3 halogen atoms, a straight-chained or branched alkenyl group having 2–6 carbon atoms, a straight-chained or branched alkynyl group having 2–6 carbon atoms, an optionally substituted straight-chained or branched alkoxy group having 1–6 carbon atoms, a straight-chained or branched alkylthio group having 1–6 carbon atoms, $NY_5Y_6$ or $COY_7$;

where $Y_5$ and $Y_6$ which may be the same or different are each a hydrogen atom, an optionally substituted straight-chained or branched alkyl group having 1–6 carbon atoms, or an optionally substituted cyclic alkyl group having 3–6 carbon atoms, an acyl group having 1–8 carbon atoms, an alkoxycarbonyl group of which the alkyl portion is a straight-chained or branched alkyl group having 1–6 carbon atoms, or $Y_5$ and $Y_6$ may combine together to form a 3- to 8-membered ring;

$Y_7$ is a hydrogen atom, a hydroxyl group, a straight-chained or branched alkyl group having 1–6 carbon atoms or a cyclic alkyl group having 3–6 carbon atoms, an alkoxy group of which the alkyl portion is a straight-chained or branched alkyl group having 1–6 carbon atoms or $NY_5Y_6$;

where $Y_5$ and $Y_6$ which may be the same or different are each a hydrogen atom, a straight-chained or branched alkyl group having 1–6 carbon atoms or a cyclic alkyl group having 3–6 carbon atoms; and n and m are each an integer of 0 or 1.

42. A therapeutic composition for cerebrovascular diseases containing a pharmaceutical carrier and as an effective ingredient an amount sufficient therefor of an N-cNOS inhibitor compound of the formula (1) according to claim 1 or a possible stereoisomer or optically active form of the compound or a pharmaceutically acceptable salt thereof, in which:

$R_1$ is $NR_7R_8$, where $R_7$ is a hydrogen atom, a straight-chained or branched alkyl group having 1–6 carbon atoms, a cyclic alkyl group having 3–8 carbon atoms or a nitro group, and $R_8$ is a hydrogen atom or a straight-chained or branched alkyl group having 1–6 carbon atoms;

$R_2$ and $R_3$ which may be the same or different are each a hydrogen atom or a straight-chained or branched alkyl group having 1–6 carbon atoms, or $R_2$ and $R_3$ may combine together to form a 3- to 8-membered ring;

$R_4$ is a hydrogen atom, a straight-chained or branched alkyl group having 1–6 carbon atoms, an alkoxycarbonyl group of which the alkyl portion is a straight-chained or branched alkyl group having 1–6 carbon atoms or an amidino group that may be substituted on the nitrogen atom with a straight-chained or branched alkyl group having 1–6 carbon atoms or a cyclic alkyl group having 3–8 carbon atoms or a nitro group, or may combine with $R_5$ to form a 3- to 8-membered ring;

$R_5$ is a hydrogen atom or a straight-chained or branched alkyl group having 1–6 carbon atoms, or may combine with $R_4$ to form a 3- to 8-membered ring;

$Y_1$, $Y_2$, $Y_3$ and $Y_4$ which may be the same or different are each a hydrogen atom, a halogen atom, a nitro group, a cyano group, a hydroxyl group, a straight-chained or branched alkyl group having 1–6 carbon atoms that may be substituted by 1–3 halogen atoms, a cyclic alkyl group having 3–6 carbon atoms that may be substituted by 1–3 halogen atoms, a straight-chained or branched alkenyl group having 2–6 carbon atoms, a straight-chained or branched alkynyl group having 2–6 carbon atoms, an optionally substituted straight-chained or branched alkoxy group having 1–6 carbon atoms, a straight-chained or branched alkylthio group having 1–6 carbon atoms, $NY_5Y_6$, or $COY_7$;

where $Y_5$ and $Y_6$ which may be the same or different are each a hydrogen atom, an optionally substituted straight-chained or branched alkyl group having 1–6 carbon atoms, or an optionally substituted cyclic alkyl group having 3–6 carbon atoms, an acyl group having 1–8 carbon atoms, an alkoxycarbonyl group of which the alkyl portion is a straight-chained or branched alkyl group having 1–6 carbon atoms, or $Y_5$ and $Y_6$ may combine together to form a 3- to 8-membered ring;

$Y_7$ is a hydrogen atom, a hydroxyl group, a straight-chained or branched alkyl group having 1–6 carbon atoms or a cyclic alkyl group having 3–6 carbon atoms, an alkoxy group of which the alkyl portion is a straight-chained or branched alkyl group having 1–6 carbon atoms or $NY_5Y_6$;

where $Y_5$ and $Y_6$ which may be the same or different are each a hydrogen atom, a straight-chained or branched alkyl group having 1–6 carbon atoms or a cyclic alkyl group having 3–6 carbon atoms; and n and m are each an integer of 0 or 1.

43. A therapeutic composition for Parkinson's disease containing as an effective ingredient an amount sufficient therefor of an iNOS inhibitor compound represented by the formula (1) of claim 1 or a possible stereoisomer or optically active form of the compound or a pharmaceutically acceptable salt thereof and a pharmaceutically acceptable adjuvant.

44. A therapeutic composition for traumatic brain injuries containing as an effective ingredient an amount sufficient therefor of an iNOS inhibitor compound represented by the formula (1) of claim 1 or a possible stereoisomer or optically active form of the compound or a pharmaceutically acceptable salt thereof and a pharmaceutically acceptable adjuvant.

45. A therapeutic composition for treatment of seizure containing as an effective ingredient an amount sufficient therefor of an iNOS inhibitor compound represented by the formula (1) of claim 1 or a possible stereoisomer or optically active form of the compound or a pharmaceutically acceptable salt thereof and a pharmaceutically acceptable adjuvant.

* * * * *